US010316323B2

(12) United States Patent
South et al.

(10) Patent No.: US 10,316,323 B2
(45) Date of Patent: Jun. 11, 2019

(54) MICROORGANISMS ENGINEERED TO USE UNCONVENTIONAL SOURCES OF NITROGEN

(71) Applicant: Novogy, Inc., Cambridge, MA (US)

(72) Inventors: Colin South, Lexington, MA (US); Arthur J Shaw, IV, Belmont, MA (US)

(73) Assignee: Novogy, Inc., Cambridge, MA (US)

( * ) Notice: Subject to any disclaimer, the term of this patent is extended or adjusted under 35 U.S.C. 154(b) by 0 days.

(21) Appl. No.: 15/679,312

(22) Filed: Aug. 17, 2017

(65) Prior Publication Data

US 2018/0051294 A1 Feb. 22, 2018

Related U.S. Application Data

(62) Division of application No. 14/759,878, filed as application No. PCT/US2014/010332 on Jan. 6, 2014, now Pat. No. 9,765,348.

(60) Provisional application No. 61/782,351, filed on Mar. 14, 2013, provisional application No. 61/748,901, filed on Jan. 4, 2013.

(51) Int. Cl.

| | |
|---|---|
| ***C12P 7/48*** | (2006.01) |
| ***C12N 15/81*** | (2006.01) |
| ***C12N 1/20*** | (2006.01) |
| ***C12N 9/14*** | (2006.01) |
| ***C12N 9/88*** | (2006.01) |
| ***C12P 3/00*** | (2006.01) |
| ***C12N 15/70*** | (2006.01) |

(52) U.S. Cl.
CPC ............ *C12N 15/815* (2013.01); *C12N 1/20* (2013.01); *C12N 9/14* (2013.01); *C12N 9/88* (2013.01); *C12N 15/70* (2013.01); *C12N 15/81* (2013.01); *C12P 3/00* (2013.01); *C12Y 308/01* (2013.01); *C12Y 402/01069* (2013.01)

(58) Field of Classification Search
CPC ........... C12N 15/815; C12N 1/20; C12N 9/14
USPC ............................................................ 435/18
See application file for complete search history.

(56) References Cited

U.S. PATENT DOCUMENTS

2011/0008809 A1 1/2011 Krebs
2011/0127108 A1 6/2011 Teichert
2011/0129566 A1 6/2011 Van Vuuren et al.

FOREIGN PATENT DOCUMENTS

WO WO 2003/040379 5/2003

OTHER PUBLICATIONS

Seffernick, et al. (2001), Journal J. Bacteriol. 183 (8), 2405-2410 (2001).*

Boundy-Mills et al., "The atzB Gene of *Pseudomonas* sp. Strain ADP Encodes the Second Enzyme of a Novel Atrazine Degradation Pathway," *Applied and Environmental Microbiology*, 1997, 63(3):916-923.

Cameron et al., "New Family of Biuret Hydrolases Involved in S-Triazine Ring Metabolism," *ACS Catal*, 2011, 1:1075-1082.

Cheng et al., "Allophanate Hydrolase, Not Urease, Function in Bacterial Cyanuric Acid Metabolism," *Appl. Environ. Microb.*, 2005, 71(8):4437-4445.

Copley, "Evolution of Efficient Pathways for Degradation of Anthropogenic Chemicals," *Nat. Chem. Biol.*, 2009, 5(8):559-566.

De Souza et al., "The atzABC Genes encoding Atrazine Catabolism Are Located on a Self-Transmissible Plasmid in *Pseudomonas* sp. Strain ADP," *Appl. Environ. Microb*, 1998, 64(6):2323-2326.

Dodge et al., "Plasmid Localization and Organization of Melamine Degradation Genes in *Rhodococcus* sp. Strain Mel." *Applied and Environmental Microbiology*, 78:1397-1403.

Eaton et al., "Cloning and analysis of s-Triazine catabolic genes from *Pseudomonas* sp. Strain NRRLB-12227," *Journal of Bacteriology*, 1991 173:1215-1222.

Eaton et al., "Cloning and comparison of the DNA encoding ammelide aminohydrolase and cyanuric acid amidohydrolase from three s-Triazine-degrading bacterial strains," *Journal of Bacteriology*, 1991, 173:1363-1366.

El-Sayed et al., "Biodegradation of melamine formaldehyde by *Micrococcus* sp. Strain MF-1 isolated from aminoplastic wastewater effluent," *International Biodeterioration & Biodegradation*, 2006, 57:75-81.

Fruchey et al., "On the Origins of Cyanuric Acid Hydrolase: Purification, Substrates, and Prevalence of AtzD from *Pseudomonas* sp. Strain ADP,"*Appl. Environ. Microb.*, 2003, 69(6):3653-3657.

International Search Report and Written Opinion issued in International Patent Application No. PCT/US2014/10332, dated Jun. 24, 2014.

Kamo et al., "Limited distribution of natural cyanamide in higher plants: Occurrence in *Vicia villosa* subsp. *varia*, *V. cracca*, and *Robinia pseudo-acacia*," *Phytochemistry*, 2008, 68:1166-1172.

Kamo et al., "Quantification of Cyanamide Contents in *Herbaceous* Plants," *Bioscience, Biotechnology, and Biochemistry*, 2006, 70:2310-2312.

(Continued)

*Primary Examiner* — Tekchand Saidha
(74) *Attorney, Agent, or Firm* — Norton Rose Fulbright US LLP

(57) ABSTRACT

Disclosed are genetically engineered organisms, such as yeast and bacteria, that have the ability to metabolize atypical nitrogen sources, such as melamine and cyanamide. Fermentation methods using the genetically engineered organisms are also described. The methods of the invention are robust processes for the industrial bioproduction of a variety of compounds, including commodities, fine chemicals, and pharmaceuticals.

7 Claims, 29 Drawing Sheets

Specification includes a Sequence Listing.

(56) References Cited

OTHER PUBLICATIONS

Karns, "Gene Sequence and Properties of an s-Triazine Ring-Cleavage Enzyme from *Pseudomonas* sp. Strain NRRLB-12227," *Applied and Environmental Microbiology*, 1999, 65:3512-3517.

Leeson et al., "Biomineralization of atrazine ozonation products. Application to the Development of a Pesticide Waste Disposal System," *J. Agric. Food Chem*., 1993, 41:983-987.

Maier-Greiner et al., "Isolation and properties of a nitrile hydratase from the soil fungus *Myrothecium verrucaria* that is highly specific for the fertilizer cyanamide and cloning of its gene," *Proceedings of the National Academy of Sciences*, 1991, 88:4260-4264.

Martinez et al., "Complete Nucleotide Sequence and Organization of the Atrazine Catabolic Plasmid pADP-1 from *Pseudomonas* sp. Strain ADP." *Journal of Bacteriology*, 2001, 183:5684-5697.

Mäser et al., "A Nucleoside Transporter from *Trypanosoma brucei* Involved in Drug Resistance," *Science*, 1999, 285:242-244.

Office action issued in corresponding Chinese Patent Application No. 201480012382.8, dated Mar. 12, 2018.

Schwarzer et al., "Physiological and electron microscopical investigations on syntrophic dicyandiamide degradation by soil bacteria," *Soil Biology and Biochemistry*, 1998, 30:385-391.

Seffemick et al., "Bacterial Ammeline Metabolism via Guanine Deaminase," *Journal of Bacteriology*, 2010, 192:1106-1112.

Seffemick et al., "Melamine Deaminse and Atrazine Chlorohydrolase: 98 Percent Identical but Functionally Different," *Journal of Bacteriology*, 2001, 183:2405-2410.

Shapir et al., "Evolution of Catabolic Pathways: Genomic Insights into Microbial s-Triazine Metabolism," *J. Bacteriol*, 2007, 189(3):674-682.

Shapir et al., "Purification and Characterization of Allophanate Hydrolase (AtzF) from *Pseudomonas* sp. Strain ADP," *J. Bacteriol*, 2005, 187(11):3731-3738.

Shapir et al., "Purification and Characterization of TrzF: Biuret Hydrolysis by Allophanate Hydrolase Supports Growth," *Applied and Environmental Microbiology*, 2006, 72:2491-2495.

Shapir et al., "Purification, Substrate Range, and Metal Center of AtzC: the N-Isopropylammelide Aminohydrolase Involved in Bacterial Atrazine Metabolism," *Journal of Bacteriology*, 184(19):5376-5384.

Shelton et al., "Metabolism and Melamine by *Klebsiella terragena*." *Applied and Environmental Microbiology*, 1997, 63:2832-5.

Strong et al., "*Arthrobacter aurescens* TC1 Metabolizes Diverse s-Triazine Ring Compounds." *Applied and Environmental Microbiology*, 2002, 68:5973-5980.

Sýkora et al., "Biodegradability of ethylenediamine-based complexing agents." *Water Research*, 2001, 35:2010-2016 .

Takagi et al., "Biodegradation of Melamine and its Hydroxy Derivatives by a Bacterial Consortium Containing a Novel *Nocardioides* Species," *Appl. Microbiol Biotechnol*, 2012, 94:1647-1656.

Ulanov et al., "Effect of the Expression of cyanamide hydratase on metabolites in cyanamide-treated soybean plants kept in the light or dark," *Journal of Experimental Botany*, 2007, 58:4319-4332.

Wackett et al., "Microbial Enzymes in Biodegradation," *Novel Approaches for Bioremediation of Organic Pollution*, Fass et al., 1999, p. 95-103.

Zeyer et al., "Microbial degradation of Ammeline." *Zbl. Bakt. Hyg., I. Abt. Orig. C*., 1981, 2:289-298.

* cited by examiner

Figure 2

| Compound | Formula | % N |
|---|---|---|
| Hydrazine | $N_2H_4$ | 88% |
| 5-Aminotetrazole | $CH_3N_5$ | 82% |
| Tetrazole | $CH_2N_4$ | 80% |
| Melamine | $C_3H_6N_6$ | 67% |
| Cyanamide | $CH_2N_2$ | 67% |
| 2-Cyanoguanidine | $C_2H_4N_4$ | 67% |
| Sodium azide | $NaN_3$ | 65% |
| Carbohydrazide | $CH_6N_4O$ | 62% |
| 1,2,3-Triazole | $C_2H_3N_3$ | 61% |
| 1,2,4-Triazole | $C_2H_3N_3$ | 61% |
| 1,3-Diaminoguanidine HCL | $CH_7N_5 \cdot HCl$ | 56% |
| Ammeline | $C_3H_5N_5O$ | 55% |
| 1,3,5-triazine | $C_3H_3N_3$ | 52% |
| Aminoacetonitrile | $C_2H_4N_2$ | 50% |
| Cyanoethylhydrazine | $C_3H_7N_3$ | 49% |
| Azodicarbonamide | $C_2H_4O_2N_4$ | 48% |
| Biurea | $C_2H_6N_4O_2$ | 47% |
| Formamidoxime | $CH_4N_2O$ | 47% |
| 1,2-Dimethylhydrazine | $C_2H_8N_2$ | 47% |
| 1,1-Dimethylhydrazine | $C_2H_8N_2$ | 47% |
| ethylhydrazine | $C_2H_8N_2$ | 47% |
| Ethylenediamine | $C_2H_8N_2$ | 47% |
| Sodium dicyanamide | $C_2N_3Na$ | 47% |
| Guanidine carbonate | $CH_5N_3 * {}^1/_2\ H_2CO_3$ | 47% |
| Methylamine | $CH_5N$ | 45% |
| Ammelide | $C_3H_4N_4O_2$ | 44% |
| Hydroxylamine | $NH_2OH$ | 42% |
| Malononitrile | $C_3H_2N_2$ | 42% |
| Biuret | $C_2H_5N_3O_2$ | 41% |
| Diethyltriamine | $C_4H_{13}N_3$ | 41% |

Figure 2 (continued)

| | | |
|---|---|---|
| Hexamethylenetetramine | $C_6H_{12}N_4$ | 40% |
| Triethylenetetramine | $C_6H_{18}N_4$ | 38% |
| 1,3-Diaminopropane | $C_3H_{10}N_2$ | 38% |
| Triethylenetetramine | $C_6H_{18}N_4$ | 38% |
| 1,3-Diaminopropane | $C_3H_{10}N_2$ | 38% |
| Hydroxyurea | $CH_4N_2O_2$ | 37% |
| Tetraethylenepentamine | $C_8H_{23}N_5$ | 37% |
| Thiourea | $CH_4N_2S$ | 37% |
| Succinonitrile | $C_4H_4N_2$ | 35% |
| Calcium cyanamide | $CaCN_2$ | 35% |
| Cyanuric acid | $C_3H_3N_3O_3$ | 33% |
| Aminoethylpiperazine | $C_6H_{15}N_3$ | 33% |
| Piperazine | $C_4H_{10}N_2$ | 33% |
| Dimethylamine | $C_2H_7N$ | 31% |
| Ethylamine | $C_2H_7N$ | 31% |
| dalfampridine | $C_5H_6N_2$ | 30% |
| Tetranitromethane | $CN_4O_8$ | 29% |
| Imidazolidinyl urea | $C_{11}H_{16}N_8O_8$ | 29% |
| Trinitromethane | $CHN_3O_6$ | 28% |
| malonamide | $C_3H_6N_2O_2$ | 27% |
| Chloramine | $NH_2Cl$ | 27% |
| Allophante | $C_2H_3N_2O_3$ | 27% |
| Trimethylamine | $C_3H_9N$ | 24% |
| Nitromethane | $CH_3NO_2$ | 23% |
| Acetaldoxime | $C_2H_5NO$ | 23% |
| Diazolidinyl urea | $C_8H_{14}N_4O_7$ | 20% |
| 1,2-Cyclohexanedione dioxime | $C_6H_{10}N_2O_2$ | 20% |
| Acetone oxime | $C_3H_7NO$ | 19% |
| Thioacetamide | $C_2H_5NS$ | 19% |
| Sodium thiocyanate | $NaSCN$ | 17% |
| Isothiazole | $C_3H_3NS$ | 16% |
| Thiazole | $C_3H_3NS$ | 16% |

Figure 2 (continued)

| | | |
|---|---|---|
| Dimethylacetamide | $C_4H_9NO$ | 16% |
| Isothiazolinone | $C_3H_3NOS$ | 14% |
| Methylene blue | $C_{16}H_{18}N_3SCl$ | 13% |
| Diethanolamine | $C_4H_{11}NO_2$ | 13% |
| Aspartame | $C_{14}H_{18}N_2O_5$ | 10% |
| Benzisothiazolinone | $C_7H_5NOS$ | 7% |
| Acesulfame potassium | $C_4H_4KNO_4S$ | 7% |

Figure 3

| Enzyme | Gene | Source | EC | Genbank | Genbank Protein or Nucleotide Region |
|---|---|---|---|---|---|
| Melamine deaminase | *trzA* | *Williamsia* sp. NRRL B-15444R (formerly *R. corallinus*) | 3.5.4.- | JN241635 | |
| Melamine deaminase | *triA* | *Pseudomonas* sp. strain NRRL B-12227 (formerly *Acidovorax citrulli*) | 3.5.4.- | AF312304 | |
| Guanine (ammeline) deaminase | *guaD* | *E. coli* K12 strain MG1566 | 3.5.4.3 | NC_000913 | REGION: 3023788..3025107 |
| Guanine (ammeline) deaminase | blr3880 | *Bradyrhizobium japonicum* USDA 110 | 3.5.4.3 | NC_004463 | REGION: 4303362..4304759 |
| Guanine (ammeline) deaminase | GUD1/YDL238C | *S. cerevisiae* | 3.5.4.3 | Z74286 | |
| Guanine (ammeline) deaminase | YALI0E25740p | *Y. lipolytica* CLIB122 | 3.5.4.3 | NC_006071 | REGION: complement(3051691..3053046) |
| ammelide hydrolase | *trzC* | *Pseudomonas* sp. strain NRRL B-12227 (formerly *Acidovorax citrulli*) | 3.5.3.- | AAK00493 | |
| ammelide hydrolase | *trzC* | *Rhodococcus* sp. Mel | 3.5.3.- | AEX65049 | |
| N-isopropylammelide isopropylamino hydrolase | *atzC* | *Pseudomonas* sp. strain ADP | 3.5.99.4 | NC_004956 | REGION: complement(70219..71430) |
| Cyanuric acid amidohydrolase | *trzD* | *Pseudomonas* sp. strain NRRL B-12227 (formerly *Acidovorax citrulli*) | 3.5.2.15 | AF086815 | |
| Cyanuric acid amidohydrolase | *atzD (trzD)* | *Rhodococcus* sp. Mel | 3.5.2.15 | JN241637 | AEX65082 |
| Cyanuric acid amidohydrolase | *atzD* | *Pseudomonas* sp. strain ADP | 3.5.2.15 | NC_004956 | REGION: 101053..102144 |
| Biuret amidohydrolase | *atzE* | *Pseudomonas* sp. strain ADP | 3.5.1.84 | NC_004956 | REGION: 102427..103800 |
| Biuret amidohydrolase | *trzE* | *Rhodococcus* sp. Mel | 3.5.1.84 | AEX65081 | |
| Biuret amidohydrolase | *trzE* | *Rhizobium leguminosarum* bv. viciae 3841 | 3.5.1.84 | YP_770628 | |
| Allophanate hydrolase | *atzF* | *Pseudomonas* sp. strain ADP | 3.5.1.54 | NC_004956 | REGION: 104283..106100 |
| Allophanate hydrolase | DUR1,2 | *S. cerevisiae* | 6.3.4.6 / 3.5.1.54 | YSCDURD | |
| Allophanate hydrolase | YALI0E07271g | *Y. lipolytica* CLIB122 | 6.3.4.6 / 3.5.1.54 | XM_503658 | |

Figure 11

| MOPS defined medium | mM |
|---|---|
| Glucose | 11.1 |
| $K_2HPO_4$ | 1.32 |
| $K_2SO_4$ | 0.28 |
| $FeSO_4$ | 0.01 |
| $CaCl_2$ | 5E-04 |
| $MgCl_2$ | 0.52 |
| NaCl | 50 |
| MOPS | 40 |
| Tricine | 4 |
| $(NH_4)_6Mo_7O_{24}$ | 3E-06 |
| $H_3BO_3$ | 4E-04 |
| $CoCl_2$ | 3E-05 |
| $CuSO_4$ | 1E-05 |
| $MnCl_2$ | 8E-05 |
| $ZnSO_4$ | 1E-05 |

| | Optical Density 600 nm | | | |
|---|---|---|---|---|
| | NS100 | NS101 | NS111 | NS112 |
| no nitrogen | 0.18 | 0.19 | 1.31 | 0.99 |
| 10 mM urea | 3.12 | 3.60 | 3.68 | 3.05 |
| 10 mM cyanamide | 0.05 | 4.66 | 3.09 | 0.15 |

| | Optical Density 600 nm | | |
|---|---|---|---|
| | NS98 | NS99 | NS100 |
| no nitrogen | 1.43 | 1.37 | 1.09 |
| 10 mM urea | 5.09 | 5.26 | 5.22 |
| 10 mM biuret | 2.55 | 2.18 | 1.21 |

Figure 29

| Plasmid | Description | Genotype |
|---|---|---|
| pNC10 | *E. coli* and *S. cerevisiae* cloning/shuttle vector | Amp, ura3 |
| pNC53 | *E. coli* promoter (pTac)-terminator (trpT') cloning vector (AJS52) | Amp, ura3 |
| pNC67 | *E. coli*, *S. cerevisiae*, and *Y. lipolytica* shuttle vector | Amp, ura3, Hyg, Nat |
| pNC85 | *E. coli triA* expression vector (AJS69) | Amp, ura3 |
| pNC86 | *E. coli trzA, guaD, trzC* expression vector (AJS67) | Amp, ura3 |
| pNC87 | *E. coli trzD, trzE*, DUR1,2 expression vector (AJS68) | Amp, ura3 |
| pNC93 | *S. cerevisiae cah* expression vector (AJS76) | Amp, ura3, Hyg |
| pNC96 | *S. cerevisiae trzE MEL* expression vector (AJS79) | Amp, ura3, Hyg |
| pNC97 | *S. cerevisiae trzE R1* expression vector (AJS80) | Amp, ura3, Hyg |
| pNC101 | E. coli *trzC*_12227, *guaD*, *triA* expression vector (AJS83) | Amp, ura3 |
| pNC120 | E. coli *trzD*_12227, *trzE*, DUR1,2 *trzC*_12227, *guaD*, *triA* expression vector (AJS88a) | Amp, ura3 |
| pNC121 | E. coli *atzD*_ADP, *trzE*, DUR1,2 *trzC*_12227, *guaD*, *triA* expression vector (AJS88b) | Amp, ura3 |

Figure 30

| Strain | Description | Culture Collection Designation |
|---|---|---|
| NS21 | Eschericha coli K12 | NRRL B-3707 |
| NS88 | Eschericha coli K12 with pNC85 | |
| NS89 | Eschericha coli K12 with pNC86 | |
| NS90 | Eschericha coli K12 with pNC87 | |
| NS91 | Eschericha coli K12 with pNC53 | |
| NS93 | Eschericha coli K12 with pNC85 selected for ammeline utilization | |
| NS103 | Eschericha coli K12 with pNC101 | |
| NS106 | Eschericha coli MG1655 | ATCC 47076 |
| NS107 | Eschericha coli B | ATCC 11303 |
| NS108 | Eschericha coli Crooks | ATCC 8739 |
| NS109 | Eschericha coli K12 with pNC120 | |
| NS110 | Eschericha coli K12 with pNC121 | |
| NS120 | Eschericha coli MG1655 with pNC53 | |
| NS121 | Eschericha coli MG1655 with pNC121 | |
| NS122 | Eschericha coli B with pNC121 | |
| NS123 | Eschericha coli Crooks with pNC53 | |
| NS124 | Eschericha coli Crooks with pNC121 | |
| NS8 | Saccharomyces cerevisiae | NRRL Y-2223 |
| NS22 | Saccharomyces cerevisiae industrial ethanol strain | |
| NS98 | Saccharomyces cerevisiae industrial ethanol strain with pNC96 | |
| NS99 | Saccharomyces cerevisiae industrial ethanol strain with pNC97 | |
| NS100 | Saccharomyces cerevisiae industrial ethanol strain with pNC67 | |
| NS101 | Saccharomyces cerevisiae industrial ethanol strain with pNC93 | |
| NS111 | Saccharomyces cerevisiae NRRL Y-2223 with pNC93 | |
| NS112 | Saccharomyces cerevisiae NRRL Y-2223 with pNC67 | |

Figure 31

*E. coli* Media

| MOPS defined medium | mM |
|---|---|
| Glucose | 11.1 |
| $K_2HPO_4$ | 1.32 |
| $K_2SO_4$ | 0.28 |
| $FeSO_4$ | 0.01 |
| $CaCl_2$ | 5E-04 |
| $MgCl_2$ | 0.52 |
| NaCl | 50 |
| MOPS | 40 |
| Tricine | 4 |
| $(NH_4)_6Mo_7O_{24}$ | 3E-06 |
| $H_3BO_3$ | 4E-04 |
| $CoCl_2$ | 3E-05 |
| $CuSO_4$ | 1E-05 |
| $MnCl_2$ | 8E-05 |
| $ZnSO_4$ | 1E-05 |
| Nitrogen source as indicated | 0.25-10 |

Additionally 100 ug/mL ampicillin is added for plasmid maintenance.

Figure 32

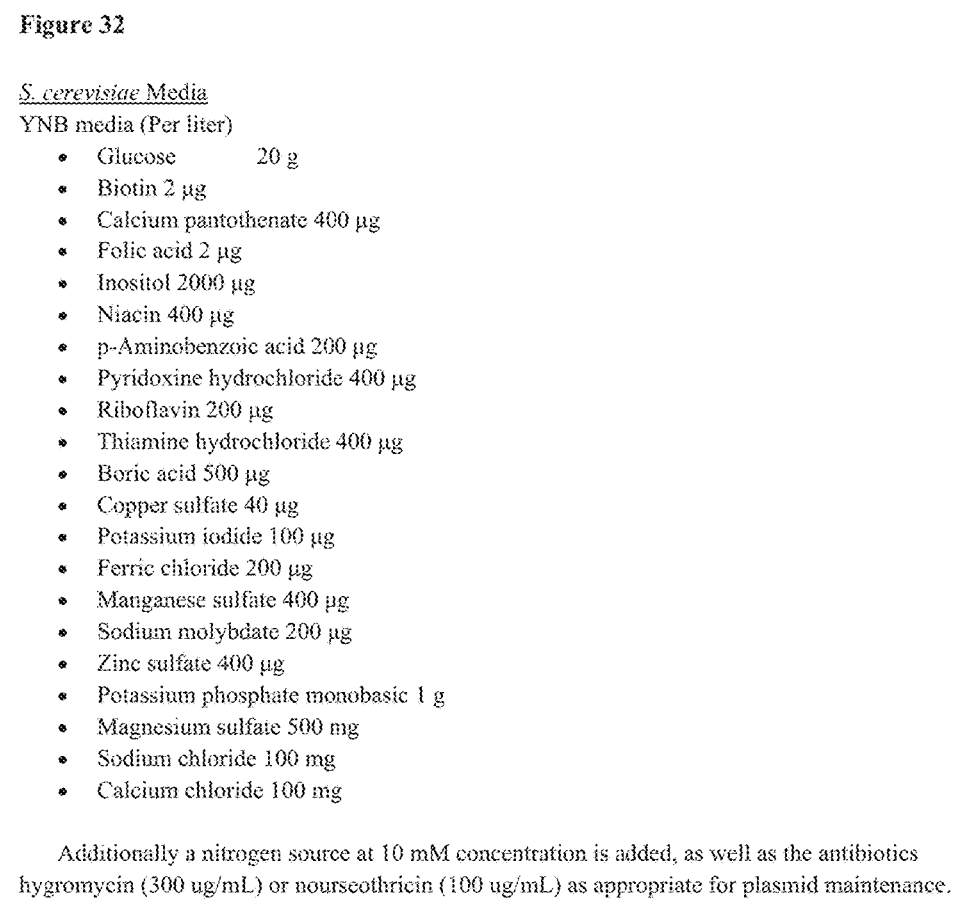

*S. cerevisiae* Media

YNB media (Per liter)

- Glucose 20 g
- Biotin 2 µg
- Calcium pantothenate 400 µg
- Folic acid 2 µg
- Inositol 2000 µg
- Niacin 400 µg
- p-Aminobenzoic acid 200 µg
- Pyridoxine hydrochloride 400 µg
- Riboflavin 200 µg
- Thiamine hydrochloride 400 µg
- Boric acid 500 µg
- Copper sulfate 40 µg
- Potassium iodide 100 µg
- Ferric chloride 200 µg
- Manganese sulfate 400 µg
- Sodium molybdate 200 µg
- Zinc sulfate 400 µg
- Potassium phosphate monobasic 1 g
- Magnesium sulfate 500 mg
- Sodium chloride 100 mg
- Calcium chloride 100 mg Additionally a nitrogen source at 10 mM concentration is added, as well as the antibiotics hygromycin (300 ug/mL) or nourseothricin (100 ug/mL) as appropriate for plasmid maintenance.

Figure 33

SC amino acid composition (total 2 g/L)

| SC amino acids | mg/L |
|---|---|
| Adenine | 21 |
| L-Alanine | 85.6 |
| L-Arginine | 85.6 |
| L-Asparagine | 85.6 |
| L-Aspartic Acid | 85.6 |
| L-Cysteine | 85.6 |
| Glutamine | 85.6 |
| L-Glutamic Acid | 85.6 |
| Glycine | 85.6 |
| L-Histidine | 85.6 |
| Myo-Inositol | 85.6 |
| L-Isoleucine | 85.6 |
| L-Leucine | 173.4 |
| L-Lysine | 85.6 |
| L-Methionine | 85.6 |
| Para-AminoBenzoic Acid (PABA) | 8.6 |
| L-Phenylalenine | 85.6 |
| L-Proline | 85.6 |
| L-Serine | 85.6 |
| L-Threonine | 85.6 |
| L-Tryptophan | 85.6 |
| L-Tyrosine | 85.6 |
| Uracil | 85.6 |
| L-Valine | 85.6 |

SEQUENCE LISTING

```
<160> NUMBER OF SEQ ID NOS: 76

<210> SEQ ID NO 1
<211> LENGTH: 1818
<212> TYPE: DNA
<213> ORGANISM: Pseudomonas sp.

<400> SEQUENCE: 1

atgaatgacc gcgcgcccca ccctgaaaga tctggtcgag tcacgccgga tcacctgacc     60

gatctggctt cctatcaggc tgcctatgcc gccggtacag acgccgccga cgtcatttcg    120

gacctgtatg cccgtatcaa agaagacggc gaaaatccga tctggattag cctgttgccc    180

ttggaaagcg cattggcgat gctggccgac gcgcagcaac gcaaggacaa gggagaagcg    240

ttgccgctct ttggcatccc cttcggcgtc aaggacaaca tcgacgtcgc aggccttccg    300

acgactgccg ggtgtacggg gttcgcgcgt acgccccgac agcacgcctt cgtcgtacag    360

cgcctggtgg acgctggcgc gatcccgatc ggaaaaacga acctcgatca attcgcgacc    420

gggttgaacg gcactcgcac gccgtttggc attccgcgct gcgtgttcaa cgagaactac    480

gtatccggcg gctccagcag tggctccgca gtggccgtcg ccaacggcac ggtaccgttc    540

tcgctcggga cggacactgc cggttccggc cgcattcctg ctgcgttcaa caatctggtg    600

ggcttgaaac cgaccaaagg cctgttctcg ggcagtggac tggttcccgc ggcgcgaagc    660

cttgactgca tcagcgtcct cgcccatacc gtagatgacg cccttgcggt cgcacgcgtc    720
```

-continued

```
gccgccggct acgatgctga tgacgctttt tcgcgcaagg cgggcgccgc cgcactgaca    780
gaaaagagtt ggcctcgtcg cttcaatttc ggggtcccag cggcggaaca tcgccagttt    840
ttcggtgacg cggaagccga ggcgcttttc aataaagcgg ttcgcaagct tgaagagatg    900
ggtggcacct gcatctcgtt tgactatacc cccttcaggc aggctgctga actgctctac    960
gccggccctt gggttgcgga gcgcctggcg gccatcgaga gccttgcgga cgagcatccc   1020
gaggtgctcc acccggtcgt tcgtgacatc atcttgtccg cgaagcgaat gagcgcagtc   1080
gacacgttca acggtatcta tcgcctggcc gaccttgtca gggctgcaga gagcacttgg   1140
gaaaagatcg atgtgatgct gctgccgacg gcgccgacca tctacactgt agaagacatg   1200
ctcgccgatc cggtacgcct caacagcaat ctgggcttct acacgaactt cgtgaacttg   1260
atggatttgt ccgcgattgc tgttcccgca ggcttccgaa ccaatggcct gccatttggc   1320
gtcactttca tcggtcgggc gttcgaagat ggggcgatcg caagcttggg aaaagctttc   1380
gtggagcacg acctcgccaa gggcaacgcg gccacggcgg cgccacccaa ggataccgtc   1440
gcaatcgccg tggtaggtgc acatctctcc gaccagccct tgaatcatca gctcacggag   1500
agcggcggaa agctacgggc aacaacgcgt actgcgccgg gatatgcctt gtacgcactc   1560
cgtgatgcga cgccggctaa gcctggaatg ttgcgcgacc agaatgcggt cgggagcatc   1620
gaagtggaaa tctgggatct gccggtcgcc gggttcggtg cgtttgtaag tgaaattccg   1680
gcgccgttgg gtatcgggac aataacactc gaagacggca gccatgtgaa aggctttctg   1740
tgcgagccac atgccatcga gacggcgctc gacatcactc actacggcgg ctggcgagca   1800
tacctcgcgg ctcaatag                                                 1818
```

```
<210> SEQ ID NO 2
<211> LENGTH: 5508
<212> TYPE: DNA
<213> ORGANISM: Saccharomyces cerevisiae

<400> SEQUENCE: 2

atgacagtta gttccgatac aactgctgaa atatcgttag gttggtcaat ccaagactgg     60
attgatttcc acaagtcatc aagctcccag gcttcactaa ggcttcttga atcactacta    120
gactctcaaa atgttgcgcc agtcgataat gcgtggatat cgctaatttc aaaggaaaat    180
ttactgcacc aattccaaat tttaaagagc agagaaaata aagaaactct acctctctac    240
ggtgtcccta ttgctgttaa ggacaacatc gacgttagag gtctacgcac caccgctgca    300
tgtccatcct ttgcatatga gccttccaaa gactctaaag tagtagaact actaagaaat    360
gcaggtgcaa taatcgtggg taagacaaac ttggaccaat ttgccacagg attagtcggc    420
acacggtctc catatgggaa aacaccttgc gcttttagca aagagcatgt atctggtggt    480
tcctccgctg ggtcagcatc ggtggtcgcc agaggtatcg taccaattgc attgggtact    540
gatacagcag gttctggtag agtcccagcc gccttgaaca acctgattgg cctaaagcca    600
acaaagggcg tcttttcctg tcaaggtgta gttcccgctt gtaaatcttt agactgcgtc    660
tccatctttg cattaaacct aagtgatgct gaacgctgct tccgcatcat gtgccagcca    720
gatcctgata atgatgaata ttctagaccc tatgtttcca acccaaagaa aaatttttca    780
agcaatgtaa cgattgctat tcctaaaaat atcccatggt atggtgaaac caagaatcct    840
gtactgtttt ccaatgctgt cgaaaatcta tcaagaacgg gcgctaacgt catagaaatt    900
gattttgagc ctcttttaga gttagctcgc tgtttatacg aaggtacttg ggtggccgag    960
cgttatcaag ctattcaatc gtttttggac agtaaaccac caaaggaatc tttggaccct   1020
```

```
actgttattt caattataga aggggccaag aaatacagtg cagtagactg cttcagtttt   1080

gaatacaaaa gacaaggcat cttgcaaaaa gtgagacgac ttctcgaatc agtcgatgtc   1140

ttgtgtgtgc ccacatgtcc cttaaatcct actatgcaac aagttgcgga tgaaccagtc   1200

ctagtcaatt caagacaagg cacatggact aattttgtca acttggcaga tttggcagcc   1260

cttgctgttc ccgcagggtt ccgagacgat ggtttgccaa atggtattac tttaatcggt   1320

aaaaaattca cagattacgc actattagag ttggctaacc gctatttcca aaatatgttc   1380

cccaacggtt ccagaacata cggtactttt acctcttctt cagtaaagcc agcaaacgat   1440

caattagtgg gaccagacta tgacccatct acgtccataa aattggctgt tgtcggtgca   1500

catcttaagg gtctgcctct acattggcaa ttggaaaagg tcaatgcaac atatttatgt   1560

acaacaaaaa catcaaaagc ttaccagctt tttgctttgc ccaaaaatgg accagtttta   1620

aaacctggtt tgagaagagt tcaagatagc aatggctctc aaatcgaatt agaagtgtac   1680

agtgttccaa aagaactgtt cggtgctttt atttccatgg ttcctgaacc attgggaata   1740

ggttcagtgg agttagaatc tggtgaatgg atcaaatcct ttatttgtga agaatctggt   1800

tacaaagcca aaggtacagt tgatatcaca aagtatggtg gatttagagc atattttgaa   1860

atgttgaaga aaaaagagtc ccaaaagaag aagttatttg ataccgtgtt aattgccaat   1920

agaggtgaaa ttgccgttcg tattatcaag acattaaaaa aattgggtat tagatcagtt   1980

gcagtttatt ccgaccctga taaatattct caacacgtta ctgatgcaga tgtttctgta   2040

ccccttcatg gcacaaccgc agcccaaact tatttagaca tgaataagat catagatgcc   2100

gctaagcaaa ctaatgcaca ggccattatt cctggttatg gtttcttgtc ggaaaatgcg   2160

gatttttctg atgcgtgcac cagtgctggc attacctttg ttggtccttc gggagatatt   2220

atcagaggtt tagggttaaa acattctgct agacagattg cacagaaggc tggcgttcct   2280

ctagtgccag gctctttgct tatcacatca gttgaagagg ctaagaaagt cgcagcggaa   2340

ttggaatacc cagttatggt gaagtcaact gctggtggcg gtggtattgg tttgcagaaa   2400

gtcgattctg aagaggacat cgagcatatt tttgagactg tgaaacatca aggtgaaaca   2460

tttttcggtg acgctggtgt atttctgaaa cggtttatcg aaaatgccag gcatgttgaa   2520

gtccaactta tgggagatgg ttttggtaag gccattgctt tgggcgaacg tgattgttct   2580

ttacagcgtc gtaaccaaaa agttatcgaa gaaactcctg caccaaattt gccagaaaag   2640

acgaggttgg cgttaagaaa ggcagctgaa agtttgggat ctttattgaa ttacaagtgt   2700

gctggtacgg ttgaatttat ttacgatgag aaaaaggacg agttttactt tttagaagtt   2760

aatacaagat tacaagttga acatccaata acagaaatgg ttacagggtt agacttggtc   2820

gagtggatga tcaggattgc cgctaatgat gcacctgatt ttgattctac aaaggtagaa   2880

gtcaatgggg tttcaatgga ggcacgttta tatgctgaaa atccattgaa aaatttcaga   2940

ccttctccag gtttacttgt cgatgtgaaa tttcctgatt gggcaagagt ggatacttgg   3000

gttaagaaag gtactaatat ttctcccgaa tatgatccaa cattggccaa aattatcgtt   3060

catgggaaag accgtgatga tgcaatttcc aagttaaatc aagcgttaga agaaacaaaa   3120

gtttacggat gtattactaa cattgactac ctgaagtcta tcattaccag tgatttcttt   3180

gctaaagcaa aagtttctac aaacattttg aactcttatc aatatgagcc taccgccatc   3240

gaaattactt tgcccggtgc acacactagt attcaggatt accccggtag agttgggtac   3300

tggagaattg gtgttccgcc ctctggtcca atggacgcat attcgtttag attggcgaac   3360
```

```
agaattgttg gtaatgacta caggactcct gccattgaag taacgttgac tggtccatcc   3420
atcgttttcc attgtgaaac tgtcattgcc attactggtg gtaccgctct atgtacatta   3480
gacggccaag aaattcccca acacaaaccg gtcgaagtta agaggggatc tactttatcc   3540
attggcaagt tgacaagcgg ctgtagagca tacttaggta tcaggggtgg cattgatgtg   3600
cctaaatact tgggctctta ttctactttc actctaggaa atgtcggtgg atacaatgga   3660
agggtgctaa aacttggaga cgtactattc ttaccaagca atgaagaaaa taaatcagtt   3720
gagtgccttc cacagaatat tcctcaatca ttaattcctc aaatttccga aactaaggaa   3780
tggagaattg gtgtaacatg tggtccccat gggtctccag atttttttaa acctgagtcc   3840
atcgaagaat ttttcagtga gaagtggaag gttcattaca actccaatag atttggtgtc   3900
cgtttgattg gacctaaacc taagtgggca agaagtaatg gtggtgaagg tggtatgcat   3960
ccttcaaaca ctcacgatta cgtttattct ctgggtgcaa ttaatttcac gggtgatgag   4020
ccagttatta ttacttgcga tggtccttcc ttaggtggtt ttgtgtgtca agctgttgtc   4080
ccagaagcag aactgtggaa ggttggacag gttaaacccg gtgattccat tcagtttgtg   4140
ccactttctt acgaaagctc gagatcctta aaggaatctc aggaagttgc aattaaatca   4200
ttggatggta ctaagttaag gcgcttagac tctgtttcaa ttttaccatc attcgaaacg   4260
cctattcttg cacaaatgga aaaagtgaat gagctttcac caaaggttgt atacagacaa   4320
gcaggtgatc gttatgtttt ggtggaatac ggtgataatg aaatgaattt taatatttcc   4380
tatagaattg aatgcctgat ctcccttgtg aaaaagaata agactattgg tattgttgaa   4440
atgtcccaag gtgttagatc tgtgttgata gaatttgatg gttacaaagt cactcaaaaa   4500
gaattgctta aagtattggt ggcatatgaa acagaaatcc agtttgatga aaattggaag   4560
ataacttcta atataataag attaccgatg gctttcgaag actcgaagac tttggcatgt   4620
gttcaaaggt atcaagaaac aattcgttcg tctgctccat ggttgccaaa taacgttgat   4680
ttcattgcca atgtaaatgg aatttcaagg aatgaagttt atgatatgtt gtattctgcc   4740
agatttatgg ttttaggttt aggtgatgtc ttcctagggt cgccttgtgc tgttccatta   4800
gatcctcgtc acagattttt gggaagcaag tacaacccaa gtagaacata tacagaaaga   4860
ggtgcagtcg gtattggcgg tatgtatatg tgcatatatg ctgctaacag tcctggtggg   4920
taccaattag tgggtagaac aataccaatt tgggacaaac tatgtctggc cgcatcttct   4980
gaggttccgt ggttgatgaa cccatttgac caagtcgaat tttacccagt ttctgaagaa   5040
gatttggata aaatgactga agattgtgat aatggtgttt ataaagtcaa tatcgaaaag   5100
agtgtttttg atcatcaaga atacttgaga tggatcaacg caaacaaaga ttccatcaca   5160
gcattccagg agggccagct tggtgaaaga gcagaggaat ttgccaaatt gattcaaaat   5220
gcaaactctg aactaaaaga aagtgtcaca gtcaaacctg acgaggaaga agacttccca   5280
gaaggtgcag aaattgtata ttctgagtat tctgggcgtt tttggaaatc catagcatct   5340
gttggagatg ttattgaagc aggtcaaggg ctactaatta ttgaagccat gaaagcggaa   5400
atgattatat ccgctcctaa atcgggtaag attatcaaga tttgccatgg caatggtgat   5460
atggttgatt ctggtgacat agtggccgtc atagagacat tggcatga               5508
```

```
<210> SEQ ID NO 3
<211> LENGTH: 5463
<212> TYPE: DNA
<213> ORGANISM: Yarrowia lipolytica

<400> SEQUENCE: 3
```

```
atgtgcaaat caatcggctg gactattgcc gaatggaagg aggcacagac caactcgtct     60
tacgaggagg cccgacatcg actgttggac ctcgtggcca ccttcaagga ctacaagcat    120
ggtgatccgg cttggatcac tgtcgcctca acagagcata tcaacaagca atggaaggag    180
cttcagttga tgaagaagaa cccagagtcc cttccccttt acggagttcc tttcgctgta    240
aaggacaaca ttgatgtcat cgactttccc acaaccgctg catgccccgc ctatctctac    300
atccccaagg aagacgccac catggtccgt ctgatcaaag aggctggagg tatcgttgtc    360
ggcaaaacca acctcgatca gttcgctact ggtctggtcg gaacccgatc tccttacgga    420
aagactccca acaccttctc cgacaagcac gtatctggag gttcgtctgc tggctctgct    480
tccgtagtcg cccgaggcct ggttcccttt tctcttggaa cagatactgc aggctcaggt    540
cgggttcccg cctctctcaa caacctggta ggcctaaagc caaccgttgg cgcattttca    600
gccaagggtg tggtacccgc ctgcaagtcg cttgattgcg tctccatttt ctcgctggtc    660
ctgtctgacg ctcagctggt gttcaacatt gccgcccact ttgacaagga cgattgctac    720
tcgcgacgtt tcccccagcg acctctcaag tcgtttggcc ccactccagt atttgccgtc    780
cccgaaaccc ctctgtggtt tggagatgag ctcaaccctg ctctcttcga cgacgccgtt    840
gagcgtttgc gacaacaggg cgtaaaggtc gtcaagattg acttcactcc tctgttcgac    900
ctcgccaagt gcctctacga aggtccctgg gtggctgagc gatacgctgc catcaaggac    960
tttgtgcaga accgaaagga agacatggac gaaactgtgt atggcattgt caagcaggct   1020
gagaacttca ctgctgcaga cgcctttgcc tacgagtaca aacgacgagc cattgtgcga   1080
aagattgagg agatcttctc ttccattgac ggtctgatcg tgcccacatg tcctctattc   1140
cccaccatgg agtctgtggc taaggagcct gtcactgtca atgcccacca gggtacctac   1200
accaactttg tcaacctcgc tgatctctct gctctagcta tccctgtcgg attccgaaag   1260
gacggtttcc cctttggaat cactctcatc tctcaaaagt tcaacgacta cgctctgctg   1320
gacatggctc agaagttcct gcctgcttct cgacctctgg gtgctctgcc aaaggacaag   1380
ttcaccgcca agaagggaga tcttcttgcc tcttctatcg tcgacaacat gcctcgaacc   1440
atccctctgg ctgttgtagg agcccatctc accggcatgc ctctcaactg gcagcttcaa   1500
aaggtcgagg ctactcttgc ccgacgaacc aaaactgccg actactaccg actctacgct   1560
ctggcgaaca ccgtgcctac aaagcctggt ctccgacggg ttcttccctc tgacactact   1620
ctccgaggcg aggctattga ggttgaaatc tgggacgtgc cttacagaaa ctttggagag   1680
ttcgtatcaa tggtccctca tcctcttggt atcggaacca ttgagcttgc cgacggaaaa   1740
tgggtcaagg gtttcatttg cgagcagctg ggatacgacg acgctgagga catcaccaag   1800
tttggcggct ggagagcgta caaggctgag actacccaga acctggagtc caagcctttc   1860
gagactgttc tggtcgccaa ccgaggtgag attgccgttc gactcatcaa aactcttcga   1920
aagatggata ttcgagctgt ggctgtcttc tccgagcctg atcggttcgc tcaacatgtt   1980
cttgatgctg atgactctgt gtctctggaa ggtaccactg ccgccgagac ttacttgtcc   2040
atccccaaga ttatcgctgc ttgcaagaag actggagccc aagccattct tcctggctac   2100
ggtttcctgt ctgagaatgc tgacttctcc gacgcctgtg ccgaggctgg tatcgtattc   2160
attggcccca ctggtgactc cattcgaaag ctcggtctca agcactctgc acgagagatt   2220
gctcttgctt ctgacgtgcc tcttgtgccc ggtacaggcc tgatcgagac tgtttccgag   2280
gcctccgagg ctgccgagaa gctcgagtac cccctgatga tcaagagtac cgctggtgga   2340
```

```
ggtggtattg gtcttcagaa ggtcgacaaa cccgaggatc tcaagcgggc ttttgagacc   2400
gtcaagcacc aaggtaagtc tttctttgga gacgatggtg tcttcatgga gcgatttgtc   2460
gagaatgctc gacacgtgga ggttcagatt cttggtgacg gcaagggcaa cgctctcgct   2520
attggcgagc gagactgttc tcttcagcga cgaaaccaga aggtcgtcga agagactcct   2580
gcccccaact tccctgctga gactcgaact cgaatgatga aggcgtccga aatgctggca   2640
aagaacctca actatcgagg tgccggcact gtggagttca ttttcgatga gaagcgaaac   2700
gagttctact tccttgaggt taacgctcgt ctgcaggtcg agcatcccat cactgagtcc   2760
gtcactggac tggatcttgt cgagtggatg attctcattg gagctggcaa ggccccagac   2820
ttcgaggccc agcgtgccaa gaccccccag ggtgcttcta tcgaggcccg tctgtacgcc   2880
gagaaccccg tcaaggactt tgtgccttct cccggtcagc tcaccgacgt gcagttccct   2940
agtgatgctc gagtcgacac ctgggtcagc cgtggaacca agatctcagc agagtacgat   3000
cccactcttg ccaagattat tgttcacggc tctgaccgag ctgacgccct gcgaaagctc   3060
cagagagctc tggacgagac agtggttgcc ggcgtgacca ccaacctgga ctaccttaag   3120
tccattgtcg gatctcagat gtttgccgag gccaaggtgt ccacccgagt actggactct   3180
tacaactaca ctcccaatgc cattgagatc acttccccccg gctcctacac cactattcag   3240
gattaccccg gtcgaaccaa gctgtggcat attggtgttc ctccttctgg acccatggat   3300
gcctacgcct tccgggtggc caaccagatt gtgggcaacc accccaaggc tcctgctatc   3360
gaagctacac ttgtgggccc ctcaattatg ttccacagcg acactgtgat tgccatcacc   3420
ggtggatctg ctgaggccac tcttaatggt gagcccatcg agttctggaa gcctgtgact   3480
gtcaaggctg gccagactct cgcaactggc cgtctcactt ctggctgcag attgtacatt   3540
gcgattcgaa acggtctgtc tattccagag taccttggtt ctcgatccac cttcgctctc   3600
ggtaaccttg gaggcttcaa cggtcgaact ctcaagtttg gcgatgtcat tttcatgggc   3660
gagcccgagc ttccctcctg ctccattcct gctcccatct ccgagcatgc tcctgcctct   3720
gatgacatga tccccaagta tggcaacgcc tggactgttg gagtcacttg cggccctcac   3780
ggctcgccag actttttgc tcacggctgg atggatacct tcttcgatgc caagtggaag   3840
atccattaca actccaaccg atttggtgtt cgtctgattg gccccaagcc cgagtgggct   3900
cgaaaggatg gaggagaggc tggtctgcat ccttccaacc agcacgacta tgtctactct   3960
ctgggtgcca tcaatttcac cggtgatgag cctgtcattc tgacctgcga tggtccttct   4020
ctcggtggct ttgtctgtgc tgctgttgtt gtagaggccg agctgtggaa gattggccag   4080
gtcaagcccg gagacactgt gcagtttgtg cccatgacta ttgactctgc tcgacagctc   4140
aagaaggccc aggacagaac cattaccaac ctgtgcggtt ccccgtacga gtctgttgat   4200
gctcttctcg ctctggagga ttacgagaac cccatcatct acaccgtccc tgcctctacc   4260
tccactcctc gagtcgtcta ccgacaggct ggagaccgat acattctggt cgagtacggt   4320
gacaacaaca tggacattaa cctgtcctat cgaatccatc ggctcattga ggaagctcag   4380
cagtctatca agggcattgt cgaaatgtct cgaggtgttc gttctgtgct gatcgagttc   4440
catccttctg cctctcgatc cactctcatg caggctttgg tcgactttga gaagcgactt   4500
cagtttgtcg agacctggca ggttccctct cgaattattc gactgccgat gtgctttgag   4560
gactccaaga ccctggacgc tgtcaaacgg taccaggaga ccattcggtc aaaggctccc   4620
tggcttccca acaacgtcga cttcattcga gacgtcaaca agttctccga ccgatctcag   4680
gtccgagaca ttgtctacac tgcccgattc ctggttctgg gtcttggaga cgtgttcctt   4740
```

```
ggtgctcctt gcgcggtacc tcttgatccc cgacacagac tgcttggaac aaagtacaat   4800

ccctctcgaa cctacactcc caacggcact gtcggaattg gaggaatgta catgtgtatc   4860

tacaccatgg aatctcctgg aggctaccag ttggttggtc gaactatccc catctgggac   4920

aagctgtctc tcggccagga ccgaccttgg ctgctgtcac ccttcgacca gattgagtac   4980

taccccgtcg acgaggagga gctcaaccac attaccaccg aggtggagaa cggtcgatat   5040

gctgtggaga tggagcagtc cgtctttgat tatggcaagt attctgcctg gctcaaggac   5100

aactctaagt ccattgaggc tcacattgct tctcaggcag agggtctgga cgacttcgcc   5160

aacctgatca aggtcgccaa cgaggatctg gcctctggaa agactggagc caccaaggag   5220

gagactcctc tgtcggcctc tgccgtccag gtcttctccg aggtcactgg ccgtttctgg   5280

aagggcctgg ttgccgtcgg agatactgtt gacaagggcc agggtatcgt tgtggtggag   5340

gccatgaaga ccgagatggt cgtcaacgcc cctgttgctg gaaaggttgt caagttgtac   5400

aacaccaatg gagatatggt ggatactgga gattgtgtgg ctgtcatcga gcccattgtt   5460

taa                                                                 5463
```

<210> SEQ ID NO 4
<211> LENGTH: 1374
<212> TYPE: DNA
<213> ORGANISM: Pseudomonas sp.

<400> SEQUENCE: 4

```
atgaagacag tagaaattat tgaaggtatc gcctctggca gaaccagtgc gcgcgacgtg     60

tgcgaagagg cgctcgcaac catcggcgcg accgatggac tcatcaatgc ctttacatgc    120

cgtacggttg aacgagcccg cgcagaggcg gatgccatcg atgttcgacg ggcgcgcggc    180

gaggtacttc cgcctcttgc cggcctcccc tacgcggtaa agaatctgtt cgacatcgaa    240

ggcgtgacga cgcttgccgg ctcgaagatc aaccgtactc tcccgcctgc gcgcgcagac    300

gccgtgctgg tgcaacggct gaaagctgcc ggcgccgtgc tcctgggcgg cctcaatatg    360

gacgagtttg cctatggatt tacgaccgaa aatacgcact atgggccgac ccggaacccg    420

catgacaccg ggcgtatcgc tggtggttcg tcaggggggt ctggagcggc aatcgctgcg    480

gggcaggtac cactatcgct cggatcggac accaacggtt ccatacgcgt gccagcatca    540

ttgtgtggcg tgtgggggct gaagcctacc ttcggccgcc tgtcccggcg agggacatac    600

ccgtttgttc acagcattga tcacctcggg ccattggccg atagcgtgga aggcttggcg    660

ttggcctacg atgcaatgca gggcccggat ccgctcgacc ccggatgcag cgcatcgcgc    720

atccaaccct cggtaccggt cctcagtcag ggtatcgctg ggctccggat cggcgtgctg    780

ggtggctggt ttcgggacaa tgccggcccg gccgcgcgag ccgcggtcga tgttgccgcg    840

cttacgctcg gcgccagcga agtcgtcatg tggcccgacg cggagatcgg gcgcgcagcc    900

gccttcgtta tcactgccag cgagggaggc tgtctgcatc tcgatgatct tcgcatccgt    960

ccgcaagact tcgagcctct gtccgtagat cgctttatct cgggggtttt acaaccggtc   1020

gcgtggtact tgcgtgcaca gcggtttcga cgtgtctatc gagataaggt gaatgctctt   1080

ttccgtgact gggacatatt aatcgctccc gcaacgccaa taagtgctcc cgcaatcggc   1140

accgaatgga tcgaggtaaa cggtacacgc catccgtgcc gcccggctat gggacttctc   1200

actcagccgg tctccttcgc aggctgtccg gtggtcgccg ctccaacgtg gcctggagaa   1260

aacgatggca tgccgatcgg ggtacagctc atcgcggcgc cctggaacga atctctatgc   1320
```

ctgcgcgcag gcaaggtatt acaagacacc ggtatcgccc gactgaaatg ttaa 1374

<210> SEQ ID NO 5
<211> LENGTH: 1092
<212> TYPE: DNA
<213> ORGANISM: Pseudomonas sp.

<400> SEQUENCE: 5
atgtatcaca tcgacgtttt ccgaatccct tgccacagcc ctggtgatac atcgggtctc 60
gaggatttga ttgaaacagg ccgcgttgcc cccgccgaca tcgtcgcggt aatgggcaag 120
accgagggca atggctgcgt caacgattac acgcgtgaat acgccaccgc catgcttgct 180
gcgtgccttg ggcgtcattt gcaactccca ccccatgagg tggaaaagcg ggtcgcgttt 240
gtgatgtcag gtgggacgga aggcgtgctg tccccccacc acacggtatt cgcaagacgt 300
ccggcaatcg acgcgcatcg tcccgctggc aaacgtctca cgcttggaat cgccttcacg 360
cgtgattttc tgccggagga aattggccgc cacgctcaga taacggagac agccggcgcc 420
gtcaaacgcg caatgcgaga tgccgggatc gcttcgattg acgatctgca ttttgtgcag 480
gtgaagtgtc cgctgctgac accagcaaag atcgcctcgg cgcgatcacg cggatgcgct 540
ccagtcacga cggatacgta tgaatcgatg ggctattcgc gcggcgcttc ggccctgggc 600
atcgctctcg ctacagaaga ggtgccctcc tcgatgctcg tagacgaatc agtgctgaat 660
gactggagtc tctcatcgtc actggcgtcg gcgtctgcag gcatcgaact ggagcacaac 720
gtggtgatcg ctattggcat gagcgagcag gccaccagtg aactggtcat tgcccacggc 780
gtgatgagcg acgcgatcga cgcggcctcg gtgcggcgaa cgattgaatc gctgggcata 840
cgtagcgatg acgagatgga tcgcatcgtc aacgtattcg ccaaagcgga ggcgagcccg 900
gacggggttg tacgaggtat gcggcacacg atgctaagtg actccgacat taattcgacc 960
cgccatgcgc gggcggtcac cggcgcggcc attgcctcgg tagttgggca tggcatggtg 1020
tatgtgtccg gtggcgccga gcatcaggga cctgccggcg gcggcccttt tgcagtcatt 1080
gcccgcgctt aa 1092

<210> SEQ ID NO 6
<211> LENGTH: 1113
<212> TYPE: DNA
<213> ORGANISM: Pseudomonas sp.

<400> SEQUENCE: 6
atgcaagcgc aagtttttcg agttccaatg agtaatccag ccgatgttag tggcgtagcc 60
aagctcatcg atgagggagt gatccgtgcc gaagaggtcg tctgcgttct cggcaagacc 120
gaaggcaacg gctgtgtcaa tgacttcacg cgtggctaca ccaccctcgc gttcaaggtc 180
tacttctccg agaaactggg cgtgtcccgg caagaggtcg gcgagcgcat cgctttcatc 240
atgtccggcg gtaccgaagg cgtcatggcg cctcactgca ccatcttcac cgtgcagaag 300
acggacaaca agcagaagac cgccgctgaa ggcaagcgac ttgccgttca gcagatcttt 360
acccgcgagt tcctgccgga ggagatcggc cgcatgccgc aggtcacgga aacagccgac 420
gctgttcgcc gcgccatgcg cgaagccggc atcgcggatg catccgatgt ccacttcgtt 480
caggtcaagt gcccactgct cactgccggc cgcatgcatg acgctgtcga gcgcgggcat 540
acggttgcca ccgaagatac ctatgagtcc atgggctact cccgcggcgc atccgcgctt 600
ggtatcgccc tggccctcgg ggaagtcgag aaggccaacc tcagtgatga agttattacc 660
gcagactaca gtctctactc ctcggttgcc tcaacttcgg cgggtatcga gttgatgaac 720

```
aacgagatca tcgtcatggg caacagccgc gcatggggtg gtgacctcgt catcggccac    780

gccgagatga aggacgccat cgacggtgca gcggtccggc aggccctgcg cgacgtcggg    840

tgctgcgaga acgacctgcc gaccgtcgac gagctcggcc gcgtggtcaa tgtatttgcc    900

aaggctgaag cctccccgga cggtgaggtt cgtaaccgcc gccacacgat gctggacgat    960

tcggacatta acagcacgcg ccatgcgcga gcggtcgtca atgcagttat cgcttcgatc   1020

gtgggagatc ccatggttta tgtctccggc ggctccgagc atcagggccc cgccggtggc   1080

ggtcccgttg cagttatcgc gcgcacagct taa                                1113
```

```
<210> SEQ ID NO 7
<211> LENGTH: 1113
<212> TYPE: DNA
<213> ORGANISM: Rhodococcus sp.

<400> SEQUENCE: 7

atgcaagcgc aagtttttcg agttccaatg agtaatccag ccgatgttag tggcgtagcc     60

aagctcatcg atgagggagt gatccgtgcc gaagaggtcg tctgcgttct cggcaagacc    120

gaaggcaacg gctgtgtcaa tgacttcacg cgtggctaca ccaccctcgc gttcaaggtc    180

tacttctccg agaaactggg cgtgtcccgg caagaggtcg gcgagcgcat cgctttcatc    240

atgtccggcg gtaccgaagg cgtcatggcg cctcactgca ccatcttcac cgtgcagaag    300

acggacaaca agcagaagac cgccgctgaa ggcaagcgac ttgccgttca gcagatcttt    360

acccgcgagt tcctgccgga ggagatcggc cgcatgccgc aggtcacgga aacagccgac    420

gctgttcgcc gcgccatgcg cgaagccggc atcgcggatg catccgatgt ccacttcgtt    480

caggtcaagt gcccactgct cactgccggc cgcatgcatg acgctgtcga gcgcgggcat    540

acggttgcca ccgaagatac ctatgagtcc atgggctact cccgcggcgc atccgcgctt    600

ggtatcgccc tggccctcgg ggaagtcgag aaggccaacc tcagtgatga agttattacc    660

gcagactaca gtctctactc ctcggttgcc tcaacttcgg cgggtatcga gttgatgaac    720

aacgagatca tcgtcatggg caacagccgc gcatggggtg gtgacctcgt catcggccac    780

gccgagatga aggacgccat cgacggtgca gcggtccggc aggccctgcg cgacgtcggg    840

tgctgcgaga acgacctgcc gaccgtcgac gagctcggcc gcgtggtcaa tgtatttgcc    900

aaggctgaag cctccccgga cggtgaggtt cgtaaccgcc gccacacgat gctggacgat    960

tcggacatta acagcacgcg ccatgcgcga gcggtcgtca atgcagttat cgcttcgatc   1020

gtgggagatc ccatggttta tgtctccggc ggctccgagc atcagggccc cgccggtggc   1080

ggtcccgttg cagttatcgc gcgcacagct taa                                1113
```

```
<210> SEQ ID NO 8
<211> LENGTH: 1320
<212> TYPE: DNA
<213> ORGANISM: Escherichia coli

<400> SEQUENCE: 8

atgatgtcag gagaacacac gttaaaagcg gtacgaggca gttttattga tgtcacccgt     60

acgatcgata acccggaaga gattgcctct gcgctgcggt ttattgagga tggtttatta    120

ctcattaaac agggaaaagt ggaatggttt ggcgaatggg aaaacggaaa gcatcaaatt    180

cctgacacca ttcgcgtgcg cgactatcgc ggcaaactga tagtaccggg ctttgtcgat    240

acacatatcc attatccgca aagtgaaatg gtgggggcct atggtgagca attgctggag    300
```

```
tggttgaata aacacacctt ccctactgaa cgtcgttatg aggatttaga gtacgcccgc    360

gaaatgtcgg cgttcttcat caagcagctt ttacgtaacg gaaccaccac ggcgctggtg    420

tttggcactg ttcatccgca atctgttgat gcgctgtttg aagccgccag tcatatcaat    480

atgcgtatga ttgccggtaa ggtgatgatg gaccgcaacg caccggatta tctgctcgac    540

actgccgaaa gcagctatca ccaaagcaaa gaactgatcg aacgctggca caaaaatggt    600

cgtctgctat atgcgattac gccacgcttc gccccgacct catctcctga acagatggcg    660

atggcgcaac gcctgaaaga agaatatccg gatacgtggg tacataccca tctctgtgaa    720

aacaaagatg aaattgcctg ggtgaaatcg ctttatcctg accatgatgg ttatctggat    780

gtttaccatc agtacggcct gaccggtaaa aactgtgtct ttgctcactg cgtccatctc    840

gaagaaaaag agtgggatcg tctcagcgaa accaaatcca gcattgcttt ctgtccgacc    900

tccaaccttt acctcggcag cggcttattc aacttgaaaa aagcatggca gaagaaagtt    960

aaagtgggca tgggaacgga tatcggtgcc ggaaccactt tcaacatgct gcaaacgctg   1020

aacgaagcct acaaagtatt gcaattacaa ggctatcgcc tctcggcata tgaagcgttt   1080

tacctggcca cgctcggcgg agcgaaatct ctgggccttg acgatttgat tggcaacttt   1140

ttacctggca aagaggctga tttcgtggtg atggaaccca ccgccactcc gctacagcag   1200

ctgcgctatg acaactctgt ttctttagtc gacaaattgt tcgtgatgat gacgttgggc   1260

gatgaccgtt cgatctaccg cacctacgtt gatggtcgtc tggtgtacga acgcaactaa   1320
```

<210> SEQ ID NO 9
<211> LENGTH: 1398
<212> TYPE: DNA
<213> ORGANISM: Bradyrhizobium japonicum

<400> SEQUENCE: 9

```
atgaccaccg tcggtattcg cggcacgttc ttcgatttcg tcgacgatcc ctggaagcac     60

atcggcaacg agcaggcggc tgcgcgcttt catcaggacg gcctcatggt cgtcaccgac    120

ggcgtcatca aggcgttcgg tccgtacgag aagatcgccg ccgcgcatcc gggcgttgag    180

atcacccata tcaaggaccg catcatcgtc ccgggcttca tcgacggcca catccatctg    240

cctcagaccc gcgtgctcgg tgcctatggc gagcagctct tgccgtggct gcagaagtcg    300

atctatcccg aggagatcaa gtacaaggat cgcaactacg cgcgcgaagg cgtgaagcgt    360

tttctcgatg cactgctcgc cgccggcacc accacctgcc aggccttcac cagctcctca    420

ccggtcgcga ccgaagagct gttcgaggag gcaagcaggc gcaacatgcg cgtgatcgcg    480

ggtctcaccg ggatcgaccg caacgcgccg gccgaattca tcgatacgcc cgagaatttc    540

tatcgcgaca gcaagcggct gatcgcgcag tatcacgaca agggccgtaa cctctacgct    600

atcacgccgc gcttcgcctt cggcgcctcg cccgagctgc tgaaggcgtg tcagcgcctc    660

aagcacgagc atccggactg ctgggtcaat acccacatct ccgagaaccc ggccgaatgc    720

agcggcgtgc tggtcgagca cccggactgc caggattatc tcggcgtcta cgagaagttc    780

gacctggtcg gcccaaagtt ctccggcggc cacggcgtct atctctcgaa caacgaattc    840

cgccgcatgt ccaagaaagg cgcggcggta gtgttctgcc cgtgctcgaa cctgttcctc    900

ggcagcggcc tgttccgtct cggccgcgcc accgatccgg agcatcgcgt gaagatgtcg    960

ttcggcaccg atgtcggcgg cggcaaccgc ttctcgatga tctccgtgct cgacgacgct   1020

tacaaggtcg gcatgtgcaa caacacgctg ctcgacggca gcatcgatcc gtcgcgcaag   1080

gacctcgcgg aagccgagcg caacaagctc tcgccctatc gtggcttctg gtcggtcacg   1140
```

```
ctcggcggcg ccgaaggcct ctacatcgac gacaagctcg gcaatttcga gcccggcaag   1200

gaggccgatt tcgtcgcgct cgatccgaac ggcggacaac tggcgcaacc ctggcaccag   1260

tcgctgattg ccgacggtgc aggtccgcgc acggttgatg aggccgcgag catgctgttc   1320

gccgtcatga tggtcggcga cgatcgctgc gtcgacgaga cctgggtgat gggcaagcgc   1380

ctctacaaga agagctga                                                 1398
```

<210> SEQ ID NO 10
<211> LENGTH: 1470
<212> TYPE: DNA
<213> ORGANISM: Saccharomyces cerevisiae

<400> SEQUENCE: 10

```
atgacaaaaa gtgatttatt atttgataaa ttcaacgaca aacatggaaa gtttctagtt     60

ttttttggta cctttgtaga taccccctaaa ttaggagagc tgagaatcag agagaaaaca    120

tctgttggag ttctcaacgg aatcatcagg tttgtgaaca gaaattcact cgatcctgtc    180

aaagattgtt tagatcacga tagtagctta tcaccagagg atgtcacggt ggttgacata    240

attggaaaag acaagactcg aaataacagc ttttattttc caggttttgt tgacacgcat    300

aaccatgtct cgcaatatcc aaatgtcggc gtatttggga attctaccct gctggattgg    360

ctagagaagt ataccttccc catagaagcc gcactagcaa acgaaaatat tgcgagagaa    420

gtttacaata aggtaataag taagacgctt tctcacggta caacgactgt ggcttactat    480

aataccattg atctcaagtc cactaagctc ttggctcaac taagctcctt attggggcag    540

cgtgttcttg ttggaaaagt gtgcatggat accaatggtc ccgagtatta tattgaagat    600

actaaaactt cctttgaaag cactgtgaaa gttgttaagt acatacggga aaccatttgt    660

gatcccctcg taaatcctat agtgacacca aggttcgcgc cctcttgttc tagagaacta    720

atgcaacagt tgtccaagct agtcaaggat gaaaacatac acgttcaaac ccacttgtcg    780

gaaaataagg aggagataca gtgggttcaa gatttatttc ccgaatgtga gagctatact    840

gatgtatacg acaaatatgg gctgctcaca gaaaaaacag tattggcaca ttgtattcat    900

ctaacagatg ccgaagcgcg tgtgattaaa cagcgtcgct gtggtatatc tcattgtccc    960

atttccaact cctctctgac ttctggagag tgtagggttc gatggttgct ggaccagggc   1020

ataaaggttg gtctaggcac cgacgtttca gccggtcatt cttgtagcat actcaccacc   1080

ggaaggcagg cctttgcagt ttcaaggcat ttggcaatga gagaaactga tcatgcaaaa   1140

ctttcagtct ccgagtgcct atttcttgct acaatgggcg gagcacaagt cttgcgtatg   1200

gatgagacct tggggacttt tgacgtcggt aagcagtttg acgctcaaat gatcgatacc   1260

aatgctcccg gctcaaacgt ggatatgttt cattggcagc taaaggagaa ggatcaaatg   1320

caagagcaag agcaagagca agggcaagac ccttataaga acccaccgct gcttactaat   1380

gaagacataa tcgcaaaatg gttctttaac ggtgatgatc gcaacaccac taaagtttgg   1440

gtagccggcc agcaagtcta ccagatttag                                    1470
```

<210> SEQ ID NO 11
<211> LENGTH: 1356
<212> TYPE: DNA
<213> ORGANISM: Yarrowia lipolytica

<400> SEQUENCE: 11

```
atgactgctt caaacaccac agtttttttc ggagccatcg tcaatcccgc cagaagagca     60
```

```
cttgaatacc tgccccaagc tgctatcggt gtcagggaag gggaaatcgt ctttttcgac    120

agacatgctg aatcggcttc ggcgtctgct gccacccaca acattaagaa cttcgacacg    180

gtggacttgt cgaaaaccac ctcgttcctt ttccccggtt tcatcgacac tcacattcat    240

gcgccccagt accccaacag cggtattttc ggcaagacca cactgctaga ctggctgact    300

acctacacct ttcccctgga gtcgtctctc aaggacccca aaatcgccca ggacgtgtac    360

tccagggtag tcaagaagac tctcgccaac ggaactacaa cggctgctta ctacgccact    420

gtccacgtgg agtccacaaa gaaactggct gacatttgtc tgtctcaagg tcagagagca    480

cttgtgggaa gagtgtgcat ggaccaaaac actcctgatt actacagaga tgcaagcgtg    540

gaggaggcca agaagagcga ccgggaagtt gttgagtata ttcagtctct taacaaaccc    600

gatcgcatcc tccccatcat cacaccccgt tttgcgccct cttgcactgg tgaaatcatg    660

tcctggcagg gagactatgc ccagaagaac aacctgcaca tccagactca catttctgaa    720

aacaagggcg agattgcctg ggtcaaggag ctgtaccctg cttgcaaatc gtatgcagac    780

acataccacc agcatggact gctgacagaa aagacgcttc tggcccatgc catctatctg    840

accgacgaag aactcaacct ggtggagcag caaaagtgtg gactttccca ttgccccatt    900

tccaactcgt cgctgacatc aggcgagttc catgctcgaa aaattctcga caggaacatt    960

ccctttggtc tgggaaccga tgtttctgga ggttacgctc cttccattct cagcacagcc   1020

agacacggtc ttctggtgtc tcgtcacgtg gccatgaagt ccgaaaacga cgccgacaag   1080

ctgtctgtgg atgaggtact gtacttggcc actctgggtg gcgccgaggc tctcaaactg   1140

gactcaaaga ttggttcttt cgaggtgggc aagaagttcg acgcccagca gattgatctc   1200

gagactaacg gttctcctgt tgacattttt gactgggaat tgcctatttc cgagggaaac   1260

aagctcgaga acctggtgca caagtggttg tttaatggag acgaccgaaa cacttctact   1320

gtctgggtca acggagacaa ggtggtgacc aagtag                             1356
```

<210> SEQ ID NO 12
<211> LENGTH: 1437
<212> TYPE: DNA
<213> ORGANISM: Williamsia sp.

<400> SEQUENCE: 12

```
atgaccagaa tcgcaatcac cggcggacga gtcctgacca tggaccccga gcgccgcgtg     60

ctcgaaccag gaacggttgt ggtcgaggac cagttcatcg cacaagtggg atccccggac    120

gacgtcgaca tccgcggcgc cgaaatcatc gacgccaccg ggatggcagt gctccccggc    180

ttcgtcaaca cccacaccca cgtcccacaa atcctcctca ggggtggtgc atcccatgac    240

cgcaacctcc tcgaatggct gcacaacgtg ctctatcccg gcctcgctgc ctacacagac    300

gacgacatcc gagtcggaac actgctgtac tgcgccgaag cccttcgttc tggcatcacc    360

actgtcgtcg acaacgagga cgtccgaccc aacgacttcg cccgcgccgg ggccgccggg    420

atcggcgcct tcaccgacgc aggaatccga gccatttacg cgcgcatgta cttcgacgcg    480

ccacgcgccg aactcgaaga actcgtcgcc accatccacg ccaaggcccc cggcgccgtg    540

cgcatggacg aatcagccag caccgaccac gtactggcag acctagacca actcatcacc    600

cgccacgacc gcacagcaga tggccgcatc agggtgtggc ccgcacccgc catccccttc    660

atggtcagtg aaaaaggaat gaaggcagcg caagagatcg cagcgagccg caccgacggc    720

tggaccatgc acgtcagcga ggatcccatc gaggcccgag tgcactccat gaacgccccg    780

gaatatttac accacctcgg ctgcctcgac gaccgactcc ttgccgcgca ctgcgtgcat    840
```

```
atcgacagcc gagacatccg cctgttccgc cagcacgacg taaaaatttc tacccaacca    900

gtatcgaaca gctacctggc ggccggaatt gcaccggtcc ccgaaatgct cgcccacggc    960

gtgaccgtgg gcatcggtac cgacgacgcc aactgcaacg acagcgtgaa cctcatctcg   1020

gacatgaaag tgctagcgct cattcaccga gctgcacatc gagatgcctc aatcatcaca   1080

cctgaaaaaa tcatcgaaat ggccaccatc gacggagccc gctgcatcgg tatggccgat   1140

cagattggtt ccctcgaggc gggtaaacgc gccgacatca tcaccctcga ccttcgtcac   1200

gcccaaacaa ccccagcgca cgacttggcg gccaccatcg tctttcaggc ctacggcaac   1260

gaggtcaacg acgtcctcgt caatggctcg gtagtgatgc gcgatcgagt actttctttt   1320

ctgccgactc cccaagaaga aaaagcgctc tacgacgatg cgtcggagcg atcggctgca   1380

atgctcgcac gggccggcct caccggcaca cgcacatggc aaacactggg atcgtag      1437


<210> SEQ ID NO 13
<211> LENGTH: 1425
<212> TYPE: DNA
<213> ORGANISM: Pseudomonas sp.

<400> SEQUENCE: 13

atgcaaacgc tcagcatcca gcacggtacc ctcgtcacga tggatcagta ccgcagagtc     60

cttggggata gctgggttca cgtgcaggat ggacggatcg tcgcgctcgg agtgcacgcc    120

gagtcggtgc ctccgccagc ggatcgggtg atcgatgcac gcggcaaggt cgtgttaccc    180

ggtttcatca atgcccacac ccatgtgaac cagatcctcc tgcgcggagg gccctcgcac    240

gggcgtcaac tctatgactg gctgttcaac gttttgtatc cgggacaaaa ggcgatgaga    300

ccggaggacg tagcggtggc ggtgaggttg tattgtgcgg aagctgtgcg cagcgggatt    360

acgacgatca acgacaacgc cgattcggcc atctacccag gcaacatcga ggccgcgatg    420

gcggtctatg gtgaggtggg tgtgagggtc gtctacgccc gcatgttctt tgatcggatg    480

gacgggcgca ttcaagggta tgtggacgcc ttgaaggctc gctctcccca agtcgaactg    540

tgctcgatca tggaggaaac ggctgtggcc aaagatcgga tcacagccct gtcagatcag    600

tatcatggca cggcaggagg tcgtatatca gtttggcccg ctcctgccat taccccggcg    660

gtgacagttg aaggaatgcg atgggcacaa gccttcgccc gtgatcgggc ggtaatgtgg    720

acgcttcaca tggcggagag cgatcatgat gagcggcttc attggatgag tcccgccgag    780

tacatggagt gttacggact cttggatgag cgtctgcagg tcgcgcattg cgtgtacttt    840

gaccggaagg atgttcggct gctgcaccgc cacaatgtga aggtcgcgtc gcaggttgtg    900

agcaatgcct acctcggctc aggggtggcc cccgtgccag agatggtgga gcgcggcatg    960

gccgtgggca ttggaacaga tgacgggaat tgtaatgact ccgtaaacat gatcggagac   1020

atgaagttta tggcccatat tcaccgcgcg gtgcatcggg atgcggacgt gctgacccca   1080

gagaagattc ttgaaatggc gacgatcgat ggggcgcgtt cgttgggaat ggaccacgag   1140

attggttcca tcgaaaccgg caagcgcgcg gaccttatcc tgcttgacct gcgtcaccct   1200

cagacgactc ctcaccatca tttggcggcc acgatcgtgt ttcaggctta cggcaatgag   1260

gtggacactg tcctgattga cggaaacgtt gtgatggaga accgccgctt gagctttctt   1320

ccccctgaac gtgagttggc gttccttgag gaagcgcaga gccgcgccac agctattttg   1380

cagcgggcga acatggtggc taacccagct tggcgcagcc tctag                   1425


<210> SEQ ID NO 14
```

```
<211> LENGTH: 1212
<212> TYPE: DNA
<213> ORGANISM: Pseudomonas sp.

<400> SEQUENCE: 14

atgagtaaag attttgattt aatcattaga aacgcctatc taagtgaaaa agacagtgta      60

tatgatattg ggattgttgg tgacagaata atcaaaatag aagctaaaat tgaaggaacc     120

gtaaaagacg aaattgatgc aaagggtaac cttgtgtctc ccggatttgt cgatgcacat     180

acccatatgg ataagtcatt tacgagcaca ggtgaaagat taccgaagtt ttggagcaga     240

ccttatacaa gggatgctgc catcgaggat ggcttgaaat attataaaaa tgctacccac     300

gaagaaataa aaagacatgt gatagaacat gctcacatgc aggtactcca tgggacttta     360

tacacccgga cccatgtaga tgtagattca gttgctaaaa caaaagcagt ggaagcagtt     420

ttagaagcca aggaagagtt aaaggatctt atcgatatac aagtcgtagc ctttgcacag     480

agtggatttt tcgttgattt ggaatctgaa tcattgatta gaaaatcctt ggatatgggc     540

tgtgatttag ttgggggagt tgatcctgct acgcgggaaa ataatgttga gggttcttta     600

gacctatgct ttaaattagc aaaggaatac gatgttgata tcgactatca catacatgat     660

attggaactg ttggagtata ttcgataaat cgtcttgccc aaaagacaat tgaaaatggg     720

tataagggta gagtaactac gagtcatgcc tggtgttttg cagatgctcc gtccgaatgg     780

ctcgatgagg caatcccatt gtacaaggat tcgggtatga aatttgttac ctgttttagt     840

agtacaccgc ctactatgcc ggtgataaag ctgcttgaag ctggcatcaa tcttggctgt     900

gcttcggaca atatcagaga tttttgggtt ccctttggca acggtgatat ggtacaaggg     960

gctctgatcg aaactcagag attagagtta aagacaaaca gagatttggg actaatttgg    1020

aaaatgataa cgtcagaggg tgctagagtt ttaggaattg aaaagaacta tgggatagaa    1080

gttggtaaaa aggccgatct tgttgtatta aattcgttgt caccacaatg ggcaataatc    1140

gaccaagcaa aaagactatg cgtaattaaa aatggacgta tcattgtgaa ggatgaggtt    1200

atagttgcct aa                                                       1212


<210> SEQ ID NO 15
<211> LENGTH: 735
<212> TYPE: DNA
<213> ORGANISM: Myrothecium verrucaria

<400> SEQUENCE: 15

atgtcttctt cagaagtcaa agccaacgga tggactgccg ttccagtcag cgcaaaggcc      60

attgttgact ccctgggaaa gcttggtgat gtctcctcat attctgtgga agatatcgcg     120

ttccctgcgg cagacaaact tgttgccgag gcacaggcct ttgtgaaggc ccgattgagt     180

cccgaaacct acaatcactc catgcgcgtt ttctactggg gaaccgtcat cgcgagacgt     240

ttacttcccg agcaagctaa agacttgtct ccaagtacat gggcactgac atgtcttctg     300

catgacgttg gtactgcgga ggcatacttt acatctacac gaatgtcctt cgatatttac     360

ggtggcatta aggctatgga ggtgctcaag gtccttggga gtagcaccga ccaggctgag     420

gctgttgccg aggccatcat tcgtcatgag gatgtggggg tagatggcaa catcacattc     480

ctcggtcagt tgatccagct ggctacgctt tatgacaatg tcggggccta cgatgggatt     540

gatgattttg gtagctgggt tgatgacacc acacgcaaca gtatcaacac ggcattccca     600

cgacatggtt ggtgttcttg gtttgcctgc acggttcgta aggaagaaag taacaagcct     660

tggtgccaca caacgcatat ccctcagttc gataaacaga tggaagcgaa cactttgatg     720
```

```
aagccttggg agtaa                                                      735

<210> SEQ ID NO 16
<211> LENGTH: 4268
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

ttatcgatga taagctgtca aagatgagaa ttaattccac ggactataga ctatactaga     60

tactccgtct actgtacgat acacttccgc tcaggtcctt gtcctttaac gaggccttac    120

cactcttttg ttactctatt gatccagctc agcaaaggca gtgtgatcta agattctatc    180

ttcgcgatgt agtaaaacta gctagaccga gaaagagact agaaatgcaa aaggcacttc    240

tacaatggct gccatcatta ttatccgatg tgacgctgca gcttctcaat gatattcgaa    300

tacgctttga ggagatacag cctaatatcc gacaaactgt tttacagatt tacgatcgta    360

cttgttaccc atcattgaat tttgaacatc cgaacctggg agttttccct gaaacagata    420

gtatatttga acctgtataa taatatatag tctagcgctt tacggaagac aatgtatgta    480

tttcggttcc tggagaaact attgcatcta ttgcataggt aatcttgcac gtcgcatccc    540

cggttcattt tctgcgtttc catcttgcac ttcaatagca tatctttgtt aacgaagcat    600

ctgtgcttca ttttgtagaa caaaaatgca acgcgagagc gctaattttt caaacaaaga    660

atctgagctg catttttaca gaacagaaat gcaacgcgaa agcgctattt taccaacgaa    720

gaatctgtgc ttcatttttg taaaacaaaa atgcaacgcg acgagagcgc taatttttca    780

aacaaagaat ctgagctgca tttttacaga acagaaatgc aacgcgagag cgctatttta    840

ccaacaaaga atctatactt ctttttttgtt ctacaaaaat gcatcccgag agcgctattt    900

ttctaacaaa gcatcttaga ttactttttt tctcctttgt gcgctctata atgcagtctc    960

ttgataactt tttgcactgt aggtccgtta aggttagaag aaggctactt tggtgtctat   1020

tttctcttcc ataaaaaaag cctgactcca cttcccgcgt ttactgatta ctagcgaagc   1080

tgcgggtgca ttttttcaag ataaaggcat ccccgattat attctatacc gatgtggatt   1140

gcgcatactt tgtgaacaga aagtgatagc gttgatgatt cttcattggt cagaaaatta   1200

tgaacggttt cttctatttt gtctctatat actacgtata ggaaatgttt acattttcgt   1260

attgttttcg attcactcta tgaatagttc ttactacaat ttttttgtct aaagagtaat   1320

actagagata aacataaaaa atgtagaggt cgagtttaga tgcaagttca aggagcgaaa   1380

ggtggatggg taggttatat agggatatag cacagagata tatagcaaag agatactttt   1440

gagcaatgtt tgtggaagcg gtattcgcaa tttaattaag tttaaacggc gcgcctttcc   1500

ataggctccg cccccctgac gagcatcaca aaaatcgacg ctcaagtcag aggtggcgaa   1560

acccgacagg actataaaga taccaggcgt ttccccctgg aagctccctc gtgcgctctc   1620

ctgttccgac cctgccgctt accggatacc tgtccgcctt tctcccttcg ggaagcgtgg   1680

cgctttctca tagctcacgc tgtaggtatc tcagttcggt gtaggtcgtt cgctccaagc   1740

tgggctgtgt gcacgaaccc cccgttcagc ccgaccgctg cgccttatcc ggtaactatc   1800

gtcttgagtc caacccggta agacacgact tatcgccact ggcagcagcc actggtaaca   1860

ggattagcag agcgaggtat gtaggcggtg ctacagagtt cttgaagtgg tggcctaact   1920

acggctacac tagaagaaca gtatttggta tctgcgctct gctgaagcca gttaccttcg   1980
```

```
gaaaaagagt tggtagctct tgatccggca aacaaaccac cgctggtagc ggtggttttt   2040
ttgtttgcaa gcagcagatt acgcgcagaa aaaaaggatc tcaagaagat cctttgatct   2100
tttctacggg gtctgacgct cagtggaacg aaaactcacg ttaagggatt ttggtcatga   2160
gattatcaaa aaggatcttc acctagatcc ttttaaatta aaaatgaagt tttaaatcaa   2220
tctaaagtat atatgagtaa acttggtctg acagttacca atgcttaatc agtgaggcac   2280
ctatctcagc gatctgtcta tttcgttcat ccatagttgc ctgactcccc gtcgtgtaga   2340
taactacgat acgggagggc ttaccatctg gccccagtgc tgcaatgata ccgcgagacc   2400
cacgctcacc ggctccagat ttatcagcaa taaaccagcc agccggaagg gccgagcgca   2460
gaagtggtcc tgcaacttta tccgcctcca tccagtctat taattgttgc cgggaagcta   2520
gagtaagtag ttcgccagtt aatagtttgc gcaacgttgt tgccattgct acaggcatcg   2580
tggtgtcacg ctcgtcgttt ggtatggctt cattcagctc cggttcccaa cgatcaaggc   2640
gagttacatg atcccccatg ttgtgcaaaa aagcggttag ctccttcggt cctccgatcg   2700
ttgtcagaag taagttggcc gcagtgttat cactcatggt tatggcagca ctgcataatt   2760
ctcttactgt catgccatcc gtaagatgct tttctgtgac tggtgagtac tcaaccaagt   2820
cattctgaga atagtgtatg cggcgaccga gttgctcttg cccggcgtca atacgggata   2880
ataccgcgcc acatagcaga actttaaaag tgctcatcat tggaaaacgt tcttcggggc   2940
gaaaactctc aaggatctta ccgctgttga gatccagttc gatgtaaccc actcgtgcac   3000
ccaactgatc ttcagcatct tttactttca ccagcgtttc tgggtgagca aaaacaggaa   3060
ggcaaaatgc cgcaaaaaag ggaataaggg cgacacggaa atgttgaata ctcatactct   3120
tcctttttca atattattga agcatttatc agggttattg tctcatgagc ggatacatat   3180
ttgaatgtat ttagaaaaat aaacagcgat cgcgcggccg cgggtaataa ctgatataat   3240
taaattgaag ctctaatttg tgagtttagt atacatgcat ttacttataa tacagttttt   3300
tagttttgct ggccgcatct tctcaaatat gcttcccagc ctgcttttct gtaacgttca   3360
ccctctacct tagcatccct tccctttgca aatagtcctc ttccaacaat aataatgtca   3420
gatcctgtag agaccacatc atccacggtt ctatactgtt gacccaatgc gtctcccttg   3480
tcatctaaac ccacaccggg tgtcataatc aaccaatcgt aaccttcatc tcttccaccc   3540
atgtctcttt gagcaataaa gccgataaca aaatctttgt cgctcttcgc aatgtcaaca   3600
gtacccttag tatattctcc agtagctagg gagcccttgc atgacaattc tgctaacatc   3660
aaaaggcctc taggttcctt tgttacttct tccgccgcct gcttcaaacc gctaacaata   3720
cctgggccca ccacaccgtg tgcattcgta atgtctgccc attctgctat tctgtataca   3780
cccgcagagt actgcaattt gactgtatta ccaatgtcag caaattttct gtcttcgaag   3840
agtaaaaaat tgtacttggc ggataatgcc tttagcggct taactgtgcc ctccatggaa   3900
aaatcagtca agatatccac atgtgttttt agtaaacaaa ttttgggacc taatgcttca   3960
actaactcca gtaattcctt ggtggtacga acatccaatg aagcacacaa gtttgtttgc   4020
ttttcgtgca tgatattaaa tagcttggca gcaacaggac taggatgagt agcagcacgt   4080
tccttatatg tagctttcga catgatttat cttcgtttcc tgcaggtttt tgttctgtgc   4140
agttgggtta agaatactgg gcaatttcat gtttcttcaa caccacatat gcgtatatat   4200
accaatctaa gtctgtgctc cttccttcgt tcttccttct gctcggagat taccgaatca   4260
aagctagc                                                            4268
```

<210> SEQ ID NO 17
<211> LENGTH: 6706
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17

```
gatacttttg agcaatgttt gtggaagcgg tattcgcaat tataaacggt attttcacaa     60

ttgcacccca gccagaccga tagccggtcg caatccgcca cccacaaccg tctacctccc    120

acagaacccc gtcacttcca cccttttcca ccagatcata tgtcccaact tgccaaatta    180

aaaccgtgcg aattttcaaa ataaactttg gcaaagaggc tgcaaaggag gggctggtga    240

gggcgtctgg aagtcgacca gagaccgggt tggcggcgca tttgtgtccc aaaaaacagc    300

cccaattgcc ccaattgacc ccaaattgac ccagtagcgg gcccaacccc ggcgagagcc    360

cccttctccc cacatatcaa acctcccccg gttcccacac ttgccgttaa gggcgtaggg    420

tactgcagtc tggaatctac gcttgttcag actttgtact agtttctttg tctggccatc    480

cgggtaaccc atgccggacg caaaatagac tactgaaaat ttttttgctt tgtggttggg    540

actttagcca agggtataaa agaccaccgt ccccgaatta cctttcctct tcttttctct    600

ctctccttgt caactcacac ccgaaatcgt taagcatttc cttctgagta taagaatcat    660

tcaaaatgac tagaatcgct atcacaggtg gtagagtttt gactatggac ccagaaagaa    720

gagtattaga accaggtaca gttgttgttg aagatcaatt cattgcacaa gtcggttcac    780

cagatgacgt agacatcaga ggtgctgaaa ttatagatgc cactggtatg gctgtattac    840

caggtttcgt taatacacat acccacgttc ctcaaatttt gttaagaggt ggtgcttcac    900

atgatagaaa tttgttggaa tggttgcaca acgtcttata tccaggtttg gctgcataca    960

ctgatgacga tatcagagtt ggtacattgt tatattgtgc tgaagcattg agatccggta   1020

ttactacagt tgtcgacaat gaagatgtta gacctaacga ttttgccaga gctggtgccg   1080

ctggtattgg tgcattcact gatgccggta tcagagcaat ctatgccaga atgtactttg   1140

atgctccaag agcagaattg gaagaattag tcgcaacaat acatgcaaaa gcccctggtg   1200

ccgtaagaat ggacgaatct gcttcaaccg atcatgtttt ggcagactta gatcaattga   1260

ttaccagaca tgacagaact gctgatggta gaattagagt atggccagct cctgcaatac   1320

cattcatggt ttctgaaaag ggtatgaagg cagcccaaga aatagctgca tccagaactg   1380

acggttggac aatgcatgtt agtgaagatc caatcgaagc cagagtccac tctatgaatg   1440

ctcctgaata tttgcatcac ttgggttgtt tagacgatag attgttagcc gctcattgcg   1500

ttcacataga ctcaagagat atcagattgt ttagacaaca tgatgttaag atatccacac   1560

aacctgtctc caatagttac ttagcagccg gtatagcacc agttcctgaa atgttggctc   1620

atggtgtcac agtaggtatt ggtaccgacg atgctaattg taacgactcc gtaaacttaa   1680

tcagtgatat gaaggttttg gcattgatac atagagctgc acacagagat gctagtatca   1740

ttaccccaga aaagataatc gaaatggcca ctattgacgg tgctagatgc attggtatgg   1800

ctgatcaaat cggttctttg gaagctggta aaagagcaga cataatcact ttggatttga   1860

gacatgcaca aaccactcct gcccacgatt tggccgctac aattgtcttt caagcttatg   1920

gtaatgaagt aaacgatgtt ttggtcaacg gttctgtagt tatgagagat agagttttgt   1980

cattcttacc aacccctcaa gaagaaaagg ctttatacga cgatgcatct gaaagatcag   2040
```

```
cagccatgtt agccagagct ggtttgactg gtacaagaac ctggcaaact ttgggttctt   2100
aagctgcttg tacctagtgc aaccccagtt tgttaaaaat tagtagtcaa aaacttctga   2160
gttagaaatt tgtgagtgta gtgagattgt agagtatcat gtgtgtccgt aagtgaagtg   2220
ttattgactc ttagttagtt tatctagtac tcgtttagtt gacactgatc tagtatttta   2280
cgaggcgtat gactttagcc aagtgttgta cttagtcttc tctccaaaca tgagagggct   2340
ctgtcactca gtcggcctat gggtgagatg gcttggtgag atctttcgat agtctcgtca   2400
agatggtagg atgatggggg aatacattac tgctctcgtc aaggaaacca caatcagatc   2460
acaccatcct ccatggtatc cgatgactct cttctccaca gttttccata ggctccgccc   2520
ccctgacgag catcacaaaa atcgacgctc aagtcagagg tggcgaaacc cgacaggact   2580
ataaagatac caggcgtttc cccctggaag ctccctcgtg cgctctcctg ttccgaccct   2640
gccgcttacc ggatacctgt ccgcctttct cccttcggga agcgtggcgc tttctcatag   2700
ctcacgctgt aggtatctca gttcggtgta ggtcgttcgc tccaagctgg gctgtgtgca   2760
cgaacccccc gttcagcccg accgctgcgc cttatccggt aactatcgtc ttgagtccaa   2820
cccggtaaga cacgacttat cgccactggc agcagccact ggtaacagga ttagcagagc   2880
gaggtatgta ggcggtgcta cagagttctt gaagtggtgg cctaactacg gctacactag   2940
aagaacagta tttggtatct gcgctctgct gaagccagtt accttcggaa aaagagttgg   3000
tagctcttga tccggcaaac aaaccaccgc tggtagcggt ggtttttttg tttgcaagca   3060
gcagattacg cgcagaaaaa aaggatctca agaagatcct ttgatctttt ctacggggtc   3120
tgacgctcag tggaacgaaa actcacgtta agggattttg gtcatgagat tatcaaaaag   3180
gatcttcacc tagatccttt taaattaaaa atgaagtttt aaatcaatct aaagtatata   3240
tgagtaaact tggtctgaca gttaccaatg cttaatcagt gaggcaccta tctcagcgat   3300
ctgtctattt cgttcatcca tagttgcctg actccccgtc gtgtagataa ctacgatacg   3360
ggagggctta ccatctggcc ccagtgctgc aatgataccg cgagacccac gctcaccggc   3420
tccagattta tcagcaataa accagccagc cggaagggcc gagcgcagaa gtggtcctgc   3480
aactttatcc gcctccatcc agtctattaa ttgttgccgg gaagctagag taagtagttc   3540
gccagttaat agtttgcgca acgttgttgc cattgctaca ggcatcgtgg tgtcacgctc   3600
gtcgtttggt atggcttcat tcagctccgg ttcccaacga tcaaggcgag ttacatgatc   3660
ccccatgttg tgcaaaaaag cggttagctc cttcggtcct ccgatcgttg tcagaagtaa   3720
gttggccgca gtgttatcac tcatggttat ggcagcactg cataattctc ttactgtcat   3780
gccatccgta agatgctttt ctgtgactgg tgagtactca accaagtcat tctgagaata   3840
gtgtatgcgg cgaccgagtt gctcttgccc ggcgtcaata cgggataata ccgcgccaca   3900
tagcagaact ttaaaagtgc tcatcattgg aaaacgttct tcggggcgaa aactctcaag   3960
gatcttaccg ctgttgagat ccagttcgat gtaacccact cgtgcaccca actgatcttc   4020
agcatctttt actttcacca gcgtttctgg gtgagcaaaa acaggaaggc aaaatgccgc   4080
aaaaaaggga ataagggcga cacggaaatg ttgaatactc atactcttcc tttttcaata   4140
ttattgaagc atttatcagg gttattgtct catgagcgga tacatatttg aatgtattta   4200
gaaaaataaa cagcgatcgc gcggccgcgg gtaataactg atataattaa attgaagctc   4260
taatttgtga gtttagtata catgcattta cttataatac agttttttag ttttgctggc   4320
cgcatcttct caaatatgct tcccagcctg cttttctgta acgttcaccc tctaccttag   4380
catcccttcc ctttgcaaat agtcctcttc caacaataat aatgtcagat cctgtagaga   4440
```

```
ccacatcatc cacggttcta tactgttgac ccaatgcgtc tcccttgtca tctaaaccca   4500
caccgggtgt cataatcaac caatcgtaac cttcatctct tccacccatg tctctttgag   4560
caataaagcc gataacaaaa tctttgtcgc tcttcgcaat gtcaacagta cccttagtat   4620
attctccagt agctagggag cccttgcatg acaattctgc taacatcaaa aggcctctag   4680
gttcctttgt tacttcttcc gccgcctgct tcaaaccgct aacaatacct gggcccacca   4740
caccgtgtgc attcgtaatg tctgcccatt ctgctattct gtatacaccc gcagagtact   4800
gcaatttgac tgtattacca atgtcagcaa attttctgtc ttcgaagagt aaaaaattgt   4860
acttggcgga taatgccttt agcggcttaa ctgtgccctc catggaaaaa tcagtcaaga   4920
tatccacatg tgtttttagt aaacaaattt tgggacctaa tgcttcaact aactccagta   4980
attccttggt ggtacgaaca tccaatgaag cacacaagtt tgtttgcttt tcgtgcatga   5040
tattaaatag cttggcagca acaggactag gatgagtagc agcacgttcc ttatatgtag   5100
ctttcgacat gatttatctt cgtttcctgc aggtttttgt tctgtgcagt tgggttaaga   5160
atactgggca atttcatgtt tcttcaacac cacatatgcg tatatatacc aatctaagtc   5220
tgtgctcctt ccttcgttct tccttctgct cggagattac cgaatcaaag ctagcttatc   5280
gatgataagc tgtcaaagat gagaattaat tccacggact atagactata ctagatactc   5340
cgtctactgt acgatacact tccgctcagg tccttgtcct ttaacgaggc cttaccactc   5400
ttttgttact ctattgatcc agctcagcaa aggcagtgtg atctaagatt ctatcttcgc   5460
gatgtagtaa aactagctag accgagaaag agactagaaa tgcaaaaggc acttctacaa   5520
tggctgccat cattattatc cgatgtgacg ctgcagcttc tcaatgatat tcgaatacgc   5580
tttgaggaga tacagcctaa tatccgacaa actgttttac agatttacga tcgtacttgt   5640
tacccatcat tgaattttga acatccgaac ctgggagttt tccctgaaac agatagtata   5700
tttgaacctg tataataata tatagtctag cgctttacgg aagacaatgt atgtatttcg   5760
gttcctggag aaactattgc atctattgca taggtaatct tgcacgtcgc atccccggtt   5820
cattttctgc gtttccatct tgcacttcaa tagcatatct ttgttaacga agcatctgtg   5880
cttcattttg tagaacaaaa atgcaacgcg agagcgctaa tttttcaaac aaagaatctg   5940
agctgcattt ttacagaaca gaaatgcaac gcgaaagcgc tattttacca acgaagaatc   6000
tgtgcttcat ttttgtaaaa caaaaatgca acgcgacgag agcgctaatt tttcaaacaa   6060
agaatctgag ctgcattttt acagaacaga aatgcaacgc gagagcgcta ttttaccaac   6120
aaagaatcta tacttctttt ttgttctaca aaaatgcatc ccgagagcgc tatttttcta   6180
acaaagcatc ttagattact ttttttctcc tttgtgcgct ctataatgca gtctcttgat   6240
aactttttgc actgtaggtc cgttaaggtt agaagaaggc tactttggtg tctattttct   6300
cttccataaa aaaagcctga ctccacttcc cgcgtttact gattactagc gaagctgcgg   6360
gtgcattttt tcaagataaa ggcatccccg attatattct ataccgatgt ggattgcgca   6420
tactttgtga acagaaagtg atagcgttga tgattcttca ttggtcagaa aattatgaac   6480
ggtttcttct attttgtctc tatatactac gtataggaaa tgtttacatt ttcgtattgt   6540
tttcgattca ctctatgaat agttcttact acaatttttt tgtctaaaga gtaatactag   6600
agataaacat aaaaaatgta gaggtcgagt ttagatgcaa gttcaaggag cgaaaggtgg   6660
atgggtaggt tatataggga tatagcacag agatatatag caaaga                  6706
```

<210> SEQ ID NO 18

```
<211> LENGTH: 8336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

gtttgtggaa gcggtattcg caatttaatt aaagctggtg acaattaatc atcggctcgt     60

ataatgtgtg gaattgaatc gatataagga ggttaatcat atgactagaa tcgctatcac    120

aggtggtaga gttttgacta tggacccaga aagaagagta ttagaaccag gtacagttgt    180

tgttgaagat caattcattg cacaagtcgg ttcaccagat gacgtagaca tcagaggtgc    240

tgaaattata gatgccactg gtatggctgt attaccaggt ttcgttaata cacataccca    300

cgttcctcaa attttgttaa gaggtggtgc ttcacatgat agaaatttgt tggaatggtt    360

gcacaacgtc ttatatccag gtttggctgc atacactgat gacgatatca gagttggtac    420

attgttatat tgtgctgaag cattgagatc cggtattact acagttgtcg acaatgaaga    480

tgttagacct aacgattttg ccagagctgg tgccgctggt attggtgcat tcactgatgc    540

cggtatcaga gcaatctatg ccagaatgta ctttgatgct ccaagagcag aattggaaga    600

attagtcgca acaatacatg caaaagcccc tggtgccgta agaatggacg aatctgcttc    660

aaccgatcat gttttggcag acttagatca attgattacc agacatgaca gaactgctga    720

tggtagaatt agagtatggc cagctcctgc aataccattc atggtttctg aaaagggtat    780

gaaggcagcc caagaaatag ctgcatccag aactgacggt tggacaatgc atgttagtga    840

agatccaatc gaagccagag tccactctat gaatgctcct gaatatttgc atcacttggg    900

ttgtttagac gatagattgt tagccgctca ttgcgttcac atagactcaa gagatatcag    960

attgtttaga caacatgatg ttaagatatc cacacaacct gtctccaata gttacttagc   1020

agccggtata gcaccagttc ctgaaatgtt ggctcatggt gtcacagtag gtattggtac   1080

cgacgatgct aattgtaacg actccgtaaa cttaatcagt gatatgaagg ttttggcatt   1140

gatacataga gctgcacaca gagatgctag tatcattacc ccagaaaaga taatcgaaat   1200

ggccactatt gacggtgcta gatgcattgg tatggctgat caaatcggtt ctttggaagc   1260

tggtaaaaga gcagacataa tcactttgga tttgagacat gcacaaacca ctcctgccca   1320

cgatttggcc gctacaattg tctttcaagc ttatggtaat gaagtaaacg atgttttggt   1380

caacggttct gtagttatga gagatagagt tttgtcattc ttaccaaccc ctcaagaaga   1440

aaaggcttta tacgacgatg catctgaaag atcagcagcc atgttagcca gagctggttt   1500

gactggtaca agaacctggc aaactttggg ttcttaagga aatccattat gatgtcagga   1560

gaacacacgt taaaagcggt acgaggcagt tttattgatg tcacccgtac gatcgataac   1620

ccggaagaga ttgcctctgc gctgcggttt attgaggatg gtttattact cattaaacag   1680

ggaaaagtgg aatggtttgg cgaatgggaa aacggaaagc atcaaattcc tgacaccatt   1740

cgcgtgcgcg actatcgcgg caaactgata gtaccgggct ttgtcgatac acatatccat   1800

tatccgcaaa gtgaaatggt gggggcctat ggtgagcaat tgctggagtg gttgaataaa   1860

cacaccttcc ctactgaacg tcgttatgag gatttagagt acgcccgcga aatgtcggcg   1920

ttcttcatca agcagctttt acgtaacgga accaccacgg cgctggtgtt tggcactgtt   1980

catccgcaat ctgttgatgc gctgtttgaa gccgccagtc atatcaatat gcgtatgatt   2040

gccggtaagg tgatgatgga ccgcaacgca ccggattatc tgctcgacac tgccgaaagc   2100
```

```
agctatcacc aaagcaaaga actgatcgaa cgctggcaca aaaatggtcg tctgctatat   2160
gcgattacgc cacgcttcgc cccgacctca tctcctgaac agatggcgat ggcgcaacgc   2220
ctgaaagaag aatatccgga tacgtgggta catacccatc tctgtgaaaa caaagatgaa   2280
attgcctggg tgaaatcgct ttatcctgac catgatggtt atctggatgt ttaccatcag   2340
tacggcctga ccggtaaaaa ctgtgtcttt gctcactgcg tccatctcga agaaaaagag   2400
tgggatcgtc tcagcgaaac caaatccagc attgctttct gtccgacctc caacctttac   2460
ctcggcagcg gcttattcaa cttgaaaaaa gcatggcaga agaaagttaa agtgggcatg   2520
ggaacggata tcggtgccgg aaccactttc aacatgctgc aaacgctgaa cgaagcctac   2580
aaagtattgc aattacaagg ctatcgcctc tcggcatatg aagcgtttta cctggccacg   2640
ctcggcggag cgaaatctct gggccttgac gatttgattg gcaacttttt acctggcaaa   2700
gaggctgatt tcgtggtgat ggaacccacc gccactccgc tacagcagct gcgctatgac   2760
aactctgttt ctttagtcga caaattgttc gtgatgatga cgttgggcga tgaccgttcg   2820
atctaccgca cctacgttga tggtcgtctg gtgtacgaac gcaactaagg aacgaccatg   2880
agagaagtcc aattgttaga tggtagaaga gttgatgtcg cctgtgctgg tcctttgatt   2940
agtgaaatag gtgcccactt agatttgact gctccagttg aaattgattg tggtggtggt   3000
ttagcaacta gaccttttac tgaacctcat ttgcacttag acaaagcagg tactgccgat   3060
agattgcctg ccggtgcttc cacaatcggt gacgctattg ctgcaatgca aagtgtcaag   3120
gtaaccgaaa gagataatgt cgccgctgta gcagccagaa tgcatagagt tttaaacaga   3180
atcgtcgatg acggttccca cgctattaga gcattggttg atgtcgacga agtttggggt   3240
ttaacagctt ttcatgctgc acaacaagtc caagccgctt tggccccaag agctgttgtc   3300
caaattgtcg ctttcccaca acacggttta acccctcaag tattggcaat gttagaacaa   3360
gcagccgctg aaggtgcagg tgccttgggt gctcatactg atgttgaccc agatcctgca   3420
gcccacgttg gtgccgtcgc tgcaatagcc gctggtgctt ccttgccatt agaagttcat   3480
actgacgaag gtgctagtcc agataaattt tatttgcctg cagtattgga agttttagat   3540
agattcccag gtttgtctac tacattagct cattgtttgt cattaggtac aattgcacct   3600
aagcaacaac aacattggat cgaagaatta gctcacagag atatcaaagt atgcgttgca   3660
ccatctattt tgggtttcgg tttgccatta gcacctgtta gagccttaat agaagctggt   3720
gtcggtatct tagtaggttc agacaatttg caagatgttt tctttccttt gggtacaggt   3780
agagcaattg aaaacgttag attgttagcc accgcagccc aattaactgc accagaattg   3840
gccggtcctt taattgctgg tgtaaccgac atagcttacg caaccgttac tggtgctgca   3900
gatgccttgg ctgttgaatc tccagctaca ttagtagttc atgatgctac ctcacctgca   3960
gaattgttaa gaggtataga cggtacaaga attaccgtta tagatggttt gttgacatct   4020
ccattgcaat tggataaagg tatcaagtaa gtttaaacta atcccacagc cgccagttcc   4080
gctggcggca ttttaacttt ctttaatggg cgcgcctttc cataggctcc gcccccctga   4140
cgagcatcac aaaaatcgac gctcaagtca gaggtggcga aacccgacag gactataaag   4200
ataccaggcg tttccccctg gaagctccct cgtgcgctct cctgttccga ccctgccgct   4260
taccggatac ctgtccgcct ttctcccttc gggaagcgtg gcgctttctc atagctcacg   4320
ctgtaggtat ctcagttcgg tgtaggtcgt tcgctccaag ctgggctgtg tgcacgaacc   4380
ccccgttcag cccgaccgct gcgccttatc cggtaactat cgtcttgagt ccaacccggt   4440
aagacacgac ttatcgccac tggcagcagc cactggtaac aggattagca gagcgaggta   4500
```

```
tgtaggcggt gctacagagt tcttgaagtg gtggcctaac tacggctaca ctagaagaac   4560
agtatttggt atctgcgctc tgctgaagcc agttaccttc ggaaaaagag ttggtagctc   4620
ttgatccggc aaacaaacca ccgctggtag cggtggtttt tttgtttgca agcagcagat   4680
tacgcgcaga aaaaaaggat ctcaagaaga tcctttgatc ttttctacgg ggtctgacgc   4740
tcagtggaac gaaaactcac gttaagggat tttggtcatg agattatcaa aaaggatctt   4800
cacctagatc cttttaaatt aaaaatgaag ttttaaatca atctaaagta tatatgagta   4860
aacttggtct gacagttacc aatgcttaat cagtgaggca cctatctcag cgatctgtct   4920
atttcgttca tccatagttg cctgactccc cgtcgtgtag ataactacga tacgggaggg   4980
cttaccatct ggccccagtg ctgcaatgat accgcgagac ccacgctcac cggctccaga   5040
tttatcagca ataaaccagc cagccggaag ggccgagcgc agaagtggtc ctgcaacttt   5100
atccgcctcc atccagtcta ttaattgttg ccgggaagct agagtaagta gttcgccagt   5160
taatagtttg cgcaacgttg ttgccattgc tacaggcatc gtggtgtcac gctcgtcgtt   5220
tggtatggct tcattcagct ccggttccca acgatcaagg cgagttacat gatcccccat   5280
gttgtgcaaa aaagcggtta gctccttcgg tcctccgatc gttgtcagaa gtaagttggc   5340
cgcagtgtta tcactcatgg ttatggcagc actgcataat tctcttactg tcatgccatc   5400
cgtaagatgc ttttctgtga ctggtgagta ctcaaccaag tcattctgag aatagtgtat   5460
gcggcgaccg agttgctctt gcccggcgtc aatacgggat aataccgcgc cacatagcag   5520
aactttaaaa gtgctcatca ttggaaaacg ttcttcgggg cgaaaactct caaggatctt   5580
accgctgttg agatccagtt cgatgtaacc cactcgtgca cccaactgat cttcagcatc   5640
ttttactttc accagcgttt ctgggtgagc aaaaacagga aggcaaaatg ccgcaaaaaa   5700
gggaataagg gcgacacgga aatgttgaat actcatactc ttcctttttc aatattattg   5760
aagcatttat cagggttatt gtctcatgag cggatacata tttgaatgta tttagaaaaa   5820
taaacagcga tcgcgcggcc gcgggtaata actgatataa ttaaattgaa gctctaattt   5880
gtgagtttag tatacatgca tttacttata atacagtttt ttagttttgc tggccgcatc   5940
ttctcaaata tgcttcccag cctgcttttc tgtaacgttc accctctacc ttagcatccc   6000
ttccctttgc aaatagtcct cttccaacaa taataatgtc agatcctgta gagaccacat   6060
catccacggt tctatactgt tgacccaatg cgtctccctt gtcatctaaa cccacaccgg   6120
gtgtcataat caaccaatcg taaccttcat ctcttccacc catgtctctt tgagcaataa   6180
agccgataac aaaatctttg tcgctcttcg caatgtcaac agtaccctta gtatattctc   6240
cagtagctag ggagcccttg catgacaatt ctgctaacat caaaaggcct ctaggttcct   6300
ttgttacttc ttccgccgcc tgcttcaaac cgctaacaat acctgggccc accacaccgt   6360
gtgcattcgt aatgtctgcc cattctgcta ttctgtatac acccgcagag tactgcaatt   6420
tgactgtatt accaatgtca gcaaattttc tgtcttcgaa gagtaaaaaa ttgtacttgg   6480
cggataatgc ctttagcggc ttaactgtgc cctccatgga aaaatcagtc aagatatcca   6540
catgtgtttt tagtaaacaa attttgggac ctaatgcttc aactaactcc agtaattcct   6600
tggtggtacg aacatccaat gaagcacaca agtttgtttg cttttcgtgc atgatattaa   6660
atagcttggc agcaacagga ctaggatgag tagcagcacg ttccttatat gtagctttcg   6720
acatgattta tcttcgtttc ctgcaggttt ttgttctgtg cagttgggtt aagaatactg   6780
ggcaatttca tgtttcttca acaccacata tgcgtatata taccaatcta agtctgtgct   6840
```

ccttccttcg ttcttccttc tgctcggaga ttaccgaatc aaagctagct tatcgatgat 6900
aagctgtcaa agatgagaat taattccacg gactatagac tatactagat actccgtcta 6960
ctgtacgata cacttccgct caggtccttg tcctttaacg aggccttacc actcttttgt 7020
tactctattg atccagctca gcaaaggcag tgtgatctaa gattctatct tcgcgatgta 7080
gtaaaactag ctagaccgag aaagagacta gaaatgcaaa aggcacttct acaatggctg 7140
ccatcattat tatccgatgt gacgctgcag cttctcaatg atattcgaat acgctttgag 7200
gagatacagc ctaatatccg acaaactgtt ttacagattt acgatcgtac ttgttaccca 7260
tcattgaatt ttgaacatcc gaacctggga gttttccctg aaacagatag tatatttgaa 7320
cctgtataat aatatatagt ctagcgcttt acggaagaca atgtatgtat ttcggttcct 7380
ggagaaacta ttgcatctat tgcataggta atcttgcacg tcgcatcccc ggttcatttt 7440
ctgcgtttcc atcttgcact tcaatagcat atctttgtta acgaagcatc tgtgcttcat 7500
tttgtagaac aaaaatgcaa cgcgagagcg ctaatttttc aaacaaagaa tctgagctgc 7560
atttttacag aacagaaatg caacgcgaaa gcgctatttt accaacgaag aatctgtgct 7620
tcatttttgt aaaacaaaaa tgcaacgcga cgagagcgct aatttttcaa acaaagaatc 7680
tgagctgcat ttttacagaa cagaaatgca acgcgagagc gctattttac caacaaagaa 7740
tctatacttc ttttttgttc tacaaaaatg catcccgaga gcgctatttt tctaacaaag 7800
catcttagat tacttttttt ctcctttgtg cgctctataa tgcagtctct tgataacttt 7860
ttgcactgta ggtccgttaa ggttagaaga aggctacttt ggtgtctatt ttctcttcca 7920
taaaaaaagc ctgactccac ttcccgcgtt tactgattac tagcgaagct gcgggtgcat 7980
tttttcaaga taaaggcatc cccgattata ttctataccg atgtggattg cgcatacttt 8040
gtgaacagaa agtgatagcg ttgatgattc ttcattggtc agaaaattat gaacggtttc 8100
ttctattttg tctctatata ctacgtatag gaaatgttta cattttcgta ttgttttcga 8160
ttcactctat gaatagttct tactacaatt tttttgtcta aagagtaata ctagagataa 8220
acataaaaaa tgtagaggtc gagtttagat gcaagttcaa ggagcgaaag gtggatgggt 8280
aggttatata gggatatagc acagagatat atagcaaaga gatacttttg agcaat 8336

<210> SEQ ID NO 19
<211> LENGTH: 8063
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19
gtttgtggaa gcggtattcg caatttaatt aaagctggtg acaattaatc atcggctcgt 60
ataatgtgtg gaattgaatc gatataagga ggttaatcat atgtcctcca cagcattata 120
caccgttcct accgcaggtc cagacgatgt tgccgccttg aaagcattag atggtcattc 180
cgcctccgat attttggctg taataggtaa aacagagggt aatggttgtg ttaacgactt 240
tagtagaacc ttatctgctg cagtttggca tccattgtta gaagattcag ccattacagt 300
cttttccggt ggtgcagaag gtgtaataag tccacatgta aacatcttcg ttagagatga 360
aagacaatat tctggtcacc ctagaggttt ggtaactgct gttggtagaa caagagttat 420
cggtccagaa gaaattggta gacctgctca agtcgatgca gtacatgaaa ccgttgtcgc 480
attgttaact gaattgggtg ttggtccaga tgacgttcac ttggtcttga ttaaatgccc 540

-continued

```
tttgttatct tcagacgcta tagcaggtgt tcatagaaga ggtttaagac ctgtcactac    600
agatacttac gaatctatgt caagatccag agccgcttct gctttgggta tagccatggc    660
tttaaaggaa tgtgatagag acagagcatt gttagccttg gaaggtagag atgacgtttg    720
gtcagcaaga gcctccgctt ccagtggtgc tgaattggat gactgccaca ttttagtagt    780
tgcagaatca gatgcagccg ctaatccatt aagagcagcc catactgcca tgagagatgc    840
tttggacatc caagctttaa cagaagtttt tgacagaatt gctgcagaag gtggtaccgt    900
cagacaaata ttcgcaaagg ccgaagctga tccttcaggt gctatcagag gttatagaca    960
taccatgtta actgattccg acgtcaatgc aacaagacac gccagagccg ctgtaggtgg   1020
tttgattgca gccttacatg gtaacggtgc tgtctatgta tcaggtggtg cagaacacca   1080
aggtccaagt ggtggtggtt ctgttactgt tatatatgat gttcctgcaa cagccaacgc   1140
taccggtgaa gcttctagat aaggaaatcc attatgatat actcaacagt caacgctaat   1200
ccttacgctt ggccttacga tggttcaata gaccctgctc acaccgcttt aatcttaatc   1260
gattggcaaa tagacttttg tggtccaggt ggttatgtcg attccatggg ttacgactta   1320
tccttgacta gaagtggttt agaacctaca gcaagagtat tggctgcagc cagagatact   1380
ggtatgacag ttatccatac tagagaaggt cacagaccag atttggctga cttgccacct   1440
aataagagat ggagatctgc atcagccggt gctgaaatcg gttcagttgg tccatgtggt   1500
agaattttag tcagaggtga acctggttgg gaaatagtac cagaagttgc acctagagaa   1560
ggtgaaccaa ttatagataa acctggtaaa ggtgctttct acgcaacaga tttggacttg   1620
ttgttgagaa caagaggtat cacccatttg attttgaccg gtataactac agatgtttgc   1680
gtccacacca ctatgagaga agccaacgat agaggttacg aatgtttaat tttgtctgat   1740
tgcaccggtg ctactgacag aaagcatcac gaagctgcat tatctatggt caccatgcaa   1800
ggtggtgtat tcggtgcaac tgcccattca gatgacttat tggccgcttt gggtacaacc   1860
gttccagcag ccgctggtcc tagagctaga acagaataag gaacgaccat gacagttagt   1920
tccgatacaa ctgctgaaat atcgttaggt tggtcaatcc aagactggat tgatttccac   1980
aagtcatcaa gctcccaggc ttcactaagg cttcttgaat cactactaga ctctcaaaat   2040
gttgcgccag tcgataatgc gtggatatcg ctaatttcaa aggaaaattt actgcaccaa   2100
ttccaaattt taaagagcag agaaaataaa gaaactctac ctctctacgg tgtccctatt   2160
gctgttaagg acaacatcga cgttagaggt ctacccacca ccgctgcatg tccatccttt   2220
gcatatgagc cttccaaaga ctctaaagta gtagaactac taagaaatgc aggtgcgata   2280
atcgtgggta agacaaactt ggaccaattt gccacaggat tagtcggcac acggtctcca   2340
tatgggaaaa caccttgcgc ttttagcaaa gagcatgtat ctggtggttc ctccgctggg   2400
tcagcatcgg tggtcgccag aggtatcgta ccaattgcat tgggtactga tacagcaggt   2460
tctggtagag tcccagccgc cttgaacaac ctgattggcc taaagccaac aaagggcgtc   2520
ttttcctgtc aaggtgtagt tcccgcttgt aaatctttag actgcgtctc catctttgca   2580
ttaaacctaa gtgatgctga acgctgcttc cgcatcatgt gccagccaga tcctgataat   2640
gatgaatatt ctagacccta tgtttccaac cctttgaaaa aattttcaag caatgtaacg   2700
attgctattc ctaaaaatat cccatggtat ggtgaaacca agaatcctgt actgttttcc   2760
aatgctgtcg aaaatctatc aagaacgggc gctaacgtca tagaaattga ttttgagcct   2820
cttttagagt tagctcgctg tttatacgaa ggtacttggg tggccgagcg ttatcaagct   2880
attcaatcgt tttggacag taaaccacca aaggaatctt tggaccctac tgttatttca   2940
```

```
attatagaag gggccaagaa atacagtgca gtagactgct tcagttttga atacaaaaga   3000
caaggcatct tgcaaaaagt gagacgactt ctcgaatcag tcgatgtatt gtgtgtgccc   3060
acatgtcctt taaatcctac tatgcaacaa gttgcggatg aaccagtcct agtcaattca   3120
agacaaggca catggactaa ttttgtcaac ttggcagatt tggcagccct tgctgttccc   3180
gcagggttcc gagacgatgg tttgccaaat ggtattactt taatcggtaa aaaattcaca   3240
gattacgcac tattagagtt ggctaaccgc tatttccaaa atatattccc caacggttcc   3300
agaacatacg gtacttttac ctcttcttca gtaaagccag caaacgatca attagtggga   3360
ccagactatg acccatctac gtccataaaa ttggctgttg tcggtgcaca tcttaagggt   3420
ctgcctctac attggcaatt ggaaaaggtc aatgcaacat atttatgtac aacaaaaaca   3480
tcaaaagctt accagctttt tgctttgccc aaaaatggac cagttttaaa acctggtttg   3540
agaagagttc aagatagcaa tggctctcaa atcgaattag aagtgtacag tgttccaaaa   3600
gaactgttcg gtgcttttat ttccatggtt cctgaaccat taggaatagg ttcagtggag   3660
ttagaatctg gtgaatggat caaatccttt atttgtgaag aatctggtta caaagccaaa   3720
ggtacagttg atatcacaaa gtatggtgga tttagagcat attttgaaat gttgtaagtt   3780
taaactaatc ccacagccgc cagttccgct ggcggcattt taactttctt taatgggcgc   3840
gcctttccat aggctccgcc cccctgacga gcatcacaaa aatcgacgct caagtcagag   3900
gtggcgaaac ccgacaggac tataaagata ccaggcgttt ccccctggaa gctccctcgt   3960
gcgctctcct gttccgaccc tgccgcttac cggatacctg tccgcctttc tcccttcggg   4020
aagcgtggcg ctttctcata gctcacgctg taggtatctc agttcggtgt aggtcgttcg   4080
ctccaagctg ggctgtgtgc acgaaccccc cgttcagccc gaccgctgcg ccttatccgg   4140
taactatcgt cttgagtcca acccggtaag acacgactta tcgccactgg cagcagccac   4200
tggtaacagg attagcagag cgaggtatgt aggcggtgct acagagttct tgaagtggtg   4260
gcctaactac ggctacacta gaagaacagt atttggtatc tgcgctctgc tgaagccagt   4320
taccttcgga aaaagagttg gtagctcttg atccggcaaa caaaccaccg ctggtagcgg   4380
tggttttttt gtttgcaagc agcagattac gcgcagaaaa aaaggatctc aagaagatcc   4440
tttgatcttt tctacggggt ctgacgctca gtggaacgaa aactcacgtt aagggatttt   4500
ggtcatgaga ttatcaaaaa ggatcttcac ctagatcctt ttaaattaaa aatgaagttt   4560
taaatcaatc taaagtatat atgagtaaac ttggtctgac agttaccaat gcttaatcag   4620
tgaggcacct atctcagcga tctgtctatt tcgttcatcc atagttgcct gactccccgt   4680
cgtgtagata actacgatac gggagggctt accatctggc cccagtgctg caatgatacc   4740
gcgagaccca cgctcaccgg ctccagattt atcagcaata aaccagccag ccggaagggc   4800
cgagcgcaga agtggtcctg caactttatc cgcctccatc cagtctatta attgttgccg   4860
ggaagctaga gtaagtagtt cgccagttaa tagtttgcgc aacgttgttg ccattgctac   4920
aggcatcgtg gtgtcacgct cgtcgtttgg tatggcttca ttcagctccg gttcccaacg   4980
atcaaggcga gttacatgat cccccatgtt gtgcaaaaaa gcggttagct ccttcggtcc   5040
tccgatcgtt gtcagaagta agttggccgc agtgttatca ctcatggtta tggcagcact   5100
gcataattct cttactgtca tgccatccgt aagatgcttt tctgtgactg gtgagtactc   5160
aaccaagtca ttctgagaat agtgtatgcg gcgaccgagt tgctcttgcc cggcgtcaat   5220
acgggataat accgcgccac atagcagaac tttaaaagtg ctcatcattg gaaaacgttc   5280
```

-continued

```
ttcggggcga aaactctcaa ggatcttacc gctgttgaga tccagttcga tgtaacccac   5340
tcgtgcaccc aactgatctt cagcatcttt tactttcacc agcgtttctg ggtgagcaaa   5400
aacaggaagg caaaatgccg caaaaaaggg aataagggcg acacggaaat gttgaatact   5460
catactcttc ctttttcaat attattgaag catttatcag ggttattgtc tcatgagcgg   5520
atacatattt gaatgtattt agaaaaataa acagcgatcg cgcggccgcg ggtaataact   5580
gatataatta aattgaagct ctaatttgtg agtttagtat acatgcattt acttataata   5640
cagtttttta gttttgctgg ccgcatcttc tcaaatatgc ttcccagcct gcttttctgt   5700
aacgttcacc ctctacctta gcatcccttc cctttgcaaa tagtcctctt ccaacaataa   5760
taatgtcaga tcctgtagag accacatcat ccacggttct atactgttga cccaatgcgt   5820
ctcccttgtc atctaaaccc acaccgggtg tcataatcaa ccaatcgtaa ccttcatctc   5880
ttccacccat gtctctttga gcaataaagc cgataacaaa atctttgtcg ctcttcgcaa   5940
tgtcaacagt acccttagta tattctccag tagctaggga gcccttgcat gacaattctg   6000
ctaacatcaa aaggcctcta ggttcctttg ttacttcttc cgccgcctgc ttcaaaccgc   6060
taacaatacc tgggcccacc acaccgtgtg cattcgtaat gtctgcccat tctgctattc   6120
tgtatacacc cgcagagtac tgcaatttga ctgtattacc aatgtcagca aattttctgt   6180
cttcgaagag taaaaaattg tacttggcgg ataatgcctt tagcggctta actgtgccct   6240
ccatggaaaa atcagtcaag atatccacat gtgtttttag taaacaaatt ttgggaccta   6300
atgcttcaac taactccagt aattccttgg tggtacgaac atccaatgaa gcacacaagt   6360
ttgtttgctt ttcgtgcatg atattaaata gcttggcagc aacaggacta ggatgagtag   6420
cagcacgttc cttatatgta gctttcgaca tgatttatct tcgtttcctg caggtttttg   6480
ttctgtgcag ttgggttaag aatactgggc aatttcatgt ttcttcaaca ccacatatgc   6540
gtatatatac caatctaagt ctgtgctcct tccttcgttc ttccttctgc tcggagatta   6600
ccgaatcaaa gctagcttat cgatgataag ctgtcaaaga tgagaattaa ttccacggac   6660
tatagactat actagatact ccgtctactg tacgatacac ttccgctcag gtccttgtcc   6720
tttaacgagg ccttaccact cttttgttac tctattgatc cagctcagca aaggcagtgt   6780
gatctaagat tctatcttcg cgatgtagta aaactagcta gaccgagaaa gagactagaa   6840
atgcaaaagg cacttctaca atggctgcca tcattattat ccgatgtgac gctgcagctt   6900
ctcaatgata ttcgaatacg ctttgaggag atacagccta atatccgaca aactgtttta   6960
cagatttacg atcgtacttg ttacccatca ttgaattttg aacatccgaa cctgggagtt   7020
ttccctgaaa cagatagtat atttgaacct gtataataat atatagtcta gcgctttacg   7080
gaagacaatg tatgtatttc ggttcctgga gaaactattg catctattgc ataggtaatc   7140
ttgcacgtcg catccccggt tcattttctg cgtttccatc ttgcacttca atagcatatc   7200
tttgttaacg aagcatctgt gcttcatttt gtagaacaaa aatgcaacgc gagagcgcta   7260
atttttcaaa caaagaatct gagctgcatt tttacagaac agaaatgcaa cgcgaaagcg   7320
ctattttacc aacgaagaat ctgtgcttca tttttgtaaa acaaaaatgc aacgcgacga   7380
gagcgctaat tttcaaaca aagaatctga gctgcatttt tacagaacag aaatgcaacg   7440
cgagagcgct attttaccaa caaagaatct atacttcttt tttgttctac aaaaatgcat   7500
cccgagagcg ctatttttct aacaaagcat cttagattac ttttttctc ctttgtgcgc   7560
tctataatgc agtctcttga taactttttg cactgtaggt ccgttaaggt tagaagaagg   7620
ctactttggt gtctattttc tcttccataa aaaaagcctg actccacttc ccgcgtttac   7680
```

```
tgattactag cgaagctgcg ggtgcatttt ttcaagataa aggcatcccc gattatattc   7740

tataccgatg tggattgcgc atactttgtg aacagaaagt gatagcgttg atgattcttc   7800

attggtcaga aaattatgaa cggtttcttc tattttgtct ctatatacta cgtataggaa   7860

atgtttacat tttcgtattg ttttcgattc actctatgaa tagttcttac tacaattttt   7920

ttgtctaaag agtaatacta gagataaaca taaaaaatgt agaggtcgag tttagatgca   7980

agttcaagga gcgaaaggtg gatgggtagg ttatataggg atatagcaca gagatatata   8040

gcaaagagat acttttgagc aat                                           8063


<210> SEQ ID NO 20
<211> LENGTH: 6004
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

gatacttttg agcaatgttt gtggaagcgg tattcgcaat tataaacggt attttcacaa     60

ttgcacccca gccagaccga tagccggtcg caatccgcca ccccacaaccg tctacctccc   120

acagaacccc gtcacttcca cccttttcca ccagatcata tgtcccaact tgccaaatta   180

aaaccgtgcg aattttcaaa ataaactttg gcaaagaggc tgcaaaggag gggctggtga   240

gggcgtctgg aagtcgacca gagaccgggt tggcggcgca tttgtgtccc aaaaaacagc   300

cccaattgcc ccaattgacc ccaaattgac ccagtagcgg gcccaacccc ggcgagagcc   360

cccttctccc cacatatcaa acctcccccg gttcccacac ttgccgttaa gggcgtaggg   420

tactgcagtc tggaatctac gcttgttcag actttgtact agtttctttg tctggccatc   480

cgggtaaccc atgccggacg caaaatagac tactgaaaat ttttttgctt tgtggttggg   540

actttagcca agggtataaa agaccaccgt ccccgaatta cctttcctct tcttttctct   600

ctctccttgt caactcacac ccgaaatcgt taagcatttc cttctgagta taagaatcat   660

tcaaaatgtc atcctcagaa gtaaaagcaa atggttggac cgcagttcct gtttccgcaa   720

aagcaatagt agactccttg ggtaaattag gagatgtctc ttcatattcc gtagaagata   780

ttgcctttcc agctgcagac aaattggtag ccgaagctca agcattcgtt aaggctagat   840

tatctcctga aacctacaac cattcaatga gagttttcta ttggggtact gtcattgcca   900

gaagattgtt accagaacaa gctaaagatt tgtctccttc aacatgggca ttaacctgtt   960

tgttacacga cgttggtact gccgaagctt attttacctc cactagaatg agtttcgata  1020

tctacggtgg tattaaagct atggaagtat tgaaggtttt aggttccagt acagatcaag  1080

cagaagccgt tgctgaagca attataagac atgaagatgt tggtgtcgac ggtaacatca  1140

catttttggg tcaattgatc caattggcaa cattgtacga taacgtcggt gcctacgacg  1200

gtattgatga cttcggttcc tgggttgatg acactacaag aaacagtata aacactgctt  1260

tcccaagaca tggttggtgt tcttggttcg catgcacagt tagaaaagaa gaatcaaaca  1320

agccttggtg ccacaccaca cacataccac aattcgacaa acaaatggaa gcaaacacct  1380

tgatgaaacc ttgggaataa gctgcttgta cctagtgcaa ccccagtttg ttaaaaatta  1440

gtagtcaaaa acttctgagt tagaaatttg tgagtgtagt gagattgtag agtatcatgt  1500

gtgtccgtaa gtgaagtgtt attgactctt agttagttta tctagtactc gtttagttga  1560

cactgatcta gtattttacg aggcgtatga ctttagccaa gtgttgtact tagtcttctc  1620
```

```
tccaaacatg agagggctct gtcactcagt cggcctatgg gtgagatggc ttggtgagat   1680
ctttcgatag tctcgtcaag atggtaggat gatgggggaa tacattactg ctctcgtcaa   1740
ggaaaccaca atcagatcac accatcctcc atggtatccg atgactctct tctccacagt   1800
tttccatagg ctccgccccc ctgacgagca tcacaaaaat cgacgctcaa gtcagaggtg   1860
gcgaaacccg acaggactat aaagatacca ggcgtttccc cctggaagct ccctcgtgcg   1920
ctctcctgtt ccgaccctgc cgcttaccgg atacctgtcc gcctttctcc cttcgggaag   1980
cgtggcgctt tctcatagct cacgctgtag gtatctcagt tcggtgtagg tcgttcgctc   2040
caagctgggc tgtgtgcacg aaccccccgt tcagcccgac cgctgcgcct tatccggtaa   2100
ctatcgtctt gagtccaacc cggtaagaca cgacttatcg ccactggcag cagccactgg   2160
taacaggatt agcagagcga ggtatgtagg cggtgctaca gagttcttga agtggtggcc   2220
taactacggc tacactagaa gaacagtatt tggtatctgc gctctgctga agccagttac   2280
cttcggaaaa agagttggta gctcttgatc cggcaaacaa accaccgctg gtagcggtgg   2340
tttttttgtt tgcaagcagc agattacgcg cagaaaaaaa ggatctcaag aagatccttt   2400
gatcttttct acggggtctg acgctcagtg gaacgaaaac tcacgttaag ggattttggt   2460
catgagatta tcaaaaagga tcttcaccta gatcctttta aattaaaaat gaagttttaa   2520
atcaatctaa agtatatatg agtaaacttg gtctgacagt taccaatgct taatcagtga   2580
ggcacctatc tcagcgatct gtctatttcg ttcatccata gttgcctgac tccccgtcgt   2640
gtagataact acgatacggg agggcttacc atctggcccc agtgctgcaa tgataccgcg   2700
agacccacgc tcaccggctc cagatttatc agcaataaac cagccagccg gaagggccga   2760
gcgcagaagt ggtcctgcaa ctttatccgc ctccatccag tctattaatt gttgccggga   2820
agctagagta agtagttcgc cagttaatag tttgcgcaac gttgttgcca ttgctacagg   2880
catcgtggtg tcacgctcgt cgtttggtat ggcttcattc agctccggtt cccaacgatc   2940
aaggcgagtt acatgatccc ccatgttgtg caaaaaagcg gttagctcct tcggtcctcc   3000
gatcgttgtc agaagtaagt tggccgcagt gttatcactc atggttatgg cagcactgca   3060
taattctctt actgtcatgc catccgtaag atgcttttct gtgactggtg agtactcaac   3120
caagtcattc tgagaatagt gtatgcggcg accgagttgc tcttgcccgg cgtcaatacg   3180
ggataatacc gcgccacata gcagaacttt aaaagtgctc atcattggaa aacgttcttc   3240
ggggcgaaaa ctctcaagga tcttaccgct gttgagatcc agttcgatgt aacccactcg   3300
tgcacccaac tgatcttcag catcttttac tttcaccagc gtttctgggt gagcaaaaac   3360
aggaaggcaa aatgccgcaa aaaagggaat aagggcgaca cggaaatgtt gaatactcat   3420
actcttcctt tttcaatatt attgaagcat ttatcagggt tattgtctca tgagcggata   3480
catatttgaa tgtatttaga aaaataaaca gcgatcgcgc ggccgcgggt aataactgat   3540
ataattaaat tgaagctcta atttgtgagt ttagtataca tgcatttact tataatacag   3600
ttttttagtt ttgctggccg catcttctca aatatgcttc ccagcctgct tttctgtaac   3660
gttcaccctc taccttagca tcccttccct ttgcaaatag tcctcttcca acaataataa   3720
tgtcagatcc tgtagagacc acatcatcca cggttctata ctgttgaccc aatgcgtctc   3780
ccttgtcatc taaacccaca ccgggtgtca taatcaacca atcgtaacct tcatctcttc   3840
cacccatgtc tctttgagca ataaagccga taacaaaatc tttgtcgctc ttcgcaatgt   3900
caacagtacc cttagtatat tctccagtag ctagggagcc cttgcatgac aattctgcta   3960
```

```
acatcaaaag gcctctaggt tcctttgtta cttcttccgc cgcctgcttc aaaccgctaa   4020
caatacctgg gcccaccaca ccgtgtgcat tcgtaatgtc tgcccattct gctattctgt   4080
atacacccgc agagtactgc aatttgactg tattaccaat gtcagcaaat tttctgtctt   4140
cgaagagtaa aaaattgtac ttggcggata atgcctttag cggcttaact gtgccctcca   4200
tggaaaaatc agtcaagata tccacatgtg tttttagtaa acaaattttg ggacctaatg   4260
cttcaactaa ctccagtaat tccttggtgg tacgaacatc caatgaagca cacaagtttg   4320
tttgcttttc gtgcatgata ttaaatagct tggcagcaac aggactagga tgagtagcag   4380
cacgttcctt atatgtagct ttcgacatga tttatcttcg tttcctgcag gtttttgttc   4440
tgtgcagttg ggttaagaat actgggcaat ttcatgtttc ttcaacacca catatgcgta   4500
tatataccaa tctaagtctg tgctccttcc ttcgttcttc cttctgctcg gagattaccg   4560
aatcaaagct agcttatcga tgataagctg tcaaagatga gaattaattc cacggactat   4620
agactatact agatactccg tctactgtac gatacacttc cgctcaggtc cttgtccttt   4680
aacgaggcct taccactctt ttgttactct attgatccag ctcagcaaag gcagtgtgat   4740
ctaagattct atcttcgcga tgtagtaaaa ctagctagac cgagaaagag actagaaatg   4800
caaaaggcac ttctacaatg gctgccatca ttattatccg atgtgacgct gcagcttctc   4860
aatgatattc gaatacgctt tgaggagata cagcctaata tccgacaaac tgttttacag   4920
atttacgatc gtacttgtta cccatcattg aattttgaac atccgaacct gggagttttc   4980
cctgaaacag atagtatatt tgaacctgta taataatata tagtctagcg ctttacggaa   5040
gacaatgtat gtatttcggt tcctggagaa actattgcat ctattgcata ggtaatcttg   5100
cacgtcgcat ccccggttca ttttctgcgt ttccatcttg cacttcaata gcatatcttt   5160
gttaacgaag catctgtgct tcattttgta gaacaaaaat gcaacgcgag agcgctaatt   5220
tttcaaacaa agaatctgag ctgcattttt acagaacaga aatgcaacgc gaaagcgcta   5280
ttttaccaac gaagaatctg tgcttcattt ttgtaaaaca aaaatgcaac gcgacgagag   5340
cgctaatttt tcaaacaaag aatctgagct gcatttttac agaacagaaa tgcaacgcga   5400
gagcgctatt ttaccaacaa agaatctata cttctttttt gttctacaaa aatgcatccc   5460
gagagcgcta tttttctaac aaagcatctt agattacttt ttttctcctt tgtgcgctct   5520
ataatgcagt ctcttgataa ctttttgcac tgtaggtccg ttaaggttag aagaaggcta   5580
ctttggtgtc tattttctct tccataaaaa aagcctgact ccacttcccg cgtttactga   5640
ttactagcga agctgcgggt gcattttttc aagataaagg catccccgat tatattctat   5700
accgatgtgg attgcgcata ctttgtgaac agaaagtgat agcgttgatg attcttcatt   5760
ggtcagaaaa ttatgaacgg tttcttctat tttgtctcta tatactacgt ataggaaatg   5820
tttacatttt cgtattgttt tcgattcact ctatgaatag ttcttactac aatttttttg   5880
tctaaagagt aatactagag ataaacataa aaaatgtaga ggtcgagttt agatgcaagt   5940
tcaaggagcg aaaggtggat gggtaggtta tatagggata tagcacagag atatatagca   6000
aaga                                                                6004
```

<210> SEQ ID NO 21
<211> LENGTH: 10640
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 21

```
gtttgtggaa gcggtattcg caatttaatt aaagctggtg acaattaatc atcggctcgt     60
ataatgtgtg gaattgaatc gatataagga ggttaatcat atgacagtta gttccgatac    120
aactgctgaa atatcgttag gttggtcaat ccaagactgg attgatttcc acaagtcatc    180
aagctcccag gcttcactaa ggcttcttga atcactacta gactctcaaa atgttgcgcc    240
agtcgataat gcgtggatat cgctaatttc aaaggaaaat ttactgcacc aattccaaat    300
tttaaagagc agagaaaata aagaaactct acctctctac ggtgtcccta ttgctgttaa    360
ggacaacatc gacgttagag gtctacccac caccgctgca tgtccatcct ttgcatatga    420
gccttccaaa gactctaaag tagtagaact actaagaaat gcaggtgcga taatcgtggg    480
taagacaaac ttggaccaat ttgccacagg attagtcggc acacggtctc catatgggaa    540
aacaccttgc gcttttagca aagagcatgt atctggtggt tcctccgctg ggtcagcatc    600
ggtggtcgcc agaggtatcg taccaattgc attgggtact gatacagcag gttctggtag    660
agtcccagcc gccttgaaca acctgattgg cctaaagcca acaaagggcg tcttttcctg    720
tcaaggtgta gttcccgctt gtaaatcttt agactgcgtc tccatctttg cattaaacct    780
aagtgatgct gaacgctgct tccgcatcat gtgccagcca gatcctgata atgatgaata    840
ttctagaccc tatgtttcca accctttgaa aaaatttcca agcaatgtaa cgattgctat    900
tcctaaaaat atcccatggt atggtgaaac caagaatcct gtactgtttt ccaatgctgt    960
cgaaaatcta tcaagaacgg gcgctaacgt catagaaatt gattttgagc ctcttttaga   1020
gttagctcgc tgtttatacg aaggtacttg ggtggccgag cgttatcaag ctattcaatc   1080
gtttttggac agtaaaccac caaaggaatc tttggaccct actgttattt caattataga   1140
aggggccaag aaatacagtg cagtagactg cttcagtttt gaatacaaaa gacaaggcat   1200
cttgcaaaaa gtgagacgac ttctcgaatc agtcgatgta ttgtgtgtgc ccacatgtcc   1260
tttaaatcct actatgcaac aagttgcgga tgaaccagtc ctagtcaatt caagacaagg   1320
cacatggact aattttgtca acttggcaga tttggcagcc cttgctgttc ccgcagggtt   1380
ccgagacgat ggtttgccaa atggtattac tttaatcggt aaaaaattca cagattacgc   1440
actattagag ttggctaacc gctatttcca aaatatattc cccaacggtt ccagaacata   1500
cggtactttt acctcttctt cagtaaagcc agcaaacgat caattagtgg gaccagacta   1560
tgacccatct acgtccataa aattggctgt tgtcggtgca catcttaagg gtctgcctct   1620
acattggcaa ttggaaaagg tcaatgcaac atatttatgt acaacaaaaa catcaaaagc   1680
ttaccagctt tttgctttgc ccaaaaatgg accagtttta aaacctggtt tgagaagagt   1740
tcaagatagc aatggctctc aaatcgaatt agaagtgtac agtgttccaa aagaactgtt   1800
cggtgctttt atttccatgg ttcctgaacc attaggaata ggttcagtgg agttagaatc   1860
tggtgaatgg atcaaatcct ttatttgtga agaatctggt tacaaagcca aaggtacagt   1920
tgatatcaca aagtatggtg gatttagagc atattttgaa atgttgaaga aaaaagagtc   1980
ccaaaagaag aagttatttg ataccgtgtt aattgccaat agaggtgaaa ttgccgttcg   2040
tattatcaag acattaaaaa aattgggtat tagatcagtt gcagtttatt ccgaccctga   2100
taaatattct caacacgtta ctgatgcaga tgtttctgta ccccttcatg gcacaaccgc   2160
agcccaaact tatttagaca tgaataagat catagatgcc gctaagcaaa ctaatgcaca   2220
ggccattatt cctggttatg gtttcttgtc ggaaaatgcg gatttttctg atgcgtgcac   2280
cagtgctggc attacctttg ttggtccttc gggagatatt atcagaggtt tagggttaaa   2340
```

```
acattctgct agacagattg cacagaaggc tggcgttcct ctagtgccag gctctttgct   2400
tatcacatca gttgaagagg ctaagaaagt cgcagcggaa ttggaatacc cagttatggt   2460
gaagtcaact gctggtggcg gtggtattgg tttgcagaaa gtcgattctg aagaggacat   2520
cgagcatatt tttgagactg tgaaacatca aggtgaaaca tttttcggtg acgctggtgt   2580
atttctggaa cggtttatcg aaaatgccag gcatgttgaa gtccaactta tgggagatgg   2640
ttttggtaag gccattgctt tgggcgaacg tgattgttct ttacagcgtc gtaaccaaaa   2700
agttatcgaa gaaactcctg caccaaattt gccagaaaag acgaggttgg cgttaagaaa   2760
ggcagctgaa agtttgggat ctttattgaa ttacaagtgt gctggtacgg ttgaatttat   2820
ttacgatgag aaaaaggacg agttttactt tttagaagtt aatacaagat tacaagttga   2880
acatccaata acagaaatgg ttacagggtt agacttggtc gagtggatga tcaggattgc   2940
cgctaatgat gcacctgatt ttgattctac aaaggtagaa gtcaatgggg tttcaatgga   3000
ggcacgttta tatgctgaaa atccattgaa aaatttcaga ccttctccag gtttacttgt   3060
cgatgtgaaa tttcctgatt gggcaagagt ggatacttgg gttaagaaag gtactaatat   3120
ttctcccgaa tatgatccaa cattggccaa aattatcgtt catgggaaag accgtgatga   3180
tgcaatttcc aagttaaatc aagcgttaga agaaacaaaa gtttacggat gtattactaa   3240
cattgactac ctgaagtcta tcattaccag tgatttcttt gctaaagcaa aagtttctac   3300
aaacattttg aactcttatc aatatgagcc taccgccatc gaaattactt tgcccggtgc   3360
acacactagt attcaggatt accccggtag agttgggtac tggagaattg gtgttccgcc   3420
ctctggtcca atggacgcat attcgtttag attggcgaac agaattgttg gtaatgacta   3480
caggactcct gccattgaag taacgttgac tggtccatcc atcgttttcc attgtgaaac   3540
tgtcattgcc attactggtg gtaccgctct atgtacatta gacggccaag aaattcccca   3600
acacaaaccg gtcgaagtta agaggggatc tactttatcc attggcaagt tgacaagcgg   3660
ctgtagagca tacttaggta tcaggggtgg cattgatgtg cctaaatact tgggctctta   3720
ttctactttc actctaggaa atgtcggtgg atacaatgga agggtgctaa aacttggaga   3780
cgtactattc ttaccaagca atgaagaaaa taaatcagtt gagtgccttc cacagaatat   3840
tcctcaatca ttaattcctc aaatttccga aactaaggaa tggagaattg gtgtaacatg   3900
tggtccccat gggtctccag atttttttaa acctgagtcc atcgaagaat tttcagtga    3960
gaagtggaag gttcattaca actccaatag atttggtgtc cgtttgattg gacctaaacc   4020
taagtgggca agaagtaatg gtggtgaagg tggtatgcat ccttcaaaca ctcacgatta   4080
cgtttattct ctgggtgcaa ttaatttcac gggtgatgag ccagttatta ttacttgcga   4140
tggtccttcc ttaggtggtt ttgtgtgtca agctgttgtc ccagaagcag aactgtggaa   4200
ggttggacag gttaaacccg gtgattccat tcagtttgtg ccactttctt acgaaagctc   4260
gagatcctta aaggaatctc aggatgttgc aattaaatca ttggatggta ctaagttaag   4320
gcgcttagac tctgtttcaa ttttaccatc attcgaaacg cctattcttg cacaaatgga   4380
aaaagtgaat gagctttcac caaaggttgt atacagacaa gcaggtgatc gttatgtttt   4440
ggtggaatac ggtgataatg aaatgaattt taatatttcc tatagaattg aatgcctgat   4500
ctcccttgtg aaaaagaata agactattgg tattgttgaa atgtcccaag gtgttagatc   4560
tgtattgata gaatttgatg gttacaaagt cactcaaaaa gaattgctta aagtattggt   4620
ggcatatgaa acagaaatcc agtttgatga aaattggaag ataacttcta atataataag   4680
```

```
attaccgatg gctttcgaag actcgaagac tttggcatgt gttcaaaggt atcaagaaac   4740
aattcgttcg tctgctccat ggttgccaaa taacgttgat ttcattgcca atgtaaatgg   4800
aatttcaagg aatgaagttt atgatatgtt gtattctgcc agatttatgg ttttaggttt   4860
aggtgatgtc ttcctagggt cgccttgtgc tgttccatta gatcctcgtc acagattttt   4920
gggaagcaag tacaacccaa gtagaacata tacagaaaga ggtgcagtcg gtattggcgg   4980
tatgtatatg tgcatatatg ctgctaacag tcctggtggg taccaattag tgggtagaac   5040
aataccaatt tgggacaaac tatgtctggc cgcatcttct gaggttccgt ggttgatgaa   5100
cccatttgac caagtcgaat ttacccagt ttctgaagaa gatttggata aaatgactga   5160
agattgtgat aatggtgttt ataaagtcaa tatcgaaaag agtgtttttg atcatcaaga   5220
atacttgaga tggatcaacg caaacaaaga ttccatcaca gcattccagg agggccagct   5280
tggtgaaaga gcagaggaat ttgccaaatt gattcaaaat gcaaactctg aactaaaaga   5340
aagtgtcaca gtcaaacctg acgaggaaga agacttccca gaaggtgcag aaattgtata   5400
ttctgagtat tctgggcgtt tttggaaatc catagcatct gttggagatg ttattgaagc   5460
aggtcaaggg ctactaatta ttgaagccat gaaagcggaa atgattatat ccgctcctaa   5520
atcgggtaag attatcaaga tttgccatgg caatggtgat atggttgatt ctggtgacat   5580
agtggccgtc atagagacat tggcatgagg aaatccatta tgtcatcctc agaagtaaaa   5640
gcaaatggtt ggaccgcagt tcctgtttcc gcaaaagcaa tagtagactc cttgggtaaa   5700
ttaggagatg tctcttcata ttccgtagaa gatattgcct ttccagctgc agacaaattg   5760
gtagccgaag ctcaagcatt cgttaaggct agattatctc ctgaaaccta caaccattca   5820
atgagagttt tctattgggg tactgtcatt gccagaagat tgttaccaga acaagctaaa   5880
gatttgtctc cttcaacatg ggcattaacc tgtttgttac acgacgttgg tactgccgaa   5940
gcttatttta cctccactag aatgagtttc gatatctacg gtggtattaa agctatggaa   6000
gtattgaagg ttttaggttc cagtacagat caagcagaag ccgttgctga agcaattata   6060
agacatgaag atgttggtgt cgacggtaac atcacatttt tggtcaatt gatccaattg   6120
gcaacattgt acgataacgt cggtgcctac gacggtattg atgacttcgg ttcctgggtt   6180
gatgacacta caagaaacag tataaacact gctttcccaa gacatggttg gtgttcttgg   6240
ttcgcatgca cagttagaaa agaagaatca aacaagcctt ggtgccacac cacacacata   6300
ccacaattcg acaaacaaat ggaagcaaac accttgatga aaccttggga ataagtttaa   6360
actaatccca cagccgccag ttccgctggc ggcattttaa ctttctttaa tgggcgcgcc   6420
tttccatagg ctccgccccc ctgacgagca tcacaaaaat cgacgctcaa gtcagaggtg   6480
gcgaaacccg acaggactat aaagatacca ggcgtttccc cctggaagct ccctcgtgcg   6540
ctctcctgtt ccgaccctgc cgcttaccgg atacctgtcc gcctttctcc cttcgggaag   6600
cgtggcgctt tctcatagct cacgctgtag gtatctcagt tcggtgtagg tcgttcgctc   6660
caagctgggc tgtgtgcacg aaccccccgt tcagcccgac cgctgcgcct tatccggtaa   6720
ctatcgtctt gagtccaacc cggtaagaca cgacttatcg ccactggcag cagccactgg   6780
taacaggatt agcagagcga ggtatgtagg cggtgctaca gagttcttga agtggtggcc   6840
taactacggc tacactagaa gaacagtatt tggtatctgc gctctgctga agccagttac   6900
cttcggaaaa agagttggta gctcttgatc cggcaaacaa accaccgctg gtagcggtgg   6960
tttttttgtt tgcaagcagc agattacgcg cagaaaaaaa ggatctcaag aagatccttt   7020
gatcttttct acggggtctg acgctcagtg gaacgaaaac tcacgttaag ggattttggt   7080
```

```
catgagatta tcaaaaagga tcttcaccta gatcctttta aattaaaaat gaagttttaa   7140
atcaatctaa agtatatatg agtaaacttg gtctgacagt taccaatgct taatcagtga   7200
ggcacctatc tcagcgatct gtctatttcg ttcatccata gttgcctgac tccccgtcgt   7260
gtagataact acgatacggg agggcttacc atctggcccc agtgctgcaa tgataccgcg   7320
agacccacgc tcaccggctc cagatttatc agcaataaac cagccagccg gaagggccga   7380
gcgcagaagt ggtcctgcaa ctttatccgc ctccatccag tctattaatt gttgccggga   7440
agctagagta agtagttcgc cagttaatag tttgcgcaac gttgttgcca ttgctacagg   7500
catcgtggtg tcacgctcgt cgtttggtat ggcttcattc agctccggtt cccaacgatc   7560
aaggcgagtt acatgatccc ccatgttgtg caaaaaagcg gttagctcct tcggtcctcc   7620
gatcgttgtc agaagtaagt tggccgcagt gttatcactc atggttatgg cagcactgca   7680
taattctctt actgtcatgc catccgtaag atgcttttct gtgactggtg agtactcaac   7740
caagtcattc tgagaatagt gtatgcggcg accgagttgc tcttgcccgg cgtcaatacg   7800
ggataatacc gcgccacata gcagaacttt aaaagtgctc atcattggaa aacgttcttc   7860
ggggcgaaaa ctctcaagga tcttaccgct gttgagatcc agttcgatgt aacccactcg   7920
tgcacccaac tgatcttcag catcttttac tttcaccagc gtttctgggt gagcaaaaac   7980
aggaaggcaa aatgccgcaa aaaagggaat aagggcgaca cggaaatgtt gaatactcat   8040
actcttcctt tttcaatatt attgaagcat ttatcagggt tattgtctca tgagcggata   8100
catatttgaa tgtatttaga aaaataaaca gcgatcgcgc ggccgcgggt aataactgat   8160
ataattaaat tgaagctcta atttgtgagt ttagtataca tgcatttact tataatacag   8220
tttttagtt ttgctggccg catcttctca aatatgcttc ccagcctgct tttctgtaac   8280
gttcaccctc taccttagca tcccttccct ttgcaaatag tcctcttcca acaataataa   8340
tgtcagatcc tgtagagacc acatcatcca cggttctata ctgttgaccc aatgcgtctc   8400
ccttgtcatc taaacccaca ccgggtgtca taatcaacca atcgtaacct tcatctcttc   8460
cacccatgtc tctttgagca ataaagccga taacaaaatc tttgtcgctc ttcgcaatgt   8520
caacagtacc cttagtatat tctccagtag ctagggagcc cttgcatgac aattctgcta   8580
acatcaaaag gcctctaggt tcctttgtta cttcttccgc cgcctgcttc aaaccgctaa   8640
caatacctgg gcccaccaca ccgtgtgcat tcgtaatgtc tgcccattct gctattctgt   8700
atacacccgc agagtactgc aatttgactg tattaccaat gtcagcaaat tttctgtctt   8760
cgaagagtaa aaaattgtac ttggcggata atgcctttag cggcttaact gtgccctcca   8820
tggaaaaatc agtcaagata tccacatgtg tttttagtaa acaaattttg ggacctaatg   8880
cttcaactaa ctccagtaat tccttggtgg tacgaacatc caatgaagca cacaagtttg   8940
tttgcttttc gtgcatgata ttaaatagct tggcagcaac aggactagga tgagtagcag   9000
cacgttcctt atatgtagct ttcgacatga tttatcttcg tttcctgcag gtttttgttc   9060
tgtgcagttg ggttaagaat actgggcaat ttcatgtttc ttcaacacca catatgcgta   9120
tatataccaa tctaagtctg tgctccttcc ttcgttcttc cttctgctcg gagattaccg   9180
aatcaaagct agcttatcga tgataagctg tcaaagatga gaattaattc cacggactat   9240
agactatact agatactccg tctactgtac gatacacttc cgctcaggtc cttgtccttt   9300
aacgaggcct taccactctt ttgttactct attgatccag ctcagcaaag gcagtgtgat   9360
ctaagattct atcttcgcga tgtagtaaaa ctagctagac cgagaaagag actagaaatg   9420
```

```
caaaaggcac ttctacaatg gctgccatca ttattatccg atgtgacgct gcagcttctc   9480
aatgatattc gaatacgctt tgaggagata cagcctaata tccgacaaac tgttttacag   9540
atttacgatc gtacttgtta cccatcattg aattttgaac atccgaacct gggagttttc   9600
cctgaaacag atagtatatt tgaacctgta taataatata tagtctagcg ctttacggaa   9660
gacaatgtat gtatttcggt tcctggagaa actattgcat ctattgcata ggtaatcttg   9720
cacgtcgcat ccccggttca ttttctgcgt ttccatcttg cacttcaata gcatatcttt   9780
gttaacgaag catctgtgct tcattttgta gaacaaaaat gcaacgcgag agcgctaatt   9840
tttcaaacaa agaatctgag ctgcattttt acagaacaga aatgcaacgc gaaagcgcta   9900
ttttaccaac gaagaatctg tgcttcattt ttgtaaaaca aaaatgcaac gcgacgagag   9960
cgctaatttt tcaaacaaag aatctgagct gcatttttac agaacagaaa tgcaacgcga  10020
gagcgctatt ttaccaacaa agaatctata cttctttttt gttctacaaa aatgcatccc  10080
gagagcgcta tttttctaac aaagcatctt agattacttt ttttctcctt tgtgcgctct  10140
ataatgcagt ctcttgataa ctttttgcac tgtaggtccg ttaaggttag aagaaggcta  10200
ctttggtgtc tattttctct tccataaaaa aagcctgact ccacttcccg cgtttactga  10260
ttactagcga agctgcgggt gcatttttttc aagataaagg catccccgat tatattctat  10320
accgatgtgg attgcgcata ctttgtgaac agaaagtgat agcgttgatg attcttcatt  10380
ggtcagaaaa ttatgaacgg tttcttctat tttgtctcta tatactacgt ataggaaatg  10440
tttacatttt cgtattgttt tcgattcact ctatgaatag ttcttactac aatttttttg  10500
tctaaagagt aatactagag ataaacataa aaaatgtaga ggtcgagttt agatgcaagt  10560
tcaaggagcg aaaggtggat gggtaggtta tatagggata tagcacagag atatatagca  10620
aagagatact tttgagcaat                                              10640
```

<210> SEQ ID NO 22
<211> LENGTH: 244
<212> TYPE: PRT
<213> ORGANISM: Fusarium oxysporum

<400> SEQUENCE: 22

```
Met Leu Pro Thr Glu Val Glu Ala Asn Gly Trp Thr Ala Val Pro Val
1               5                   10                  15

Ser Ala Lys Ala Ile Lys Asp Ser Val Gly Gln Leu Val Pro Thr Gln
            20                  25                  30

Thr Tyr Thr Leu Gln Asp Ile Val Phe Pro Ser Glu Asp Lys Leu Val
        35                  40                  45

Ser Glu Ala Gln Ala Phe Val Lys Ala Arg Leu Ser Gln Glu Ala Tyr
    50                  55                  60

Asn His Ser Met Arg Val Phe Tyr Trp Gly Ser Ile Ile Ala Lys Arg
65                  70                  75                  80

Leu Leu Pro Lys His Ala Glu Ala Leu Ser Pro Ser Thr Trp Ala Leu
                85                  90                  95

Thr Cys Leu Leu His Asp Ile Gly Thr Ala Glu Ala Tyr Phe Thr Ser
            100                 105                 110

Thr Arg Met Ser Phe Asp Ile Tyr Gly Gly Ile Lys Ala Met Glu Val
        115                 120                 125

Leu Lys Val Leu Gly Ser Ser Asp Asp Gln Ala Glu Ala Val Ala Glu
    130                 135                 140

Ala Ile Ile Arg His Glu Asp Met Gly Val Asp Gly Ser Ile Thr Phe
145                 150                 155                 160
```

```
Leu Gly Gln Leu Ile Gln Leu Ala Thr Leu Tyr Asp Asn Val Gly Thr
                165                 170                 175

Tyr Glu Gly Ile Asp Asp Phe Gly Gly Trp Ile Asp Glu Ala Thr Arg
            180                 185                 190

Asp Asn Val Asn Lys Ala Ile Pro Arg His Gly Trp Cys Ser Trp Phe
        195                 200                 205

Ala Cys Thr Val Arg Lys Glu Glu Ser Asn Lys Pro Trp Cys His Thr
    210                 215                 220

Thr His Ile Pro Gln Phe Asp Lys Gln Met Glu Ala Asn Thr Leu Met
225                 230                 235                 240

Lys Gln Trp Glu


<210> SEQ ID NO 23
<211> LENGTH: 735
<212> TYPE: DNA
<213> ORGANISM: Fusarium oxysporum

<400> SEQUENCE: 23

atgttgccca ccgaagtcga ggccaacggc tggactgccg tgcctgtcag cgccaaggca      60

atcaaggact cggtcggaca gcttgtaccc acgcaaacct acactctcca agacatcgtt     120

ttcccctctg aggacaaact tgtgtctgaa gctcaagcct ttgtcaaggc acggctaagt     180

caagaagctt ataaccactc tatgcgagtt ttctactggg gatccattat tgccaagcgt     240

ttgctaccca agcacgcaga ggccctgtcc ccgtccacct gggcgctgac atgtcttttg     300

catgatatcg gtactgctga ggcttacttc acttcaactc gcatgtcttt tgatatctat     360

ggtggaatca aggcaatgga ggtgctcaaa gtcctcggta gcagcgacga tcaggccgag     420

gcagtcgcag aggctatcat ccgtcatgaa gacatgggcg tggacggttc gattactttc     480

ctaggccagt taattcagct tgctacgctg tatgacaacg ttgggacgta cgagggcatt     540

gacgattttg gcggctggat tgacgaagct actcgggata atgtcaacaa agctattcct     600

cgtcacggtt ggtgctcctg gtttgcctgt actgtccgca aggaggaatc caacaagcct     660

tggtgccata ctacccatat tcctcaattt gataagcaga tggaggcaaa cactttgatg     720

aaacagtggg agtag                                                      735


<210> SEQ ID NO 24
<211> LENGTH: 245
<212> TYPE: PRT
<213> ORGANISM: Fusarium pseudograminearum

<400> SEQUENCE: 24

Met Ser Ser Pro Glu Val Lys Ile Asn Gly Trp Thr Ala Val Pro Leu
1               5                   10                  15

Asn Ala Lys Asn Ile Leu Asp Ser Val Gly Lys Leu Ala Glu Val Pro
            20                  25                  30

Thr Tyr Lys Ala Glu Asp Ile Lys Phe Pro Ser Asn Asp Lys Leu Val
        35                  40                  45

Ala Glu Ala Gln Ala Phe Val Lys Ala Arg Leu Ser Pro Glu Ala Tyr
    50                  55                  60

Asn His Ser Met Arg Val Phe Tyr Trp Gly Asn Ile Leu Ala Lys Arg
65                  70                  75                  80

Leu Leu Pro Glu His Phe Glu Ala Leu Ser Thr Ser Thr Trp Ala Leu
                85                  90                  95

Thr Cys Leu Leu His Asp Ile Gly Thr Ala Asp Ala Phe Phe Thr Ser
```

```
            100                 105                 110

Thr His Met Ser Phe Asp Leu Tyr Gly Gly Ile Lys Ala Met Glu Val
        115                 120                 125

Leu Lys Val Leu Gly Gly Thr Thr Asp Gln Ala Glu Ala Val Ala Glu
    130                 135                 140

Ala Ile Ile Arg His Gln Asp Val Gly Val Asp Gly Thr Ile Thr Phe
145                 150                 155                 160

Leu Gly Gln Leu Ile Gln Leu Ala Thr Leu Tyr Asp Asn Val Gly Val
                165                 170                 175

Tyr Glu Gly Ile Glu Asp Tyr Gly Ser Trp Val Asp Glu Val Thr Arg
            180                 185                 190

Asp Asn Ile Asn Arg Glu Phe Pro Arg His Lys Trp Ala Ser Cys Phe
        195                 200                 205

Ala Ser Val Ile Arg Gln Glu Glu Ser Asn Lys Pro Trp Cys His Ser
    210                 215                 220

Thr His Ile Val Gly Phe Pro Glu Lys Leu Glu Ala Asn Thr Leu Met
225                 230                 235                 240

Lys Pro Trp Glu Glu
                245


<210> SEQ ID NO 25
<211> LENGTH: 738
<212> TYPE: DNA
<213> ORGANISM: Fusarium pseudograminearum

<400> SEQUENCE: 25

atgtcttcac ctgaagtcaa gattaacggt tggactgctg tccccctcaa cgccaagaac      60

attctcgatt ctgtaggaaa actcgcagaa gttcccacct acaaggcaga ggatattaaa     120

ttcccatcaa atgacaagct cgtcgccgaa gcccaggcct ttgtcaaggc gcgactgagc     180

ccagaagcgt ataatcactc catgagagta ttttactggg gaaacattct tgcaaagcgt     240

ttgctgcccg agcattttga agctttgtcc acgtctacct gggcactcac ctgtctctta     300

cacgacatag gaacggccga tgccttcttc acctccacgc acatgtcgtt cgatctctat     360

ggcggcataa aggctatgga agtgctcaag gtgctcggcg gtactaccga ccaagctgaa     420

gctgtcgccg aggccatcat acgtcatcag gatgtgggcg tggacggcac catcactttt     480

cttgggcagc tgattcaact tgccacactt tacgacaacg tcggcgttta tgagggcatt     540

gaggactatg gcagttgggt tgatgaggtc actcgcgata atatcaatag ggaatttcct     600

cggcacaagt gggcatcttg ctttgcttct gtcattcgtc aggaggagtc caacaaaccc     660

tggtgccatt ctacacatat tgtaggcttt cctgaaaagc ttgaggccaa cactcttatg     720

aagccttggg aggagtag                                                   738


<210> SEQ ID NO 26
<211> LENGTH: 245
<212> TYPE: PRT
<213> ORGANISM: Fusarium graminearum

<400> SEQUENCE: 26

Met Ser Ser Pro Glu Ala Lys Thr Asn Gly Trp Thr Ala Val Pro Leu
1               5                   10                  15

Asn Ala Lys Asn Ile Leu Asp Thr Val Gly Lys Leu Ala Glu Val Pro
            20                  25                  30

Thr Tyr Lys Ala Glu Asp Ile Gln Phe Pro Ser Asp Asp Lys Leu Val
        35                  40                  45
```

```
Ala Glu Ala Gln Ala Phe Ala Lys Ala Arg Leu Ser Pro Glu Ala Tyr
    50                  55                  60

Asn His Ser Met Arg Val Phe Tyr Trp Gly Asn Ile Leu Ala Lys Arg
65                  70                  75                  80

Leu Leu Pro Glu His Phe Gly Ala Leu Ser Thr Ser Thr Trp Ala Leu
                85                  90                  95

Thr Cys Leu Leu His Asp Ile Gly Thr Ala Asp Val Phe Phe Thr Ser
            100                 105                 110

Thr His Met Ser Phe Asp Leu Tyr Gly Gly Ile Lys Ala Met Glu Val
        115                 120                 125

Leu Lys Val Leu Gly Gly Thr Thr Asp Gln Ala Glu Ala Val Ala Glu
    130                 135                 140

Ala Ile Ile Arg His Gln Asp Val Gly Val Asp Gly Thr Ile Thr Phe
145                 150                 155                 160

Leu Gly Gln Leu Ile Gln Leu Ala Thr Leu Tyr Asp Asn Val Gly Val
                165                 170                 175

Tyr Glu Gly Ile Gln Asp Tyr Gly Ser Trp Val Asp Glu Ala Thr Arg
            180                 185                 190

Asp Asn Ile Asn Arg Ala Phe Pro Arg His Lys Trp Thr Ser Cys Phe
        195                 200                 205

Ala Ser Val Ile Arg Gln Glu Glu Ser Asn Lys Pro Trp Cys His Ser
    210                 215                 220

Thr His Ile Val Asp Phe Pro Glu Lys Leu Glu Ala Asn Thr Leu Met
225                 230                 235                 240

Lys Pro Trp Glu Glu
                245
```

<210> SEQ ID NO 27
<211> LENGTH: 738
<212> TYPE: DNA
<213> ORGANISM: Fusarium graminearum

<400> SEQUENCE: 27

```
atgtcttcac ctgaagccaa aactaacggt tggactgctg tccccctcaa cgctaagaat      60

attctcgaca ctgtaggaaa gctcgcagaa gttcccacct acaaggcaga ggatattcaa     120

tttccatcag acgacaagct agtcgccgaa gcccaagcct ttgccaaggc acgactaagc     180

cctgaagcct ataatcactc catgcgagta ttttactggg gaaacattct tgcaaagcgt     240

ttgctgccag agcattttgg agctttgtcc acgtctacct gggcactcac ctgtctctta     300

cacgacatag gaacggccga tgtcttcttc acatccacac acatgtcgtt cgatctctat     360

ggcggcataa aggctatgga agtgctcaag gtgctcggtg gtaccaccga ccaagctgaa     420

gctgtcgccg aggccatcat acgtcatcag gatgtgggcg tggacggcac catcactttt     480

cttgggcagc tgattcaact tgccacactt tatgataacg tcggcgttta tgagggcatt     540

caagactatg gcagttgggt tgatgaggcc actcgcgata atatcaatag ggcatttcct     600

cgacacaagt ggacgtcttg ctttgcttcc gtcattcgtc aggaggagtc caacaaaccc     660

tggtgccatt ctacacatat tgtggacttt cctgaaaagc ttgaggccaa cactcttatg     720

aagccttggg aggagtag                                                  738
```

<210> SEQ ID NO 28
<211> LENGTH: 244
<212> TYPE: PRT
<213> ORGANISM: Aspergillus kawachii

<400> SEQUENCE: 28

Met Cys Asn Asp Glu Ile Lys Ala Asn Gly Trp Ser Ser Met Pro Ala
1               5                   10                  15

Asn Ala Gly Ala Ile Phe Thr Asp Gln Ser Phe Ile Glu Arg Ala Glu
            20                  25                  30

Ala Met Gln Leu Asp Thr Ile Ile Phe Pro Phe Asp Asp Pro Val Val
        35                  40                  45

Ser Lys Thr Trp Glu Tyr Ala Arg Ala Val Leu His Pro Gln Thr Leu
    50                  55                  60

Asn His Ser Met Arg Val Tyr Phe Tyr Gly Met Val Ile Thr Thr Gln
65                  70                  75                  80

Gln Phe Pro Glu Ile Ala Ala Ser Leu Asn Pro Val Thr Trp Ala Leu
                85                  90                  95

Thr Cys Leu Leu His Asp Ile Gly Thr Ala Glu Glu Asn Leu Thr Ala
            100                 105                 110

Thr Arg Met Ser Phe Asp Ile Tyr Gly Gly Ile Lys Ala Leu His Val
        115                 120                 125

Leu Lys Glu Phe Gly Ala Thr Ala Asp Gln Ala Glu Ala Val Ala Glu
    130                 135                 140

Ala Ile Ile Arg His Glu Asp Met Gly Val Asp Gly Thr Ile Thr Tyr
145                 150                 155                 160

Phe Gly Gln Leu Ile Gln Leu Ala Thr Thr Tyr Asp Asn Thr Gly Val
                165                 170                 175

His Pro His Val Lys Ser Phe Glu Gly Leu Val His Gln Thr Thr Arg
            180                 185                 190

Lys Gln Ile Asn Glu Ala Tyr Pro Arg Leu Lys Trp Cys Glu Phe Phe
        195                 200                 205

Ser Gly Met Ile Arg Lys Glu Glu Thr Ile Lys Pro Trp Cys His Ser
    210                 215                 220

Thr His Leu Val Asp Phe Asp Arg Glu Ile Glu Glu Asn Thr Leu Met
225                 230                 235                 240

Arg Glu Trp Glu

<210> SEQ ID NO 29
<211> LENGTH: 735
<212> TYPE: DNA
<213> ORGANISM: Aspergillus kawachii

<400> SEQUENCE: 29
atgtgcaacg acgaaataaa agccaacggc tggtccagca tgcccgccaa tgccggtgcc 60
atatttacgg accaatcctt catcgaaagg gcagaagcca tgcagctcga tacaatcata 120
ttccccttcg acgatcctgt cgtttcaaag acctgggaat acgccagggc tgttcttcac 180
ccccagacat tgaaccattc catgagggtc tacttctacg gaatggtaat caccacccag 240
caattccctg aaatagcagc atccctcaac ccagtcacct gggctctgac ctgcctcctc 300
cacgacatcg gtactgcgga ggagaaccta actgcaacgc gcatgtcatt cgatatctat 360
ggcggtatca aggccctcca tgtgctgaag gagtttggtg ccactgcgga ccaggccgag 420
gccgttgctg aggcgatcat tcgacatgag gatatgggcg tcgatggaac tattacatat 480
ttcggtcagc ttattcagtt ggctactaca tatgataata ccggagttca tccgcatgtg 540
aagagttttg agggcttggt gcatcagaca actcgcaaac agatcaatga ggcgtatccg 600
cggttgaagt ggtgtgaatt tttctcgggg atgattagga aggaagagac gatcaagcct 660

```
tggtgtcatt cgacccattt ggtggacttt gacagggaga tagaagagaa tacgcttatg    720

agggagtggg agtaa                                                     735


<210> SEQ ID NO 30
<211> LENGTH: 244
<212> TYPE: PRT
<213> ORGANISM: Aspergillus niger

<400> SEQUENCE: 30

Met Cys His Asp Glu Ile Lys Ala Asn Gly Trp Ser Ser Thr Pro Ala
1               5                   10                  15

Asn Ala Gly Ala Ile Phe Thr Asp Gln Ser Phe Ile Glu Arg Ala Glu
            20                  25                  30

Ala Val Glu Leu Asp Thr Ile Gln Phe Pro Phe Asp Asp Pro Val Val
        35                  40                  45

Ser Lys Thr Leu Glu Tyr Val Lys Ala Val Leu His Pro Glu Thr Leu
    50                  55                  60

Asn His Ser Met Arg Val Tyr Tyr Tyr Gly Met Val Ile Thr Thr Gln
65                  70                  75                  80

Gln Phe Pro Glu Gln Ala Ala Ser Ile Asn Pro Val Thr Trp Ala Leu
                85                  90                  95

Thr Cys Leu Leu His Asp Leu Gly Thr Ala Glu Glu Asn Leu Thr Ala
            100                 105                 110

Thr Arg Met Ser Phe Asp Ile Tyr Gly Gly Ile Lys Ala Leu His Val
        115                 120                 125

Leu Lys Glu Phe Gly Ala Thr Ala Asp Gln Ala Glu Ala Ala Ala Glu
    130                 135                 140

Ala Ile Ile Arg His Glu Asp Met Gly Val Asp Gly Thr Ile Thr Tyr
145                 150                 155                 160

Phe Gly Gln Leu Ile Gln Leu Ala Thr Thr Tyr Asp Asn Thr Gly Ile
                165                 170                 175

His Pro His Val Lys Gly Phe Glu Gly Leu Val His Arg Thr Thr Arg
            180                 185                 190

Lys Gln Ile Asn Glu Ala Tyr Pro Arg Leu Lys Trp Cys Ala Phe Phe
        195                 200                 205

Ser Gly Leu Ile Arg Lys Glu Glu Thr Ile Lys Pro Trp Cys His Ser
    210                 215                 220

Thr His Leu Val Asp Phe Asp Lys Glu Ile Glu Glu Asn Thr Leu Met
225                 230                 235                 240

Arg Glu Trp Glu


<210> SEQ ID NO 31
<211> LENGTH: 735
<212> TYPE: DNA
<213> ORGANISM: Aspergillus niger

<400> SEQUENCE: 31

atgtgccacg acgaaatcaa agccaacggc tggtccagca ctcccgccaa tgccggtgcc     60

atatttacgg accaatcctt cattgaaagg gcagaagccg tggagctcga tacgatccag    120

ttcccctttg acgaccctgt agtctcgaag acattggaat atgtcaaggc tgttcttcac    180

cccgagactt tgaatcattc catgagggtt tactattacg gaatggtaat caccacccaa    240

caattccccg aacaagcagc atccataaac ccagtgacct gggctctgac ttgtctcctc    300

cacgacctcg gaaccgcgga ggagaacctc accgcaacgc gcatgtcatt cgatatctac    360
```

```
ggcggcatca aagccctcca tgtgctgaag gagtttggtg ccactgcgga ccaggccgaa    420

gcagcagctg aggcaatcat tcgacatgaa gatatgggag tcgatggaac gattacctac    480

ttcggtcagc ttattcagct ggctacgacg tatgataata ccgggattca tccgcatgtg    540

aagggctttg aggggttggt ccatcgcacg actcgcaagc agattaatga ggcgtatccg    600

cggttgaagt ggtgtgcgtt tttctccggg ttgattagaa aggaggagac gattaagcct    660

tggtgtcatt cgactcattt ggtggatttt gataaggaga tcgaggagaa tacgcttatg    720

agggagtggg agtaa                                                     735
```

<210> SEQ ID NO 32
<211> LENGTH: 241
<212> TYPE: PRT
<213> ORGANISM: Aspergillus niger

<400> SEQUENCE: 32

```
Met Cys His Asp Lys Ile Pro Leu Asn Gly Trp Thr Ser Thr Pro Ala
1               5                   10                  15

Asn Ala Gly Ala Ile Phe Pro Asp Lys Pro Phe Ile His Pro Pro Thr
            20                  25                  30

Pro Ile Ser Ile Thr Asp Ile Pro Phe Pro Ser Thr Asp Pro Leu Val
        35                  40                  45

Ala Lys Thr Leu Glu Tyr Val Gln Ser Leu Leu Pro Arg Glu Thr Val
    50                  55                  60

Asn His Ser Met Arg Val Tyr Ser Tyr Gly Met Ile Leu Leu Thr Gln
65                  70                  75                  80

Gln Phe Pro Ser His His Leu Ser Pro Thr Thr Trp Ala Leu Thr Cys
                85                  90                  95

Leu Leu His Asp Ile Gly Thr Ala Pro Ser Leu Leu Thr Ser Thr Asn
            100                 105                 110

Met Ser Phe Asp Leu Tyr Gly Gly Ile Lys Ala His Ser Val Leu Thr
        115                 120                 125

Ser Phe Asp Cys Pro Ala Asp Val Ala Asp Ala Val Ala Glu Ala Ile
    130                 135                 140

Ile Arg His Gln Asp Leu Gly Val Asp Gly Asn Ile Thr Phe Leu Gly
145                 150                 155                 160

Gln Leu Ile Gln Leu Ala Thr Ile Tyr Asp Asn Val Gly Glu His Pro
                165                 170                 175

His Val Lys Asp Phe Gly Gly Leu Ile His Glu Asp Ala Arg Arg Glu
            180                 185                 190

Val Asn Glu Arg Trp Arg Arg Glu Gly Trp Cys Gly Val Phe Ala Asp
        195                 200                 205

Val Val Lys Leu Glu Val Gly Arg Lys Pro Trp Cys His Ser Thr His
    210                 215                 220

Ile Val Gly Phe Glu Gly Lys Val Arg Gly Asn Ala Leu Phe Gly Glu
225                 230                 235                 240

Lys
```

<210> SEQ ID NO 33
<211> LENGTH: 726
<212> TYPE: DNA
<213> ORGANISM: Aspergillus niger

<400> SEQUENCE: 33

```
atgtgccacg acaagatccc cctcaacggc tggaccagca cccccgccaa cgctggtgcc     60
```

```
atcttccccg acaagccctt catccaccca cccacgccca tctccatcac cgacatcccc    120

ttcccctcca ccgatcccct cgtcgccaag accctcgaat acgtccaatc cctcctcccc    180

cgcgagaccg tcaaccactc catgcgcgta tactcctacg gaatgatcct cctcacccag    240

caattccctt cccaccatct atctccaaca acctgggccc taacctgcct tctgcatgac    300

atcggcaccg ccccctccct cctcacctca acaaacatgt cctttgacct ctacggcggc    360

atcaaagccc actccgtact tacttccttc gactgtcccg ctgatgttgc tgacgccgta    420

gcggaagcta ttatccggca tcaggatcta ggcgtggatg ggaatatcac gttcctggga    480

cagttgatcc agctggctac catttatgat aatgtggggg aacatccgca cgtcaaggac    540

tttggagggt tgattcatga ggatgcgagg agggaggtta atgagcgctg gagaagggag    600

ggatggtgtg gggtgtttgc tgatgtggtg aagttggagg tggggaggaa gccgtggtgt    660

cattcgacgc atattgtggg gtttgagggg aaggttaggg ggaatgcgct tttggggag    720

aaatag                                                               726
```

```
<210> SEQ ID NO 34
<211> LENGTH: 242
<212> TYPE: PRT
<213> ORGANISM: Aspergillus oryzae

<400> SEQUENCE: 34

Met Ser Pro Thr Arg Ala Ala Gln Val Glu Glu Tyr Gly Trp Thr Ala
1               5                   10                  15

Val Ser Cys Asp Pro Gln Gln Arg Ala Ala Thr Asn Pro Pro Thr Lys
            20                  25                  30

Pro Ser Val Pro Gln Leu Val Lys Asp Thr Thr Leu Pro Asp Thr Pro
        35                  40                  45

Leu Val Lys Asp Ala Met Glu Tyr Val Lys Ala Glu Leu Pro Ala His
    50                  55                  60

Thr Phe Asn His Ser Met Arg Val Tyr Tyr Tyr Gly Leu Ala Ile Ala
65                  70                  75                  80

Arg Gln His Phe Pro Glu Trp Lys Phe Ser Asp Glu Thr Trp Leu Leu
                85                  90                  95

Thr Cys Leu Phe His Asp Ile Gly Thr Ile Asp Lys Tyr Thr Gln Asp
            100                 105                 110

Val Phe Met Ser Phe Asp Ile Tyr Gly Gly Ile Val Ala Leu Asn Val
        115                 120                 125

Leu Thr Glu Lys Gly Ala Pro Ala Pro Gln Ala Glu Ser Val Ala Glu
    130                 135                 140

Ala Ile Ile Arg His Gln Asp Pro Val Lys Val Gly Thr Ile His Ser
145                 150                 155                 160

Val Gly Leu Leu Ile Gln Leu Ala Thr Gln Phe Asp Asn Leu Gly Ala
                165                 170                 175

His Lys Glu Tyr Val His Pro Asp Thr Val Glu Asp Val Asn Gln His
            180                 185                 190

Tyr Pro Arg Arg Gln Trp Ser Lys Cys Phe Ser Ser Lys Leu Arg Glu
        195                 200                 205

Glu Ile Gly Leu Lys Pro Trp Cys His Thr Thr Ala Glu Gly Glu Gly
    210                 215                 220

Phe Pro Val Gly Ile Glu Asn Asn Thr Leu Met Glu Pro Tyr Asp Gly
225                 230                 235                 240

Arg Phe
```

<210> SEQ ID NO 35
<211> LENGTH: 729
<212> TYPE: DNA
<213> ORGANISM: Aspergillus oryzae

<400> SEQUENCE: 35

```
atgtcaccca ccagagcagc tcaagtcgaa gaatacggtt ggacagcggt gtcctgcgat      60

cctcagcagc gagctgctac aaacccacct accaagcctt ctgttcccca gttggtcaaa     120

gatacaactc ttcccgatac tcctctagtc aaagatgcca tggaatatgt taaggcagag     180

ctacccgctc acacttttaa ccacagcatg cgtgtctact attatggcct tgcaatcgcc     240

agacaacact tcccagaatg gaagttcagc gatgaaacct ggcttctcac ctgcctcttc     300

cacgacatcg gcactatcga caagtacacc caagacgtct ttatgtcctt cgatatctac     360

ggtggaattg tcgctctgaa cgtcctcacg gagaaaggtg cgccagcacc ccaggctgaa     420

agtgtcgcag aagccatcat ccgtcatcag gatccggtga aagttgggac tattcattct     480

gtcggtttac ttattcagct tgctacgcag tttgacaacc ttggtgccca caaggagtat     540

gtccaccctg atactgtgga agatgtgaac cagcattatc cgcgtcgtca gtggtcgaag     600

tgcttctcga gtaagctgag ggaggaaatt gggctcaagc cttggtgcca tactactgcg     660

gagggcgagg ggttccctgt tgggatcgag aacaacactt tgatggagcc ttatgatgga     720

cgcttctag                                                             729
```

<210> SEQ ID NO 36
<211> LENGTH: 243
<212> TYPE: PRT
<213> ORGANISM: Saccharomyces cerevisiae

<400> SEQUENCE: 36

```
Met Lys Leu Leu Arg Thr Val Phe Leu Pro Cys Ser Ser Ser Lys Glu
1               5                   10                  15

Ser Ile Met Ser Gln Tyr Gly Phe Val Arg Val Pro Arg Glu Val Glu
            20                  25                  30

Lys Ala Ile Pro Val Val Asn Ala Ser Arg Pro Arg Ala Val Val Pro
        35                  40                  45

Pro Pro Asn Ser Glu Thr Ala Arg Leu Val Arg Glu Tyr Ala Ala Lys
    50                  55                  60

Glu Leu Thr Ala Pro Val Leu Asn His Ser Leu Arg Val Phe Gln Tyr
65                  70                  75                  80

Ser Leu Ala Ile Ile Arg Asp Gln Phe Pro Ala Trp Asp Leu Asp Gln
                85                  90                  95

Glu Val Leu Tyr Val Thr Cys Leu Leu His Asp Ile Ala Thr Thr Asp
            100                 105                 110

Lys Asn Met Arg Ala Thr Lys Met Ser Phe Glu Tyr Tyr Gly Gly Ile
        115                 120                 125

Leu Ser Arg Glu Leu Val Phe Asn Ala Thr Gly Gly Asn Gln Asp Tyr
    130                 135                 140

Ala Asp Ala Val Thr Glu Ala Ile Ile Arg His Gln Asp Leu Thr Gly
145                 150                 155                 160

Thr Gly Tyr Ile Thr Thr Leu Gly Leu Ile Leu Gln Ile Ala Thr Thr
                165                 170                 175

Leu Asp Asn Val Gly Ser Asn Thr Asp Leu Ile His Ile Asp Thr Val
            180                 185                 190
```

```
Arg Ala Ile Asn Glu Gln Phe Pro Arg Leu His Trp Leu Ser Cys Phe
        195                 200                 205

Ala Thr Val Val Asn Thr Glu Asn Ser Arg Lys Pro Trp Gly His Thr
    210                 215                 220

Ser Ser Leu Gly Asp Asp Phe Ser Lys Lys Val Ile Cys Asn Thr Phe
225                 230                 235                 240

Gly Tyr Asn


<210> SEQ ID NO 37
<211> LENGTH: 732
<212> TYPE: DNA
<213> ORGANISM: Saccharomyces cerevisiae

<400> SEQUENCE: 37

ttagttatac ccaaatgtat tgcatatgac tttctttgaa aaatcatcac ccaaagaact      60

ggtgtggccc cacggttttc tcgagttttc agtgttcacc accgtagcaa aacatgataa     120

ccagtgcagt cttggaaatt gctcattaat ggctctaact gtatcgatat gaatcagatc     180

ggtattggat ccgacattgt caagcgtagt agcaatctgc agaatgagcc ccaaggtggt     240

aatgtagcca gtcccagtca aatcctggtg acgaatgatg gcctcagtta ctgcatctgc     300

atagtcctga tttccacctg tcgcattaaa tacaagctcc cttgaaagta tgccaccata     360

atactcaaat gacatcttcg tggctctcat attcttatct gttgttgcaa tatcatgaag     420

taagcaggtg acgtacaaaa cttcctgatc caagtcccat gctggaaatt ggtctcttat     480

gatagctaaa ctatattgaa aaacacgcaa agagtggttt agaacggggg cagtcaattc     540

tttagcggca tattcccgaa caagcctagc agtttcactg tttggaggcg gaacaacggc     600

ccgtggtcta gatgcattca ccactggaat ggccttttct acctctctag gaactcttac     660

aaatccgtac tgtgacatga ttgattcttt tgaagaggag caaggcaaaa aaacagtacg     720

aagcaacttc at                                                         732


<210> SEQ ID NO 38
<211> LENGTH: 390
<212> TYPE: PRT
<213> ORGANISM: Rhodococcus sp.

<400> SEQUENCE: 38

Met Arg Glu Val Gln Leu Leu Asp Gly Arg Arg Val Asp Val Ala Cys
1               5                   10                  15

Ala Gly Pro Leu Ile Ser Glu Ile Gly Ala His Leu Asp Leu Thr Ala
            20                  25                  30

Pro Val Glu Ile Asp Cys Gly Gly Gly Leu Ala Thr Arg Pro Phe Thr
        35                  40                  45

Glu Pro His Leu His Leu Asp Lys Ala Gly Thr Ala Asp Arg Leu Pro
    50                  55                  60

Ala Gly Ala Ser Thr Ile Gly Asp Ala Ile Ala Ala Met Gln Ser Val
65                  70                  75                  80

Lys Val Thr Glu Arg Asp Asn Val Ala Ala Val Ala Ala Arg Met His
                85                  90                  95

Arg Val Leu Asn Arg Ile Val Asp Asp Gly Ser His Ala Ile Arg Ala
            100                 105                 110

Leu Val Asp Val Asp Glu Val Trp Gly Leu Thr Ala Phe His Ala Ala
        115                 120                 125

Gln Gln Val Gln Ala Ala Leu Ala Pro Arg Ala Val Val Gln Ile Val
    130                 135                 140
```

```
Ala Phe Pro Gln His Gly Leu Thr Pro Gln Val Leu Ala Met Leu Glu
145                 150                 155                 160

Gln Ala Ala Ala Glu Gly Ala Gly Ala Leu Gly Ala His Thr Asp Val
                165                 170                 175

Asp Pro Asp Pro Ala Ala His Val Gly Ala Val Ala Ala Ile Ala Ala
            180                 185                 190

Gly Ala Ser Leu Pro Leu Glu Val His Thr Asp Glu Gly Ala Ser Pro
        195                 200                 205

Asp Lys Phe Tyr Leu Pro Ala Val Leu Glu Val Leu Asp Arg Phe Pro
    210                 215                 220

Gly Leu Ser Thr Thr Leu Ala His Cys Leu Ser Leu Gly Thr Ile Ala
225                 230                 235                 240

Pro Lys Gln Gln Gln His Trp Ile Glu Glu Leu Ala His Arg Asp Ile
                245                 250                 255

Lys Val Cys Val Ala Pro Ser Ile Leu Gly Phe Gly Leu Pro Leu Ala
            260                 265                 270

Pro Val Arg Ala Leu Ile Glu Ala Gly Val Gly Ile Leu Val Gly Ser
        275                 280                 285

Asp Asn Leu Gln Asp Val Phe Phe Pro Leu Gly Thr Gly Arg Ala Ile
    290                 295                 300

Glu Asn Val Arg Leu Leu Ala Thr Ala Ala Gln Leu Thr Ala Pro Glu
305                 310                 315                 320

Leu Ala Gly Pro Leu Ile Ala Gly Val Thr Asp Ile Ala Tyr Ala Thr
                325                 330                 335

Val Thr Gly Ala Ala Asp Ala Leu Ala Val Glu Ser Pro Ala Thr Leu
            340                 345                 350

Val Val His Asp Ala Thr Ser Pro Ala Glu Leu Leu Arg Gly Ile Asp
        355                 360                 365

Gly Thr Arg Ile Thr Val Ile Asp Gly Leu Leu Thr Ser Pro Leu Gln
    370                 375                 380

Leu Asp Lys Gly Ile Lys
385                 390


<210> SEQ ID NO 39
<211> LENGTH: 412
<212> TYPE: PRT
<213> ORGANISM: Pseudomonas sp.

<400> SEQUENCE: 39

Met Ser Met Glu Thr His Ser Tyr Val Asp Val Ala Ile Arg Asn Ala
1               5                   10                  15

Arg Leu Ala Asp Thr Glu Gly Ile Val Asp Ile Leu Ile His Asp Gly
            20                  25                  30

Arg Ile Ala Ser Ile Val Lys Ser Thr Lys Thr Lys Gly Ser Val Glu
        35                  40                  45

Ile Asp Ala His Glu Gly Leu Val Thr Ser Gly Leu Val Glu Pro His
    50                  55                  60

Ile His Leu Asp Lys Ala Leu Thr Ala Asp Arg Val Pro Ala Gly Ser
65                  70                  75                  80

Ile Gly Asp Leu Arg Thr Arg Arg Gly Leu Glu Met Ala Ile Arg Ala
                85                  90                  95

Thr Arg Asp Ile Lys Arg Thr Phe Thr Val Glu Asp Val Arg Glu Arg
            100                 105                 110

Ala Ile Arg Ala Ala Leu Met Ala Ser Arg Ala Gly Thr Thr Ala Leu
```

```
        115                 120                 125

Arg Thr His Val Asp Val Asp Pro Ile Val Gly Leu Ala Gly Ile Arg
    130                 135                 140

Gly Val Leu Glu Ala Arg Glu Val Cys Ala Gly Leu Ile Asp Ile Gln
145                 150                 155                 160

Ile Val Ala Phe Pro Gln Glu Gly Leu Phe Cys Ser Ala Gly Ala Val
                165                 170                 175

Asp Leu Met Arg Glu Ala Ile Lys Leu Gly Ala Asp Ala Val Gly Gly
            180                 185                 190

Ala Pro Ala Leu Asp Asp Arg Pro Gln Asp His Val Arg Ala Val Phe
        195                 200                 205

Asp Leu Ala Ala Glu Phe Gly Leu Pro Val Asp Met His Val Asp Glu
    210                 215                 220

Ser Asp Arg Arg Glu Asp Phe Thr Leu Pro Phe Val Ile Glu Ala Ala
225                 230                 235                 240

Arg Glu Arg Arg Val Pro Asn Val Thr Val Ala His Ile Ser Ser Leu
                245                 250                 255

Ser Val Gln Thr Asp Asp Val Ala Arg Ser Thr Ile Ala Ala Leu Ala
            260                 265                 270

Asp Ala Asp Val Asn Val Val Val Asn Pro Ile Ile Val Lys Ile Thr
        275                 280                 285

Arg Leu Ser Glu Leu Leu Asp Ala Gly Val Ser Val Met Phe Gly Ser
    290                 295                 300

Asp Asn Leu Arg Asp Pro Phe Tyr Pro Leu Gly Ala Ala Asn Pro Leu
305                 310                 315                 320

Gly Ser Ala Ile Phe Ala Cys Gln Ile Ala Ala Leu Gly Thr Pro Gln
                325                 330                 335

Asp Leu Arg Arg Val Phe Asp Ala Val Thr Ile Asn Ala Ala Arg Met
            340                 345                 350

Leu Gly Phe Pro Ser Leu Leu Gly Val Val Glu Gly Ala Val Ala Asp
        355                 360                 365

Leu Ala Val Phe Pro Ser Ala Thr Pro Glu Glu Val Val Leu Asp Gln
    370                 375                 380

Gln Ser Pro Leu Phe Val Leu Lys Gly Gly Arg Val Val Ala Met Arg
385                 390                 395                 400

Leu Ala Ala Gly Ser Thr Ser Phe Arg Asp Tyr Ser
                405                 410


<210> SEQ ID NO 40
<211> LENGTH: 241
<212> TYPE: PRT
<213> ORGANISM: Rhodococcus sp.

<400> SEQUENCE: 40

Met Ile Tyr Ser Thr Val Asn Ala Asn Pro Tyr Ala Trp Pro Tyr Asp
1               5                   10                  15

Gly Ser Ile Asp Pro Ala His Thr Ala Leu Ile Leu Ile Asp Trp Gln
            20                  25                  30

Ile Asp Phe Cys Gly Pro Gly Gly Tyr Val Asp Ser Met Gly Tyr Asp
        35                  40                  45

Leu Ser Leu Thr Arg Ser Gly Leu Glu Pro Thr Ala Arg Val Leu Ala
    50                  55                  60

Ala Ala Arg Asp Thr Gly Met Thr Val Ile His Thr Arg Glu Gly His
65                  70                  75                  80
```

```
Arg Pro Asp Leu Ala Asp Leu Pro Pro Asn Lys Arg Trp Arg Ser Ala
                85                  90                  95

Ser Ala Gly Ala Glu Ile Gly Ser Val Gly Pro Cys Gly Arg Ile Leu
            100                 105                 110

Val Arg Gly Glu Pro Gly Trp Glu Ile Val Pro Glu Val Ala Pro Arg
        115                 120                 125

Glu Gly Glu Pro Ile Ile Asp Lys Pro Gly Lys Gly Ala Phe Tyr Ala
    130                 135                 140

Thr Asp Leu Asp Leu Leu Leu Arg Thr Arg Gly Ile Thr His Leu Ile
145                 150                 155                 160

Leu Thr Gly Ile Thr Thr Asp Val Cys Val His Thr Thr Met Arg Glu
                165                 170                 175

Ala Asn Asp Arg Gly Tyr Glu Cys Leu Ile Leu Ser Asp Cys Thr Gly
            180                 185                 190

Ala Thr Asp Arg Lys His His Glu Ala Ala Leu Ser Met Val Thr Met
        195                 200                 205

Gln Gly Gly Val Phe Gly Ala Thr Ala His Ser Asp Asp Leu Leu Ala
    210                 215                 220

Ala Leu Gly Thr Thr Val Pro Ala Ala Ala Gly Pro Arg Ala Arg Thr
225                 230                 235                 240

Glu


<210> SEQ ID NO 41
<211> LENGTH: 233
<212> TYPE: PRT
<213> ORGANISM: Rhizobium leguminosarum

<400> SEQUENCE: 41

Met Asp Ala Met Val Glu Thr Asn Arg His Phe Ile Asp Ala Asp Pro
1               5                   10                  15

Tyr Pro Trp Pro Tyr Asn Gly Ala Leu Arg Pro Asp Asn Thr Ala Leu
            20                  25                  30

Ile Ile Ile Asp Met Gln Thr Asp Phe Cys Gly Lys Gly Gly Tyr Val
        35                  40                  45

Asp His Met Gly Tyr Asp Leu Ser Leu Val Gln Ala Pro Ile Glu Pro
    50                  55                  60

Ile Lys Arg Val Leu Ala Ala Met Arg Ala Lys Gly Tyr His Ile Ile
65                  70                  75                  80

His Thr Arg Glu Gly His Arg Pro Asp Leu Ala Asp Leu Pro Ala Asn
                85                  90                  95

Lys Arg Trp Arg Ser Gln Arg Ile Gly Ala Gly Ile Gly Asp Pro Gly
            100                 105                 110

Pro Cys Gly Arg Ile Leu Thr Arg Gly Glu Pro Gly Trp Asp Ile Ile
        115                 120                 125

Pro Glu Leu Tyr Pro Ile Glu Gly Glu Thr Ile Ile Asp Lys Pro Gly
    130                 135                 140

Lys Gly Ser Phe Cys Ala Thr Asp Leu Glu Leu Val Leu Asn Gln Lys
145                 150                 155                 160

Arg Ile Glu Asn Ile Ile Leu Thr Gly Ile Thr Thr Asp Val Cys Val
                165                 170                 175

Ser Thr Thr Met Arg Glu Ala Asn Asp Arg Gly Tyr Glu Cys Leu Leu
            180                 185                 190

Leu Glu Asp Cys Cys Gly Ala Thr Asp Tyr Gly Asn His Leu Ala Ala
        195                 200                 205
```

```
Ile Lys Met Val Lys Met Gln Gly Gly Val Phe Gly Ser Val Ser Asn
    210                 215                 220

Ser Ala Ala Leu Val Glu Ala Leu Pro
225                 230


<210> SEQ ID NO 42
<211> LENGTH: 4268
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42

gtttgtggaa gcggtattcg caatttaatt aagtttaaac ggcgcgcctt tccataggct     60

ccgccccccct gacgagcatc acaaaaatcg acgctcaagt cagaggtggc gaaacccgac    120

aggactataa agataccagg cgtttccccc tggaagctcc ctcgtgcgct ctcctgttcc    180

gaccctgccg cttaccggat acctgtccgc ctttctccct tcgggaagcg tggcgctttc    240

tcatagctca cgctgtaggt atctcagttc ggtgtaggtc gttcgctcca agctgggctg    300

tgtgcacgaa ccccccgttc agcccgaccg ctgcgcctta tccggtaact atcgtcttga    360

gtccaacccg gtaagacacg acttatcgcc actggcagca gccactggta acaggattag    420

cagagcgagg tatgtaggcg gtgctacaga gttcttgaag tggtggccta actacggcta    480

cactagaaga acagtatttg gtatctgcgc tctgctgaag ccagttacct tcggaaaaag    540

agttggtagc tcttgatccg gcaaacaaac caccgctggt agcggtggtt tttttgtttg    600

caagcagcag attacgcgca gaaaaaaagg atctcaagaa gatcctttga tcttttctac    660

ggggtctgac gctcagtgga acgaaaactc acgttaaggg attttggtca tgagattatc    720

aaaaaggatc ttcacctaga tccttttaaa ttaaaaatga agttttaaat caatctaaag    780

tatatatgag taaacttggt ctgacagtta ccaatgctta atcagtgagg cacctatctc    840

agcgatctgt ctatttcgtt catccatagt tgcctgactc cccgtcgtgt agataactac    900

gatacgggag ggcttaccat ctggccccag tgctgcaatg ataccgcgag acccacgctc    960

accggctcca gatttatcag caataaacca gccagccgga agggccgagc gcagaagtgg   1020

tcctgcaact ttatccgcct ccatccagtc tattaattgt tgccgggaag ctagagtaag   1080

tagttcgcca gttaatagtt tgcgcaacgt tgttgccatt gctacaggca tcgtggtgtc   1140

acgctcgtcg tttggtatgg cttcattcag ctccggttcc caacgatcaa ggcgagttac   1200

atgatccccc atgttgtgca aaaaagcggt tagctccttc ggtcctccga tcgttgtcag   1260

aagtaagttg gccgcagtgt tatcactcat ggttatggca gcactgcata attctcttac   1320

tgtcatgcca tccgtaagat gcttttctgt gactggtgag tactcaacca agtcattctg   1380

agaatagtgt atgcggcgac cgagttgctc ttgcccggcg tcaatacggg ataataccgc   1440

gccacatagc agaactttaa aagtgctcat cattggaaaa cgttcttcgg ggcgaaaact   1500

ctcaaggatc ttaccgctgt tgagatccag ttcgatgtaa cccactcgtg cacccaactg   1560

atcttcagca tcttttactt tcaccagcgt ttctgggtga gcaaaaacag gaaggcaaaa   1620

tgccgcaaaa aagggaataa gggcgacacg gaaatgttga atactcatac tcttcctttt   1680

tcaatattat tgaagcattt atcagggtta ttgtctcatg agcggataca tatttgaatg   1740

tatttagaaa aataaacagc gatcgcgcgg ccgcgggtaa taactgatat aattaaattg   1800

aagctctaat ttgtgagttt agtatacatg catttactta taatacagtt ttttagtttt   1860
```

```
gctggccgca tcttctcaaa tatgcttccc agcctgcttt tctgtaacgt tcaccctcta   1920
ccttagcatc ccttcccttt gcaaatagtc ctcttccaac aataataatg tcagatcctg   1980
tagagaccac atcatccacg gttctatact gttgacccaa tgcgtctccc ttgtcatcta   2040
aacccacacc gggtgtcata atcaaccaat cgtaaccttc atctcttcca cccatgtctc   2100
tttgagcaat aaagccgata acaaaatctt tgtcgctctt cgcaatgtca acagtaccct   2160
tagtatattc tccagtagct agggagccct tgcatgacaa ttctgctaac atcaaaaggc   2220
ctctaggttc ctttgttact tcttccgccg cctgcttcaa accgctaaca atacctgggc   2280
ccaccacacc gtgtgcattc gtaatgtctg cccattctgc tattctgtat acacccgcag   2340
agtactgcaa tttgactgta ttaccaatgt cagcaaattt tctgtcttcg aagagtaaaa   2400
aattgtactt ggcggataat gcctttagcg gcttaactgt gccctccatg gaaaaatcag   2460
tcaagatatc cacatgtgtt tttagtaaac aaattttggg acctaatgct tcaactaact   2520
ccagtaattc cttggtggta cgaacatcca atgaagcaca caagtttgtt tgcttttcgt   2580
gcatgatatt aaatagcttg gcagcaacag gactaggatg agtagcagca cgttccttat   2640
atgtagcttt cgacatgatt tatcttcgtt tcctgcaggt tttgttctg tgcagttggg   2700
ttaagaatac tgggcaattt catgtttctt caacaccaca tatgcgtata tataccaatc   2760
taagtctgtg ctccttcctt cgttcttcct tctgctcgga gattaccgaa tcaaagctag   2820
cttatcgatg ataagctgtc aaagatgaga attaattcca cggactatag actatactag   2880
atactccgtc tactgtacga tacacttccg ctcaggtcct tgtcctttaa cgaggcctta   2940
ccactctttt gttactctat tgatccagct cagcaaaggc agtgtgatct aagattctat   3000
cttcgcgatg tagtaaaact agctagaccg agaaagagac tagaaatgca aaaggcactt   3060
ctacaatggc tgccatcatt attatccgat gtgacgctgc agcttctcaa tgatattcga   3120
atacgctttg aggagataca gcctaatatc cgacaaactg ttttacagat ttacgatcgt   3180
acttgttacc catcattgaa ttttgaacat ccgaacctgg gagttttccc tgaaacagat   3240
agtatatttg aacctgtata ataatatata gtctagcgct ttacggaaga caatgtatgt   3300
atttcggttc ctggagaaac tattgcatct attgcatagg taatcttgca cgtcgcatcc   3360
ccggttcatt ttctgcgttt ccatcttgca cttcaatagc atatctttgt taacgaagca   3420
tctgtgcttc attttgtaga acaaaaatgc aacgcgagag cgctaatttt tcaaacaaag   3480
aatctgagct gcatttttac agaacagaaa tgcaacgcga aagcgctatt ttaccaacga   3540
agaatctgtg cttcattttt gtaaaacaaa aatgcaacgc gacgagagcg ctaatttttc   3600
aaacaaagaa tctgagctgc atttttacag aacagaaatg caacgcgaga gcgctatttt   3660
accaacaaag aatctatact tctttttgt tctacaaaaa tgcatcccga gagcgctatt   3720
tttctaacaa agcatcttag attacttttt ttctcctttg tgcgctctat aatgcagtct   3780
cttgataact ttttgcactg taggtccgtt aaggttagaa gaaggctact ttggtgtcta   3840
ttttctcttc cataaaaaaa gcctgactcc acttcccgcg tttactgatt actagcgaag   3900
ctgcgggtgc attttttcaa gataaaggca tccccgatta tattctatac cgatgtggat   3960
tgcgcatact ttgtgaacag aaagtgatag cgttgatgat tcttcattgg tcagaaaatt   4020
atgaacggtt tcttctattt tgtctctata tactacgtat aggaaatgtt tacattttcg   4080
tattgttttc gattcactct atgaatagtt cttactacaa tttttttgtc taaagagtaa   4140
tactagagat aaacataaaa aatgtagagg tcgagtttag atgcaagttc aaggagcgaa   4200
aggtggatgg gtaggttata tagggatata gcacagagat atatagcaaa gagatacttt   4260
```

```
tgagcaat                                                          4268

<210> SEQ ID NO 43
<211> LENGTH: 4399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43

gtttgtggaa gcggtattcg caatttaatt aaagctggtg acaattaatc atcggctcgt     60

ataatgtgtg gaattgaatc gatataagga ggttaatcat gtttaaaccc tcaaaatata    120

ttttccctct atcttctcgt tgcgcttaat ttgactaatt ctcattagcg aggcgcgcct    180

ttccataggc tccgcccccc tgacgagcat cacaaaaatc gacgctcaag tcagaggtgg    240

cgaaacccga caggactata aagataccag gcgtttcccc ctggaagctc cctcgtgcgc    300

tctcctgttc cgaccctgcc gcttaccgga tacctgtccg cctttctccc ttcgggaagc    360

gtggcgcttt ctcatagctc acgctgtagg tatctcagtt cggtgtaggt cgttcgctcc    420

aagctgggct gtgtgcacga accccccgtt cagcccgacc gctgcgcctt atccggtaac    480

tatcgtcttg agtccaaccc ggtaagacac gacttatcgc cactggcagc agccactggt    540

aacaggatta gcagagcgag gtatgtaggc ggtgctacag agttcttgaa gtggtggcct    600

aactacggct acactagaag aacagtattt ggtatctgcg ctctgctgaa gccagttacc    660

ttcggaaaaa gagttggtag ctcttgatcc ggcaaacaaa ccaccgctgg tagcggtggt    720

tttttgtttt gcaagcagca gattacgcgc agaaaaaaag gatctcaaga agatcctttg    780

atcttttcta cggggtctga cgctcagtgg aacgaaaact cacgttaagg gattttggtc    840

atgagattat caaaaaggat cttcacctag atccttttaa attaaaaatg aagttttaaa    900

tcaatctaaa gtatatatga gtaaacttgg tctgacagtt accaatgctt aatcagtgag    960

gcacctatct cagcgatctg tctatttcgt tcatccatag ttgcctgact ccccgtcgtg   1020

tagataacta cgatacggga gggcttacca tctggcccca gtgctgcaat gataccgcga   1080

gacccacgct caccggctcc agatttatca gcaataaacc agccagccgg aagggccgag   1140

cgcagaagtg gtcctgcaac tttatccgcc tccatccagt ctattaattg ttgccgggaa   1200

gctagagtaa gtagttcgcc agttaatagt ttgcgcaacg ttgttgccat tgctacaggc   1260

atcgtggtgt cacgctcgtc gtttggtatg gcttcattca gctccggttc ccaacgatca   1320

aggcgagtta catgatcccc catgttgtgc aaaaaagcgg ttagctcctt cggtcctccg   1380

atcgttgtca gaagtaagtt ggccgcagtg ttatcactca tggttatggc agcactgcat   1440

aattctctta ctgtcatgcc atccgtaaga tgcttttctg tgactggtga gtactcaacc   1500

aagtcattct gagaatagtg tatgcggcga ccgagttgct cttgcccggc gtcaatacgg   1560

gataataccg cgccacatag cagaacttta aaagtgctca tcattggaaa acgttcttcg   1620

gggcgaaaac tctcaaggat cttaccgctg ttgagatcca gttcgatgta acccactcgt   1680

gcacccaact gatcttcagc atcttttact ttcaccagcg tttctgggtg agcaaaaaca   1740

ggaaggcaaa atgccgcaaa aaagggaata agggcgacac ggaaatgttg aatactcata   1800

ctcttccttt ttcaatatta ttgaagcatt tatcagggtt attgtctcat gagcggatac   1860

atatttgaat gtatttagaa aaataaacag cgatcgcgcg gccgcgggta ataactgata   1920

taattaaatt gaagctctaa tttgtgagtt tagtatacat gcatttactt ataatacagt   1980
```

```
tttttagttt tgctggccgc atcttctcaa atatgcttcc cagcctgctt ttctgtaacg   2040
ttcaccctct accttagcat cccttccctt tgcaaatagt cctcttccaa caataataat   2100
gtcagatcct gtagagacca catcatccac ggttctatac tgttgaccca atgcgtctcc   2160
cttgtcatct aaacccacac cgggtgtcat aatcaaccaa tcgtaacctt catctcttcc   2220
acccatgtct ctttgagcaa taaagccgat aacaaaatct ttgtcgctct tcgcaatgtc   2280
aacagtaccc ttagtatatt ctccagtagc tagggagccc ttgcatgaca attctgctaa   2340
catcaaaagg cctctaggtt cctttgttac ttcttccgcc gcctgcttca aaccgctaac   2400
aatacctggg cccaccacac cgtgtgcatt cgtaatgtct gcccattctg ctattctgta   2460
tacacccgca gagtactgca atttgactgt attaccaatg tcagcaaatt ttctgtcttc   2520
gaagagtaaa aaattgtact tggcggataa tgcctttagc ggcttaactg tgccctccat   2580
ggaaaaatca gtcaagatat ccacatgtgt ttttagtaaa caaattttgg gacctaatgc   2640
ttcaactaac tccagtaatt ccttggtggt acgaacatcc aatgaagcac acaagtttgt   2700
ttgcttttcg tgcatgatat taaatagctt ggcagcaaca ggactaggat gagtagcagc   2760
acgttcctta tatgtagctt tcgacatgat ttatcttcgt ttcctgcagg tttttgttct   2820
gtgcagttgg gttaagaata ctgggcaatt tcatgtttct tcaacaccac atatgcgtat   2880
atataccaat ctaagtctgt gctccttcct tcgttcttcc ttctgctcgg agattaccga   2940
atcaaagcta gcttatcgat gataagctgt caaagatgag aattaattcc acggactata   3000
gactatacta gatactccgt ctactgtacg atacacttcc gctcaggtcc ttgtccttta   3060
acgaggcctt accactcttt tgttactcta ttgatccagc tcagcaaagg cagtgtgatc   3120
taagattcta tcttcgcgat gtagtaaaac tagctagacc gagaaagaga ctagaaatgc   3180
aaaaggcact tctacaatgg ctgccatcat tattatccga tgtgacgctg cagcttctca   3240
atgatattcg aatacgcttt gaggagatac agcctaatat ccgacaaact gttttacaga   3300
tttacgatcg tacttgttac ccatcattga attttgaaca tccgaacctg ggagttttcc   3360
ctgaaacaga tagtatattt gaacctgtat aataatatat agtctagcgc tttacggaag   3420
acaatgtatg tatttcggtt cctggagaaa ctattgcatc tattgcatag gtaatcttgc   3480
acgtcgcatc cccggttcat ttctgcgttt ccatcttgc acttcaatag catatctttg   3540
ttaacgaagc atctgtgctt cattttgtag aacaaaaatg caacgcgaga gcgctaattt   3600
ttcaaacaaa gaatctgagc tgcattttta cagaacagaa atgcaacgcg aaagcgctat   3660
tttaccaacg aagaatctgt gcttcatttt tgtaaaacaa aaatgcaacg cgacgagagc   3720
gctaattttt caaacaaaga atctgagctg catttttaca gaacagaaat gcaacgcgag   3780
agcgctattt taccaacaaa gaatctatac ttcttttttg ttctacaaaa atgcatcccg   3840
agagcgctat ttttctaaca aagcatctta gattactttt tttctccttt gtgcgctcta   3900
taatgcagtc tcttgataac tttttgcact gtaggtccgt taaggttaga agaaggctac   3960
tttggtgtct attttctctt ccataaaaaa agcctgactc cacttcccgc gtttactgat   4020
tactagcgaa gctgcgggtg catttttttca agataaaggc atccccgatt atattctata   4080
ccgatgtgga ttgcgcatac tttgtgaaca gaaagtgata gcgttgatga ttcttcattg   4140
gtcagaaaat tatgaacggt ttcttctatt ttgtctctat atactacgta taggaaatgt   4200
ttacattttc gtattgtttt cgattcactc tatgaatagt tcttactaca attttttttgt   4260
ctaaagagta atactagaga taaacataaa aaatgtagag gtcgagttta gatgcaagtt   4320
```

```
caaggagcga aaggtggatg ggtaggttat atagggatat agcacagaga tatatagcaa   4380

agagatactt ttgagcaat                                                4399


<210> SEQ ID NO 44
<211> LENGTH: 8762
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44

gtttgtggaa gcggtattcg caatcattta gtcgtgcaat gtatgacttt aagatttgtg     60

agcaggaaga aaagggagaa tcttctaacg ataaaccctt gaaaaactgg gtagactacg    120

ctatgttgag ttgctacgca ggctgcacaa ttacacgaga atgctcccgc ctaggattta    180

aggctaaggg acgtgcaatg cagacgacag atctaaatga ccgtgtcggt gaagtgttcg    240

ccaaactttt cggttaacac atgcagtgat gcacgcgcga tggtgctaag ttacatatat    300

atatatatat atatatatat atatatatag ccatagtgat gtctaagtaa cctttatggt    360

atatttctta atgtggaaag atactagcgc gcgcacccac acacaagctt cgtctttttct    420

tgaagaaaag aggaagctcg ctaaatggga ttccactttc cgttccctgc cagctgatgg    480

aaaaaggtta gtggaacgat gaagaataaa aagagagatc cactgaggtg aaatttcagc    540

tgacagcgag tttcatgatc gtgatgaaca atggtaacga gttgtggctg ttgccaggga    600

gggtggttct caacttttaa tgtatggcca aatcgctact tgggtttgtt atataacaaa    660

gaagaaataa tgaactgatt ctcttcctcc ttcttgtcct ttcttaattc tgttgtaatt    720

accttccttt gtaatttttt ttgtaattat tcttcttaat aatccaaaca aacacacata    780

ttacaataat gaagaagccc gagctgaccg ctacctctgt tgagaagttc ctgattgaga    840

agtttgattc cgtttccgac ctgatgcagc tgtccgaggg cgaggagtct cgagccttct    900

cctttgacgt gggcggacga ggttacgttc tgcgagtgaa ctcgtgtgcc gacggcttct    960

acaaggatcg atacgtctac cgacactttg cttctgccgc tctgcccatc cctgaggttc   1020

tcgacattgg cgagttctct gagtccctca cctactgcat ctctcgacga gctcagggag   1080

tcaccctgca ggacctccct gagactgagc tgcctgctgt cctccagcct gttgctgagg   1140

ccatggacgc tatcgctgct gctgatctgt cccagacctc gggtttcggc ccctttggac   1200

ctcagggaat tggacagtac accacttggc gagacttcat ctgtgctatt gccgatcctc   1260

acgtctacca ttggcagacc gttatggacg atactgtgtc ggcttctgtc gctcaggctc   1320

tggacgagct gatgctctgg gccgaggatt gccccgaggt tcgacacctg gtgcatgctg   1380

acttcggttc caacaacgtt ctcaccgaca acggccgaat cactgccgtg attgactggt   1440

ccgaggctat gtttggcgac tcgcagtacg aggtggccaa catcttcttt tggcgaccct   1500

ggctggcttg tatggagcag cagacccgat acttcgagcg acgacatcct gagctcgctg   1560

gatcccctcg actgcgagct tacatgctcc gaattggtct ggaccagctc taccagtcgc   1620

tggtggatgg caactttgac gatgctgcct gggctcaggg acgatgtgac gccatcgtgc   1680

gatctggcgc tggaaccgtc ggacgaactc agattgcccg acgatccgct gctgtctgga   1740

ccgacggatg cgtggaggtc ctggctgatt cgggtaaccg acgaccctct actcgacctc   1800

gagctaagga gtaataaacg gcgcgccgtc tgaagaatga atgatttgat gatttctttt   1860

tccctccatt tttcttactg aatatatcaa tgatatagac ttgtatagtt tattatttca   1920
```

-continued

```
aattaagtag ctatatatag tcaagataac gtttgtttga cacgattaca ttattcgtcg   1980
acatcttttt tcagcctgtc gtggtagcaa tttgaggagt attattaatt gaataggttc   2040
attttgcgct cgcataaaca gttttcgtca gggacagtat gttggaatga gtggtaatta   2100
atggtgacat gacatgttat agcaataacc ttgatgttta catcgtagtt taatgtacac   2160
cccgcgaatt cgttcaagta ggagtgcacc aattgcaaag ggaaaagctg aatgggcagt   2220
tcgaatagta ctttttccat aggctccgcc cccctgacga gcatcacaaa aatcgacgct   2280
caagtcagag gtggcgaaac ccgacaggac tataaagata ccaggcgttt ccccctggaa   2340
gctccctcgt gcgctctcct gttccgaccc tgccgcttac cggatacctg tccgcctttc   2400
tcccttcggg aagcgtggcg ctttctcata gctcacgctg taggtatctc agttcggtgt   2460
aggtcgttcg ctccaagctg ggctgtgtgc acgaaccccc cgttcagccc gaccgctgcg   2520
ccttatccgg taactatcgt cttgagtcca acccggtaag acacgactta tcgccactgg   2580
cagcagccac tggtaacagg attagcagag cgaggtatgt aggcggtgct acagagttct   2640
tgaagtggtg gcctaactac ggctacacta gaagaacagt atttggtatc tgcgctctgc   2700
tgaagccagt taccttcgga aaaagagttg gtagctcttg atccggcaaa caaaccaccg   2760
ctggtagcgg tggttttttt gtttgcaagc agcagattac gcgcagaaaa aaaggatctc   2820
aagaagatcc tttgatcttt tctacggggt ctgacgctca gtggaacgaa aactcacgtt   2880
aagggatttt ggtcatgaga ttatcaaaaa ggatcttcac ctagatcctt ttaaattaaa   2940
aatgaagttt taaatcaatc taaagtatat atgagtaaac ttggtctgac agttaccaat   3000
gcttaatcag tgaggcacct atctcagcga tctgtctatt tcgttcatcc atagttgcct   3060
gactccccgt cgtgtagata actacgatac gggagggctt accatctggc cccagtgctg   3120
caatgatacc gcgagaccca cgctcaccgg ctccagattt atcagcaata aaccagccag   3180
ccggaagggc cgagcgcaga agtggtcctg caactttatc cgcctccatc cagtctatta   3240
attgttgccg ggaagctaga gtaagtagtt cgccagttaa tagtttgcgc aacgttgttg   3300
ccattgctac aggcatcgtg gtgtcacgct cgtcgtttgg tatggcttca ttcagctccg   3360
gttcccaacg atcaaggcga gttacatgat cccccatgtt gtgcaaaaaa gcggttagct   3420
ccttcggtcc tccgatcgtt gtcagaagta agttggccgc agtgttatca ctcatggtta   3480
tggcagcact gcataattct cttactgtca tgccatccgt aagatgcttt tctgtgactg   3540
gtgagtactc aaccaagtca ttctgagaat agtgtatgcg gcgaccgagt tgctcttgcc   3600
cggcgtcaat acgggataat accgcgccac atagcagaac tttaaaagtg ctcatcattg   3660
gaaaacgttc ttcggggcga aaactctcaa ggatcttacc gctgttgaga tccagttcga   3720
tgtaacccac tcgtgcaccc aactgatctt cagcatcttt tactttcacc agcgtttctg   3780
ggtgagcaaa aacaggaagg caaaatgccg caaaaaaggg aataagggcg acacggaaat   3840
gttgaatact catactcttc ctttttcaat attattgaag catttatcag ggttattgtc   3900
tcatgagcgg atacatattt gaatgtattt agaaaaataa acagcgatcg cagctagctc   3960
gtcgtgttca ggaactgttc gatggttcgg agagagtcgc cgcccagaac atacgcgcac   4020
cgatgtcagc agacagcctt attacaagta tattcaagca agtatatccg tagggtgcgg   4080
gtgatttgga tctaaggttc gtactcaaca ctcacgagca gcttgcctat gttacatcct   4140
tttatcagac ataacataat tggagtttac ttacacacgg ggtgtacctg tatgagcacc   4200
acctacaatt gtagcactgg tacttgtaca aagaatttat tcgtacgaat cacagggacg   4260
gccgccctca ccgaaccagc gaatacctca gcggtcccct gcagtgactc aacaaagcga   4320
```

```
tatgaacatc ttgcgatggt atcctgctga tagtttttac tgtacaaaca cctgtgtagc   4380
tccttctagc atttttaagt tattcacacc tcaaggggag ggataaatta aataaattcc   4440
aaaagcgaag atcgagaaac taaattaaaa ttccaaaaac gaagttggaa cacaaccccc   4500
cgaaaaaaaa caacaaacaa aaaacccaac aaaataaaca aaaacaaaat aaatatataa   4560
ctaccagtat ctgactaaaa gttcaaatac tcgtacttac aacaaataga aatgagccgg   4620
ccaaaattct gcagaaaaaa atttcaaaca agtactggta taattaaatt aaaaaacaca   4680
tcaaagtatc ataacgttag ttattttatt ttatttaata aaagaaaaca acaagatggg   4740
ctcaaaactt tcaacttata cgatacatac caaataacaa tttagtattt atctaagtgc   4800
ttttcgtaga taatggaata caaatggata tccagagtat acacatggat agtatacact   4860
gacacgacaa ttctgtatct ctttatgtta actactgtga ggcattaaat agagcttgat   4920
atataaaatg ttacatttca cagtctgaac ttttgcagat tacctaattt ggtaagatat   4980
taattatgaa ctgaaagttg atggcggccg catagcttca aaatgtttct actccttttt   5040
tactcttcca gattttctcg gactccgcgc atcgccgtac cacttcaaaa cacccaagca   5100
cagcatacta aatttcccct ctttcttcct ctagggtgtc gttaattacc cgtactaaag   5160
gtttggaaaa gaaaaaagag accgcctcgt ttctttttct tcgtcgaaaa aggcaataaa   5220
aatttttatc acgtttcttt ttcttgaaaa tttttttttt tgattttttt ctctttcgat   5280
gacctcccat tgatatttaa gttaataaac ggtcttcaat ttctcaagtt tcagtttcat   5340
ttttcttgtt ctattacaac tttttttact tcttgctcat tagaaagaaa gcatagcaat   5400
ctaatctaag ttttaattac aaaatgacca ctctggatga caccgcttac cgataccgaa   5460
cttccgttcc tggcgatgcc gaggctattg aggctctgga tggatctttc accactgaca   5520
ccgttttccg agtgaccgct actggcgacg gcttcaccct gcgagaggtg cctgtcgacc   5580
ctcctctcac caaggttttc cctgacgatg agtcggacga tgagtctgac gctggagagg   5640
acggcgaccc tgactctcga actttcgtgg cttacggcga cgatggagac ctggccggct   5700
ttgtggtcgt ttcttactcc ggatggaacc gacgactgac cgtggaggac atcgaggtcg   5760
ctcctgagca ccgaggtcat ggtgtcggac gagctctgat gggtctcgct actgagttcg   5820
ctcgagagcg aggtgctggc cacctgtggc tcgaggtcac caacgttaac gcccctgcta   5880
ttcatgccta ccgacgaatg ggttttaccc tgtgtggcct cgatactgcc ctgtacgacg   5940
gaaccgcttc cgatggagag caggccctct acatgtcgat gccctgccct taaacaggcc   6000
ccttttcctt tgtcgatatc atgtaattag ttatgtcacg cttacattca cgccctcctc   6060
ccacatccgc tctaaccgaa aaggaaggag ttagacaacc tgaagtctag gtccctattt   6120
attttttta atagttatgt tagtattaag aacgttattt atatttcaaa tttttctttt   6180
ttttctgtac aaacgcgtgt acgcatgtaa cattatactg aaaaccttgc ttgagaaggt   6240
tttgggacgc tcgaaggctt taatttgcgg gtaataactg atataattaa attgaagctc   6300
taatttgtga gtttagtata catgcattta cttataatac agttttttag ttttgctggc   6360
cgcatcttct caaatatgct tcccagcctg cttttctgta acgttcaccc tctaccttag   6420
catcccttcc ctttgcaaat agtcctcttc caacaataat aatgtcagat cctgtagaga   6480
ccacatcatc cacggttcta tactgttgac ccaatgcgtc tcccttgtca tctaaaccca   6540
caccgggtgt cataatcaac caatcgtaac cttcatctct tccacccatg tctctttgag   6600
caataaagcc gataacaaaa tctttgtcgc tcttcgcaat gtcaacagta cccttagtat   6660
```

-continued

```
attctccagt agctagggag cccttgcatg acaattctgc taacatcaaa aggcctctag   6720
gttcctttgt tacttcttcc gccgcctgct tcaaaccgct aacaatacct gggcccacca   6780
caccgtgtgc attcgtaatg tctgcccatt ctgctattct gtatacaccc gcagagtact   6840
gcaatttgac tgtattacca atgtcagcaa attttctgtc ttcgaagagt aaaaaattgt   6900
acttggcgga taatgccttt agcggcttaa ctgtgccctc catggaaaaa tcagtcaaga   6960
tatccacatg tgtttttagt aaacaaattt tgggacctaa tgcttcaact aactccagta   7020
attccttggt ggtacgaaca tccaatgaag cacacaagtt tgtttgcttt tcgtgcatga   7080
tattaaatag cttggcagca acaggactag gatgagtagc agcacgttcc ttatatgtag   7140
ctttcgacat gatttatctt cgtttcctgc aggtttttgt tctgtgcagt tgggttaaga   7200
atactgggca atttcatgtt tcttcaacac cacatatgcg tatatatacc aatctaagtc   7260
tgtgctcctt ccttcgttct tccttctgct cggagattac cgaatcaaag ctagcttatc   7320
gatgataagc tgtcaaagat gagaattaat tccacggact atagactata ctagatactc   7380
cgtctactgt acgatacact tccgctcagg tccttgtcct ttaacgaggc cttaccactc   7440
ttttgttact ctattgatcc agctcagcaa aggcagtgtg atctaagatt ctatcttcgc   7500
gatgtagtaa aactagctag accgagaaag agactagaaa tgcaaaaggc acttctacaa   7560
tggctgccat cattattatc cgatgtgacg ctgcagcttc tcaatgatat tcgaatacgc   7620
tttgaggaga tacagcctaa tatccgacaa actgttttac agatttacga tcgtacttgt   7680
tacccatcat tgaattttga acatccgaac ctgggagttt tccctgaaac agatagtata   7740
tttgaacctg tataataata tatagtctag cgctttacgg aagacaatgt atgtatttcg   7800
gttcctggag aaactattgc atctattgca taggtaatct tgcacgtcgc atccccggtt   7860
cattttctgc gtttccatct tgcacttcaa tagcatatct ttgttaacga agcatctgtg   7920
cttcattttg tagaacaaaa atgcaacgcg agagcgctaa tttttcaaac aaagaatctg   7980
agctgcattt ttacagaaca gaaatgcaac gcgaaagcgc tattttacca acgaagaatc   8040
tgtgcttcat ttttgtaaaa caaaaatgca acgcgacgag agcgctaatt tttcaaacaa   8100
agaatctgag ctgcattttt acagaacaga aatgcaacgc gagagcgcta ttttaccaac   8160
aaagaatcta tacttctttt ttgttctaca aaaatgcatc ccgagagcgc tatttttcta   8220
acaaagcatc ttagattact ttttttctcc tttgtgcgct ctataatgca gtctcttgat   8280
aactttttgc actgtaggtc cgttaaggtt agaagaaggc tactttggtg tctattttct   8340
cttccataaa aaaagcctga ctccacttcc cgcgtttact gattactagc gaagctgcgg   8400
gtgcattttt tcaagataaa ggcatccccg attatattct ataccgatgt ggattgcgca   8460
tactttgtga acagaaagtg atagcgttga tgattcttca ttggtcagaa aattatgaac   8520
ggtttcttct attttgtctc tatatactac gtataggaaa tgtttacatt ttcgtattgt   8580
tttcgattca ctctatgaat agttcttact acaatttttt tgtctaaaga gtaatactag   8640
agataaacat aaaaaatgta gaggtcgagt ttagatgcaa gttcaaggag cgaaaggtgg   8700
atgggtaggt tatataggga tatagcacag agatatatag caaagagata cttttgagca   8760
at                                                                  8762
```

<210> SEQ ID NO 45
<211> LENGTH: 5824
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 45

```
gtttgtggaa gcggtattcg caatttaatt aaagctggtg acaattaatc atcggctcgt     60
ataatgtgtg gaattgaatc gatataagga ggttaatcat atgcaaacgc tcagcatcca    120
gcacggtacc ctcgtcacga tggatcagta ccgcagagtc cttggggata gctgggttca    180
cgtgcaggat ggacggatcg tcgcgctcgg agtgcacgcc gagtcggtgc ctccgccagc    240
ggatcgggtg atcgatgcac gcggcaaggt cgtgttaccc ggtttcatca atgcccacac    300
ccatgtgaac cagatcctcc tgcgcggagg gccctcgcac gggcgtcaac tctatgactg    360
gctgttcaac gttttgtatc cgggacaaaa ggcgatgaga ccggaggacg tagcggtggc    420
ggtgaggttg tattgtgcgg aagctgtgcg cagcgggatt acgacgatca acgacaacgc    480
cgattcggcc atctacccag gcaacatcga ggccgcgatg gcggtctatg gtgaggtggg    540
tgtgagggtc gtctacgccc gcatgttctt tgatcggatg gacgggcgca ttcaagggta    600
tgtggacgcc ttgaaggctc gctctcccca agtcgaactg tgctcgatca tggaggaaac    660
ggctgtggcc aaagatcgga tcacagccct gtcagatcag tatcatggca cggcaggagg    720
tcgtatatca gtttggcccg ctcctgccat taccccggcg gtgacagttg aaggaatgcg    780
atgggcacaa gccttcgccc gtgatcgggc ggtaatgtgg acgcttcaca tggcggagag    840
cgatcatgat gagcggcttc attggatgag tcccgccgag tacatggagt gttacggact    900
cttggatgag cgtctgcagg tcgcgcattg cgtgtacttt gaccggaagg atgttcggct    960
gctgcaccgc cacaatgtga aggtcgcgtc gcaggttgtg agcaatgcct acctcggctc   1020
aggggtggcc cccgtgccag agatggtgga gcgcggcatg gccgtgggca ttggaacaga   1080
tgacgggaat tgtaatgact ccgtaaacat gatcggagac atgaagttta tggcccatat   1140
tcaccgcgcg gtgcatcggg atgcggacgt gctgacccca gagaagattc ttgaaatggc   1200
gacgatcgat ggggcgcgtt cgttgggaat ggaccacgag attggttcca tcgaaaccgg   1260
caagcgcgcg gaccttatcc tgcttgacct gcgtcaccct cagacgactc ctcaccatca   1320
tttggcggcc acgatcgtgt ttcaggctta cggcaatgag gtggacactg tcctgattga   1380
cggaaacgtt gtgatggaga accgccgctt gagctttctt ccccctgaac gtgagttggc   1440
gttccttgag gaagcgcaga gccgcgccac agctattttg cagcgggcga acatggtggc   1500
taacccagct tggcgcagcc tctaggttta aaccctcaaa atatattttc cctctatctt   1560
ctcgttgcgc ttaatttgac taattctcat tagcgaggcg cgcctttcca taggctccgc   1620
ccccctgacg agcatcacaa aaatcgacgc tcaagtcaga ggtggcgaaa cccgacagga   1680
ctataaagat accaggcgtt tccccctgga agctccctcg tgcgctctcc tgttccgacc   1740
ctgccgctta ccggatacct gtccgccttt ctcccttcgg gaagcgtggc gctttctcat   1800
agctcacgct gtaggtatct cagttcggtg taggtcgttc gctccaagct gggctgtgtg   1860
cacgaacccc ccgttcagcc cgaccgctgc gccttatccg gtaactatcg tcttgagtcc   1920
aacccggtaa gacacgactt atcgccactg gcagcagcca ctggtaacag gattagcaga   1980
gcgaggtatg taggcggtgc tacagagttc ttgaagtggt ggcctaacta cggctacact   2040
agaagaacag tatttggtat ctgcgctctg ctgaagccag ttaccttcgg aaaaagagtt   2100
ggtagctctt gatccggcaa acaaaccacc gctggtagcg gtggtttttt tgtttgcaag   2160
cagcagatta cgcgcagaaa aaaaggatct caagaagatc ctttgatctt ttctacgggg   2220
tctgacgctc agtggaacga aaactcacgt taagggattt tggtcatgag attatcaaaa   2280
```

```
aggatcttca cctagatcct tttaaattaa aaatgaagtt ttaaatcaat ctaaagtata   2340
tatgagtaaa cttggtctga cagttaccaa tgcttaatca gtgaggcacc tatctcagcg   2400
atctgtctat ttcgttcatc catagttgcc tgactccccg tcgtgtagat aactacgata   2460
cgggagggct taccatctgg ccccagtgct gcaatgatac cgcgagaccc acgctcaccg   2520
gctccagatt tatcagcaat aaaccagcca gccggaaggg ccgagcgcag aagtggtcct   2580
gcaactttat ccgcctccat ccagtctatt aattgttgcc gggaagctag agtaagtagt   2640
tcgccagtta atagtttgcg caacgttgtt gccattgcta caggcatcgt ggtgtcacgc   2700
tcgtcgtttg gtatggcttc attcagctcc ggttcccaac gatcaaggcg agttacatga   2760
tcccccatgt tgtgcaaaaa agcggttagc tccttcggtc ctccgatcgt tgtcagaagt   2820
aagttggccg cagtgttatc actcatggtt atggcagcac tgcataattc tcttactgtc   2880
atgccatccg taagatgctt ttctgtgact ggtgagtact caaccaagtc attctgagaa   2940
tagtgtatgc ggcgaccgag ttgctcttgc ccggcgtcaa tacgggataa taccgcgcca   3000
catagcagaa ctttaaaagt gctcatcatt ggaaaacgtt cttcggggcg aaaactctca   3060
aggatcttac cgctgttgag atccagttcg atgtaaccca ctcgtgcacc caactgatct   3120
tcagcatctt ttactttcac cagcgtttct gggtgagcaa aaacaggaag gcaaaatgcc   3180
gcaaaaaagg gaataagggc gacacggaaa tgttgaatac tcatactctt cctttttcaa   3240
tattattgaa gcatttatca gggttattgt ctcatgagcg gatacatatt tgaatgtatt   3300
tagaaaaata aacagcgatc gcgcggccgc gggtaataac tgatataatt aaattgaagc   3360
tctaatttgt gagtttagta tacatgcatt tacttataat acagtttttt agttttgctg   3420
gccgcatctt ctcaaatatg cttcccagcc tgcttttctg taacgttcac cctctacctt   3480
agcatccctt ccctttgcaa atagtcctct tccaacaata ataatgtcag atcctgtaga   3540
gaccacatca tccacggttc tatactgttg acccaatgcg tctcccttgt catctaaacc   3600
cacaccgggt gtcataatca accaatcgta accttcatct cttccaccca tgtctctttg   3660
agcaataaag ccgataacaa aatctttgtc gctcttcgca atgtcaacag taccettagt   3720
atattctcca gtagctaggg agcccttgca tgacaattct gctaacatca aaaggcctct   3780
aggttccttt gttacttctt ccgccgcctg cttcaaaccg ctaacaatac ctgggcccac   3840
cacaccgtgt gcattcgtaa tgtctgccca ttctgctatt ctgtatacac ccgcagagta   3900
ctgcaatttg actgtattac caatgtcagc aaattttctg tcttcgaaga gtaaaaaatt   3960
gtacttggcg gataatgcct ttagcggctt aactgtgccc tccatggaaa aatcagtcaa   4020
gatatccaca tgtgttttta gtaaacaaat tttgggacct aatgcttcaa ctaactccag   4080
taattccttg gtggtacgaa catccaatga agcacacaag tttgtttgct tttcgtgcat   4140
gatattaaat agcttggcag caacaggact aggatgagta gcagcacgtt ccttatatgt   4200
agctttcgac atgatttatc ttcgtttcct gcaggttttt gttctgtgca gttgggttaa   4260
gaatactggg caatttcatg tttcttcaac accacatatg cgtatatata ccaatctaag   4320
tctgtgctcc ttccttcgtt cttccttctg ctcggagatt accgaatcaa agctagctta   4380
tcgatgataa gctgtcaaag atgagaatta attccacgga ctatagacta tactagatac   4440
tccgtctact gtacgataca cttccgctca ggtccttgtc ctttaacgag gccttaccac   4500
tcttttgtta ctctattgat ccagctcagc aaaggcagtg tgatctaaga ttctatcttc   4560
gcgatgtagt aaaactagct agaccgagaa agagactaga aatgcaaaag gcacttctac   4620
```

```
aatggctgcc atcattatta tccgatgtga cgctgcagct tctcaatgat attcgaatac   4680

gctttgagga gatacagcct aatatccgac aaactgtttt acagatttac gatcgtactt   4740

gttacccatc attgaatttt gaacatccga acctgggagt tttccctgaa acagatagta   4800

tatttgaacc tgtataataa tatatagtct agcgctttac ggaagacaat gtatgtattt   4860

cggttcctgg agaaactatt gcatctattg cataggtaat cttgcacgtc gcatccccgg   4920

ttcattttct gcgtttccat cttgcacttc aatagcatat ctttgttaac gaagcatctg   4980

tgcttcattt tgtagaacaa aaatgcaacg cgagagcgct aatttttcaa acaaagaatc   5040

tgagctgcat ttttacagaa cagaaatgca acgcgaaagc gctattttac caacgaagaa   5100

tctgtgcttc atttttgtaa aacaaaaatg caacgcgacg agagcgctaa tttttcaaac   5160

aaagaatctg agctgcattt ttacagaaca gaaatgcaac gcgagagcgc tattttacca   5220

acaaagaatc tatacttctt ttttgttcta caaaaatgca tcccgagagc gctatttttc   5280

taacaaagca tcttagatta cttttttttct cctttgtgcg ctctataatg cagtctcttg   5340

ataacttttt gcactgtagg tccgttaagg ttagaagaag gctactttgg tgtctatttt   5400

ctcttccata aaaaaagcct gactccactt cccgcgttta ctgattacta gcgaagctgc   5460

gggtgcattt tttcaagata aaggcatccc cgattatatt ctataccgat gtggattgcg   5520

catactttgt gaacagaaag tgatagcgtt gatgattctt cattggtcag aaaattatga   5580

acggtttctt ctattttgtc tctatatact acgtatagga aatgtttaca ttttcgtatt   5640

gttttcgatt cactctatga atagttctta ctacaatttt tttgtctaaa gagtaatact   5700

agagataaac ataaaaaatg tagaggtcga gtttagatgc aagttcaagg agcgaaaggt   5760

ggatgggtag gttatatagg gatatagcac agagatatat agcaaagaga tacttttgag   5820

caat                                                                5824
```

<210> SEQ ID NO 46
<211> LENGTH: 8336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 46

```
gtttgtggaa gcggtattcg caatttaatt aaagctggtg acaattaatc atcggctcgt     60

ataatgtgtg gaattgaatc gatataagga ggttaatcat atgactagaa tcgctatcac    120

aggtggtaga gttttgacta tggacccaga aagaagagta ttagaaccag gtacagttgt    180

tgttgaagat caattcattg cacaagtcgg ttcaccagat gacgtagaca tcagaggtgc    240

tgaaattata gatgccactg gtatggctgt attaccaggt ttcgttaata cacataccca    300

cgttcctcaa attttgttaa gaggtggtgc ttcacatgat agaaatttgt tggaatggtt    360

gcacaacgtc ttatatccag gtttggctgc atacactgat gacgatatca gagttggtac    420

attgttatat tgtgctgaag cattgagatc cggtattact acagttgtcg acaatgaaga    480

tgttagacct aacgattttg ccagagctgg tgccgctggt attggtgcat tcactgatgc    540

cggtatcaga gcaatctatg ccagaatgta ctttgatgct ccaagagcag aattggaaga    600

attagtcgca acaatacatg caaaagcccc tggtgccgta agaatggacg aatctgcttc    660

aaccgatcat gttttggcag acttagatca attgattacc agacatgaca gaactgctga    720

tggtagaatt agagtatggc cagctcctgc aataccattc atggtttctg aaaagggtat    780
```

-continued

```
gaaggcagcc caagaaatag ctgcatccag aactgacggt tggacaatgc atgttagtga    840
agatccaatc gaagccagag tccactctat gaatgctcct gaatatttgc atcacttggg    900
ttgtttagac gatagattgt tagccgctca ttgcgttcac atagactcaa gagatatcag    960
attgtttaga caacatgatg ttaagatatc cacacaacct gtctccaata gttacttagc   1020
agccggtata gcaccagttc ctgaaatgtt ggctcatggt gtcacagtag gtattggtac   1080
cgacgatgct aattgtaacg actccgtaaa cttaatcagt gatatgaagg ttttggcatt   1140
gatacataga gctgcacaca gagatgctag tatcattacc ccagaaaaga taatcgaaat   1200
ggccactatt gacggtgcta gatgcattgg tatggctgat caaatcggtt ctttggaagc   1260
tggtaaaaga gcagacataa tcactttgga tttgagacat gcacaaacca ctcctgccca   1320
cgatttggcc gctacaattg tctttcaagc ttatggtaat gaagtaaacg atgttttggt   1380
caacggttct gtagttatga gagatagagt tttgtcattc ttaccaaccc ctcaagaaga   1440
aaaggcttta tacgacgatg catctgaaag atcagcagcc atgttagcca gagctggttt   1500
gactggtaca agaacctggc aaactttggg ttcttaagga aatccattat gatgtcagga   1560
gaacacacgt taaaagcggt acgaggcagt tttattgatg tcacccgtac gatcgataac   1620
ccggaagaga ttgcctctgc gctgcggttt attgaggatg gtttattact cattaaacag   1680
ggaaaagtgg aatggtttgg cgaatgggaa aacggaaagc atcaaattcc tgacaccatt   1740
cgcgtgcgcg actatcgcgg caaactgata gtaccgggct ttgtcgatac acatatccat   1800
tatccgcaaa gtgaaatggt gggggcctat ggtgagcaat tgctggagtg gttgaataaa   1860
cacaccttcc ctactgaacg tcgttatgag gatttagagt acgcccgcga aatgtcggcg   1920
ttcttcatca agcagctttt acgtaacgga accaccacgg cgctggtgtt tggcactgtt   1980
catccgcaat ctgttgatgc gctgtttgaa gccgccagtc atatcaatat gcgtatgatt   2040
gccggtaagg tgatgatgga ccgcaacgca ccggattatc tgctcgacac tgccgaaagc   2100
agctatcacc aaagcaaaga actgatcgaa cgctggcaca aaaatggtcg tctgctatat   2160
gcgattacgc cacgcttcgc cccgacctca tctcctgaac agatggcgat ggcgcaacgc   2220
ctgaaagaag aatatccgga tacgtgggta catacccatc tctgtgaaaa caaagatgaa   2280
attgcctggg tgaaatcgct ttatcctgac catgatggtt atctggatgt ttaccatcag   2340
tacggcctga ccggtaaaaa ctgtgtcttt gctcactgcg tccatctcga agaaaaagag   2400
tgggatcgtc tcagcgaaac caaatccagc attgctttct gtccgacctc caacctttac   2460
ctcggcagcg gcttattcaa cttgaaaaaa gcatggcaga agaaagttaa agtgggcatg   2520
ggaacggata tcggtgccgg aaccactttc aacatgctgc aaacgctgaa cgaagcctac   2580
aaagtattgc aattacaagg ctatcgcctc tcggcatatg aagcgtttta cctggccacg   2640
ctcggcggag cgaaatctct gggccttgac gatttgattg gcaacttttt acctggcaaa   2700
gaggctgatt tcgtggtgat ggaacccacc gccactccgc tacagcagct gcgctatgac   2760
aactctgttt ctttagtcga caaattgttc gtgatgatga cgttgggcga tgaccgttcg   2820
atctaccgca cctacgttga tggtcgtctg gtgtacgaac gcaactaagg aacgaccatg   2880
agagaagtcc aattgttaga tggtagaaga gttgatgtcg cctgtgctgg tcctttgatt   2940
agtgaaatag gtgcccactt agatttgact gctccagttg aaattgattg tggtggtggt   3000
ttagcaacta gaccttttac tgaacctcat ttgcacttag acaaagcagg tactgccgat   3060
agattgcctg ccggtgcttc cacaatcggt gacgctattg ctgcaatgca aagtgtcaag   3120
gtaaccgaaa gagataatgt cgccgctgta gcagccagaa tgcatagagt tttaaacaga   3180
```

```
atcgtcgatg acggttccca cgctattaga gcattggttg atgtcgacga agtttggggt   3240
ttaacagctt ttcatgctgc acaacaagtc caagccgctt tggccccaag agctgttgtc   3300
caaattgtcg ctttcccaca acacggttta acccctcaag tattggcaat gttagaacaa   3360
gcagccgctg aaggtgcagg tgccttgggt gctcatactg atgttgaccc agatcctgca   3420
gcccacgttg gtgccgtcgc tgcaatagcc gctggtgctt ccttgccatt agaagttcat   3480
actgacgaag gtgctagtcc agataaattt tatttgcctg cagtattgga agttttagat   3540
agattcccag gtttgtctac tacattagct cattgtttgt cattaggtac aattgcacct   3600
aagcaacaac aacattggat cgaagaatta gctcacagag atatcaaagt atgcgttgca   3660
ccatctattt tgggtttcgg tttgccatta gcacctgtta gagccttaat agaagctggt   3720
gtcggtatct tagtaggttc agacaatttg caagatgttt tctttccttt gggtacaggt   3780
agagcaattg aaaacgttag attgttagcc accgcagccc aattaactgc accagaattg   3840
gccggtcctt taattgctgg tgtaaccgac atagcttacg caaccgttac tggtgctgca   3900
gatgccttgg ctgttgaatc tccagctaca ttagtagttc atgatgctac ctcacctgca   3960
gaattgttaa gaggtataga cggtacaaga attaccgtta tagatggttt gttgacatct   4020
ccattgcaat tggataaagg tatcaagtaa gtttaaacta atcccacagc cgccagttcc   4080
gctggcggca ttttaacttt ctttaatggg cgcgcctttc cataggctcc gcccccctga   4140
cgagcatcac aaaaatcgac gctcaagtca gaggtggcga aacccgacag gactataaag   4200
ataccaggcg tttccccctg gaagctccct cgtgcgctct cctgttccga ccctgccgct   4260
taccggatac ctgtccgcct ttctcccttc gggaagcgtg gcgctttctc atagctcacg   4320
ctgtaggtat ctcagttcgg tgtaggtcgt tcgctccaag ctgggctgtg tgcacgaacc   4380
ccccgttcag cccgaccgct gcgccttatc cggtaactat cgtcttgagt ccaacccggt   4440
aagacacgac ttatcgccac tggcagcagc cactggtaac aggattagca gagcgaggta   4500
tgtaggcggt gctacagagt tcttgaagtg gtggcctaac tacggctaca ctagaagaac   4560
agtatttggt atctgcgctc tgctgaagcc agttaccttc ggaaaaagag ttggtagctc   4620
ttgatccggc aaacaaacca ccgctggtag cggtggtttt tttgtttgca agcagcagat   4680
tacgcgcaga aaaaaaggat ctcaagaaga tcctttgatc ttttctacgg ggtctgacgc   4740
tcagtggaac gaaaactcac gttaagggat tttggtcatg agattatcaa aaaggatctt   4800
cacctagatc cttttaaatt aaaaatgaag ttttaaatca atctaaagta tatatgagta   4860
aacttggtct gacagttacc aatgcttaat cagtgaggca cctatctcag cgatctgtct   4920
atttcgttca tccatagttg cctgactccc cgtcgtgtag ataactacga tacgggaggg   4980
cttaccatct ggccccagtg ctgcaatgat accgcgagac ccacgctcac cggctccaga   5040
tttatcagca ataaaccagc cagccggaag ggccgagcgc agaagtggtc ctgcaacttt   5100
atccgcctcc atccagtcta ttaattgttg ccgggaagct agagtaagta gttcgccagt   5160
taatagtttg cgcaacgttg ttgccattgc tacaggcatc gtggtgtcac gctcgtcgtt   5220
tggtatggct tcattcagct ccggttccca acgatcaagg cgagttacat gatcccccat   5280
gttgtgcaaa aaagcggtta gctccttcgg tcctccgatc gttgtcagaa gtaagttggc   5340
cgcagtgtta tcactcatgg ttatggcagc actgcataat tctcttactg tcatgccatc   5400
cgtaagatgc ttttctgtga ctggtgagta ctcaaccaag tcattctgag aatagtgtat   5460
gcggcgaccg agttgctctt gcccggcgtc aatacgggat aataccgcgc cacatagcag   5520
```

```
aactttaaaa gtgctcatca ttggaaaacg ttcttcgggg cgaaaactct caaggatctt   5580
accgctgttg agatccagtt cgatgtaacc cactcgtgca cccaactgat cttcagcatc   5640
ttttactttc accagcgttt ctgggtgagc aaaaacagga aggcaaaatg ccgcaaaaaa   5700
gggaataagg gcgacacgga aatgttgaat actcatactc ttcctttttc aatattattg   5760
aagcatttat cagggttatt gtctcatgag cggatacata tttgaatgta tttagaaaaa   5820
taaacagcga tcgcgcggcc gcgggtaata actgatataa ttaaattgaa gctctaattt   5880
gtgagtttag tatacatgca tttacttata atacagtttt ttagttttgc tggccgcatc   5940
ttctcaaata tgcttcccag cctgcttttc tgtaacgttc accctctacc ttagcatccc   6000
ttccctttgc aaatagtcct cttccaacaa taataatgtc agatcctgta gagaccacat   6060
catccacggt tctatactgt tgacccaatg cgtctccctt gtcatctaaa cccacaccgg   6120
gtgtcataat caaccaatcg taaccttcat ctcttccacc catgtctctt tgagcaataa   6180
agccgataac aaaatctttg tcgctcttcg caatgtcaac agtaccctta gtatattctc   6240
cagtagctag ggagcccttg catgacaatt ctgctaacat caaaaggcct ctaggttcct   6300
ttgttacttc ttccgccgcc tgcttcaaac cgctaacaat acctgggccc accacaccgt   6360
gtgcattcgt aatgtctgcc cattctgcta ttctgtatac acccgcagag tactgcaatt   6420
tgactgtatt accaatgtca gcaaattttc tgtcttcgaa gagtaaaaaa ttgtacttgg   6480
cggataatgc ctttagcggc ttaactgtgc cctccatgga aaaatcagtc aagatatcca   6540
catgtgtttt tagtaaacaa attttgggac ctaatgcttc aactaactcc agtaattcct   6600
tggtggtacg aacatccaat gaagcacaca agtttgtttg cttttcgtgc atgatattaa   6660
atagcttggc agcaacagga ctaggatgag tagcagcacg ttccttatat gtagctttcg   6720
acatgattta tcttcgtttc ctgcaggttt ttgttctgtg cagttgggtt aagaatactg   6780
ggcaatttca tgtttcttca acaccacata tgcgtatata taccaatcta agtctgtgct   6840
ccttccttcg ttcttccttc tgctcggaga ttaccgaatc aaagctagct tatcgatgat   6900
aagctgtcaa agatgagaat taattccacg gactatagac tatactagat actccgtcta   6960
ctgtacgata cacttccgct caggtccttg tcctttaacg aggccttacc actcttttgt   7020
tactctattg atccagctca gcaaaggcag tgtgatctaa gattctatct tcgcgatgta   7080
gtaaaactag ctagaccgag aaagagacta gaaatgcaaa aggcacttct acaatggctg   7140
ccatcattat tatccgatgt gacgctgcag cttctcaatg atattcgaat acgctttgag   7200
gagatacagc ctaatatccg acaaactgtt ttacagattt acgatcgtac ttgttaccca   7260
tcattgaatt ttgaacatcc gaacctggga gttttccctg aaacagatag tatatttgaa   7320
cctgtataat aatatatagt ctagcgcttt acggaagaca atgtatgtat ttcggttcct   7380
ggagaaacta ttgcatctat tgcataggta atcttgcacg tcgcatcccc ggttcatttt   7440
ctgcgtttcc atcttgcact tcaatagcat atctttgtta acgaagcatc tgtgcttcat   7500
tttgtagaac aaaaatgcaa cgcgagagcg ctaatttttc aaacaaagaa tctgagctgc   7560
atttttacag aacagaaatg caacgcgaaa gcgctatttt accaacgaag aatctgtgct   7620
tcatttttgt aaaacaaaaa tgcaacgcga cgagagcgct aatttttcaa acaaagaatc   7680
tgagctgcat ttttacagaa cagaaatgca acgcgagagc gctattttac caacaaagaa   7740
tctatacttc ttttttgttc tacaaaaatg catcccgaga gcgctatttt tctaacaaag   7800
catcttagat tacttttttt ctcctttgtg cgctctataa tgcagtctct tgataacttt   7860
ttgcactgta ggtccgttaa ggttagaaga aggctacttt ggtgtctatt ttctcttcca   7920
```

```
taaaaaaagc ctgactccac ttcccgcgtt tactgattac tagcgaagct gcgggtgcat   7980

tttttcaaga taaaggcatc cccgattata ttctataccg atgtggattg cgcatacttt   8040

gtgaacagaa agtgatagcg ttgatgattc ttcattggtc agaaaattat gaacggtttc   8100

ttctattttg tctctatata ctacgtatag gaaatgttta cattttcgta ttgttttcga   8160

ttcactctat gaatagttct tactacaatt tttttgtcta aagagtaata ctagagataa   8220

acataaaaaa tgtagaggtc gagtttagat gcaagttcaa ggagcgaaag gtggatgggt   8280

aggttatata gggatatagc acagagatat atagcaaaga gatacttttg agcaat       8336
```

```
<210> SEQ ID NO 47
<211> LENGTH: 8063
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
```

```
gtttgtggaa gcggtattcg caatttaatt aaagctggtg acaattaatc atcggctcgt     60

ataatgtgtg gaattgaatc gatataagga ggttaatcat atgtcctcca cagcattata    120

caccgttcct accgcaggtc cagacgatgt tgccgccttg aaagcattag atggtcattc    180

cgcctccgat attttggctg taataggtaa aacagagggt aatggttgtg ttaacgactt    240

tagtagaacc ttatctgctg cagtttggca tccattgtta gaagattcag ccattacagt    300

cttttccggt ggtgcagaag gtgtaataag tccacatgta aacatcttcg ttagagatga    360

aagacaatat tctggtcacc ctagaggttt ggtaactgct gttggtagaa caagagttat    420

cggtccagaa gaaattggta gacctgctca agtcgatgca gtacatgaaa ccgttgtcgc    480

attgttaact gaattgggtg ttggtccaga tgacgttcac ttggtcttga ttaaatgccc    540

tttgttatct tcagacgcta tagcaggtgt tcatagaaga ggtttaagac ctgtcactac    600

agatacttac gaatctatgt caagatccag agccgcttct gctttgggta tagccatggc    660

tttaaaggaa tgtgatagag acagagcatt gttagccttg gaaggtagag atgacgtttg    720

gtcagcaaga gcctccgctt ccagtggtgc tgaattggat gactgccaca ttttagtagt    780

tgcagaatca gatgcagccg ctaatccatt aagagcagcc catactgcca tgagagatgc    840

tttggacatc caagctttaa cagaagtttt tgacagaatt gctgcagaag gtggtaccgt    900

cagacaaata ttcgcaaagg ccgaagctga tccttcaggt gctatcagag gttatagaca    960

taccatgtta actgattccg acgtcaatgc aacaagacac gccagagccg ctgtaggtgg   1020

tttgattgca gccttacatg gtaacggtgc tgtctatgta tcaggtggtg cagaacacca   1080

aggtccaagt ggtggtggtt ctgttactgt tatatatgat gttcctgcaa cagccaacgc   1140

taccggtgaa gcttctagat aaggaaatcc attatgatat actcaacagt caacgctaat   1200

ccttacgctt ggccttacga tggttcaata gaccctgctc acaccgcttt aatcttaatc   1260

gattggcaaa tagacttttg tggtccaggt ggttatgtcg attccatggg ttacgactta   1320

tccttgacta gaagtggttt agaacctaca gcaagagtat tggctgcagc cagagatact   1380

ggtatgacag ttatccatac tagagaaggt cacagaccag atttggctga cttgccacct   1440

aataagagat ggagatctgc atcagccggt gctgaaatcg gttcagttgg tccatgtggt   1500

agaattttag tcagaggtga acctggttgg gaaatagtac cagaagttgc acctagagaa   1560

ggtgaaccaa ttatagataa acctggtaaa ggtgctttct acgcaacaga tttggacttg   1620
```

```
ttgttgagaa caagaggtat cacccatttg attttgaccg gtataactac agatgtttgc   1680
gtccacacca ctatgagaga agccaacgat agaggttacg aatgtttaat tttgtctgat   1740
tgcaccggtg ctactgacag aaagcatcac gaagctgcat tatctatggt caccatgcaa   1800
ggtggtgtat tcggtgcaac tgcccattca gatgacttat tggccgcttt gggtacaacc   1860
gttccagcag ccgctggtcc tagagctaga acagaataag gaacgaccat gacagttagt   1920
tccgatacaa ctgctgaaat atcgttaggt tggtcaatcc aagactggat tgatttccac   1980
aagtcatcaa gctcccaggc ttcactaagg cttcttgaat cactactaga ctctcaaaat   2040
gttgcgccag tcgataatgc gtggatatcg ctaatttcaa aggaaaattt actgcaccaa   2100
ttccaaattt taaagagcag agaaaataaa gaaactctac ctctctacgg tgtccctatt   2160
gctgttaagg acaacatcga cgttagaggt ctacccacca ccgctgcatg tccatccttt   2220
gcatatgagc cttccaaaga ctctaaagta gtagaactac taagaaatgc aggtgcgata   2280
atcgtgggta agacaaactt ggaccaattt gccacaggat tagtcggcac acggtctcca   2340
tatgggaaaa caccttgcgc ttttagcaaa gagcatgtat ctggtggttc ctccgctggg   2400
tcagcatcgg tggtcgccag aggtatcgta ccaattgcat tgggtactga tacagcaggt   2460
tctggtagag tcccagccgc cttgaacaac ctgattggcc taaagccaac aaagggcgtc   2520
ttttcctgtc aaggtgtagt tcccgcttgt aaatctttag actgcgtctc catctttgca   2580
ttaaacctaa gtgatgctga acgctgcttc cgcatcatgt gccagccaga tcctgataat   2640
gatgaatatt ctagacccta tgtttccaac cctttgaaaa aattttcaag caatgtaacg   2700
attgctattc ctaaaaatat cccatggtat ggtgaaacca agaatcctgt actgttttcc   2760
aatgctgtcg aaaatctatc aagaacgggc gctaacgtca tagaaattga ttttgagcct   2820
cttttagagt tagctcgctg tttatacgaa ggtacttggg tggccgagcg ttatcaagct   2880
attcaatcgt tttggacag taaaccacca aaggaatctt tggaccctac tgttatttca   2940
attatagaag gggccaagaa atacagtgca gtagactgct tcagttttga atacaaaaga   3000
caaggcatct tgcaaaaagt gagacgactt ctcgaatcag tcgatgtatt gtgtgtgccc   3060
acatgtcctt taaatcctac tatgcaacaa gttgcggatg aaccagtcct agtcaattca   3120
agacaaggca catggactaa ttttgtcaac ttggcagatt tggcagccct tgctgttccc   3180
gcagggttcc gagacgatgg tttgccaaat ggtattactt taatcggtaa aaaattcaca   3240
gattacgcac tattagagtt ggctaaccgc tatttccaaa atatattccc caacggttcc   3300
agaacatacg gtactttac ctcttcttca gtaaagccag caaacgatca attagtggga   3360
ccagactatg acccatctac gtccataaaa ttggctgttg tcggtgcaca tcttaagggt   3420
ctgcctctac attggcaatt ggaaaaggtc aatgcaacat atttatgtac aacaaaaaca   3480
tcaaaagctt accagctttt tgctttgccc aaaaatggac cagttttaaa acctggtttg   3540
agaagagttc aagatagcaa tggctctcaa atcgaattag aagtgtacag tgttccaaaa   3600
gaactgttcg gtgcttttat ttccatggtt cctgaaccat taggaatagg ttcagtggag   3660
ttagaatctg gtgaatggat caaatccttt atttgtgaag aatctggtta caaagccaaa   3720
ggtacagttg atatcacaaa gtatggtgga tttagagcat attttgaaat gttgtaagtt   3780
taaactaatc ccacagccgc cagttccgct ggcggcattt taactttctt taatgggcgc   3840
gcctttccat aggctccgcc cccctgacga gcatcacaaa aatcgacgct caagtcagag   3900
gtggcgaaac ccgacaggac tataaagata ccaggcgttt ccccctggaa gctccctcgt   3960
```

```
gcgctctcct gttccgaccc tgccgcttac cggatacctg tccgcctttc tcccttcggg   4020

aagcgtggcg ctttctcata gctcacgctg taggtatctc agttcggtgt aggtcgttcg   4080

ctccaagctg ggctgtgtgc acgaaccccc cgttcagccc gaccgctgcg ccttatccgg   4140

taactatcgt cttgagtcca acccggtaag acacgactta tcgccactgg cagcagccac   4200

tggtaacagg attagcagag cgaggtatgt aggcggtgct acagagttct tgaagtggtg   4260

gcctaactac ggctacacta gaagaacagt atttggtatc tgcgctctgc tgaagccagt   4320

taccttcgga aaaagagttg gtagctcttg atccggcaaa caaaccaccg ctggtagcgg   4380

tggttttttt gtttgcaagc agcagattac gcgcagaaaa aaaggatctc aagaagatcc   4440

tttgatcttt tctacggggt ctgacgctca gtggaacgaa aactcacgtt aagggatttt   4500

ggtcatgaga ttatcaaaaa ggatcttcac ctagatcctt ttaaattaaa aatgaagttt   4560

taaatcaatc taaagtatat atgagtaaac ttggtctgac agttaccaat gcttaatcag   4620

tgaggcacct atctcagcga tctgtctatt tcgttcatcc atagttgcct gactccccgt   4680

cgtgtagata actacgatac gggagggctt accatctggc cccagtgctg caatgatacc   4740

gcgagaccca cgctcaccgg ctccagattt atcagcaata aaccagccag ccggaagggc   4800

cgagcgcaga agtggtcctg caactttatc cgcctccatc cagtctatta attgttgccg   4860

ggaagctaga gtaagtagtt cgccagttaa tagtttgcgc aacgttgttg ccattgctac   4920

aggcatcgtg gtgtcacgct cgtcgtttgg tatggcttca ttcagctccg gttcccaacg   4980

atcaaggcga gttacatgat cccccatgtt gtgcaaaaaa gcggttagct ccttcggtcc   5040

tccgatcgtt gtcagaagta agttggccgc agtgttatca ctcatggtta tggcagcact   5100

gcataattct cttactgtca tgccatccgt aagatgcttt tctgtgactg gtgagtactc   5160

aaccaagtca ttctgagaat agtgtatgcg gcgaccgagt tgctcttgcc cggcgtcaat   5220

acgggataat accgcgccac atagcagaac tttaaaagtg ctcatcattg gaaaacgttc   5280

ttcggggcga aaactctcaa ggatcttacc gctgttgaga tccagttcga tgtaacccac   5340

tcgtgcaccc aactgatctt cagcatcttt tactttcacc agcgtttctg ggtgagcaaa   5400

aacaggaagg caaaatgccg caaaaaaggg aataagggcg acacggaaat gttgaatact   5460

catactcttc ctttttcaat attattgaag catttatcag ggttattgtc tcatgagcgg   5520

atacatattt gaatgtattt agaaaaataa acagcgatcg cgcggccgcg ggtaataact   5580

gatataatta aattgaagct ctaatttgtg agtttagtat acatgcattt acttataata   5640

cagtttttta gttttgctgg ccgcatcttc tcaaatatgc ttcccagcct gcttttctgt   5700

aacgttcacc ctctacctta gcatcccttc cctttgcaaa tagtcctctt ccaacaataa   5760

taatgtcaga tcctgtagag accacatcat ccacggttct atactgttga cccaatgcgt   5820

ctcccttgtc atctaaaccc acaccgggtg tcataatcaa ccaatcgtaa ccttcatctc   5880

ttccacccat gtctctttga gcaataaagc cgataacaaa atctttgtcg ctcttcgcaa   5940

tgtcaacagt acccttagta tattctccag tagctaggga gcccttgcat gacaattctg   6000

ctaacatcaa aaggcctcta ggttcctttg ttacttcttc cgccgcctgc ttcaaaccgc   6060

taacaatacc tgggcccacc acaccgtgtg cattcgtaat gtctgcccat tctgctattc   6120

tgtatacacc cgcagagtac tgcaatttga ctgtattacc aatgtcagca aattttctgt   6180

cttcgaagag taaaaaattg tacttggcgg ataatgcctt tagcggctta actgtgccct   6240

ccatggaaaa atcagtcaag atatccacat gtgtttttag taaacaaatt ttgggaccta   6300

atgcttcaac taactccagt aattccttgg tggtacgaac atccaatgaa gcacacaagt   6360
```

```
ttgtttgctt ttcgtgcatg atattaaata gcttggcagc aacaggacta ggatgagtag   6420

cagcacgttc cttatatgta gctttcgaca tgatttatct tcgtttcctg caggtttttg   6480

ttctgtgcag ttgggttaag aatactgggc aatttcatgt ttcttcaaca ccacatatgc   6540

gtatatatac caatctaagt ctgtgctcct tccttcgttc ttccttctgc tcggagatta   6600

ccgaatcaaa gctagcttat cgatgataag ctgtcaaaga tgagaattaa ttccacggac   6660

tatagactat actagatact ccgtctactg tacgatacac ttccgctcag gtccttgtcc   6720

tttaacgagg ccttaccact cttttgttac tctattgatc cagctcagca aaggcagtgt   6780

gatctaagat tctatcttcg cgatgtagta aaactagcta gaccgagaaa gagactagaa   6840

atgcaaaagg cacttctaca atggctgcca tcattattat ccgatgtgac gctgcagctt   6900

ctcaatgata ttcgaatacg ctttgaggag atacagccta atatccgaca aactgtttta   6960

cagatttacg atcgtacttg ttacccatca ttgaattttg aacatccgaa cctgggagtt   7020

ttccctgaaa cagatagtat atttgaacct gtataataat atatagtcta gcgctttacg   7080

gaagacaatg tatgtatttc ggttcctgga gaaactattg catctattgc ataggtaatc   7140

ttgcacgtcg catccccggt tcattttctg cgtttccatc ttgcacttca atagcatatc   7200

tttgttaacg aagcatctgt gcttcatttt gtagaacaaa aatgcaacgc gagagcgcta   7260

atttttcaaa caaagaatct gagctgcatt tttacagaac agaaatgcaa cgcgaaagcg   7320

ctatttttacc aacgaagaat ctgtgcttca tttttgtaaa acaaaaatgc aacgcgacga   7380

gagcgctaat tttcaaaca aagaatctga gctgcatttt tacagaacag aaatgcaacg   7440

cgagagcgct attttaccaa caaagaatct atacttcttt tttgttctac aaaaatgcat   7500

cccgagagcg ctatttttct aacaaagcat cttagattac ttttttctc ctttgtgcgc   7560

tctataatgc agtctcttga taacttttttg cactgtaggt ccgttaaggt tagaagaagg   7620

ctactttggt gtctattttc tcttccataa aaaaagcctg actccacttc ccgcgtttac   7680

tgattactag cgaagctgcg ggtgcatttt ttcaagataa aggcatcccc gattatattc   7740

tataccgatg tggattgcgc atactttgtg aacagaaagt gatagcgttg atgattcttc   7800

attggtcaga aaattatgaa cggtttcttc tattttgtct ctatatacta cgtataggaa   7860

atgtttacat tttcgtattg ttttcgattc actctatgaa tagttcttac tacaattttt   7920

ttgtctaaag agtaatacta gagataaaca taaaaaatgt agaggtcgag tttagatgca   7980

agttcaagga gcgaaaggtg gatgggtagg ttatataggg atatagcaca gagatatata   8040

gcaaagagat acttttgagc aat                                           8063
```

<210> SEQ ID NO 48
<211> LENGTH: 8927
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 48

```
gtttgtggaa gcggtattcg caatcattta gtcgtgcaat gtatgacttt aagatttgtg     60

agcaggaaga aaagggagaa tcttctaacg ataaaccctt gaaaaactgg gtagactacg    120

ctatgttgag ttgctacgca ggctgcacaa ttacacgaga atgctcccgc ctaggattta    180

aggctaaggg acgtgcaatg cagacgacag atctaaatga ccgtgtcggt gaagtgttcg    240

ccaaactttt cggttaacac atgcagtgat gcacgcgcga tggtgctaag ttacatatat    300
```

-continued

```
atatatatat atatatatat atatatatag ccatagtgat gtctaagtaa cctttatggt    360
atatttctta atgtggaaag atactagcgc gcgcacccac acacaagctt cgtcttttct    420
tgaagaaaag aggaagctcg ctaaatggga ttccactttc cgttccctgc cagctgatgg    480
aaaaaggtta gtggaacgat gaagaataaa aagagagatc cactgaggtg aaatttcagc    540
tgacagcgag tttcatgatc gtgatgaaca atggtaacga gttgtggctg ttgccaggga    600
gggtggttct caacttttaa tgtatggcca aatcgctact tgggtttgtt atataacaaa    660
gaagaaataa tgaactgatt ctcttcctcc ttcttgtcct ttcttaattc tgttgtaatt    720
accttccttt gtaatttttt ttgtaattat tcttcttaat aatccaaaca aacacacata    780
ttacaataat gaagaagccc gagctgaccg ctacctctgt tgagaagttc ctgattgaga    840
agtttgattc cgtttccgac ctgatgcagc tgtccgaggg cgaggagtct cgagccttct    900
cctttgacgt gggcggacga ggttacgttc tgcgagtgaa ctcgtgtgcc gacggcttct    960
acaaggatcg atacgtctac cgacactttg cttctgccgc tctgcccatc cctgaggttc   1020
tcgacattgg cgagttctct gagtccctca cctactgcat ctctcgacga gctcagggag   1080
tcaccctgca ggacctccct gagactgagc tgcctgctgt cctccagcct gttgctgagg   1140
ccatggacgc tatcgctgct gctgatctgt cccagacctc gggtttcggc ccctttggac   1200
ctcagggaat tggacagtac accacttggc gagacttcat ctgtgctatt gccgatcctc   1260
acgtctacca ttggcagacc gttatggacg atactgtgtc ggcttctgtc gctcaggctc   1320
tggacgagct gatgctctgg gccgaggatt gccccgaggt tcgacacctg gtgcatgctg   1380
acttcggttc caacaacgtt ctcaccgaca acggccgaat cactgccgtg attgactggt   1440
ccgaggctat gtttggcgac tcgcagtacg aggtggccaa catcttcttt tggcgaccct   1500
ggctggcttg tatggagcag cagacccgat acttcgagcg acgacatcct gagctcgctg   1560
gatcccctcg actgcgagct tacatgctcc gaattggtct ggaccagctc taccagtcgc   1620
tggtggatgg caactttgac gatgctgcct gggctcaggg acgatgtgac gccatcgtgc   1680
gatctggcgc tggaaccgtc ggacgaactc agattgcccg acgatccgct gctgtctgga   1740
ccgacggatg cgtggaggtc ctggctgatt cgggtaaccg acgaccctct actcgacctc   1800
gagctaagga gtaataaacg gcgcgccgtc tgaagaatga atgatttgat gatttctttt   1860
tccctccatt tttcttactg aatatatcaa tgatatagac ttgtatagtt tattatttca   1920
aattaagtag ctatatatag tcaagataac gtttgtttga cacgattaca ttattcgtcg   1980
acatcttttt tcagcctgtc gtggtagcaa tttgaggagt attattaatt gaataggttc   2040
attttgcgct cgcataaaca gttttcgtca gggacagtat gttggaatga gtggtaatta   2100
atggtgacat gacatgttat agcaataacc ttgatgttta catcgtagtt taatgtacac   2160
cccgcgaatt cgttcaagta ggagtgcacc aattgcaaag ggaaaagctg aatgggcagt   2220
tcgaatagta ctttttccat aggctccgcc cccctgacga gcatcacaaa aatcgacgct   2280
caagtcagag gtggcgaaac ccgacaggac tataaagata ccaggcgttt ccccctggaa   2340
gctccctcgt gcgctctcct gttccgaccc tgccgcttac cggatacctg tccgcctttc   2400
tcccttcggg aagcgtggcg ctttctcata gctcacgctg taggtatctc agttcggtgt   2460
aggtcgttcg ctccaagctg ggctgtgtgc acgaaccccc cgttcagccc gaccgctgcg   2520
ccttatccgg taactatcgt cttgagtcca acccggtaag acacgactta tcgccactgg   2580
cagcagccac tggtaacagg attagcagag cgaggtatgt aggcggtgct acagagttct   2640
```

-continued

```
tgaagtggtg gcctaactac ggctacacta gaagaacagt atttggtatc tgcgctctgc   2700
tgaagccagt taccttcgga aaaagagttg gtagctcttg atccggcaaa caaaccaccg   2760
ctggtagcgg tggttttttt gtttgcaagc agcagattac gcgcagaaaa aaaggatctc   2820
aagaagatcc tttgatcttt tctacggggt ctgacgctca gtggaacgaa aactcacgtt   2880
aagggatttt ggtcatgaga ttatcaaaaa ggatcttcac ctagatcctt ttaaattaaa   2940
aatgaagttt taaatcaatc taaagtatat atgagtaaac ttggtctgac agttaccaat   3000
gcttaatcag tgaggcacct atctcagcga tctgtctatt tcgttcatcc atagttgcct   3060
gactccccgt cgtgtagata actacgatac gggagggctt accatctggc cccagtgctg   3120
caatgatacc gcgagaccca cgctcaccgg ctccagattt atcagcaata aaccagccag   3180
ccggaagggc cgagcgcaga agtggtcctg caactttatc cgcctccatc cagtctatta   3240
attgttgccg ggaagctaga gtaagtagtt cgccagttaa tagtttgcgc aacgttgttg   3300
ccattgctac aggcatcgtg gtgtcacgct cgtcgtttgg tatggcttca ttcagctccg   3360
gttcccaacg atcaaggcga gttacatgat cccccatgtt gtgcaaaaaa gcggttagct   3420
ccttcggtcc tccgatcgtt gtcagaagta agttggccgc agtgttatca ctcatggtta   3480
tggcagcact gcataattct cttactgtca tgccatccgt aagatgcttt tctgtgactg   3540
gtgagtactc aaccaagtca ttctgagaat agtgtatgcg gcgaccgagt tgctcttgcc   3600
cggcgtcaat acgggataat accgcgccac atagcagaac tttaaaagtg ctcatcattg   3660
gaaaacgttc ttcggggcga aaactctcaa ggatcttacc gctgttgaga tccagttcga   3720
tgtaacccac tcgtgcaccc aactgatctt cagcatcttt tactttcacc agcgtttctg   3780
ggtgagcaaa aacaggaagg caaaatgccg caaaaaaggg aataagggcg acacggaaat   3840
gttgaatact catactcttc ctttttcaat attattgaag catttatcag ggttattgtc   3900
tcatgagcgg atacatattt gaatgtattt agaaaaataa acagcgatcg cagctagctc   3960
gtcgtgttca ggaactgttc gatggttcgg agagagtcgc cgcccagaac atacgcgcac   4020
cgatgtcagc agacagcctt attacaagta tattcaagca agtatatccg tagggtgcgg   4080
gtgatttgga tctaaggttc gtactcaaca ctcacgagca gcttgcctat gttacatcct   4140
tttatcagac ataacataat tggagtttac ttacacacgg ggtgtacctg tatgagcacc   4200
acctacaatt gtagcactgg tacttgtaca aagaatttat tcgtacgaat cacagggacg   4260
gccgccctca ccgaaccagc gaatacctca gcggtcccct gcagtgactc aacaaagcga   4320
tatgaacatc ttgcgatggt atcctgctga tagtttttac tgtacaaaca cctgtgtagc   4380
tccttctagc atttttaagt tattcacacc tcaaggggag ggataaatta aataaattcc   4440
aaaagcgaag atcgagaaac taaattaaaa ttccaaaaac gaagttggaa cacaaccccc   4500
cgaaaaaaaa caacaaacaa aaaacccaac aaaataaaca aaaacaaaat aaatatataa   4560
ctaccagtat ctgactaaaa gttcaaatac tcgtacttac aacaaataga aatgagccgg   4620
ccaaaattct gcagaaaaaa atttcaaaca agtactggta taattaaatt aaaaaacaca   4680
tcaaagtatc ataacgttag ttattttatt ttatttaata aaagaaaaca acaagatggg   4740
ctcaaaactt tcaacttata cgatacatac caaataacaa tttagtattt atctaagtgc   4800
ttttcgtaga taatggaata caaatggata tccagagtat acacatggat agtatacact   4860
gacacgacaa ttctgtatct ctttatgtta actactgtga ggcattaaat agagcttgat   4920
atataaaatg ttacatttca cagtctgaac ttttgcagat tacctaattt ggtaagatat   4980
taattatgaa ctgaaagttg atggcggccg catagcttca aaatgtttct actccttttt   5040
```

```
tactcttcca gattttctcg gactccgcgc atcgccgtac cacttcaaaa cacccaagca   5100
cagcatacta aatttcccct ctttcttcct ctagggtgtc gttaattacc cgtactaaag   5160
gtttggaaaa gaaaaaagag accgcctcgt ttctttttct tcgtcgaaaa aggcaataaa   5220
aatttttatc acgtttcttt ttcttgaaaa tttttttttt tgattttttt ctctttcgat   5280
gacctcccat tgatatttaa gttaataaac ggtcttcaat ttctcaagtt tcagtttcat   5340
ttttcttgtt ctattacaac tttttttact tcttgctcat tagaaagaaa gcatagcaat   5400
ctaatctaag ttttaattac aaaatgtcat cctcagaagt aaaagcaaat ggttggaccg   5460
cagttcctgt ttccgcaaaa gcaatagtag actccttggg taaattagga gatgtctctt   5520
catattccgt agaagatatt gcctttccag ctgcagacaa attggtagcc gaagctcaag   5580
cattcgttaa ggctagatta tctcctgaaa cctacaacca ttcaatgaga gttttctatt   5640
ggggtactgt cattgccaga agattgttac cagaacaagc taaagatttg tctccttcaa   5700
catgggcatt aacctgtttg ttacacgacg ttggtactgc cgaagcttat tttacctcca   5760
ctagaatgag tttcgatatc tacggtggta ttaaagctat ggaagtattg aaggttttag   5820
gttccagtac agatcaagca gaagccgttg ctgaagcaat tataagacat gaagatgttg   5880
gtgtcgacgg taacatcaca tttttgggtc aattgatcca attggcaaca ttgtacgata   5940
acgtcggtgc ctacgacggt attgatgact tcggttcctg ggttgatgac actacaagaa   6000
acagtataaa cactgctttc ccaagacatg gttggtgttc ttggttcgca tgcacagtta   6060
gaaaagaaga atcaaacaag ccttggtgcc acaccacaca cataccacaa ttcgacaaac   6120
aaatggaagc aaacaccttg atgaaacctt gggaataaac aggcccccttt tcctttgtcg   6180
atatcatgta attagttatg tcacgcttac attcacgccc tcctcccaca tccgctctaa   6240
ccgaaaagga aggagttaga caacctgaag tctaggtccc tatttatttt ttttaatagt   6300
tatgttagta ttaagaacgt tatttatatt tcaaattttt cttttttttc tgtacaaacg   6360
cgtgtacgca tgtaacatta tactgaaaac cttgcttgag aaggttttgg gacgctcgaa   6420
ggctttaatt tgcgggtaat aactgatata attaaattga agctctaatt tgtgagttta   6480
gtatacatgc atttacttat aatacagttt tttagttttg ctggccgcat cttctcaaat   6540
atgcttccca gcctgctttt ctgtaacgtt caccctctac cttagcatcc cttccctttg   6600
caaatagtcc tcttccaaca ataataatgt cagatcctgt agagaccaca tcatccacgg   6660
ttctatactg ttgacccaat gcgtctccct tgtcatctaa acccacaccg ggtgtcataa   6720
tcaaccaatc gtaaccttca tctcttccac ccatgtctct ttgagcaata aagccgataa   6780
caaaatcttt gtcgctcttc gcaatgtcaa cagtaccctt agtatattct ccagtagcta   6840
gggagccctt gcatgacaat tctgctaaca tcaaaaggcc tctaggttcc tttgttactt   6900
cttccgccgc ctgcttcaaa ccgctaacaa tacctgggcc caccacaccg tgtgcattcg   6960
taatgtctgc ccattctgct attctgtata cacccgcaga gtactgcaat ttgactgtat   7020
taccaatgtc agcaaatttt ctgtcttcga agagtaaaaa attgtacttg gcggataatg   7080
cctttagcgg cttaactgtg ccctccatgg aaaaatcagt caagatatcc acatgtgttt   7140
ttagtaaaca aattttggga cctaatgctt caactaactc cagtaattcc ttggtggtac   7200
gaacatccaa tgaagcacac aagtttgttt gcttttcgtg catgatatta aatagcttgg   7260
cagcaacagg actaggatga gtagcagcac gttccttata tgtagctttc gacatgattt   7320
atcttcgttt cctgcaggtt tttgttctgt gcagttgggt taagaatact gggcaatttc   7380
```

```
atgtttcttc aacaccacat atgcgtatat ataccaatct aagtctgtgc tccttccttc   7440

gttcttcctt ctgctcggag attaccgaat caaagctagc ttatcgatga taagctgtca   7500

aagatgagaa ttaattccac ggactataga ctatactaga tactccgtct actgtacgat   7560

acacttccgc tcaggtcctt gtcctttaac gaggccttac cactcttttg ttactctatt   7620

gatccagctc agcaaaggca gtgtgatcta agattctatc ttcgcgatgt agtaaaacta   7680

gctagaccga gaaagagact agaaatgcaa aaggcacttc tacaatggct gccatcatta   7740

ttatccgatg tgacgctgca gcttctcaat gatattcgaa tacgctttga ggagatacag   7800

cctaatatcc gacaaactgt tttacagatt tacgatcgta cttgttaccc atcattgaat   7860

tttgaacatc cgaacctggg agttttccct gaaacagata gtatatttga acctgtataa   7920

taatatatag tctagcgctt tacggaagac aatgtatgta tttcggttcc tggagaaact   7980

attgcatcta ttgcataggt aatcttgcac gtcgcatccc cggttcattt tctgcgtttc   8040

catcttgcac ttcaatagca tatctttgtt aacgaagcat ctgtgcttca ttttgtagaa   8100

caaaaatgca acgcgagagc gctaattttt caaacaaaga atctgagctg catttttaca   8160

gaacagaaat gcaacgcgaa agcgctattt taccaacgaa gaatctgtgc ttcatttttg   8220

taaaacaaaa atgcaacgcg acgagagcgc taatttttca aacaaagaat ctgagctgca   8280

tttttacaga acagaaatgc aacgcgagag cgctatttta ccaacaaaga atctatactt   8340

ctttttgtt ctacaaaaat gcatcccgag agcgctattt ttctaacaaa gcatcttaga   8400

ttactttttt tctcctttgt gcgctctata atgcagtctc ttgataactt tttgcactgt   8460

aggtccgtta aggttagaag aaggctactt tggtgtctat ttctcttcc ataaaaaaag   8520

cctgactcca cttcccgcgt ttactgatta ctagcgaagc tgcgggtgca tttttcaag   8580

ataaaggcat ccccgattat attctatacc gatgtggatt gcgcatactt tgtgaacaga   8640

aagtgatagc gttgatgatt cttcattggt cagaaaatta tgaacggttt cttctatttt   8700

gtctctatat actacgtata ggaaatgttt acattttcgt attgttttcg attcactcta   8760

tgaatagttc ttactacaat ttttttgtct aaagagtaat actagagata aacataaaaa   8820

atgtagaggt cgagtttaga tgcaagttca aggagcgaaa ggtggatggg taggttatat   8880

agggatatag cacagagata tatagcaaag agatactttt gagcaat                 8927
```

<210> SEQ ID NO 49
<211> LENGTH: 8918
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 49

```
gtttgtggaa gcggtattcg caatcattta gtcgtgcaat gtatgacttt aagatttgtg     60

agcaggaaga aaagggagaa tcttctaacg ataaaccctt gaaaaactgg gtagactacg    120

ctatgttgag ttgctacgca ggctgcacaa ttacacgaga atgctcccgc ctaggattta    180

aggctaaggg acgtgcaatg cagacgacag atctaaatga ccgtgtcggt gaagtgttcg    240

ccaaactttt cggttaacac atgcagtgat gcacgcgcga tggtgctaag ttacatatat    300

atatatatat atatatatat atatatatag ccatagtgat gtctaagtaa cctttatggt    360

atatttctta atgtggaaag atactagcgc gcgcacccac acacaagctt cgtcttttct    420

tgaagaaaag aggaagctcg ctaaatggga ttccactttc cgttccctgc cagctgatgg    480
```

-continued

```
aaaaaggtta gtggaacgat gaagaataaa aagagagatc cactgaggtg aaatttcagc    540
tgacagcgag tttcatgatc gtgatgaaca atggtaacga gttgtggctg ttgccaggga    600
gggtggttct caacttttaa tgtatggcca aatcgctact tgggtttgtt atataacaaa    660
gaagaaataa tgaactgatt ctcttcctcc ttcttgtcct ttcttaattc tgttgtaatt    720
accttccttt gtaatttttt ttgtaattat tcttcttaat aatccaaaca aacacacata    780
ttacaataat gaagaagccc gagctgaccg ctacctctgt tgagaagttc ctgattgaga    840
agtttgattc cgtttccgac ctgatgcagc tgtccgaggg cgaggagtct cgagccttct    900
cctttgacgt gggcggacga ggttacgttc tgcgagtgaa ctcgtgtgcc gacggcttct    960
acaaggatcg atacgtctac cgacactttg cttctgccgc tctgcccatc cctgaggttc   1020
tcgacattgg cgagttctct gagtccctca cctactgcat ctctcgacga gctcagggag   1080
tcaccctgca ggacctccct gagactgagc tgcctgctgt cctccagcct gttgctgagg   1140
ccatggacgc tatcgctgct gctgatctgt cccagacctc gggtttcggc ccctttggac   1200
ctcagggaat tggacagtac accacttggc gagacttcat ctgtgctatt gccgatcctc   1260
acgtctacca ttggcagacc gttatggacg atactgtgtc ggcttctgtc gctcaggctc   1320
tggacgagct gatgctctgg gccgaggatt gccccgaggt tcgacacctg gtgcatgctg   1380
acttcggttc caacaacgtt ctcaccgaca acggccgaat cactgccgtg attgactggt   1440
ccgaggctat gtttggcgac tcgcagtacg aggtggccaa catcttcttt tggcgaccct   1500
ggctggcttg tatggagcag cagacccgat acttcgagcg acgacatcct gagctcgctg   1560
gatcccctcg actgcgagct tacatgctcc gaattggtct ggaccagctc taccagtcgc   1620
tggtggatgg caactttgac gatgctgcct gggctcaggg acgatgtgac gccatcgtgc   1680
gatctggcgc tggaaccgtc ggacgaactc agattgcccg acgatccgct gctgtctgga   1740
ccgacggatg cgtggaggtc ctggctgatt cgggtaaccg acgaccctct actcgacctc   1800
gagctaagga gtaataaacg gcgcgccgtc tgaagaatga atgatttgat gatttctttt   1860
tccctccatt tttcttactg aatatatcaa tgatatagac ttgtatagtt tattatttca   1920
aattaagtag ctatatatag tcaagataac gtttgtttga cacgattaca ttattcgtcg   1980
acatcttttt tcagcctgtc gtggtagcaa tttgaggagt attattaatt gaataggttc   2040
attttgcgct cgcataaaca gttttcgtca gggacagtat gttggaatga gtggtaatta   2100
atggtgacat gacatgttat agcaataacc ttgatgttta catcgtagtt taatgtacac   2160
cccgcgaatt cgttcaagta ggagtgcacc aattgcaaag ggaaaagctg aatgggcagt   2220
tcgaatagta ctttttccat aggctccgcc cccctgacga gcatcacaaa aatcgacgct   2280
caagtcagag gtggcgaaac ccgacaggac tataaagata ccaggcgttt ccccctggaa   2340
gctccctcgt gcgctctcct gttccgaccc tgccgcttac cggatacctg tccgcctttc   2400
tcccttcggg aagcgtggcg ctttctcata gctcacgctg taggtatctc agttcggtgt   2460
aggtcgttcg ctccaagctg ggctgtgtgc acgaaccccc cgttcagccc gaccgctgcg   2520
ccttatccgg taactatcgt cttgagtcca acccggtaag acacgactta tcgccactgg   2580
cagcagccac tggtaacagg attagcagag cgaggtatgt aggcggtgct acagagttct   2640
tgaagtggtg gcctaactac ggctacacta gaagaacagt atttggtatc tgcgctctgc   2700
tgaagccagt taccttcgga aaaagagttg gtagctcttg atccggcaaa caaaccaccg   2760
ctggtagcgg tggttttttt gtttgcaagc agcagattac gcgcagaaaa aaaggatctc   2820
aagaagatcc tttgatcttt tctacggggt ctgacgctca gtggaacgaa aactcacgtt   2880
```

```
aagggatttt ggtcatgaga ttatcaaaaa ggatcttcac ctagatcctt ttaaattaaa   2940
aatgaagttt taaatcaatc taaagtatat atgagtaaac ttggtctgac agttaccaat   3000
gcttaatcag tgaggcacct atctcagcga tctgtctatt tcgttcatcc atagttgcct   3060
gactccccgt cgtgtagata actacgatac gggagggctt accatctggc cccagtgctg   3120
caatgatacc gcgagaccca cgctcaccgg ctccagattt atcagcaata aaccagccag   3180
ccggaagggc cgagcgcaga agtggtcctg caactttatc cgcctccatc cagtctatta   3240
attgttgccg ggaagctaga gtaagtagtt cgccagttaa tagtttgcgc aacgttgttg   3300
ccattgctac aggcatcgtg gtgtcacgct cgtcgtttgg tatggcttca ttcagctccg   3360
gttcccaacg atcaaggcga gttacatgat cccccatgtt gtgcaaaaaa gcggttagct   3420
ccttcggtcc tccgatcgtt gtcagaagta agttggccgc agtgttatca ctcatggtta   3480
tggcagcact gcataattct cttactgtca tgccatccgt aagatgcttt tctgtgactg   3540
gtgagtactc aaccaagtca ttctgagaat agtgtatgcg gcgaccgagt tgctcttgcc   3600
cggcgtcaat acgggataat accgcgccac atagcagaac tttaaaagtg ctcatcattg   3660
gaaaacgttc ttcggggcga aaactctcaa ggatcttacc gctgttgaga tccagttcga   3720
tgtaacccac tcgtgcaccc aactgatctt cagcatcttt tactttcacc agcgtttctg   3780
ggtgagcaaa aacaggaagg caaaatgccg caaaaaaggg aataagggcg acacggaaat   3840
gttgaatact catactcttc ctttttcaat attattgaag catttatcag ggttattgtc   3900
tcatgagcgg atacatattt gaatgtattt agaaaaataa acagcgatcg cagctagctc   3960
gtcgtgttca ggaactgttc gatggttcgg agagagtcgc cgcccagaac atacgcgcac   4020
cgatgtcagc agacagcctt attacaagta tattcaagca agtatatccg tagggtgcgg   4080
gtgatttgga tctaaggttc gtactcaaca ctcacgagca gcttgcctat gttacatcct   4140
tttatcagac ataacataat tggagtttac ttacacacgg ggtgtacctg tatgagcacc   4200
acctacaatt gtagcactgg tacttgtaca aagaatttat tcgtacgaat cacagggacg   4260
gccgccctca ccgaaccagc gaatacctca gcggtcccct gcagtgactc aacaaagcga   4320
tatgaacatc ttgcgatggt atcctgctga tagtttttac tgtacaaaca cctgtgtagc   4380
tccttctagc atttttaagt tattcacacc tcaaggggag ggataaatta aataaattcc   4440
aaaagcgaag atcgagaaac taaattaaaa ttccaaaaac gaagttggaa cacaaccccc   4500
cgaaaaaaaa caacaaacaa aaaacccaac aaaataaaca aaaacaaaat aaatatataa   4560
ctaccagtat ctgactaaaa gttcaaatac tcgtacttac aacaaataga aatgagccgg   4620
ccaaaattct gcagaaaaaa atttcaaaca agtactggta taattaaatt aaaaaacaca   4680
tcaaagtatc ataacgttag ttattttatt ttatttaata aaagaaaaca acaagatggg   4740
ctcaaaactt tcaacttata cgatacatac caaataacaa tttagtattt atctaagtgc   4800
ttttcgtaga taatggaata caaatggata tccagagtat acacatggat agtatacact   4860
gacacgacaa ttctgtatct ctttatgtta actactgtga ggcattaaat agagcttgat   4920
atataaaatg ttacatttca cagtctgaac ttttgcagat tacctaattt ggtaagatat   4980
taattatgaa ctgaaagttg atggcggccg catagcttca aaatgtttct actccttttt   5040
tactcttcca gattttctcg gactccgcgc atcgccgtac cacttcaaaa cacccaagca   5100
cagcatacta aatttcccct ctttcttcct ctagggtgtc gttaattacc cgtactaaag   5160
gtttggaaaa gaaaaaagag accgcctcgt ttctttttct tcgtcgaaaa aggcaataaa   5220
```

```
aatttttatc acgtttcttt ttcttgaaaa tttttttttt tgattttttt ctctttcgat   5280
gacctcccat tgatatttaa gttaataaac ggtcttcaat ttctcaagtt tcagtttcat   5340
ttttcttgtt ctattacaac ttttttttact tcttgctcat tagaaagaaa gcatagcaat   5400
ctaatctaag ttttaattac aaaatgatat actcaacagt caacgctaat ccttacgctt   5460
ggccttacga tggttcaata gaccctgctc acaccgcttt aatcttaatc gattggcaaa   5520
tagacttttg tggtccaggt ggttatgtcg attccatggg ttacgactta tccttgacta   5580
gaagtggttt agaacctaca gcaagagtat tggctgcagc cagagatact ggtatgacag   5640
ttatccatac tagagaaggt cacagaccag atttggctga cttgccacct aataagagat   5700
ggagatctgc atcagccggt gctgaaatcg gttcagttgg tccatgtggt agaattttag   5760
tcagaggtga acctggttgg gaaatagtac cagaagttgc acctagagaa ggtgaaccaa   5820
ttatagataa acctggtaaa ggtgctttct acgcaacaga tttggacttg ttgttgagaa   5880
caagaggtat cacccatttg attttgaccg gtataactac agatgtttgc gtccacacca   5940
ctatgagaga agccaacgat agaggttacg aatgtttaat tttgtctgat tgcaccggtg   6000
ctactgacag aaagcatcac gaagctgcat tatctatggt caccatgcaa ggtggtgtat   6060
tcggtgcaac tgcccattca gatgacttat tggccgcttt gggtacaacc gttccagcag   6120
ccgctggtcc tagagctaga acagaataaa caggcccctt ttcctttgtc gatatcatgt   6180
aattagttat gtcacgctta cattcacgcc ctcctcccac atccgctcta accgaaaagg   6240
aaggagttag acaacctgaa gtctaggtcc ctatttattt tttttaatag ttatgttagt   6300
attaagaacg ttatttatat ttcaaatttt tctttttttt ctgtacaaac gcgtgtacgc   6360
atgtaacatt atactgaaaa ccttgcttga gaaggttttg ggacgctcga aggctttaat   6420
ttgcgggtaa taactgatat aattaaattg aagctctaat ttgtgagttt agtatacatg   6480
catttactta taatacagtt ttttagtttt gctggccgca tcttctcaaa tatgcttccc   6540
agcctgcttt tctgtaacgt tcaccctcta ccttagcatc ccttcccttt gcaaatagtc   6600
ctcttccaac aataataatg tcagatcctg tagagaccac atcatccacg gttctatact   6660
gttgacccaa tgcgtctccc ttgtcatcta aacccacacc gggtgtcata atcaaccaat   6720
cgtaaccttc atctcttcca cccatgtctc tttgagcaat aaagccgata acaaaatctt   6780
tgtcgctctt cgcaatgtca acagtaccct tagtatattc tccagtagct agggagccct   6840
tgcatgacaa ttctgctaac atcaaaaggc ctctaggttc ctttgttact tcttccgccg   6900
cctgcttcaa accgctaaca atacctgggc ccaccacacc gtgtgcattc gtaatgtctg   6960
cccattctgc tattctgtat acacccgcag agtactgcaa tttgactgta ttaccaatgt   7020
cagcaaattt tctgtcttcg aagagtaaaa aattgtactt ggcggataat gcctttagcg   7080
gcttaactgt gccctccatg gaaaaatcag tcaagatatc cacatgtgtt tttagtaaac   7140
aaattttggg acctaatgct tcaactaact ccagtaattc cttggtggta cgaacatcca   7200
atgaagcaca caagtttgtt tgcttttcgt gcatgatatt aaatagcttg gcagcaacag   7260
gactaggatg agtagcagca cgttccttat atgtagcttt cgacatgatt tatcttcgtt   7320
tcctgcaggt ttttgttctg tgcagttggg ttaagaatac tgggcaattt catgtttctt   7380
caacaccaca tatgcgtata tataccaatc taagtctgtg ctccttcctt cgttcttcct   7440
tctgctcgga gattaccgaa tcaaagctag cttatcgatg ataagctgtc aaagatgaga   7500
attaattcca cggactatag actatactag atactccgtc tactgtacga tacacttccg   7560
ctcaggtcct tgtcctttaa cgaggcctta ccactctttt gttactctat tgatccagct   7620
```

```
cagcaaaggc agtgtgatct aagattctat cttcgcgatg tagtaaaact agctagaccg   7680
agaaagagac tagaaatgca aaaggcactt ctacaatggc tgccatcatt attatccgat   7740
gtgacgctgc agcttctcaa tgatattcga atacgctttg aggagataca gcctaatatc   7800
cgacaaactg ttttacagat ttacgatcgt acttgttacc catcattgaa ttttgaacat   7860
ccgaacctgg gagttttccc tgaaacagat agtatatttg aacctgtata ataatatata   7920
gtctagcgct ttacggaaga caatgtatgt atttcggttc ctggagaaac tattgcatct   7980
attgcatagg taatcttgca cgtcgcatcc ccggttcatt ttctgcgttt ccatcttgca   8040
cttcaatagc atatctttgt taacgaagca tctgtgcttc attttgtaga acaaaaatgc   8100
aacgcgagag cgctaatttt tcaaacaaag aatctgagct gcatttttac agaacagaaa   8160
tgcaacgcga aagcgctatt ttaccaacga agaatctgtg cttcattttt gtaaaacaaa   8220
aatgcaacgc gacgagagcg ctaatttttc aaacaaagaa tctgagctgc atttttacag   8280
aacagaaatg caacgcgaga gcgctatttt accaacaaag aatctatact tcttttttgt   8340
tctacaaaaa tgcatcccga gagcgctatt tttctaacaa agcatcttag attacttttt   8400
ttctcctttg tgcgctctat aatgcagtct cttgataact tttgcactg taggtccgtt    8460
aaggttagaa gaaggctact ttggtgtcta ttttctcttc cataaaaaaa gcctgactcc   8520
acttcccgcg tttactgatt actagcgaag ctgcgggtgc atttttcaa gataaaggca    8580
tccccgatta tattctatac cgatgtggat tgcgcatact ttgtgaacag aaagtgatag   8640
cgttgatgat tcttcattgg tcagaaaatt atgaacggtt tcttctattt tgtctctata   8700
tactacgtat aggaaatgtt tacattttcg tattgttttc gattcactct atgaatagtt   8760
cttactacaa ttttttgtc taaagagtaa tactagagat aaacataaaa aatgtagagg    8820
tcgagtttag atgcaagttc aaggagcgaa aggtggatgg gtaggttata tagggatata   8880
gcacagagat atatagcaaa gagatacttt tgagcaat                           8918
```

```
<210> SEQ ID NO 50
<211> LENGTH: 8894
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
```

```
gtttgtggaa gcggtattcg caatcattta gtcgtgcaat gtatgacttt aagatttgtg     60
agcaggaaga aaagggagaa tcttctaacg ataaaccctt gaaaaactgg gtagactacg    120
ctatgttgag ttgctacgca ggctgcacaa ttacacgaga atgctcccgc ctaggattta    180
aggctaaggg acgtgcaatg cagacgacag atctaaatga ccgtgtcggt gaagtgttcg    240
ccaaactttt cggttaacac atgcagtgat gcacgcgcga tggtgctaag ttacatatat    300
atatatatat atatatatat atatatatag ccatagtgat gtctaagtaa cctttatggt    360
atatttctta atgtggaaag atactagcgc gcgcacccac acacaagctt cgtcttttct    420
tgaagaaaag aggaagctcg ctaaatggga ttccactttc cgttccctgc cagctgatgg    480
aaaaaggtta gtggaacgat gaagaataaa aagagagatc cactgaggtg aaatttcagc    540
tgacagcgag tttcatgatc gtgatgaaca atggtaacga gttgtggctg ttgccaggga    600
gggtggttct caacttttaa tgtatggcca aatcgctact tgggtttgtt atataacaaa    660
gaagaaataa tgaactgatt ctcttcctcc ttcttgtcct ttcttaattc tgttgtaatt    720
```

```
accttccttt gtaatttttt ttgtaattat tcttcttaat aatccaaaca aacacacata    780
ttacaataat gaagaagccc gagctgaccg ctacctctgt tgagaagttc ctgattgaga    840
agtttgattc cgtttccgac ctgatgcagc tgtccgaggg cgaggagtct cgagccttct    900
cctttgacgt gggcggacga ggttacgttc tgcgagtgaa ctcgtgtgcc gacggcttct    960
acaaggatcg atacgtctac cgacactttg cttctgccgc tctgcccatc cctgaggttc   1020
tcgacattgg cgagttctct gagtccctca cctactgcat ctctcgacga gctcagggag   1080
tcaccctgca ggacctccct gagactgagc tgcctgctgt cctccagcct gttgctgagg   1140
ccatggacgc tatcgctgct gctgatctgt cccagacctc gggtttcggc ccctttggac   1200
ctcagggaat tggacagtac accacttggc gagacttcat ctgtgctatt gccgatcctc   1260
acgtctacca ttggcagacc gttatggacg atactgtgtc ggcttctgtc gctcaggctc   1320
tggacgagct gatgctctgg gccgaggatt gccccgaggt tcgacacctg gtgcatgctg   1380
acttcggttc caacaacgtt ctcaccgaca acggccgaat cactgccgtg attgactggt   1440
ccgaggctat gtttggcgac tcgcagtacg aggtggccaa catcttcttt tggcgaccct   1500
ggctggcttg tatggagcag cagacccgat acttcgagcg acgacatcct gagctcgctg   1560
gatcccctcg actgcgagct tacatgctcc gaattggtct ggaccagctc taccagtcgc   1620
tggtggatgg caactttgac gatgctgcct gggctcaggg acgatgtgac gccatcgtgc   1680
gatctggcgc tggaaccgtc ggacgaactc agattgcccg acgatccgct gctgtctgga   1740
ccgacggatg cgtggaggtc ctggctgatt cgggtaaccg acgaccctct actcgacctc   1800
gagctaagga gtaataaacg gcgcgccgtc tgaagaatga atgatttgat gatttctttt   1860
tccctccatt tttcttactg aatatatcaa tgatatagac ttgtatagtt tattatttca   1920
aattaagtag ctatatatag tcaagataac gtttgtttga cacgattaca ttattcgtcg   1980
acatcttttt tcagcctgtc gtggtagcaa tttgaggagt attattaatt gaataggttc   2040
attttgcgct cgcataaaca gttttcgtca gggacagtat gttggaatga gtggtaatta   2100
atggtgacat gacatgttat agcaataacc ttgatgttta catcgtagtt taatgtacac   2160
cccgcgaatt cgttcaagta ggagtgcacc aattgcaaag ggaaaagctg aatgggcagt   2220
tcgaatagta ctttttccat aggctccgcc cccctgacga gcatcacaaa aatcgacgct   2280
caagtcagag gtggcgaaac ccgacaggac tataaagata ccaggcgttt ccccctggaa   2340
gctccctcgt gcgctctcct gttccgaccc tgccgcttac cggatacctg tccgcctttc   2400
tcccttcggg aagcgtggcg ctttctcata gctcacgctg taggtatctc agttcggtgt   2460
aggtcgttcg ctccaagctg ggctgtgtgc acgaaccccc cgttcagccc gaccgctgcg   2520
ccttatccgg taactatcgt cttgagtcca acccggtaag acacgactta tcgccactgg   2580
cagcagccac tggtaacagg attagcagag cgaggtatgt aggcggtgct acagagttct   2640
tgaagtggtg gcctaactac ggctacacta gaagaacagt atttggtatc tgcgctctgc   2700
tgaagccagt taccttcgga aaaagagttg gtagctcttg atccggcaaa caaaccaccg   2760
ctggtagcgg tggttttttt gtttgcaagc agcagattac gcgcagaaaa aaaggatctc   2820
aagaagatcc tttgatcttt tctacggggt ctgacgctca gtggaacgaa aactcacgtt   2880
aagggatttt ggtcatgaga ttatcaaaaa ggatcttcac ctagatcctt ttaaattaaa   2940
aatgaagttt taaatcaatc taaagtatat atgagtaaac ttggtctgac agttaccaat   3000
gcttaatcag tgaggcacct atctcagcga tctgtctatt tcgttcatcc atagttgcct   3060
```

-continued

```
gactccccgt cgtgtagata actacgatac gggagggctt accatctggc cccagtgctg   3120
caatgatacc gcgagaccca cgctcaccgg ctccagattt atcagcaata aaccagccag   3180
ccggaagggc cgagcgcaga agtggtcctg caactttatc cgcctccatc cagtctatta   3240
attgttgccg ggaagctaga gtaagtagtt cgccagttaa tagtttgcgc aacgttgttg   3300
ccattgctac aggcatcgtg gtgtcacgct cgtcgtttgg tatggcttca ttcagctccg   3360
gttcccaacg atcaaggcga gttacatgat cccccatgtt gtgcaaaaaa gcggttagct   3420
ccttcggtcc tccgatcgtt gtcagaagta agttggccgc agtgttatca ctcatggtta   3480
tggcagcact gcataattct cttactgtca tgccatccgt aagatgcttt tctgtgactg   3540
gtgagtactc aaccaagtca ttctgagaat agtgtatgcg gcgaccgagt tgctcttgcc   3600
cggcgtcaat acgggataat accgcgccac atagcagaac tttaaaagtg ctcatcattg   3660
gaaaacgttc ttcggggcga aaactctcaa ggatcttacc gctgttgaga tccagttcga   3720
tgtaacccac tcgtgcaccc aactgatctt cagcatcttt tactttcacc agcgtttctg   3780
ggtgagcaaa aacaggaagg caaaatgccg caaaaaaggg aataagggcg acacggaaat   3840
gttgaatact catactcttc ctttttcaat attattgaag catttatcag ggttattgtc   3900
tcatgagcgg atacatattt gaatgtattt agaaaaataa acagcgatcg cagctagctc   3960
gtcgtgttca ggaactgttc gatggttcgg agagagtcgc cgcccagaac atacgcgcac   4020
cgatgtcagc agacagcctt attacaagta tattcaagca agtatatccg tagggtgcgg   4080
gtgatttgga tctaaggttc gtactcaaca ctcacgagca gcttgcctat gttacatcct   4140
tttatcagac ataacataat tggagtttac ttacacacgg ggtgtacctg tatgagcacc   4200
acctacaatt gtagcactgg tacttgtaca aagaatttat tcgtacgaat cacagggacg   4260
gccgccctca ccgaaccagc gaatacctca gcggtcccct gcagtgactc aacaaagcga   4320
tatgaacatc ttgcgatggt atcctgctga tagtttttac tgtacaaaca cctgtgtagc   4380
tccttctagc atttttaagt tattcacacc tcaaggggag ggataaatta aataaattcc   4440
aaaagcgaag atcgagaaac taaattaaaa ttccaaaaac gaagttggaa cacaaccccc   4500
cgaaaaaaaa caacaaacaa aaaacccaac aaaataaaca aaaacaaaat aaatatataa   4560
ctaccagtat ctgactaaaa gttcaaatac tcgtacttac aacaaataga aatgagccgg   4620
ccaaaattct gcagaaaaaa atttcaaaca agtactggta taattaaatt aaaaaacaca   4680
tcaaagtatc ataacgttag ttattttatt ttatttaata aaagaaaaca acaagatggg   4740
ctcaaaactt tcaacttata cgatacatac caaataacaa tttagtattt atctaagtgc   4800
ttttcgtaga taatggaata caaatggata tccagagtat acacatggat agtatacact   4860
gacacgacaa ttctgtatct ctttatgtta actactgtga ggcattaaat agagcttgat   4920
atataaaatg ttacatttca cagtctgaac ttttgcagat tacctaattt ggtaagatat   4980
taattatgaa ctgaaagttg atggcggccg catagcttca aaatgtttct actccttttt   5040
tactcttcca gattttctcg gactccgcgc atcgccgtac cacttcaaaa cacccaagca   5100
cagcatacta aatttcccct ctttcttcct ctagggtgtc gttaattacc cgtactaaag   5160
gtttggaaaa gaaaaaagag accgcctcgt ttctttttct tcgtcgaaaa aggcaataaa   5220
aatttttatc acgtttcttt ttcttgaaaa tttttttttt tgattttttt ctctttcgat   5280
gacctcccat tgatatttaa gttaataaac ggtcttcaat ttctcaagtt tcagtttcat   5340
ttttcttgtt ctattacaac tttttttact tcttgctcat tagaaagaaa gcatagcaat   5400
ctaatctaag ttttaattac aaaatggacg caatggtaga aacaaataga cacttcatag   5460
```

```
atgccgaccc ttacccttgg ccttacaacg gtgccttgag acctgataac acagccttga   5520
ttataatcga tatgcaaacc gacttttgtg gtaaaggtgg ttatgtcgat catatgggtt   5580
acgacttatc attggtacaa gccccaatcg aacctattaa aagagtttta gctgcaatga   5640
gagctaaggg ttatcatatt atacacacaa gagaaggtca cagaccagat ttggctgact   5700
tacctgcaaa caagagatgg agatctcaaa gaataggtgc tggtatcggt gacccaggtc   5760
cttgtggtag aattttgacc agaggtgaac caggttggga tatcattcca gaattgtacc   5820
ctatagaagg tgaaactatc atcgataaac ctggtaaagg tagtttttgc gcaacagact   5880
tagaattggt tttgaaccaa aagagaatcg aaaacatcat cttgaccggt atcactacag   5940
atgtttgtgt ctctaccact atgagagaag caaacgatag aggttacgaa tgcttgttgt   6000
tggaagattg ttgcggtgcc actgactacg gtaaccattt ggccgctatt aaaatggtca   6060
agatgcaagg tggtgtattc ggttctgttt caaattccgc agccttggtt gaagcattac   6120
cataaacagg ccccttttcc tttgtcgata tcatgtaatt agttatgtca cgcttacatt   6180
cacgccctcc tcccacatcc gctctaaccg aaaaggaagg agttagacaa cctgaagtct   6240
aggtccctat ttattttttt taatagttat gttagtatta agaacgttat ttatatttca   6300
aatttttctt ttttttctgt acaaacgcgt gtacgcatgt aacattatac tgaaaacctt   6360
gcttgagaag gttttgggac gctcgaaggc tttaatttgc gggtaataac tgatataatt   6420
aaattgaagc tctaatttgt gagtttagta tacatgcatt tacttataat acagtttttt   6480
agttttgctg gccgcatctt ctcaaatatg cttcccagcc tgcttttctg taacgttcac   6540
cctctacctt agcatccctt ccctttgcaa atagtcctct tccaacaata ataatgtcag   6600
atcctgtaga gaccacatca tccacggttc tatactgttg acccaatgcg tctcccttgt   6660
catctaaacc cacaccgggt gtcataatca accaatcgta accttcatct cttccaccca   6720
tgtctctttg agcaataaag ccgataacaa aatctttgtc gctcttcgca atgtcaacag   6780
tacccttagt atattctcca gtagctaggg agcccttgca tgacaattct gctaacatca   6840
aaaggcctct aggttccttt gttacttctt ccgccgcctg cttcaaaccg ctaacaatac   6900
ctgggcccac cacaccgtgt gcattcgtaa tgtctgccca ttctgctatt ctgtatacac   6960
ccgcagagta ctgcaatttg actgtattac caatgtcagc aaattttctg tcttcgaaga   7020
gtaaaaaatt gtacttggcg gataatgcct ttagcggctt aactgtgccc tccatggaaa   7080
aatcagtcaa gatatccaca tgtgttttta gtaaacaaat tttgggacct aatgcttcaa   7140
ctaactccag taattccttg gtggtacgaa catccaatga agcacacaag tttgtttgct   7200
tttcgtgcat gatattaaat agcttggcag caacaggact aggatgagta gcagcacgtt   7260
ccttatatgt agctttcgac atgatttatc ttcgtttcct gcaggttttt gttctgtgca   7320
gttgggttaa gaatactggg caatttcatg tttcttcaac accacatatg cgtatatata   7380
ccaatctaag tctgtgctcc ttccttcgtt cttccttctg ctcggagatt accgaatcaa   7440
agctagctta tcgatgataa gctgtcaaag atgagaatta attccacgga ctatagacta   7500
tactagatac tccgtctact gtacgataca cttccgctca ggtccttgtc ctttaacgag   7560
gccttaccac tcttttgtta ctctattgat ccagctcagc aaaggcagtg tgatctaaga   7620
ttctatcttc gcgatgtagt aaaactagct agaccgagaa agagactaga aatgcaaaag   7680
gcacttctac aatggctgcc atcattatta tccgatgtga cgctgcagct tctcaatgat   7740
attcgaatac gctttgagga gatacagcct aatatccgac aaactgtttt acagatttac   7800
```

```
gatcgtactt gttacccatc attgaatttt gaacatccga acctgggagt tttccctgaa   7860

acagatagta tatttgaacc tgtataataa tatatagtct agcgctttac ggaagacaat   7920

gtatgtattt cggttcctgg agaaactatt gcatctattg cataggtaat cttgcacgtc   7980

gcatccccgg ttcattttct gcgtttccat cttgcacttc aatagcatat ctttgttaac   8040

gaagcatctg tgcttcattt tgtagaacaa aaatgcaacg cgagagcgct aatttttcaa   8100

acaaagaatc tgagctgcat ttttacagaa cagaaatgca acgcgaaagc gctattttac   8160

caacgaagaa tctgtgcttc atttttgtaa aacaaaaatg caacgcgacg agagcgctaa   8220

tttttcaaac aaagaatctg agctgcattt ttacagaaca gaaatgcaac gcgagagcgc   8280

tattttacca acaaagaatc tatacttctt ttttgttcta caaaaatgca tcccgagagc   8340

gctatttttc taacaaagca tcttagatta cttttttttct cctttgtgcg ctctataatg   8400

cagtctcttg ataacttttt gcactgtagg tccgttaagg ttagaagaag gctactttgg   8460

tgtctatttt ctcttccata aaaaaagcct gactccactt cccgcgttta ctgattacta   8520

gcgaagctgc gggtgcattt tttcaagata aaggcatccc cgattatatt ctataccgat   8580

gtggattgcg catactttgt gaacagaaag tgatagcgtt gatgattctt cattggtcag   8640

aaaattatga acggtttctt ctattttgtc tctatatact acgtatagga aatgtttaca   8700

ttttcgtatt gttttcgatt cactctatga atagttctta ctacaatttt tttgtctaaa   8760

gagtaatact agagataaac ataaaaaatg tagaggtcga gtttagatgc aagttcaagg   8820

agcgaaaggt ggatgggtag gttatatagg gatatagcac agagatatat agcaaagaga   8880

tacttttgag caat                                                     8894
```

<210> SEQ ID NO 51
<211> LENGTH: 8395
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 51

```
gtttgtggaa gcggtattcg caatttaatt aaagctggtg acaattaatc atcggctcgt     60

ataatgtgtg gaattgaatc gatataagga ggttaatcat atgtcaatgg aaacccatag    120

ttatgtagac gtcgcaattc gtaacgcgcg tcttgccgat acggagggaa ttgtcgatat    180

tcttattcac gatgggcgca ttgcgtccat cgtgaagtcg acaaaaacaa aaggatcggt    240

ggagatcgat gctcatgagg gtctggtcac ttccggcctg gtagagcctc acatccatct    300

cgataaggcc ctgacggcag atcgggttcc cgcaggaagc attggcgacc ttcgaacgcg    360

acgaggcctt gagatggcaa ttcgggccac ccgtgatatc aagcgtacgt tcacggttga    420

agatgttcga gaacgggcca tacgtgcggc cctgatggca tcccgtgcgg gaaccaccgc    480

attgcggaca cacgtcgatg tcgacccgat tgtcggcctc gcaggtatcc gtggtgtcct    540

tgaggcgcgt gaagtctgcg cgggattgat cgatatccag atcgtcgcct tccctcagga    600

gggactcttc tgctctgcgg gggccgtgga cctcatgcgg gaggcgatca aactgggcgc    660

ggatgccgtc ggcggcgcac ccgcgctgga tgatcgcccg caggaccatg tccgagccgt    720

ttttgacctt gctgctgagt tcggcctgcc cgtagacatg cacgtcgatg agtccgaccg    780

gcgggaagac tttacgcttc cctttgtgat tgaagctgcc cgtgaacggc gtgtgcccaa    840

tgtgaccgtc gcgcacatca gctcgctgtc cgtacagacg gatgacgtag cacggtcgac    900
```

```
cattgccgcc cttgcggacg ccgatgttaa tgtcgtggtt aatccgatca ttgtcaaaat    960
tacgcggctg agtgaattac tcgatgccgg agtctccgta atgtttggct cggacaacct   1020
gcgggatccg ttctatccgc tcggagcggc gaatcccctt ggatcagcca tttttgcctg   1080
tcaaattgcc gcgctgggaa caccgcaaga tctcagacgg gtattcgatg cggtcaccat   1140
caacgctgcc cgcatgctgg gattcccctc acttttaggc gtcgtggaag gggcagtcgc   1200
ggatctcgca gtattcccat cggcgacgcc cgaggaggtt gttctggatc aacagtctcc   1260
gctcttcgta ctcaagggcg gacgtgtcgt tgccatgcga ttggccgctg gatcaacgtc   1320
gttccgcgac tactcatgag gaaatccatt atgatgtcag gagaacacac gttaaaagcg   1380
gtacgaggca gttttattga tgtcacccgt acgatcgata acccggaaga gattgcctct   1440
gcgctgcggt ttattgagga tggtttatta ctcattaaac agggaaaagt ggaatggttt   1500
ggcgaatggg aaaacggaaa gcatcaaatt cctgacacca ttcgcgtgcg cgactatcgc   1560
ggcaaactga tagtaccggg ctttgtcgat acacatatcc attatccgca aagtgaaatg   1620
gtgggggcct atggtgagca attgctggag tggttgaata aacacacctt ccctactgaa   1680
cgtcgttatg aggatttaga gtacgcccgc gaaatgtcgg cgttcttcat caagcagctt   1740
ttacgtaacg gaaccaccac ggcgctggtg tttggcactg ttcatccgca atctgttgat   1800
gcgctgtttg aagccgccag tcatatcaat atgcgtatga ttgccggtaa ggtgatgatg   1860
gaccgcaacg caccggatta tctgctcgac actgccgaaa gcagctatca ccaaagcaaa   1920
gaactgatcg aacgctggca caaaaatggt cgtctgctat atgcgattac gccacgcttc   1980
gccccgacct catctcctga acagatggcg atggcgcaac gcctgaaaga agaatatccg   2040
gatacgtggg tacataccca tctctgtgaa aacaaagatg aaattgcctg ggtgaaatcg   2100
ctttatcctg accatgatgg ttatctggat gtttaccatc agtacggcct gaccggtaaa   2160
aactgtgtct ttgctcactg cgtccatctc gaagaaaaag agtgggatcg tctcagcgaa   2220
accaaatcca gcattgcttt ctgtccgacc tccaaccttt acctcggcag cggcttattc   2280
aacttgaaaa aagcatggca gaagaaagtt aaagtgggca tgggaacgga tatcggtgcc   2340
ggaaccactt tcaacatgct gcaaacgctg aacgaagcct acaaagtatt gcaattacaa   2400
ggctatcgcc tctcggcata tgaagcgttt tacctggcca cgctcggcgg agcgaaatct   2460
ctgggccttg acgatttgat tggcaacttt ttacctggca aagaggctga tttcgtggtg   2520
atggaaccca ccgccactcc gctacagcag ctgcgctatg acaactctgt ttctttagtc   2580
gacaaattgt tcgtgatgat gacgttgggc gatgaccgtt cgatctaccg cacctacgtt   2640
gatggtcgtc tggtgtacga acgcaactaa ggaacgacca tgcaaacgct cagcatccag   2700
cacggtaccc tcgtcacgat ggatcagtac cgcagagtcc ttggggatag ctgggttcac   2760
gtgcaggatg gacggatcgt cgcgctcgga gtgcacgccg agtcggtgcc tccgccagcg   2820
gatcgggtga tcgatgcacg cggcaaggtc gtgttacccg gtttcatcaa tgcccacacc   2880
catgtgaacc agatcctcct gcgcggaggg ccctcgcacg ggcgtcaact ctatgactgg   2940
ctgttcaacg ttttgtatcc gggacaaaag gcgatgagac cggaggacgt agcggtggcg   3000
gtgaggttgt attgtgcgga agctgtgcgc agcgggatta cgacgatcaa cgacaacgcc   3060
gattcggcca tctacccagg caacatcgag gccgcgatgg cggtctatgg tgaggtgggt   3120
gtgagggtcg tctacgcccg catgttcttt gatcggatgg acgggcgcat tcaagggtat   3180
gtggacgcct tgaaggctcg ctctccccaa gtcgaactgt gctcgatcat ggaggaaacg   3240
gctgtggcca aagatcggat cacagccctg tcagatcagt atcatggcac ggcaggaggt   3300
```

```
cgtatatcag tttggcccgc tcctgccatt accccggcgg tgacagttga aggaatgcga   3360
tgggcacaag ccttcgcccg tgatcgggcg gtaatgtgga cgcttcacat ggcggagagc   3420
gatcatgatg agcggcttca ttggatgagt cccgccgagt acatggagtg ttacggactc   3480
ttggatgagc gtctgcaggt cgcgcattgc gtgtactttg accggaagga tgttcggctg   3540
ctgcaccgcc acaatgtgaa ggtcgcgtcg caggttgtga gcaatgccta cctcggctca   3600
ggggtggccc ccgtgccaga gatggtggag cgcggcatgg ccgtgggcat tggaacagat   3660
gacgggaatt gtaatgactc cgtaaacatg atcggagaca tgaagtttat ggcccatatt   3720
caccgcgcgg tgcatcggga tgcggacgtg ctgaccccag agaagattct tgaaatggcg   3780
acgatcgatg gggcgcgttc gttgggaatg gaccacgaga ttggttccat cgaaaccggc   3840
aagcgcgcgg accttatcct gcttgacctg cgtcaccctc agacgactcc tcaccatcat   3900
ttggcggcca cgatcgtgtt tcaggcttac ggcaatgagg tggacactgt cctgattgac   3960
ggaaacgttg tgatggagaa ccgccgcttg agctttcttc cccctgaacg tgagttggcg   4020
ttccttgagg aagcgcagag ccgcgccaca gctattttgc agcgggcgaa catggtggct   4080
aacccagctt ggcgcagcct ctagcctcaa aatatatttt ccctctatct tctcgttgcg   4140
cttaatttga ctaattctca ttagcgaggc gcgcctttcc ataggctccg ccccccctgac   4200
gagcatcaca aaaatcgacg ctcaagtcag aggtggcgaa acccgacagg actataaaga   4260
taccaggcgt ttccccctgg aagctccctc gtgcgctctc ctgttccgac cctgccgctt   4320
accggatacc tgtccgcctt tctcccttcg ggaagcgtgg cgctttctca tagctcacgc   4380
tgtaggtatc tcagttcggt gtaggtcgtt cgctccaagc tgggctgtgt gcacgaaccc   4440
cccgttcagc ccgaccgctg cgccttatcc ggtaactatc gtcttgagtc caacccggta   4500
agacacgact tatcgccact ggcagcagcc actggtaaca ggattagcag agcgaggtat   4560
gtaggcggtg ctacagagtt cttgaagtgg tggcctaact acggctacac tagaagaaca   4620
gtatttggta tctgcgctct gctgaagcca gttaccttcg gaaaaagagt tggtagctct   4680
tgatccggca aacaaaccac cgctggtagc ggtggttttt ttgtttgcaa gcagcagatt   4740
acgcgcagaa aaaaaggatc tcaagaagat cctttgatct tttctacggg gtctgacgct   4800
cagtggaacg aaaactcacg ttaagggatt ttggtcatga gattatcaaa aaggatcttc   4860
acctagatcc ttttaaatta aaaatgaagt tttaaatcaa tctaaagtat atatgagtaa   4920
acttggtctg acagttacca atgcttaatc agtgaggcac ctatctcagc gatctgtcta   4980
tttcgttcat ccatagttgc ctgactcccc gtcgtgtaga taactacgat acgggagggc   5040
ttaccatctg gccccagtgc tgcaatgata ccgcgagacc cacgctcacc ggctccagat   5100
ttatcagcaa taaaccagcc agccggaagg gccgagcgca gaagtggtcc tgcaacttta   5160
tccgcctcca tccagtctat taattgttgc cgggaagcta gagtaagtag ttcgccagtt   5220
aatagtttgc gcaacgttgt tgccattgct acaggcatcg tggtgtcacg ctcgtcgttt   5280
ggtatggctt cattcagctc cggttcccaa cgatcaaggc gagttacatg atcccccatg   5340
ttgtgcaaaa aagcggttag ctccttcggt cctccgatcg ttgtcagaag taagttggcc   5400
gcagtgttat cactcatggt tatggcagca ctgcataatt ctcttactgt catgccatcc   5460
gtaagatgct tttctgtgac tggtgagtac tcaaccaagt cattctgaga atagtgtatg   5520
cggcgaccga gttgctcttg cccggcgtca atacgggata ataccgcgcc acatagcaga   5580
actttaaaag tgctcatcat tggaaaacgt tcttcggggc gaaaactctc aaggatctta   5640
```

-continued

```
ccgctgttga gatccagttc gatgtaaccc actcgtgcac ccaactgatc ttcagcatct   5700
tttactttca ccagcgtttc tgggtgagca aaaacaggaa ggcaaaatgc cgcaaaaaag   5760
ggaataaggg cgacacggaa atgttgaata ctcatactct tcctttttca atattattga   5820
agcatttatc agggttattg tctcatgagc ggatacatat ttgaatgtat ttagaaaaat   5880
aaacagcgat cgcgcggccg cgggtaataa ctgatataat taaattgaag ctctaatttg   5940
tgagtttagt atacatgcat ttacttataa tacagttttt tagttttgct ggccgcatct   6000
tctcaaatat gcttcccagc ctgcttttct gtaacgttca ccctctacct tagcatccct   6060
tccctttgca aatagtcctc ttccaacaat aataatgtca gatcctgtag agaccacatc   6120
atccacggtt ctatactgtt gacccaatgc gtctcccttg tcatctaaac ccacaccggg   6180
tgtcataatc aaccaatcgt aaccttcatc tcttccaccc atgtctcttt gagcaataaa   6240
gccgataaca aaatctttgt cgctcttcgc aatgtcaaca gtacccttag tatattctcc   6300
agtagctagg gagcccttgc atgacaattc tgctaacatc aaaaggcctc taggttcctt   6360
tgttacttct tccgccgcct gcttcaaacc gctaacaata cctgggccca ccacaccgtg   6420
tgcattcgta atgtctgccc attctgctat tctgtataca cccgcagagt actgcaattt   6480
gactgtatta ccaatgtcag caaattttct gtcttcgaag agtaaaaaat tgtacttggc   6540
ggataatgcc tttagcggct taactgtgcc ctccatggaa aaatcagtca agatatccac   6600
atgtgttttt agtaaacaaa ttttgggacc taatgcttca actaactcca gtaattcctt   6660
ggtggtacga acatccaatg aagcacacaa gtttgtttgc ttttcgtgca tgatattaaa   6720
tagcttggca gcaacaggac taggatgagt agcagcacgt tccttatatg tagctttcga   6780
catgatttat cttcgtttcc tgcaggtttt tgttctgtgc agttgggtta agaatactgg   6840
gcaatttcat gtttcttcaa caccacatat gcgtatatat accaatctaa gtctgtgctc   6900
cttccttcgt tcttccttct gctcggagat taccgaatca aagctagctt atcgatgata   6960
agctgtcaaa gatgagaatt aattccacgg actatagact atactagata ctccgtctac   7020
tgtacgatac acttccgctc aggtccttgt cctttaacga ggccttacca ctcttttgtt   7080
actctattga tccagctcag caaaggcagt gtgatctaag attctatctt cgcgatgtag   7140
taaaactagc tagaccgaga aagagactag aaatgcaaaa ggcacttcta caatggctgc   7200
catcattatt atccgatgtg acgctgcagc ttctcaatga tattcgaata cgctttgagg   7260
agatacagcc taatatccga caaactgttt tacagattta cgatcgtact tgttacccat   7320
cattgaattt tgaacatccg aacctgggag ttttccctga aacagatagt atatttgaac   7380
ctgtataata atatatagtc tagcgcttta cggaagacaa tgtatgtatt tcggttcctg   7440
gagaaactat tgcatctatt gcataggtaa tcttgcacgt cgcatccccg gttcattttc   7500
tgcgtttcca tcttgcactt caatagcata tctttgttaa cgaagcatct gtgcttcatt   7560
ttgtagaaca aaaatgcaac gcgagagcgc taatttttca aacaaagaat ctgagctgca   7620
tttttacaga acagaaatgc aacgcgaaag cgctatttta ccaacgaaga atctgtgctt   7680
catttttgta aaacaaaaat gcaacgcgac gagagcgcta atttttcaaa caaagaatct   7740
gagctgcatt tttacagaac agaaatgcaa cgcgagagcg ctattttacc aacaaagaat   7800
ctatacttct tttttgttct acaaaaatgc atcccgagag cgctattttt ctaacaaagc   7860
atcttagatt actttttttc tcctttgtgc gctctataat gcagtctctt gataactttt   7920
tgcactgtag gtccgttaag gttagaagaa ggctactttg gtgtctattt tctcttccat   7980
aaaaaaagcc tgactccact tcccgcgttt actgattact agcgaagctg cgggtgcatt   8040
```

```
ttttcaagat aaaggcatcc ccgattatat tctataccga tgtggattgc gcatactttg   8100

tgaacagaaa gtgatagcgt tgatgattct tcattggtca gaaaattatg aacggtttct   8160

tctattttgt ctctatatac tacgtatagg aaatgtttac attttcgtat tgttttcgat   8220

tcactctatg aatagttctt actacaattt ttttgtctaa agagtaatac tagagataaa   8280

cataaaaaat gtagaggtcg agtttagatg caagttcaag gagcgaaagg tggatgggta   8340

ggttatatag ggatatagca cagagatata tagcaaagag atacttttga gcaat        8395
```

<210> SEQ ID NO 52
<211> LENGTH: 12133
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 52

```
gtttgtggaa gcggtattcg caatttaatt aaagctggtg acaattaatc atcggctcgt     60

ataatgtgtg gaattgaatc gatataagga ggttaatcat atgcaagcgc aagtttttcg    120

agttccaatg agtaatccag ccgatgttag tggcgtagcc aagctcatcg atgagggagt    180

gatccgtgcc gaagaggtcg tctgcgttct cggcaagacc gaaggcaacg gctgtgtcaa    240

tgacttcacg cgtggctaca ccaccctcgc gttcaaggtc tacttctccg agaaactggg    300

cgtgtcccgg caagaggtcg gcgagcgcat cgctttcatc atgtccggcg gtaccgaagg    360

cgtcatggcg cctcactgca ccatcttcac cgtgcagaag acggacaaca agcagaagac    420

cgccgctgaa ggcaagcgac ttgccgttca gcagatcttt acccgcgagt tcctgccgga    480

ggagatcggc cgcatgccgc aggtcacgga aacagccgac gctgttcgcc gcgccatgcg    540

cgaagccggc atcgcggatg catccgatgt ccacttcgtt caggtcaagt gcccactgct    600

cactgccggc cgcatgcatg acgctgtcga gcgcgggcat acggttgcca ccgaagatac    660

ctatgagtcc atgggctact cccgcggcgc atccgcgctt ggtatcgccc tggccctcgg    720

ggaagtcgag aaggccaacc tcagtgatga agttattacc gcagactaca gtctctactc    780

ctcggttgcc tcaacttcgg cgggtatcga gttgatgaac aacgagatca tcgtcatggg    840

caacagccgc gcatggggtg gtgacctcgt catcggccac gccgagatga aggacgccat    900

cgacggtgca gcggtccggc aggccctgcg cgacgtcggg tgctgcgaga acgacctgcc    960

gaccgtcgac gagctcggcc gcgtggtcaa tgtatttgcc aaggctgaag cctccccgga   1020

cggtgaggtt cgtaaccgcc gccacacgat gctggacgat tcggacatta acagcacgcg   1080

ccatgcgcga gcggtcgtca atgcagttat cgcttcgatc gtgggagatc ccatggttta   1140

tgtctccggc ggctccgagc atcagggccc cgccggtggc ggtcccgttg cagttatcgc   1200

gcgcacagct taaggaaatc cattatgata tactcaacag tcaacgctaa tccttacgct   1260

tggccttacg atggttcaat agaccctgct cacaccgctt taatcttaat cgattggcaa   1320

atagactttt gtggtccagg tggttatgtc gattccatgg gttacgactt atccttgact   1380

agaagtggtt tagaacctac agcaagagta ttggctgcag ccagagatac tggtatgaca   1440

gttatccata ctagagaagg tcacagacca gatttggctg acttgccacc taataagaga   1500

tggagatctg catcagccgg tgctgaaatc ggttcagttg gtccatgtgg tagaatttta   1560

gtcagaggtg aacctggttg ggaaatagta ccagaagttg cacctagaga aggtgaacca   1620

attatagata aacctggtaa aggtgctttc tacgcaacag atttggactt gttgttgaga   1680
```

```
acaagaggta tcacccattt gattttgacc ggtataacta cagatgtttg cgtccacacc   1740
actatgagag aagccaacga tagaggttac gaatgtttaa ttttgtctga ttgcaccggt   1800
gctactgaca gaaagcatca cgaagctgca ttatctatgg tcaccatgca aggtggtgta   1860
ttcggtgcaa ctgcccattc agatgactta ttggccgctt tgggtacaac cgttccagca   1920
gccgctggtc ctagagctag aacagaataa ggaacgacca tgacagttag ttccgataca   1980
actgctgaaa tatcgttagg ttggtcaatc caagactgga ttgatttcca caagtcatca   2040
agctcccagg cttcactaag gcttcttgaa tcactactag actctcaaaa tgttgcgcca   2100
gtcgataatg cgtggatatc gctaatttca aaggaaaatt tactgcacca attccaaatt   2160
ttaaagagca gagaaaataa agaaactcta cctctctacg gtgtccctat tgctgttaag   2220
gacaacatcg acgttagagg tctacccacc accgctgcat gtccatcctt tgcatatgag   2280
ccttccaaag actctaaagt agtagaacta ctaagaaatg caggtgcgat aatcgtgggt   2340
aagacaaact tggaccaatt tgccacagga ttagtcggca cacggtctcc atatgggaaa   2400
acaccttgcg cttttagcaa agagcatgta tctggtggtt cctccgctgg gtcagcatcg   2460
gtggtcgcca gaggtatcgt accaattgca ttgggtactg atacagcagg ttctggtaga   2520
gtcccagccg ccttgaacaa cctgattggc ctaaagccaa caaagggcgt cttttcctgt   2580
caaggtgtag ttcccgcttg taaatcttta gactgcgtct ccatctttgc attaaaccta   2640
agtgatgctg aacgctgctt ccgcatcatg tgccagccag atcctgataa tgatgaatat   2700
tctagaccct atgtttccaa ccctttgaaa aaattttcaa gcaatgtaac gattgctatt   2760
cctaaaaata tcccatggta tggtgaaacc aagaatcctg tactgttttc caatgctgtc   2820
gaaaatctat caagaacggg cgctaacgtc atagaaattg attttgagcc tcttttagag   2880
ttagctcgct gtttatacga aggtacttgg gtggccgagc gttatcaagc tattcaatcg   2940
tttttggaca gtaaaccacc aaaggaatct ttggacccta ctgttatttc aattatagaa   3000
ggggccaaga aatacagtgc agtagactgc ttcagttttg aatacaaaag acaaggcatc   3060
ttgcaaaaag tgagacgact tctcgaatca gtcgatgtat tgtgtgtgcc cacatgtcct   3120
ttaaatccta ctatgcaaca agttgcggat gaaccagtcc tagtcaattc aagacaaggc   3180
acatggacta attttgtcaa cttggcagat ttggcagccc ttgctgttcc cgcagggttc   3240
cgagacgatg gtttgccaaa tggtattact ttaatcggta aaaaattcac agattacgca   3300
ctattagagt tggctaaccg ctatttccaa aatatattcc ccaacggttc cagaacatac   3360
ggtactttta cctcttcttc agtaaagcca gcaaacgatc aattagtggg accagactat   3420
gacccatcta cgtccataaa attggctgtt gtcggtgcac atcttaaggg tctgcctcta   3480
cattggcaat tggaaaaggt caatgcaaca tatttatgta caacaaaaac atcaaaagct   3540
taccagcttt ttgctttgcc caaaaatgga ccagttttaa aacctggttt gagaagagtt   3600
caagatagca atggctctca aatcgaatta gaagtgtaca gtgttccaaa agaactgttc   3660
ggtgctttta tttccatggt tcctgaacca ttaggaatag gttcagtgga gttagaatct   3720
ggtgaatgga tcaaatcctt tatttgtgaa gaatctggtt acaaagccaa aggtacagtt   3780
gatatcacaa agtatggtgg atttagagca tattttgaaa tgttgtaagg acacgataat   3840
gtcaatggaa acccatagtt atgtagacgt cgcaattcgt aacgcgcgtc ttgccgatac   3900
ggagggaatt gtcgatattc ttattcacga tgggcgcatt gcgtccatcg tgaagtcgac   3960
aaaaacaaaa ggatcggtgg agatcgatgc tcatgagggt ctggtcactt ccggcctggt   4020
```

```
agagcctcac atccatctcg ataaggccct gacggcagat cgggttcccg caggaagcat   4080
tggcgacctt cgaacgcgac gaggccttga gatggcaatt cgggccaccc gtgatatcaa   4140
gcgtacgttc acggttgaag atgttcgaga acgggccata cgtgcggccc tgatggcatc   4200
ccgtgcggga accaccgcat tgcggacaca cgtcgatgtc gacccgattg tcggcctcgc   4260
aggtatccgt ggtgtccttg aggcgcgtga agtctgcgcg ggattgatcg atatccagat   4320
cgtcgccttc cctcaggagg gactcttctg ctctgcgggg gccgtggacc tcatgcggga   4380
ggcgatcaaa ctgggcgcgg atgccgtcgg cggcgcaccc gcgctggatg atcgcccgca   4440
ggaccatgtc cgagccgttt ttgaccttgc tgctgagttc ggcctgcccg tagacatgca   4500
cgtcgatgag tccgaccggc gggaagactt tacgcttccc tttgtgattg aagctgcccg   4560
tgaacggcgt gtgcccaatg tgaccgtcgc gcacatcagc tcgctgtccg tacagacgga   4620
tgacgtagca cggtcgacca ttgccgccct tgcggacgcc gatgttaatg tcgtggttaa   4680
tccgatcatt gtcaaaatta cgcggctgag tgaattactc gatgccggag tctccgtaat   4740
gtttggctcg gacaacctgc gggatccgtt ctatccgctc ggagcggcga atccccttgg   4800
atcagccatt tttgcctgtc aaattgccgc gctgggaaca ccgcaagatc tcagacgggt   4860
attcgatgcg gtcaccatca acgctgcccg catgctggga ttcccctcac ttttaggcgt   4920
cgtggaaggg gcagtcgcgg atctcgcagt attcccatcg gcgacgcccg aggaggttgt   4980
tctggatcaa cagtctccgc tcttcgtact caagggcgga cgtgtcgttg ccatgcgatt   5040
ggccgctgga tcaacgtcgt tccgcgacta ctcatgagga aatccattat gatgtcagga   5100
gaacacacgt taaaagcggt acgaggcagt tttattgatg tcacccgtac gatcgataac   5160
ccggaagaga ttgcctctgc gctgcggttt attgaggatg gtttattact cattaaacag   5220
ggaaaagtgg aatggtttgg cgaatgggaa aacggaaagc atcaaattcc tgacaccatt   5280
cgcgtgcgcg actatcgcgg caaactgata gtaccgggct ttgtcgatac acatatccat   5340
tatccgcaaa gtgaaatggt gggggcctat ggtgagcaat tgctggagtg gttgaataaa   5400
cacaccttcc ctactgaacg tcgttatgag gatttagagt acgcccgcga aatgtcggcg   5460
ttcttcatca agcagctttt acgtaacgga accaccacgg cgctggtgtt tggcactgtt   5520
catccgcaat ctgttgatgc gctgtttgaa gccgccagtc atatcaatat gcgtatgatt   5580
gccggtaagg tgatgatgga ccgcaacgca ccggattatc tgctcgacac tgccgaaagc   5640
agctatcacc aaagcaaaga actgatcgaa cgctggcaca aaaatggtcg tctgctatat   5700
gcgattacgc cacgcttcgc ccgacctca tctcctgaac agatggcgat ggcgcaacgc   5760
ctgaaagaag aatatccgga tacgtgggta catacccatc tctgtgaaaa caaagatgaa   5820
attgcctggg tgaaatcgct ttatcctgac catgatggtt atctggatgt ttaccatcag   5880
tacggcctga ccggtaaaaa ctgtgtcttt gctcactgcg tccatctcga agaaaaagag   5940
tgggatcgtc tcagcgaaac caaatccagc attgctttct gtccgacctc caacctttac   6000
ctcggcagcg gcttattcaa cttgaaaaaa gcatggcaga agaaagttaa agtgggcatg   6060
ggaacggata tcggtgccgg aaccactttc aacatgctgc aaacgctgaa cgaagcctac   6120
aaagtattgc aattacaagg ctatcgcctc tcggcatatg aagcgtttta cctggccacg   6180
ctcggcggag cgaaatctct gggccttgac gatttgattg gcaacttttt acctggcaaa   6240
gaggctgatt tcgtggtgat ggaacccacc gccactccgc tacagcagct gcgctatgac   6300
aactctgttt ctttagtcga caaattgttc gtgatgatga cgttgggcga tgaccgttcg   6360
atctaccgca cctacgttga tggtcgtctg gtgtacgaac gcaactaagg aacgaccatg   6420
```

```
caaacgctca gcatccagca cggtaccctc gtcacgatgg atcagtaccg cagagtcctt   6480
ggggatagct gggttcacgt gcaggatgga cggatcgtcg cgctcggagt gcacgccgag   6540
tcggtgcctc cgccagcgga tcgggtgatc gatgcacgcg gcaaggtcgt gttacccggt   6600
ttcatcaatg cccacaccca tgtgaaccag atcctcctgc gcggagggcc ctcgcacggg   6660
cgtcaactct atgactggct gttcaacgtt ttgtatccgg gacaaaaggc gatgagaccg   6720
gaggacgtag cggtggcggt gaggttgtat tgtgcggaag ctgtgcgcag cgggattacg   6780
acgatcaacg acaacgccga ttcggccatc tacccaggca acatcgaggc cgcgatggcg   6840
gtctatggtg aggtgggtgt gagggtcgtc tacgcccgca tgttctttga tcggatggac   6900
gggcgcattc aagggtatgt ggacgccttg aaggctcgct ctccccaagt cgaactgtgc   6960
tcgatcatgg aggaaacggc tgtggccaaa gatcggatca cagccctgtc agatcagtat   7020
catggcacgg caggaggtcg tatatcagtt tggcccgctc ctgccattac cccggcggtg   7080
acagttgaag gaatgcgatg ggcacaagcc ttcgcccgtg atcgggcggt aatgtggacg   7140
cttcacatgg cggagagcga tcatgatgag cggcttcatt ggatgagtcc cgccgagtac   7200
atggagtgtt acggactctt ggatgagcgt ctgcaggtcg cgcattgcgt gtactttgac   7260
cggaaggatg ttcggctgct gcaccgccac aatgtgaagg tcgcgtcgca ggttgtgagc   7320
aatgcctacc tcggctcagg ggtggccccc gtgccagaga tggtggagcg cggcatggcc   7380
gtgggcattg gaacagatga cgggaattgt aatgactccg taaacatgat cggagacatg   7440
aagtttatgg cccatattca ccgcgcggtg catcgggatg cggacgtgct gaccccagag   7500
aagattcttg aaatggcgac gatcgatggg gcgcgttcgt tgggaatgga ccacgagatt   7560
ggttccatcg aaaccggcaa gcgcgcggac cttatcctgc ttgacctgcg tcaccctcag   7620
acgactcctc accatcattt ggcggccacg atcgtgtttc aggcttacgg caatgaggtg   7680
gacactgtcc tgattgacgg aaacgttgtg atggagaacc gccgcttgag ctttcttccc   7740
cctgaacgtg agttggcgtt ccttgaggaa gcgcagagcc gcgccacagc tattttgcag   7800
cgggcgaaca tggtggctaa cccagcttgg cgcagcctct agcctcaaaa tatattttcc   7860
ctctatcttc tcgttgcgct taatttgact aattctcatt agcgaggcgc gcctttccat   7920
aggctccgcc cccctgacga gcatcacaaa aatcgacgct caagtcagag gtggcgaaac   7980
ccgacaggac tataaagata ccaggcgttt ccccctggaa gctccctcgt gcgctctcct   8040
gttccgaccc tgccgcttac cggatacctg tccgcctttc tcccttcggg aagcgtggcg   8100
ctttctcata gctcacgctg taggtatctc agttcggtgt aggtcgttcg ctccaagctg   8160
ggctgtgtgc acgaaccccc cgttcagccc gaccgctgcg ccttatccgg taactatcgt   8220
cttgagtcca acccggtaag acacgactta tcgccactgg cagcagccac tggtaacagg   8280
attagcagag cgaggtatgt aggcggtgct acagagttct tgaagtggtg gcctaactac   8340
ggctacacta gaagaacagt atttggtatc tgcgctctgc tgaagccagt taccttcgga   8400
aaaagagttg gtagctcttg atccggcaaa caaaccaccg ctggtagcgg tggttttttt   8460
gtttgcaagc agcagattac gcgcagaaaa aaaggatctc aagaagatcc tttgatcttt   8520
tctacggggt ctgacgctca gtggaacgaa aactcacgtt aagggatttt ggtcatgaga   8580
ttatcaaaaa ggatcttcac ctagatcctt ttaaattaaa aatgaagttt taaatcaatc   8640
taaagtatat atgagtaaac ttggtctgac agttaccaat gcttaatcag tgaggcacct   8700
atctcagcga tctgtctatt tcgttcatcc atagttgcct gactccccgt cgtgtagata   8760
```

```
actacgatac gggagggctt accatctggc cccagtgctg caatgatacc gcgagaccca   8820
cgctcaccgg ctccagattt atcagcaata aaccagccag ccggaagggc cgagcgcaga   8880
agtggtcctg caactttatc cgcctccatc cagtctatta attgttgccg ggaagctaga   8940
gtaagtagtt cgccagttaa tagtttgcgc aacgttgttg ccattgctac aggcatcgtg   9000
gtgtcacgct cgtcgtttgg tatggcttca ttcagctccg gttcccaacg atcaaggcga   9060
gttacatgat cccccatgtt gtgcaaaaaa gcggttagct ccttcggtcc tccgatcgtt   9120
gtcagaagta agttggccgc agtgttatca ctcatggtta tggcagcact gcataattct   9180
cttactgtca tgccatccgt aagatgcttt tctgtgactg gtgagtactc aaccaagtca   9240
ttctgagaat agtgtatgcg gcgaccgagt tgctcttgcc cggcgtcaat acgggataat   9300
accgcgccac atagcagaac tttaaaagtg ctcatcattg gaaaacgttc ttcggggcga   9360
aaactctcaa ggatcttacc gctgttgaga tccagttcga tgtaacccac tcgtgcaccc   9420
aactgatctt cagcatcttt tactttcacc agcgtttctg ggtgagcaaa aacaggaagg   9480
caaaatgccg caaaaaaggg aataagggcg acacggaaat gttgaatact catactcttc   9540
ctttttcaat attattgaag catttatcag ggttattgtc tcatgagcgg atacatattt   9600
gaatgtattt agaaaaataa acagcgatcg cgcggccgcg ggtaataact gatataatta   9660
aattgaagct ctaatttgtg agtttagtat acatgcattt acttataata cagtttttta   9720
gttttgctgg ccgcatcttc tcaaatatgc ttcccagcct gcttttctgt aacgttcacc   9780
ctctacctta gcatcccttc cctttgcaaa tagtcctctt ccaacaataa taatgtcaga   9840
tcctgtagag accacatcat ccacggttct atactgttga cccaatgcgt ctcccttgtc   9900
atctaaaccc acaccgggtg tcataatcaa ccaatcgtaa ccttcatctc ttccacccat   9960
gtctctttga gcaataaagc cgataacaaa atctttgtcg ctcttcgcaa tgtcaacagt  10020
acccttagta tattctccag tagctaggga gcccttgcat gacaattctg ctaacatcaa  10080
aaggcctcta ggttcctttg ttacttcttc cgccgcctgc ttcaaaccgc taacaatacc  10140
tgggcccacc acaccgtgtg cattcgtaat gtctgcccat tctgctattc tgtatacacc  10200
cgcagagtac tgcaatttga ctgtattacc aatgtcagca aattttctgt cttcgaagag  10260
taaaaaattg tacttggcgg ataatgcctt tagcggctta actgtgccct ccatggaaaa  10320
atcagtcaag atatccacat gtgtttttag taaacaaatt ttgggaccta atgcttcaac  10380
taactccagt aattccttgg tggtacgaac atccaatgaa gcacacaagt ttgtttgctt  10440
ttcgtgcatg atattaaata gcttggcagc aacaggacta ggatgagtag cagcacgttc  10500
cttatatgta gctttcgaca tgatttatct tcgtttcctg caggtttttg ttctgtgcag  10560
ttgggttaag aatactgggc aatttcatgt ttcttcaaca ccacatatgc gtatatatac  10620
caatctaagt ctgtgctcct tccttcgttc ttccttctgc tcggagatta ccgaatcaaa  10680
gctagcttat cgatgataag ctgtcaaaga tgagaattaa ttccacggac tatagactat  10740
actagatact ccgtctactg tacgatacac ttccgctcag gtccttgtcc tttaacgagg  10800
ccttaccact cttttgttac tctattgatc cagctcagca aaggcagtgt gatctaagat  10860
tctatcttcg cgatgtagta aaactagcta gaccgagaaa gagactagaa atgcaaaagg  10920
cacttctaca atggctgcca tcattattat ccgatgtgac gctgcagctt ctcaatgata  10980
ttcgaatacg ctttgaggag atacagccta atatccgaca aactgtttta cagatttacg  11040
atcgtacttg ttacccatca ttgaattttg aacatccgaa cctgggagtt ttccctgaaa  11100
cagatagtat atttgaacct gtataataat atatagtcta gcgctttacg gaagacaatg  11160
```

```
tatgtatttc ggttcctgga gaaactattg catctattgc ataggtaatc ttgcacgtcg  11220

catccccggt tcattttctg cgtttccatc ttgcacttca atagcatatc tttgttaacg  11280

aagcatctgt gcttcatttt gtagaacaaa aatgcaacgc gagagcgcta atttttcaaa  11340

caaagaatct gagctgcatt tttacagaac agaaatgcaa cgcgaaagcg ctattttacc  11400

aacgaagaat ctgtgcttca tttttgtaaa acaaaaatgc aacgcgacga gagcgctaat  11460

ttttcaaaca aagaatctga gctgcatttt tacagaacag aaatgcaacg cgagagcgct  11520

attttaccaa caaagaatct atacttcttt tttgttctac aaaaatgcat cccgagagcg  11580

ctatttttct aacaaagcat cttagattac ttttttttctc ctttgtgcgc tctataatgc  11640

agtctcttga taacttttttg cactgtaggt ccgttaaggt tagaagaagg ctactttggt  11700

gtctattttc tcttccataa aaaaagcctg actccacttc ccgcgtttac tgattactag  11760

cgaagctgcg ggtgcatttt ttcaagataa aggcatcccc gattatattc tataccgatg  11820

tggattgcgc atactttgtg aacagaaagt gatagcgttg atgattcttc attggtcaga  11880

aaattatgaa cggtttcttc tattttgtct ctatatacta cgtataggaa atgtttacat  11940

tttcgtattg ttttcgattc actctatgaa tagttcttac tacaattttt ttgtctaaag  12000

agtaatacta gagataaaca taaaaaatgt agaggtcgag tttagatgca agttcaagga  12060

gcgaaaggtg gatgggtagg ttatataggg atatagcaca gagatatata gcaaagagat  12120

acttttgagc aat                                                   12133
```

```
<210> SEQ ID NO 53
<211> LENGTH: 12112
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53

gtttgtggaa gcggtattcg caatttaatt aaagctggtg acaattaatc atcggctcgt     60

ataatgtgtg gaattgaatc gatataagga ggttaatcat atgtaccata tagatgtatt    120

cagaatccct tgccatagtc caggtgacac ttcaggttta gaagatttga tagaaacagg    180

tagagtcgct ccagcagata ttgttgctgt catgggtaaa acagagggta atggttgtgt    240

taacgactat acaagagaat acgccaccgc tatgttggct gcatgcttag gtagacattt    300

gcaattacca cctcacgaag ttgaaaagag agtagctttt gttatgtccg gtggtacaga    360

aggtgtattg tctccacatc acaccgtttt cgctagaaga ccagcaatag atgcccatag    420

acctgcaggt aaaagattga ctttaggtat cgcttttaca agagatttct tgcctgaaga    480

aattggtaga catgcacaaa taaccgaaac tgcaggtgcc gttaagagag ctatgagaga    540

tgctggtatc gcatcaatag atgacttaca tttcgtacag gttaagtgtc cattgttgac    600

tcctgcaaag atcgcttcag caagatccag aggttgcgct ccagtcacta cagatacata    660

tgaaagtatg ggttactcta gaggtgcctc agctttgggt attgcattag ccaccgaaga    720

agttccttct tcaatgttgg tcgatgaatc cgtattaaat gactggagtt tgtccagttc    780

tttagcttca gcatccgccg gtatagaatt ggaacataac gttgtcattg ccataggcat    840

gtccgaacaa gctacaagtg aattagttat cgcacacggt gtcatgtctg atgccattga    900

cgccgcttca gttagaagaa ctatagaatc tttgggtatc agatcagatg acgaaatgga    960

tagaatagtc aacgtattcg ctaaagcaga agcctctcca gacggtgtag ttagaggcat   1020
```

```
gagacatact atgttgagtg attctgacat caactctacc agacacgcta gagcagttac   1080
tggtgcagcc atagcttctg tcgtaggtca tggtatggtt tatgtctcag gtggtgccga   1140
acaccaaggt ccagctggtg gtggtccttt cgcagttatt gccagagctt aaggaaatcc   1200
attatgatat actcaacagt caacgctaat ccttacgctt ggccttacga tggttcaata   1260
gaccctgctc acaccgcttt aatcttaatc gattggcaaa tagacttttg tggtccaggt   1320
ggttatgtcg attccatggg ttacgactta tccttgacta gaagtggttt agaacctaca   1380
gcaagagtat tggctgcagc cagagatact ggtatgacag ttatccatac tagagaaggt   1440
cacagaccag atttggctga cttgccacct aataagagat ggagatctgc atcagccggt   1500
gctgaaatcg gttcagttgg tccatgtggt agaattttag tcagaggtga acctggttgg   1560
gaaatagtac cagaagttgc acctagagaa ggtgaaccaa ttatagataa acctggtaaa   1620
ggtgctttct acgcaacaga tttggacttg ttgttgagaa caagaggtat cacccatttg   1680
attttgaccg gtataactac agatgtttgc gtccacacca ctatgagaga agccaacgat   1740
agaggttacg aatgtttaat tttgtctgat tgcaccggtg ctactgacag aaagcatcac   1800
gaagctgcat tatctatggt caccatgcaa ggtggtgtat tcggtgcaac tgcccattca   1860
gatgacttat tggccgcttt gggtacaacc gttccagcag ccgctggtcc tagagctaga   1920
acagaataag gaacgaccat gacagttagt tccgatacaa ctgctgaaat atcgttaggt   1980
tggtcaatcc aagactggat tgatttccac aagtcatcaa gctcccaggc ttcactaagg   2040
cttcttgaat cactactaga ctctcaaaat gttgcgccag tcgataatgc gtggatatcg   2100
ctaatttcaa aggaaaattt actgcaccaa ttccaaattt taaagagcag agaaaataaa   2160
gaaactctac ctctctacgg tgtccctatt gctgttaagg acaacatcga cgttagaggt   2220
ctacccacca ccgctgcatg tccatccttt gcatatgagc cttccaaaga ctctaaagta   2280
gtagaactac taagaaatgc aggtgcgata atcgtgggta agacaaactt ggaccaattt   2340
gccacaggat tagtcggcac acggtctcca tatgggaaaa caccttgcgc ttttagcaaa   2400
gagcatgtat ctggtggttc ctccgctggg tcagcatcgg tggtcgccag aggtatcgta   2460
ccaattgcat tgggtactga tacagcaggt tctggtagag tcccagccgc cttgaacaac   2520
ctgattggcc taaagccaac aaagggcgtc ttttcctgtc aaggtgtagt tcccgcttgt   2580
aaatctttag actgcgtctc catctttgca ttaaacctaa gtgatgctga acgctgcttc   2640
cgcatcatgt gccagccaga tcctgataat gatgaatatt ctagacccta tgtttccaac   2700
cctttgaaaa aattttcaag caatgtaacg attgctattc ctaaaaatat cccatggtat   2760
ggtgaaacca agaatcctgt actgttttcc aatgctgtcg aaaatctatc aagaacgggc   2820
gctaacgtca tagaaattga ttttgagcct cttttagagt tagctcgctg tttatacgaa   2880
ggtacttggg tggccgagcg ttatcaagct attcaatcgt tttggacag taaaccacca    2940
aaggaatctt tggaccctac tgttatttca attatagaag ggccaagaa atacagtgca    3000
gtagactgct tcagttttga atacaaaaga caaggcatct tgcaaaaagt gagacgactt   3060
ctcgaatcag tcgatgtatt gtgtgtgccc acatgtcctt taaatcctac tatgcaacaa   3120
gttgcggatg aaccagtcct agtcaattca agacaaggca catggactaa ttttgtcaac   3180
ttggcagatt tggcagccct tgctgttccc gcagggttcc gagacgatgg tttgccaaat   3240
ggtattactt taatcggtaa aaaattcaca gattacgcac tattagagtt ggctaaccgc   3300
tatttccaaa atatattccc caacggttcc agaacatacg gtacttttac ctcttcttca   3360
```

-continued

```
gtaaagccag caaacgatca attagtggga ccagactatg acccatctac gtccataaaa   3420
ttggctgttg tcggtgcaca tcttaagggt ctgcctctac attggcaatt ggaaaaggtc   3480
aatgcaacat atttatgtac aacaaaaaca tcaaaagctt accagctttt tgctttgccc   3540
aaaaatggac cagttttaaa acctggtttg agaagagttc aagatagcaa tggctctcaa   3600
atcgaattag aagtgtacag tgttccaaaa gaactgttcg gtgcttttat ttccatggtt   3660
cctgaaccat taggaatagg ttcagtggag ttagaatctg gtgaatggat caaatccttt   3720
atttgtgaag aatctggtta caaagccaaa ggtacagttg atatcacaaa gtatggtgga   3780
tttagagcat attttgaaat gttgtaagga cacgataatg tcaatggaaa cccatagtta   3840
tgtagacgtc gcaattcgta acgcgcgtct tgccgatacg gagggaattg tcgatattct   3900
tattcacgat gggcgcattg cgtccatcgt gaagtcgaca aaaacaaaag gatcggtgga   3960
gatcgatgct catgagggtc tggtcacttc cggcctggta gagcctcaca tccatctcga   4020
taaggccctg acggcagatc gggttcccgc aggaagcatt ggcgaccttc gaacgcgacg   4080
aggccttgag atggcaattc gggccacccg tgatatcaag cgtacgttca cggttgaaga   4140
tgttcgagaa cgggccatac gtgcggccct gatggcatcc cgtgcgggaa ccaccgcatt   4200
gcggacacac gtcgatgtcg acccgattgt cggcctcgca ggtatccgtg gtgtccttga   4260
ggcgcgtgaa gtctgcgcgg gattgatcga tatccagatc gtcgccttcc ctcaggaggg   4320
actcttctgc tctgcggggg ccgtggacct catgcgggag gcgatcaaac tgggcgcgga   4380
tgccgtcggc ggcgcacccg cgctggatga tcgcccgcag gaccatgtcc gagccgtttt   4440
tgaccttgct gctgagttcg gcctgcccgt agacatgcac gtcgatgagt ccgaccggcg   4500
ggaagacttt acgcttccct ttgtgattga agctgcccgt gaacggcgtg tgcccaatgt   4560
gaccgtcgcg cacatcagct cgctgtccgt acagacggat gacgtagcac ggtcgaccat   4620
tgccgccctt gcggacgccg atgttaatgt cgtggttaat ccgatcattg tcaaaattac   4680
gcggctgagt gaattactcg atgccggagt ctccgtaatg tttggctcgg acaacctgcg   4740
ggatccgttc tatccgctcg gagcggcgaa tccccttgga tcagccattt ttgcctgtca   4800
aattgccgcg ctgggaacac cgcaagatct cagacgggta ttcgatgcgg tcaccatcaa   4860
cgctgcccgc atgctgggat tcccctcact tttaggcgtc gtggaagggg cagtcgcgga   4920
tctcgcagta ttcccatcgg cgacgcccga ggaggttgtt ctggatcaac agtctccgct   4980
cttcgtactc aagggcggac gtgtcgttgc catgcgattg gccgctggat caacgtcgtt   5040
ccgcgactac tcatgaggaa atccattatg atgtcaggag aacacacgtt aaaagcggta   5100
cgaggcagtt ttattgatgt cacccgtacg atcgataacc cggaagagat tgcctctgcg   5160
ctgcggttta ttgaggatgg tttattactc attaaacagg gaaaagtgga atggtttggc   5220
gaatgggaaa acggaaagca tcaaattcct gacaccattc gcgtgcgcga ctatcgcggc   5280
aaactgatag taccgggctt tgtcgataca catatccatt atccgcaaag tgaaatggtg   5340
ggggcctatg gtgagcaatt gctggagtgg ttgaataaac acaccttccc tactgaacgt   5400
cgttatgagg atttagagta cgcccgcgaa atgtcggcgt tcttcatcaa gcagctttta   5460
cgtaacggaa ccaccacggc gctggtgttt ggcactgttc atccgcaatc tgttgatgcg   5520
ctgtttgaag ccgccagtca tatcaatatg cgtatgattg ccggtaaggt gatgatggac   5580
cgcaacgcac cggattatct gctcgacact gccgaaagca gctatcacca aagcaaagaa   5640
ctgatcgaac gctggcacaa aaatggtcgt ctgctatatg cgattacgcc acgcttcgcc   5700
ccgacctcat ctcctgaaca gatggcgatg gcgcaacgcc tgaaagaaga atatccggat   5760
```

```
acgtgggtac atacccatct ctgtgaaaac aaagatgaaa ttgcctgggt gaaatcgctt   5820
tatcctgacc atgatggtta tctggatgtt taccatcagt acggcctgac cggtaaaaac   5880
tgtgtctttg ctcactgcgt ccatctcgaa gaaaaagagt gggatcgtct cagcgaaacc   5940
aaatccagca ttgctttctg tccgacctcc aacctttacc tcggcagcgg cttattcaac   6000
ttgaaaaaag catggcagaa gaaagttaaa gtgggcatgg gaacggatat cggtgccgga   6060
accactttca acatgctgca aacgctgaac gaagcctaca aagtattgca attacaaggc   6120
tatcgcctct cggcatatga agcgttttac ctggccacgc tcggcggagc gaaatctctg   6180
ggccttgacg atttgattgg caacttttta cctggcaaag aggctgattt cgtggtgatg   6240
gaacccaccg ccactccgct acagcagctg cgctatgaca actctgtttc tttagtcgac   6300
aaattgttcg tgatgatgac gttgggcgat gaccgttcga tctaccgcac ctacgttgat   6360
ggtcgtctgg tgtacgaacg caactaagga acgaccatgc aaacgctcag catccagcac   6420
ggtaccctcg tcacgatgga tcagtaccgc agagtccttg ggatagctgg ggttcacgtg   6480
caggatggac ggatcgtcgc gctcggagtg cacgccgagt cggtgcctcc gccagcggat   6540
cgggtgatcg atgcacgcgg caaggtcgtg ttacccggtt tcatcaatgc ccacacccat   6600
gtgaaccaga tcctcctgcg cggagggccc tcgcacgggc gtcaactcta tgactggctg   6660
ttcaacgttt tgtatccggg acaaaaggcg atgagaccgg aggacgtagc ggtggcggtg   6720
aggttgtatt gtgcggaagc tgtgcgcagc gggattacga cgatcaacga caacgccgat   6780
tcggccatct acccaggcaa catcgaggcc gcgatggcgg tctatggtga ggtgggtgtg   6840
agggtcgtct acgcccgcat gttctttgat cggatggacg ggcgcattca agggtatgtg   6900
gacgccttga aggctcgctc tccccaagtc gaactgtgct cgatcatgga ggaaacggct   6960
gtggccaaag atcggatcac agccctgtca gatcagtatc atggcacggc aggaggtcgt   7020
atatcagttt ggcccgctcc tgccattacc ccggcggtga cagttgaagg aatgcgatgg   7080
gcacaagcct tcgcccgtga tcgggcggta atgtggacgc ttcacatggc ggagagcgat   7140
catgatgagc ggcttcattg gatgagtccc gccgagtaca tggagtgtta cggactcttg   7200
gatgagcgtc tgcaggtcgc gcattgcgtg tactttgacc ggaaggatgt tcggctgctg   7260
caccgccaca atgtgaaggt cgcgtcgcag gttgtgagca atgcctacct cggctcaggg   7320
gtggcccccg tgccagagat ggtggagcgc ggcatggccg tgggcattgg aacagatgac   7380
gggaattgta atgactccgt aaacatgatc ggagacatga agtttatggc ccatattcac   7440
cgcgcggtgc atcgggatgc ggacgtgctg accccagaga agattcttga aatggcgacg   7500
atcgatgggg cgcgttcgtt gggaatggac cacgagattg gttccatcga aaccggcaag   7560
cgcgcggacc ttatcctgct tgacctgcgt caccctcaga cgactcctca ccatcatttg   7620
gcggccacga tcgtgtttca ggcttacggc aatgaggtgg acactgtcct gattgacgga   7680
aacgttgtga tggagaaccg ccgcttgagc tttcttcccc ctgaacgtga gttggcgttc   7740
cttgaggaag cgcagagccg cgccacagct attttgcagc gggcgaacat ggtggctaac   7800
ccagcttggc gcagcctcta gcctcaaaat atattttccc tctatcttct cgttgcgctt   7860
aatttgacta attctcatta gcgaggcgcg cctttccata ggctccgccc ccctgacgag   7920
catcacaaaa atcgacgctc aagtcagagg tggcgaaacc cgacaggact ataaagatac   7980
caggcgtttc cccctggaag ctccctcgtg cgctctcctg ttccgaccct gccgcttacc   8040
ggatacctgt ccgcctttct cccttcggga agcgtggcgc tttctcatag ctcacgctgt   8100
```

-continued

```
aggtatctca gttcggtgta ggtcgttcgc tccaagctgg gctgtgtgca cgaacccccc   8160
gttcagcccg accgctgcgc cttatccggt aactatcgtc ttgagtccaa cccggtaaga   8220
cacgacttat cgccactggc agcagccact ggtaacagga ttagcagagc gaggtatgta   8280
ggcggtgcta cagagttctt gaagtggtgg cctaactacg gctacactag aagaacagta   8340
tttggtatct gcgctctgct gaagccagtt accttcggaa aaagagttgg tagctcttga   8400
tccggcaaac aaaccaccgc tggtagcggt ggtttttttg tttgcaagca gcagattacg   8460
cgcagaaaaa aaggatctca agaagatcct ttgatctttt ctacggggtc tgacgctcag   8520
tggaacgaaa actcacgtta agggattttg gtcatgagat tatcaaaaag gatcttcacc   8580
tagatccttt taaattaaaa atgaagtttt aaatcaatct aaagtatata tgagtaaact   8640
tggtctgaca gttaccaatg cttaatcagt gaggcaccta tctcagcgat ctgtctattt   8700
cgttcatcca tagttgcctg actccccgtc gtgtagataa ctacgatacg ggagggctta   8760
ccatctggcc ccagtgctgc aatgataccg cgagacccac gctcaccggc tccagattta   8820
tcagcaataa accagccagc cggaagggcc gagcgcagaa gtggtcctgc aactttatcc   8880
gcctccatcc agtctattaa ttgttgccgg gaagctagag taagtagttc gccagttaat   8940
agtttgcgca acgttgttgc cattgctaca ggcatcgtgg tgtcacgctc gtcgtttggt   9000
atggcttcat tcagctccgg ttcccaacga tcaaggcgag ttacatgatc ccccatgttg   9060
tgcaaaaaag cggttagctc cttcggtcct ccgatcgttg tcagaagtaa gttggccgca   9120
gtgttatcac tcatggttat ggcagcactg cataattctc ttactgtcat gccatccgta   9180
agatgctttt ctgtgactgg tgagtactca accaagtcat tctgagaata gtgtatgcgg   9240
cgaccgagtt gctcttgccc ggcgtcaata cgggataata ccgcgccaca tagcagaact   9300
ttaaaagtgc tcatcattgg aaaacgttct tcggggcgaa aactctcaag gatcttaccg   9360
ctgttgagat ccagttcgat gtaacccact cgtgcaccca actgatcttc agcatctttt   9420
actttcacca gcgtttctgg gtgagcaaaa acaggaaggc aaaatgccgc aaaaaaggga   9480
ataagggcga cacggaaatg ttgaatactc atactcttcc tttttcaata ttattgaagc   9540
atttatcagg gttattgtct catgagcgga tacatatttg aatgtattta gaaaaataaa   9600
cagcgatcgc gcggccgcgg gtaataactg atataattaa attgaagctc taatttgtga   9660
gtttagtata catgcattta cttataatac agtttttag ttttgctggc cgcatcttct   9720
caaatatgct tcccagcctg cttttctgta acgttcaccc tctaccttag catcccttcc   9780
ctttgcaaat agtcctcttc caacaataat aatgtcagat cctgtagaga ccacatcatc   9840
cacggttcta tactgttgac ccaatgcgtc tcccttgtca tctaaaccca caccgggtgt   9900
cataatcaac caatcgtaac cttcatctct tccacccatg tctctttgag caataaagcc   9960
gataacaaaa tctttgtcgc tcttcgcaat gtcaacagta cccttagtat attctccagt  10020
agctagggag cccttgcatg acaattctgc taacatcaaa aggcctctag gttcctttgt  10080
tacttcttcc gccgcctgct tcaaaccgct aacaatacct gggcccacca caccgtgtgc  10140
attcgtaatg tctgcccatt ctgctattct gtatacaccc gcagagtact gcaatttgac  10200
tgtattacca atgtcagcaa attttctgtc ttcgaagagt aaaaaattgt acttggcgga  10260
taatgccttt agcggcttaa ctgtgccctc catggaaaaa tcagtcaaga tatccacatg  10320
tgtttttagt aaacaaattt tgggacctaa tgcttcaact aactccagta attccttggt  10380
ggtacgaaca tccaatgaag cacacaagtt tgtttgcttt tcgtgcatga tattaaatag  10440
cttggcagca acaggactag gatgagtagc agcacgttcc ttatatgtag ctttcgacat  10500
```

```
gatttatctt cgtttcctgc aggtttttgt tctgtgcagt tgggttaaga atactgggca  10560

atttcatgtt tcttcaacac cacatatgcg tatatatacc aatctaagtc tgtgctcctt  10620

ccttcgttct tccttctgct cggagattac cgaatcaaag ctagcttatc gatgataagc  10680

tgtcaaagat gagaattaat tccacggact atagactata ctagatactc cgtctactgt  10740

acgatacact tccgctcagg tccttgtcct ttaacgaggc cttaccactc ttttgttact  10800

ctattgatcc agctcagcaa aggcagtgtg atctaagatt ctatcttcgc gatgtagtaa  10860

aactagctag accgagaaag agactagaaa tgcaaaaggc acttctacaa tggctgccat  10920

cattattatc cgatgtgacg ctgcagcttc tcaatgatat tcgaatacgc tttgaggaga  10980

tacagcctaa tatccgacaa actgttttac agatttacga tcgtacttgt tacccatcat  11040

tgaattttga acatccgaac ctgggagttt tccctgaaac agatagtata tttgaacctg  11100

tataataata tatagtctag cgctttacgg aagacaatgt atgtatttcg gttcctggag  11160

aaactattgc atctattgca taggtaatct tgcacgtcgc atccccggtt cattttctgc  11220

gtttccatct tgcacttcaa tagcatatct ttgttaacga agcatctgtg cttcattttg  11280

tagaacaaaa atgcaacgcg agagcgctaa tttttcaaac aaagaatctg agctgcattt  11340

ttacagaaca gaaatgcaac gcgaaagcgc tattttacca acgaagaatc tgtgcttcat  11400

ttttgtaaaa caaaaatgca acgcgacgag agcgctaatt tttcaaacaa agaatctgag  11460

ctgcattttt acagaacaga aatgcaacgc gagagcgcta ttttaccaac aaagaatcta  11520

tacttctttt ttgttctaca aaaatgcatc ccgagagcgc tatttttcta acaaagcatc  11580

ttagattact ttttttctcc tttgtgcgct ctataatgca gtctcttgat aactttttgc  11640

actgtaggtc cgttaaggtt agaagaaggc tactttggtg tctattttct cttccataaa  11700

aaaagcctga ctccacttcc cgcgtttact gattactagc gaagctgcgg gtgcattttt  11760

tcaagataaa ggcatccccg attatattct ataccgatgt ggattgcgca tactttgtga  11820

acagaaagtg atagcgttga tgattcttca ttggtcagaa aattatgaac ggtttcttct  11880

attttgtctc tatatactac gtataggaaa tgtttacatt ttcgtattgt tttcgattca  11940

ctctatgaat agttcttact acaatttttt tgtctaaaga gtaatactag agataaacat  12000

aaaaaatgta gaggtcgagt ttagatgcaa gttcaaggag cgaaaggtgg atgggtaggt  12060

tatataggga tatagcacag agatatatag caaagagata cttttgagca at          12112
```

<210> SEQ ID NO 54
<211> LENGTH: 1173
<212> TYPE: DNA
<213> ORGANISM: Rhodococcus sp.

<400> SEQUENCE: 54

```
ttgcgggaag tccaactgct cgacggccgc cgagttgatg ttgcatgcgc cggaccgttg     60

atctccgaaa tcggcgccca tctcgacctc accgctccag tggagatcga ctgtggcggc    120

ggcctggcga cgcgaccgtt caccgaaccc catttgcacc tcgacaaggc ggggaccgcc    180

gatcgtctac cggcaggcgc cagcaccatc ggtgatgcga tcgccgccat gcaatcggtg    240

aaagtcactg agcgcgacaa tgtggcggcg gtcgccgcac gaatgcaccg cgtcctgaac    300

cgcattgtcg acgatggttc ccacgccatt cgcgctctcg tcgacgtcga tgaggtctgg    360

ggattgaccg cttttcatgc agcccaacaa gtccaagctg ctctcgcgcc gcgcgcggta    420

gtacaaatcg tggccttccc acaacatggc ctcaccccgc aggtacttgc catgctcgag    480
```

caagcggccg cagaaggtgc aggagcactc ggcgcccaca ccgacgtcga ccctgaccca 540
gcggcgcacg tcggtgctgt ggccgccatt gccgccgggg catcgctacc gctcgaagtc 600
cacactgatg aaggcgccag tcccgacaag ttctacttgc ctgcagtact ggaggtcctc 660
gaccggtttc ctggactctc gacgaccctc gcacactgtc tgtcactcgg aacgatcgcg 720
ccgaaacaac agcagcactg gattgaggaa ctggcccatc gggacatcaa agtctgtgtc 780
gcgcctagca ttttaggttt cggcctgccc ttggcgccag tccgggcact catcgaggcc 840
ggcgtcggaa tacttgtcgg atcagacaac ctgcaggacg ttttctttcc gctcggtacg 900
ggccgcgcca tcgaaaacgt gcgtctgctg gcgaccgcag cacagctcac cgcacctgag 960
ctcgctggcc cgctcatcgc aggtgtcacc gacatcgcgt acgccaccgt gaccggcgca 1020
gcagatgcac tggcggtgga atcccccgca accctcgtcg tccacgacgc gacctcgccg 1080
gcggagctgc ttcgcggcat cgacggtact cgaatcaccg ttatcgacgg cctgttgaca 1140
tccccgctcc aactcgacaa aggaatcaag tga 1173

<210> SEQ ID NO 55
<211> LENGTH: 1239
<212> TYPE: DNA
<213> ORGANISM: Pseudomonas sp.

<400> SEQUENCE: 55
atgtcaatgg aaacccatag ttatgtagac gtcgcaattc gtaacgcgcg tcttgccgat 60
acggagggaa ttgtcgatat tcttattcac gatgggcgca ttgcgtccat cgtgaagtcg 120
acaaaaacaa aaggatcggt ggagatcgat gctcatgagg gtctggtcac ttccggcctg 180
gtagagcctc acatccatct cgataaggcc ctgacggcag atcgggttcc cgcaggaagc 240
attggcgacc ttcgaacgcg acgaggcctt gagatggcaa ttcgggccac ccgtgatatc 300
aagcgtacgt tcacggttga agatgttcga gaacgggcca tacgtgcggc cctgatggca 360
tcccgtgcgg gaaccaccgc attgcggaca cacgtcgatg tcgacccgat tgtcggcctc 420
gcaggtatcc gtggtgtcct tgaggcgcgt gaagtctgcg cgggattgat cgatatccag 480
atcgtcgcct tccctcagga gggactcttc tgctctgcgg gggccgtgga cctcatgcgg 540
gaggcgatca aactgggcgc ggatgccgtc ggcggcgcac ccgcgctgga tgatcgcccg 600
caggaccatg tccgagccgt ttttgacctt gctgctgagt tcggcctgcc cgtagacatg 660
cacgtcgatg agtccgaccg gcgggaagac tttacgcttc cctttgtgat tgaagctgcc 720
cgtgaacggc gtgtgcccaa tgtgaccgtc gcgcacatca gctcgctgtc cgtacagacg 780
gatgacgtag cacggtcgac cattgccgcc cttgcggacg ccgatgttaa tgtcgtggtt 840
aatccgatca ttgtcaaaat tacgcggctg agtgaattac tcgatgccgg agtctccgta 900
atgtttggct cggacaacct gcgggatccg ttctatccgc tcggagcggc gaatcccctt 960
ggatcagcca tttttgcctg tcaaattgcc gcgctgggaa caccgcaaga tctcagacgg 1020
gtattcgatg cggtcaccat caacgctgcc cgcatgctgg gattccccctc acttttaggc 1080 gtcgtggaag ggcagtcgc ggatctcgca gtattcccat cggcgacgcc cgaggaggtt 1140
gttctggatc aacagtctcc gctcttcgta ctcaagggcg gacgtgtcgt tgccatgcga 1200
ttggccgctg gatcaacgtc gttccgcgac tactcatga 1239

<210> SEQ ID NO 56
<211> LENGTH: 726
<212> TYPE: DNA
<213> ORGANISM: Rhodococcus sp.

<400> SEQUENCE: 56

```
atgatatact caacagtcaa cgctaatcct tacgcttggc cttacgatgg ttcaatagac     60

cctgctcaca ccgctttaat cttaatcgat tggcaaatag acttttgtgg tccaggtggt    120

tatgtcgatt ccatgggtta cgacttatcc ttgactagaa gtggtttaga acctacagca    180

agagtattgg ctgcagccag agatactggt atgacagtta tccatactag agaaggtcac    240

agaccagatt tggctgactt gccacctaat aagagatgga gatctgcatc agccggtgct    300

gaaatcggtt cagttggtcc atgtggtaga attttagtca gaggtgaacc tggttgggaa    360

atagtaccag aagttgcacc tagagaaggt gaaccaatta tagataaacc tggtaaaggt    420

gctttctacg caacagattt ggacttgttg ttgagaacaa gaggtatcac ccatttgatt    480

ttgaccggta taactacaga tgtttgcgtc cacaccacta tgagagaagc caacgataga    540

ggttacgaat gtttaatttt gtctgattgc accggtgcta ctgacagaaa gcatcacgaa    600

gctgcattat ctatggtcac catgcaaggt ggtgtattcg gtgcaactgc ccattcagat    660

gacttattgg ccgctttggg tacaaccgtt ccagcagccg ctggtcctag agctagaaca    720

gaataa                                                               726
```

<210> SEQ ID NO 57
<211> LENGTH: 702
<212> TYPE: DNA
<213> ORGANISM: Rhizobium leguminosarum

<400> SEQUENCE: 57

```
atggacgcga tggtcgaaac caaccggcat tttatcgacg ccgatccgta tccgtggccc     60

tataacggag ctctgaggcc tgacaatacc gccctcatca tcatcgacat gcagacggat    120

ttctgcggca agggcggtta tgtcgaccac atgggctacg acctgtcgct ggtgcaggcg    180

ccgatcgaac ccatcaaacg cgtgcttgcc gccatgcggg ccaagggtta tcacatcatc    240

cacacccgcg agggccaccg ccccgacctc gccgatctgc cagcaaacaa acgctggcgc    300

tcgcaacgga tcggggccgg catcggtgat cccggcccct gcggccgaat cctgacgcgt    360

ggcgaacccg gctgggacat catccccgaa ctctacccga tcgaaggcga gacgatcatc    420

gacaagcccg gcaagggttc gttctgcgcc accgacctcg aactcgtcct caaccagaaa    480

cgcatcgaga acattatcct caccgggatc accaccgatg tctgcgtctc gacgacgatg    540

cgcgaggcga acgaccgcgg ctacgaatgc ctgctgctgg aggactgctg tggtgcgacc    600

gactacggaa accacctcgc cgccatcaag atggtgaaga tgcagggcgg cgtcttcggc    660

tcggtctcca attccgcggc tctagtcgag gcgctgccct ga                       702
```

<210> SEQ ID NO 58
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

```
Met Gln Thr Leu Ser Ile Gln His Gly Thr Leu Val Thr Met Asp Gln
1               5                   10                  15

Tyr Arg Arg Val Leu Gly Asp Ser Trp Val His Val Gln Asp Gly Arg
            20                  25                  30

Ile Val Ala Leu Gly Val His Ala Glu Ser Val Pro Pro Pro Ala Asp
```

-continued

```
        35                  40                  45

Arg Val Ile Asp Ala Arg Gly Lys Val Val Leu Pro Gly Phe Ile Asn
    50                  55                  60

Ala His Thr His Val Asn Gln Ile Leu Leu Arg Gly Gly Pro Ser His
65                  70                  75                  80

Gly Arg Gln Leu Tyr Asp Trp Leu Phe Asn Val Leu Tyr Pro Gly Gln
                85                  90                  95

Lys Ala Met Arg Pro Glu Asp Val Ala Val Ala Val Arg Leu Tyr Cys
            100                 105                 110

Ala Glu Ala Val Arg Ser Gly Ile Thr Thr Ile Asn Asp Asn Ala Asp
        115                 120                 125

Ser Ala Ile Tyr Pro Gly Asn Ile Glu Ala Ala Met Ala Val Tyr Gly
    130                 135                 140

Glu Val Gly Val Arg Val Val Tyr Ala Arg Met Phe Phe Asp Arg Met
145                 150                 155                 160

Asp Gly Arg Ile Gln Gly Tyr Val Asp Ala Leu Lys Ala Arg Ser Pro
                165                 170                 175

Gln Val Glu Leu Cys Ser Ile Met Glu Glu Thr Ala Val Ala Lys Asp
            180                 185                 190

Arg Ile Thr Ala Leu Ser Asp Gln Tyr His Gly Thr Ala Gly Gly Arg
        195                 200                 205

Ile Ser Val Trp Pro Ala Pro Ala Ile Thr Pro Ala Val Thr Val Glu
    210                 215                 220

Gly Met Arg Trp Ala Gln Ala Phe Ala Arg Asp Arg Ala Val Met Trp
225                 230                 235                 240

Thr Leu His Met Ala Glu Ser Asp His Asp Glu Arg Leu His Trp Met
                245                 250                 255

Ser Pro Ala Glu Tyr Met Glu Cys Tyr Gly Leu Leu Asp Glu Arg Leu
            260                 265                 270

Gln Val Ala His Cys Val Tyr Phe Asp Arg Lys Asp Val Arg Leu Leu
        275                 280                 285

His Arg His Asn Val Lys Val Ala Ser Gln Val Val Ser Asn Ala Tyr
    290                 295                 300

Leu Gly Ser Gly Val Ala Pro Val Pro Glu Met Val Glu Arg Gly Met
305                 310                 315                 320

Ala Val Gly Ile Gly Thr Asp Asp Gly Asn Cys Asn Asp Ser Val Asn
                325                 330                 335

Met Ile Gly Asp Met Lys Phe Met Ala His Ile His Arg Ala Val His
            340                 345                 350

Arg Asp Ala Asp Val Leu Thr Pro Glu Lys Ile Leu Glu Met Ala Thr
        355                 360                 365

Ile Asp Gly Ala Arg Ser Leu Gly Met Asp His Glu Ile Gly Ser Ile
    370                 375                 380

Glu Thr Gly Lys Arg Ala Asp Leu Ile Leu Leu Asp Leu Arg His Pro
385                 390                 395                 400

Gln Thr Thr Pro His His His Leu Ala Ala Thr Ile Val Phe Gln Ala
                405                 410                 415

Tyr Gly Asn Glu Val Asp Thr Val Leu Ile Asp Gly Asn Val Val Met
            420                 425                 430

Glu Asn Arg Arg Leu Ser Phe Leu Pro Pro Glu Arg Glu Leu Ala Phe
        435                 440                 445

Leu Glu Glu Ala Gln Ser Arg Ala Thr Ala Ile Leu Gln Arg Ala Asn
    450                 455                 460
```

```
Met Val Ala Asn Pro Ala Trp Arg Ser Leu
465                 470

<210> SEQ ID NO 59
<211> LENGTH: 423
<212> TYPE: DNA
<213> ORGANISM: Saccharomyces cerevisiae

<400> SEQUENCE: 59

aggaacccat caggttggtg gaagattacc cgttctaaga cttttcagct tcctctattg     60

atgttacacc tggacacccc ttttctggca tccagttttt aatcttcagt ggcatgtgag    120

attctccgaa attaattaaa gcaatcacac aattctctcg gataccacct cggttgaaac    180

tgacaggtgg tttgttacgc atgctaatgc aaaggagcct atatacottt ggctcggctg    240

ctgtaacagg gaatataaag ggcagcataa tttaggagtt tagtgaactt gcaacattta    300

ctattttccc ttcttacgta aatatttttc tttttaattc taaatcaatc tttttcaatt    360

ttttgtttgt attcttttct tgcttaaatc tataactaca aaaaacacat acataaacta    420

aaa                                                                  423

<210> SEQ ID NO 60
<211> LENGTH: 658
<212> TYPE: DNA
<213> ORGANISM: Saccharomyces cerevisiae

<400> SEQUENCE: 60

ttgctacgca ggctgcacaa ttacacgaga atgctcccgc ctaggattta aggctaaggg     60

acgtgcaatg cagacgacag atctaaatga ccgtgtcggt gaagtgttcg ccaaactttt    120

cggttaacac atgcagtgat gcacgcgcga tggtgctaag ttacatatat atatatatat    180

atatatatat atatatatag ccatagtgat gtctaagtaa cctttatggt atatttctta    240

atgtggaaag atactagcgc gcgcacccac acacaagctt cgtcttttct tgaagaaaag    300

aggaagctcg ctaaatggga ttccactttc cgttccctgc cagctgatgg aaaaaggtta    360

gtggaacgat gaagaataaa aagagagatc cactgaggtg aaatttcagc tgacagcgag    420

tttcatgatc gtgatgaaca atggtaacga gttgtggctg ttgccaggga gggtggttct    480

caacttttaa tgtatggcca aatcgctact tgggtttgtt atataacaaa gaagaaataa    540

tgaactgatt ctcttcctcc ttcttgtcct ttcttaattc tgttgtaatt accttccttt    600

gtaatttttt ttgtaattat tcttcttaat aatccaaaca aacacacata ttacaata      658

<210> SEQ ID NO 61
<211> LENGTH: 573
<212> TYPE: DNA
<213> ORGANISM: Saccharomyces cerevisiae

<400> SEQUENCE: 61

tgctgtaacc cgtacatgcc caaaataggg ggcgggttac acagaatata taacatcgta     60

ggtgtctggg tgaacagttt attcctggca tccactaaat ataatggagc ccgcttttta    120

agctggcatc cagaaaaaaa aagaatccca gcaccaaaat attgttttct tcaccaacca    180

tcagttcata ggtccattct cttagcgcaa ctacagagaa caggggcaca aacaggcaaa    240

aaacgggcac aacctcaatg gagtgatgca acctgcctgg agtaaatgat gacacaaggc    300

aattgaccca cgcatgtatc tatctcattt tcttacacct tctattacct tctgctctct    360

ctgatttgga aaaagctgaa aaaaaaggtt gaaaccagtt ccctgaaatt attcccctac    420
```

```
ttgactaata agtatataaa gacggtaggt attgattgta attctgtaaa tctatttctt    480

aaacttctta aattctactt ttatagttag tcttttttt agttttaaaa caccaagaac    540

ttagtttcga ataaacacac ataaacaaac aaa                                573
```

<210> SEQ ID NO 62
<211> LENGTH: 812
<212> TYPE: DNA
<213> ORGANISM: Saccharomyces cerevisiae

<400> SEQUENCE: 62

```
gcaccgctgg cttgaacaac aataccagcc ttccaacttc tgtaaataac ggcggtacgc     60

cagtgccacc agtaccgtta cctttcggta tacctccttt ccccatgttt ccaatgccct    120

tcatgcctcc aacggctact atcacaaatc ctcatcaagc tgacgcaagc cctaagaaat    180

gaataacaat actgacagta ctaaataatt gcctacttgg cttcacatac gttgcatacg    240

tcgatataga taataatgat aatgacagca ggattatcgt aatacgtaat agttgaaaat    300

ctcaaaaatg tgtgggtcat tacgtaaata atgataggaa tgggattctt ctatttttcc    360

tttttccatt ctagcagccg tcgggaaaac gtggcatcct ctctttcggg ctcaattgga    420

gtcacgctgc cgtgagcatc ctctctttcc atatctaaca actgagcacg taaccaatgg    480

aaaagcatga gcttagcgtt gctccaaaaa agtattggat ggttaatacc atttgtctgt    540

tctcttctga ctttgactcc tcaaaaaaaa aaaatctaca atcaacagat cgcttcaatt    600

acgccctcac aaaaactttt ttccttcttc ttcgcccacg ttaaatttta tccctcatgt    660

tgtctaacgg atttctgcac ttgatttatt ataaaaagac aaagacataa tacttctcta    720

tcaatttcag ttattgttct tccttgcgtt attcttctgt tcttcttttt cttttgtcat    780

atataaccat aaccaagtaa tacatattca aa                                 812
```

<210> SEQ ID NO 63
<211> LENGTH: 625
<212> TYPE: DNA
<213> ORGANISM: Yarrowia lipolytica

<400> SEQUENCE: 63

```
tataaacggt attttcacaa ttgcacccca gccagaccga tagccggtcg caatccgcca     60

cccacaaccg tctacctccc acagaacccc gtcacttcca cccttttcca ccagatcata    120

tgtcccaact tgccaaatta aaaccgtgcg aattttcaaa ataaactttg gcaaagaggc    180

tgcaaaggag gggctggtga gggcgtctgg aagtcgacca gagaccgggt tggcggcgca    240

tttgtgtccc aaaaaacagc cccaattgcc ccaattgacc ccaaattgac ccagtagcgg    300

gcccaacccc ggcgagagcc cccttctccc cacatatcaa acctcccccg gttcccacac    360

ttgccgttaa gggcgtaggg tactgcagtc tggaatctac gcttgttcag actttgtact    420

agtttctttg tctggccatc cgggtaaccc atgccggacg caaaatagac tactgaaaat    480

tttttgctt tgtggttggg actttagcca agggtataaa agaccaccgt ccccgaatta    540

cctttcctct tcttttctct ctctccttgt caactcacac ccgaaatcgt taagcatttc    600

cttctgagta taagaatcat tcaaa                                         625
```

<210> SEQ ID NO 64
<211> LENGTH: 318
<212> TYPE: DNA
<213> ORGANISM: Saccharomyces cerevisiae

<400> SEQUENCE: 64

```
gcataatatt gtccgctgcc cgtttttctg ttagacggtg tcttgatcta cttgctatcg     60
ttcaacacca ccttattttc taactatttt ttttttagct catttgaatc agcttatggt    120
gatggcacat ttttgcataa acctagctgt cctcgttgaa cataggaaaa aaaaatatat    180
aaacaaggct ctttcactct ccttggaatc agatttgggt ttgttccctt tattttcata    240
tttcttgtca tattcttttc tcaattatta tcttctactc ataacctcac gcaaaataac    300
acagtcaaat caatcaaa                                                  318
```

<210> SEQ ID NO 65
<211> LENGTH: 413
<212> TYPE: DNA
<213> ORGANISM: Saccharomyces cerevisiae

<400> SEQUENCE: 65

```
catagcttca aaatgtttct actccttttt tactcttcca gattttctcg gactccgcgc     60
atcgccgtac cacttcaaaa cacccaagca cagcatacta aatttcccct ctttcttcct    120
ctagggtgtc gttaattacc cgtactaaag gtttggaaaa gaaaaaagag accgcctcgt    180
ttctttttct tcgtcgaaaa aggcaataaa aatttttatc acgtttcttt ttcttgaaaa    240
tttttttttt tgattttttt ctctttcgat gacctcccat tgatatttaa gttaataaac    300
ggtcttcaat ttctcaagtt tcagtttcat ttttcttgtt ctattacaac tttttttact    360
tcttgctcat tagaaagaaa gcatagcaat ctaatctaag ttttaattac aaa           413
```

<210> SEQ ID NO 66
<211> LENGTH: 330
<212> TYPE: DNA
<213> ORGANISM: Saccharomyces cerevisiae

<400> SEQUENCE: 66

```
taagattaat ataattatat aaaaatatta tcttcttttc tttatatcta gtgttatgta     60
aaataaattg atgactacgg aaagcttttt tatattgttt ctttttcatt ctgagccact    120
taaatttcgt gaatgttctt gtaagggacg gtagatttac aagtgataca acaaaaagca    180
aggcgctttt tctaataaaa agaagaaaag catttaacaa ttgaacacct ctatatcaac    240
gaagaatatt actttgtctc taaatccttg taaaatgtgt acgatctcta tatgggttac    300
tcataagtgt accgaagact gcattgaaag                                     330
```

<210> SEQ ID NO 67
<211> LENGTH: 377
<212> TYPE: DNA
<213> ORGANISM: Saccharomyces cerevisiae

<400> SEQUENCE: 67

```
gtctgaagaa tgaatgattt gatgatttct ttttccctcc atttttctta ctgaatatat     60
caatgatata gacttgtata gtttattatt tcaaattaag tagctatata tagtcaagat    120
aacgtttgtt tgacacgatt acattattcg tcgacatctt ttttcagcct gtcgtggtag    180
caatttgagg agtattatta attgaatagg ttcattttgc gctcgcataa acagttttcg    240
tcagggacag tatgttggaa tgagtggtaa ttaatggtga catgacatgt tatagcaata    300
accttgatgt ttacatcgta gtttaatgta caccccgcga attcgttcaa gtaggagtgc    360
accaattgca aagggaa                                                   377
```

<210> SEQ ID NO 68
<211> LENGTH: 506
<212> TYPE: DNA
<213> ORGANISM: Saccharomyces cerevisiae

<400> SEQUENCE: 68
gtgaatttac tttaaatctt gcatttaaat aaattttctt tttatagctt tatgacttag 60
tttcaattta tatactattt taatgacatt ttcgattcat tgattgaaag ctttgtgttt 120
tttcttgatg cgctattgca ttgttcttgt ctttttcgcc acatgtaata tctgtagtag 180
atacctgata cattgtggat gctgagtgaa attttagtta ataatggagg cgctcttaat 240
aattttgggg atattggctt ttttttttaa agtttacaaa tgaatttttt ccgccaggat 300
aacgattctg aagttactct tagcgttcct atcggtacag ccatcaaatc atgcctataa 360
atcatgccta tatttgcgtg cagtcagtat catctacatg aaaaaaactc ccgcaatttc 420
ttatagaata cgttgaaaat taaatgtacg cgccaagata agataacata tatctagatg 480
cagtaatata cacagattcc cgcgga 506

<210> SEQ ID NO 69
<211> LENGTH: 199
<212> TYPE: DNA
<213> ORGANISM: Saccharomyces cerevisiae

<400> SEQUENCE: 69
gttaattcaa attaattgat atagtttttt aatgagtatt gaatctgttt agaaataatg 60
gaatattatt tttatttatt tatttatatt attggtcggc tcttttcttc tgaaggtcaa 120
tgacaaaatg atatgaagga aataatgatt tctaaaattt tacaacgtaa gatattttta 180
caaaagccta gctcatctt 199

<210> SEQ ID NO 70
<211> LENGTH: 400
<212> TYPE: DNA
<213> ORGANISM: Yarrowia lipolytica

<400> SEQUENCE: 70
gctgcttgta cctagtgcaa ccccagtttg ttaaaaatta gtagtcaaaa acttctgagt 60
tagaaatttg tgagtgtagt gagattgtag agtatcatgt gtgtccgtaa gtgaagtgtt 120
attgactctt agttagttta tctagtactc gtttagttga cactgatcta gtattttacg 180
aggcgtatga ctttagccaa gtgttgtact tagtcttctc tccaaacatg agagggctct 240
gtcactcagt cggcctatgg gtgagatggc ttggtgagat ctttcgatag tctcgtcaag 300
atggtaggat gatgggggaa tacattactg ctctcgtcaa ggaaaccaca atcagatcac 360
accatcctcc atggtatccg atgactctct tctccacagt 400

<210> SEQ ID NO 71
<211> LENGTH: 203
<212> TYPE: DNA
<213> ORGANISM: Saccharomyces cerevisiae

<400> SEQUENCE: 71
acaagctaag ttgactgctg ctaccaacgc taagcaataa gcgatttaat ctctaattat 60
tagttaaagt tttataagca tttttatgta acgaaaaata aattggttca tattattact 120
gcactgtcac ttaccatgga aagaccagac aagaagttgc cgacacgaca gtctgttgaa 180
ttggcttaag tctgggtccg ctt 203

<210> SEQ ID NO 72
<211> LENGTH: 274
<212> TYPE: DNA
<213> ORGANISM: Saccharomyces cerevisiae

<400> SEQUENCE: 72
caggcccctt ttcctttgtc gatatcatgt aattagttat gtcacgctta cattcacgcc 60
ctcctcccac atccgctcta accgaaaagg aaggagttag acaacctgaa gtctaggtcc 120
ctatttattt tttttaatag ttatgttagt attaagaacg ttatttatat ttcaaatttt 180
tctttttttt ctgtacaaac gcgtgtacgc atgtaacatt atactgaaaa ccttgcttga 240
gaaggttttg ggacgctcga aggctttaat ttgc 274

<210> SEQ ID NO 73
<211> LENGTH: 67
<212> TYPE: DNA
<213> ORGANISM: Escherichia coli

<400> SEQUENCE: 73
agctggtgac aattaatcat cggctcgtat aatgtgtgga attgaatcga tataaggagg 60
ttaatca 67

<210> SEQ ID NO 74
<211> LENGTH: 89
<212> TYPE: DNA
<213> ORGANISM: Escherichia coli

<400> SEQUENCE: 74
ctcaaaatat attttccctc tatcttctcg ttgcgcttaa tttgactaat tctcattagc 60
gaggcgcgcc tttccatagg ctccgcccc 89

<210> SEQ ID NO 75
<211> LENGTH: 11
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 75
ggaaatccat t 11

<210> SEQ ID NO 76
<211> LENGTH: 9
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 76 ggaacgacc 9

MICROORGANISMS ENGINEERED TO USE UNCONVENTIONAL SOURCES OF NITROGEN

CROSS-REFERENCE TO RELATED APPLICATIONS

This application is a divisional of U.S. patent application Ser. No. 14/759,878 filed Jul. 8, 2015, which claims priority from PCT/US2014/010332 filed Jan. 6, 2014, which claims priority to U.S. Provisional Application No. 61/782,351, filed Mar. 14, 2013, and U.S. Provisional Application No. 61/748,901, filed Jan. 4, 2013, which are incorporated herein by reference in their entireties for all purposes.

RELATED APPLICATIONS

This application claims the benefit of priority to U.S. Provisional Patent Application Ser. Nos. 61/748,901, filed Jan. 4, 2013, and 61/782,351, filed Mar. 14, 2013; the contents of both of which are hereby incorporated by reference.

SEQUENCE LISTING

The instant application contains a Sequence Listing which has been submitted electronically in ASCII format and is hereby incorporated by reference in its entirety. Said ASCII copy, created on Feb. 13, 2015, is named NGX-16.25_SL.txt and is 284,885 bytes in size.

BACKGROUND

In the fermentation industry, cell culture media is typically formulated to provide all nutrients necessary for the growth of a host cell line, with particular emphasis on meeting the cell line's requirements for carbon, nitrogen, phosphorus, sulfur, and other major nutrients. Some cell lines require additional components, including amino acids, trace minerals and metals, and complex growth factors. The presence of these nutrients provides a suitable growth environment for the organism of choice and, unfortunately, for any potential contaminating organisms. In this environment the production organism is required to compete directly with any contaminant organism in the cell culture.

Even in robust hosts, the combination of opportunistic infections of the culture and the metabolic burden resulting from the demands of product manufacture is a major concern in monoculture operations. Industrial robustness is typically considered a multigenic trait specific to the host strain and thus difficult to engineer predictably into organisms late in the development process. Addition of selective growth inhibitors, such as bacterial antibiotics, is one method used to create a more robust fermentation environment for host organisms that are resistant to the growth inhibitor. However, antibiotic addition is often undesirable or unfeasible, and spontaneously resistant contaminations frequently result.

Accordingly, there exists a need for rationally engineered traits that, when engineered into a host organism, create a robust monoculture fermentation environment.

SUMMARY OF THE INVENTION

In certain embodiments, the invention relates to a genetically engineered organism, wherein the genetically engineered organism has been transformed by a nucleic acid molecule comprising any one or more of the sequences disclosed herein.

In certain embodiments, the invention relates to a genetically engineered organism, wherein the genetically engineered organism has been transformed by a nucleic acid molecule; the nucleic acid molecule comprises a non-native gene; and the non-native gene encodes for a non-native enzyme selected from the group consisting of allophanate hydrolase, biuret amidohydrolase, cyanuric acid amidohydrolase, guanine deaminase, melamine deaminase, isopropylammelide isopropylaminohydrolase, cyanamide hydratase, urease, and urea carboxylase.

In certain embodiments, the invention relates to a method, comprising the step of contacting any one of the aforementioned genetically engineered organisms with a substrate, wherein the substrate comprises a nitrogen-containing fraction and a non-nitrogen-containing fraction;

the nitrogen-containing fraction comprises, in an amount from about 10% by weight to about 100% by weight, a nitrogen-containing compound of any one of Formulas I-III, or a salt thereof;

a native organism of the same species as the genetically engineered organism could not metabolize (i.e., use as a source of nitrogen) the nitrogen-containing compound;

the genetically engineered organism converts the substrate to a product; and the compound of formula I is $$\text{(A)}\!-\!(R)_n \qquad \text{I}$$

wherein, independently for each occurrence, $$\text{(A)}$$

is a five-, six, nine-, or ten-membered aryl or heteroaryl group;

R is —OH, —$CO_2$H, —$NO_2$, —CN, substituted or unsubstituted amino, or substituted or unsubstituted alkyl; and n is 0, 1, 2, 3, 4, or 5;

the compound of formula II is

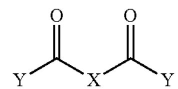

II wherein, independently for each occurrence,

X is —NH—, —N(alkyl)-, —O—, —C($R^1$)$_2$—, —S—, or absent;

Y is —H, —$NH_2$, —N(H)(alkyl), —N(alkyl)$_2$, —$CO_2$H, —CN, or substituted or unsubstituted alkyl; and $R^1$ is —H, —OH, —$CO_2$H, —$NO_2$, —CN, substituted or unsubstituted amino, or substituted or unsubstituted alkyl; and the compound of formula III is

III

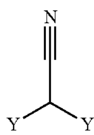

wherein, independently for each occurrence,

Y is —H, —$NH_2$, —N(H)(alkyl), —$N(alkyl)_2$, —$CO_2H$, —CN, or substituted or unsubstituted alkyl.

In certain embodiments, the invention relates to a method, comprising the step of contacting any one of the aforementioned genetically engineered organisms with a substrate, wherein the substrate comprises a nitrogen-containing fraction and a non-nitrogen-containing fraction;

the nitrogen-containing fraction comprises, in an amount from about 10% by weight to about 100% by weight, a nitrogen-containing compound selected from the group consisting of triazine, urea, melamine, cyanamide, 2-cyanoguanidine, ammeline, guanidine carbonate, ethylenediamine, ammelide, biuret, diethylenetriamine, triethylenetetramine, 1,3-diaminopropane, calcium cyanamide, cyanuric acid, aminoethylpiperazine, piperazine, and allophante; and the genetically engineered organism converts the substrate to a product.

In certain embodiments, the invention relates to a method, comprising the step of contacting any one of the aforementioned genetically engineered organisms with a substrate, wherein the substrate comprises a nitrogen-containing fraction and a non-nitrogen-containing fraction;

the nitrogen containing fraction consists essentially of a nitrogen-containing compound selected from the group consisting of triazine, urea, melamine, cyanamide, 2-cyanoguanidine, ammeline, guanidine carbonate, ethylenediamine, ammelide, biuret, diethylenetriamine, triethylenetetramine, 1,3-diaminopropane, calcium cyanamide, cyanuric acid, aminoethylpiperazine, piperazine, and allophante; and the genetically engineered organism converts the substrate to a product.

In certain embodiments, the invention relates to a method comprising the step of contacting any one of the aforementioned genetically engineered organisms with a substrate, wherein the substrate consists of a nitrogen-containing fraction and a non-nitrogen-containing fraction;

the nitrogen containing fraction consists of a nitrogen-containing compound selected from the group consisting of triazine, urea, melamine, cyanamide, 2-cyanoguanidine, ammeline, guanidine carbonate, ethylenediamine, ammelide, biuret, diethylenetriamine, triethylenetetramine, 1,3-diaminopropane, calcium cyanamide, cyanuric acid, aminoethylpiperazine, piperazine, and allophante; and the genetically engineered organism converts the substrate to a product.

In certain embodiments, the invention relates to a product made by any one of the aforementioned methods.

In certain embodiments, the invention relates to a recombinant vector comprising a gene operably linked to a promoter, wherein the gene encodes an enzyme; and the enzyme is allophanate hydrolase, biuret amidohydrolase, cyanuric acid amidohydrolase, guanine deaminase, melamine deaminase, isopropylammelide isopropylaminohydrolase, cyanamide hydratase, urease, or urea carboxylase.

BRIEF DESCRIPTION OF THE FIGURES

FIG. 2 tabulates exemplary compounds capable of delivering nitrogen that could be accessed by an engineered organism.

FIG. 3 tabulates DNA and protein sequences encoding the melamine degradation pathway.

FIG. 11 tabulates the concentrations of the components in the MOPS medium used in Example 9.

FIG. 29 tabulates a summary of various plasmids of the invention.

FIG. 30 tabulates a summary of various organisms of the invention.

FIG. 31 tabulates the components and molar concentrations of each component in a MOPS defined medium, which is used, for example, with *E. coli*.

FIG. 32 tabulates the components and weight concentrations of each component in a YNB medium, which is used, for example, with *S. cerevisiae*.

FIG. 33 tabulates the components and weight concentrations of each component in a SC amino acid medium.

DETAILED DESCRIPTION OF THE INVENTION

Overview

Figure 1:
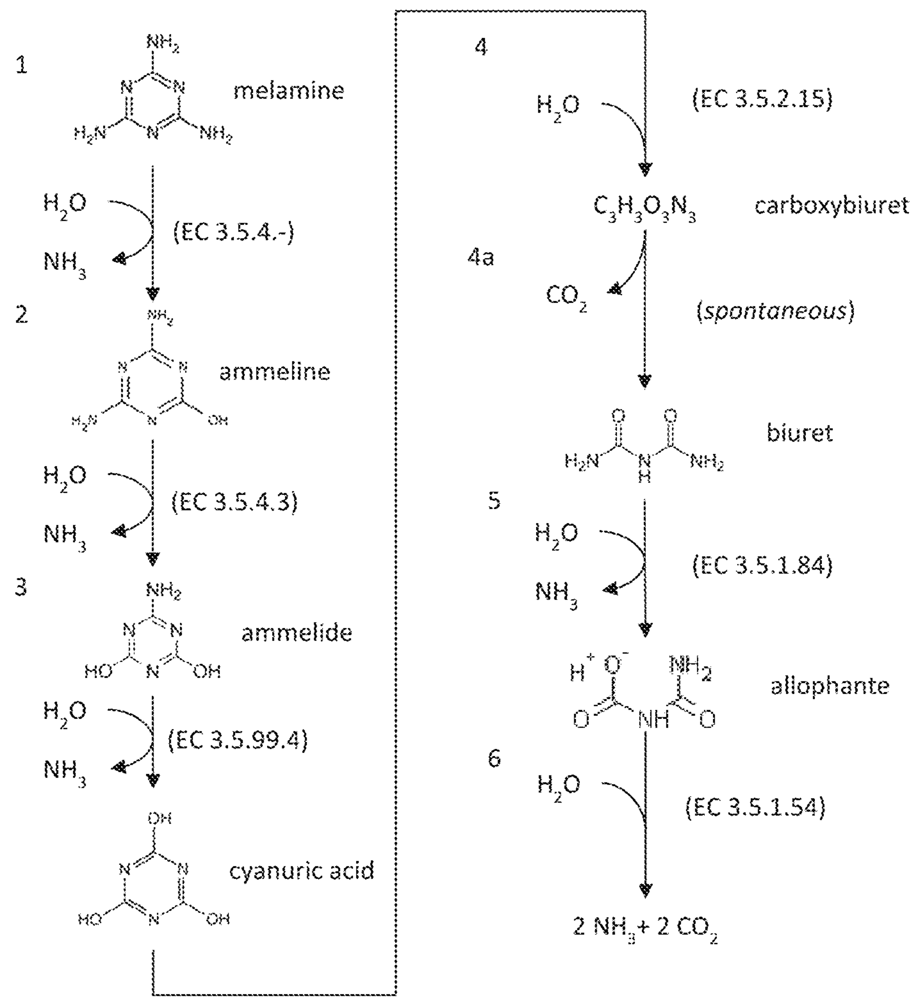
FIG. 1 depicts a schematic representation of the melamine degradation pathway. 1—Melamine deaminase (tzrA) (EC 3.5.4.-); 2—Ammeline deaminase (guanine deaminase) (EC 3.5.4.3); 3—N-isopropylammelide isopropylamino (Ammelide) hydrolyase (EC 3.5.99.4); 4—Cyanuric acid hydrolyase (EC 3.5.2.15); 4a—Carboxybiuret decarboxylase, spontaneous reaction; 5—Biuret amidohydrolase (EC 3.5.1.84); 6—Allophanate hydrolyase (EC 3.5.1.54). Nitrogen can be assimilated (as $NH_3$) by the action of the complete pathway acting on melamine, liberating 6 mol $NH_3$ per mol melamine, or via a subset of enzymes acting on pathway intermediates (e.g., steps 4, 4a, 5, and 6 acting on cyanuric acid releasing 3 mol $NH_3$ per mol cyanuric acid).
Figure 4:
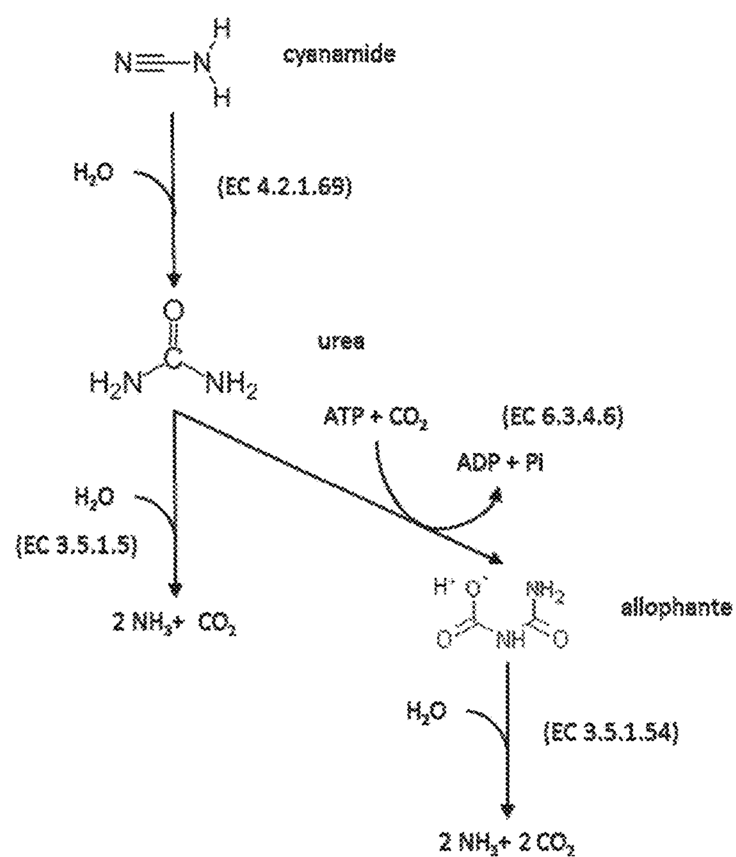
FIG. 4 depicts a schematic representation of the cyanamide assimilation pathway. After conversion of cyanamide to urea by cyanamide hydratase (EC 4.2.1.69), urea can be degraded either via urease (EC 3.5.1.5) or by urea carboxylase (EC 6.3.4.6) and allophante hydrolyase (EC 3.5.1.54).

In certain embodiments, the invention relates to a genetically engineered host organism, wherein the genetically engineered host organism has a non-native ability to obtain a growth-limiting nutrient from a complex substrate; and the complex substrate could not have been metabolized or used as a nutrient by the native host organism. In certain embodiments, the non-native ability will provide the organism with a significant competitive advantage, and provide a major barrier to the success of contaminants in a fermentation. In certain embodiments, the genetically engineered host organism is a bacterium, a yeast, a fungus, a mammalian cell, or an insect cell. In certain embodiments, the genetically engineered host organism is a bacterium or a yeast.

In certain embodiments, the invention relates to a method of using the above-mentioned genetically engineered host organism, comprising contacting the genetically engineered host organism with a modified cell culture medium. In certain embodiments, the invention relates to a method of using the above-mentioned genetically engineered host organism, comprising contacting the genetically engineered host organism with a modified cell culture medium, wherein the genetically engineered host organism converts the cell culture medium to a product. In certain embodiments, using this approach provides a unique and targeted manner to promote the growth of the desired genetically engineered host organism. In certain embodiments, the above-mentioned methods minimize the growth of contaminant organisms, provide a valuable competitive advantage, and allow management of production of a range of valuable products.

In certain embodiments, the inventive methods decrease or eliminate the need for use of prophylactic antibiotics in large scale yeast cultures. Avoiding unnecessary antibiotics is an important benefit due to emerging environmental considerations and societal pressures. Additionally, in certain embodiments, the technique can be applied to bacterial systems in which antibiotics may not be added.

In certain embodiments, the genetically engineered host organism is a yeast; and the product is ethanol, isobutanol, lactic acid, an isoprenoid, a lipid, and enzyme product, or a high value specialty chemical.

In certain embodiments, the genetically engineered host organism is a bacterium; and the product is butanol, ethanol, isopropanol, 1,3-propanediol (PDO), 1,4-butanediol (BDO), succinic acid, itaconic acid, an enzyme product, a polyol, a protein product, or a high value specialty chemical.

In certain embodiments, the inventive technology is applicable in the production of one or more commodities, fine chemicals, and pharmaceuticals.

Definitions

"Dry weight" and "dry cell weight" mean weight determined in the relative absence of water. For example, reference to oleaginous cells as comprising a specified percentage of a particular component by dry weight means that the percentage is calculated based on the weight of the cell after substantially all water has been removed.

"Exogenous gene" is a nucleic acid that codes for the expression of an RNA and/or protein that has been introduced into a cell (e.g., by transformation/transfection), and is also referred to as a "transgene." A cell comprising an exogenous gene may be referred to as a recombinant cell, into which additional exogenous gene(s) may be introduced. The exogenous gene may be from a different species (and so heterologous), or from the same species (and so homologous), relative to the cell being transformed. Thus, an exogenous gene can include a homologous gene that occupies a different location in the genome of the cell or is under different control, relative to the endogenous copy of the gene. An exogenous gene may be present in more than one copy in the cell. An exogenous gene may be maintained in a cell as an insertion into the genome (nuclear or plastid) or as an episomal molecule.

"Expression vector" or "expression construct" or "plasmid" or "recombinant DNA construct" is a vehicle for introducing a nucleic acid into a host cell. The nucleic acid can be one that has been generated via human intervention, including by recombinant means or direct chemical synthesis, with a series of specified nucleic acid elements that permit transcription and/or translation of a particular nucleic acid. The expression vector can be part of a plasmid, virus, or nucleic acid fragment, or other suitable vehicle. Typically, the expression vector includes a nucleic acid to be transcribed operably linked to a promoter.

"Inducible promoter" is a promoter that mediates transcription of an operably linked gene in response to a particular stimulus.

"In operable linkage" is a functional linkage between two nucleic acid sequences, such a control sequence (typically a promoter) and the linked sequence (typically a sequence that encodes a protein, also called a coding sequence). A promoter is in operable linkage with an exogenous gene if it can mediate transcription of the gene.

"Lysate" is a solution containing the contents of lysed cells.

"Lysis" is the breakage of the plasma membrane and optionally the cell wall of a biological organism sufficient to release at least some intracellular content, often by mechanical, viral or osmotic mechanisms that compromise its integrity.

"Lysing" is disrupting the cellular membrane and optionally the cell wall of a biological organism or cell sufficient to release at least some intracellular content.

"Osmotic shock" is the rupture of cells in a solution following a sudden reduction in osmotic pressure. Osmotic shock is sometimes induced to release cellular components of such cells into a solution.

The terms "plasmid", "vector" and "cassette" refer to an extra chromosomal element often carrying genes that are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements, in addition to the foreign gene, that facilitate transformation of a particular host cell. "Expression cassette" refers to a specific vector containing a foreign gene and having elements in addition to the foreign gene that allow for enhanced expression of that gene in a foreign host.

"Promoter" is a nucleic acid control sequence that directs transcription of a nucleic acid. As used herein, a promoter includes necessary nucleic acid sequences near the start site of transcription. A promoter also optionally includes distal enhancer or repressor elements, which can be located as much as several thousand base pairs from the start site of transcription.

"Recombinant" is a cell, nucleic acid, protein, or vector, which has been modified due to the introduction of an exogenous nucleic acid or the alteration of a native nucleic acid. Thus, e.g., recombinant cells can express genes that are not found within the native (non-recombinant) form of the cell or express native genes differently than those genes are expressed by a non-recombinant cell. Recombinant cells can, without limitation, include recombinant nucleic acids that encode for a gene product or for suppression elements such as mutations, knockouts, antisense, interfering RNA (RNAi) or dsRNA that reduce the levels of active gene product in a cell. A "recombinant nucleic acid" is a nucleic acid originally formed in vitro, in general, by the manipulation of nucleic acid, e.g., using polymerases, ligases, exonucleases, and endonucleases, or otherwise is in a form not normally found in nature. Recombinant nucleic acids may be produced, for example, to place two or more nucleic acids in operable linkage. Thus, an isolated nucleic acid or an expression vector formed in vitro by ligating DNA molecules that are not normally joined in nature, are both considered recombinant for the purposes of this invention. Once a recombinant nucleic acid is made and introduced into a host cell or organism, it may replicate using the in vivo cellular machinery of the host cell; however, such nucleic acids, once produced recombinantly, although subsequently replicated intracellularly, are still considered recombinant for purposes of this invention. Similarly, a "recombinant protein" is a protein made using recombinant techniques, i.e., through the expression of a recombinant nucleic acid.

"Sonication" is a process of disrupting biological materials, such as a cell, by use of sound wave energy.

"Transformation" refers to the transfer of a nucleic acid fragment into a host organism or the genome of a host organism, resulting in genetically stable inheritance. Host organisms containing the transformed nucleic acid fragments are referred to as "recombinant", "transgenic" or "transformed" organisms. Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. Typically, expression vectors include, for example, one or more cloned genes under the transcriptional control of 5' and 3' regulatory sequences and a selectable marker. Such vectors also can contain a promoter regulatory region (e.g., a regulatory region controlling inducible or constitutive, environmentally- or developmentally-regulated, or location-specific expression), a transcription initiation start site, a ribosome binding site, a transcription termination site, and/or a polyadenylation signal.

Microbe Engineering

A. Overview

In certain embodiments of the invention, a microorganism is genetically modified to improve or provide de novo growth characteristics on a variety of feedstock materials.

Genes and gene products may be introduced into microbial host cells. Suitable host cells for expression of the genes and nucleic acid molecules are microbial hosts that can be found broadly within the fungal or bacterial families and which grow over a wide range of temperature, pH values, and solvent tolerances. Examples of suitable host strains include but are not limited to fungal or yeast species, such as *Aspergillus, Trichoderma, Saccharomyces, Pichia, Candida, Hansenula, Kluyveromyces*, or bacterial species, such as member of the proteobacteria and actinomycetes as well as the specific genera *Acinetobacter, Arthrobacter, Brevibacterium, Acidovorax, Bacillus, Clostridia, Streptomyces, Escherichia, Salmonella, Pseudomonas*, and *Cornyebacterium.*

*E. coli* is well suited to use as the host microorganism in the invention fermentative processes.

Microbial expression systems and expression vectors containing regulatory sequences that direct high level expression of foreign proteins are well known to those skilled in the art. Any of these could be used to construct chimeric genes to produce the any one of the gene products of the instant sequences. These chimeric genes could then be introduced into appropriate microorganisms via transformation techniques to provide high-level expression of the enzymes.

For example, a gene encoding an enzyme can be cloned in a suitable plasmid, and the aforementioned starting parent strain as a host can be transformed with the resulting plasmid. This approach can increase the copy number of each of the genes encoding the enzymes and, as a result, the activities of these enzymes can be increased. The plasmid is not particularly limited so long as it can autonomously replicate in the microorganism.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene harboring transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Promoters, cDNAs, and 3'UTRs, as well as other elements of the vectors, can be generated through cloning techniques using fragments isolated from native sources (see, for example, Molecular Cloning: A Laboratory Manual, Sambrook et al. (3d edition, 2001, Cold Spring Harbor Press; and U.S. Pat. No. 4,683,202 (incorporated by reference)). Alternatively, elements can be generated synthetically using known methods (see, for example, Gene. 1995 Oct. 16; 164(1):49-53).

B. Homologous Recombination

Homologous recombination is the ability of complementary DNA sequences to align and exchange regions of homology. Transgenic DNA ("donor") containing sequences homologous to the genomic sequences being targeted ("template") is introduced into the organism and then undergoes recombination into the genome at the site of the corresponding genomic homologous sequences.

The ability to carry out homologous recombination in a host organism has many practical implications for what can be carried out at the molecular genetic level and is useful in the generation of an oleaginous microbe that can produced tailored oils. By its very nature homologous recombination is a precise gene targeting event, hence, most transgenic lines generated with the same targeting sequence will be essentially identical in terms of phenotype, necessitating the screening of far fewer transformation events. Homologous recombination also targets gene insertion events into the host chromosome, potentially resulting in excellent genetic stability, even in the absence of genetic selection. Because different chromosomal loci will likely impact gene expression, even from heterologous promoters/UTRs, homologous recombination can be a method of querying loci in an unfamiliar genome environment and to assess the impact of these environments on gene expression.

A particularly useful genetic engineering approach using homologous recombination is to co-opt specific host regulatory elements such as promoters/UTRs to drive heterologous gene expression in a highly specific fashion.

Because homologous recombination is a precise gene targeting event, it can be used to precisely modify any nucleotide(s) within a gene or region of interest, so long as sufficient flanking regions have been identified. Therefore, homologous recombination can be used as a means to modify regulatory sequences impacting gene expression of RNA and/or proteins. It can also be used to modify protein coding regions in an effort to modify enzyme activities such as substrate specificity, affinities and Km, and thus affecting the desired change in metabolism of the host cell. Homologous recombination provides a powerful means to manipulate the host genome resulting in gene targeting, gene conversion, gene deletion, gene duplication, gene inversion and exchanging gene expression regulatory elements such as promoters, enhancers and 3'UTRs.

Homologous recombination can be achieved by using targeting constructs containing pieces of endogenous sequences to "target" the gene or region of interest within the endogenous host cell genome. Such targeting sequences can either be located 5' of the gene or region of interest, 3' of the gene/region of interest or even flank the gene/region of interest. Such targeting constructs can be transformed into the host cell either as a supercoiled plasmid DNA with additional vector backbone, a PCR product with no vector backbone, or as a linearized molecule. In some cases, it may be advantageous to first expose the homologous sequences within the transgenic DNA (donor DNA) with a restriction enzyme. This step can increase the recombination efficiency and decrease the occurrence of undesired events. Other methods of increasing recombination efficiency include using PCR to generate transforming transgenic DNA containing linear ends homologous to the genomic sequences being targeted.

C. Vectors and Vector Components

Vectors for transformation of microorganisms in accordance with the present invention can be prepared by known techniques familiar to those skilled in the art in view of the disclosure herein. A vector typically contains one or more genes, in which each gene codes for the expression of a desired product (the gene product) and is operably linked to one or more control sequences that regulate gene expression or target the gene product to a particular location in the recombinant cell.

This subsection is divided into subsections. Subsection 1 describes control sequences typically contained on vectors as well as novel control sequences provided by the present invention. Subsection 2 describes genes typically contained in vectors as well as novel codon optimization methods and genes prepared using them provided by the invention.

1. Control Sequences

Control sequences are nucleic acids that regulate the expression of a coding sequence or direct a gene product to a particular location in or outside a cell. Control sequences that regulate expression include, for example, promoters that regulate transcription of a coding sequence and terminators that terminate transcription of a coding sequence. Another control sequence is a 3' untranslated sequence located at the end of a coding sequence that encodes a polyadenylation signal. Control sequences that direct gene products to particular locations include those that encode signal peptides, which direct the protein to which they are attached to a particular location in or outside the cell.

Thus, an exemplary vector design for expression of an exogenous gene in a microbe contains a coding sequence for a desired gene product (for example, a selectable marker, or an enzyme) in operable linkage with a promoter active in microalgae. Alternatively, if the vector does not contain a promoter in operable linkage with the coding sequence of interest, the coding sequence can be transformed into the cells such that it becomes operably linked to an endogenous promoter at the point of vector integration.

The promoter used to express an exogenous gene can be the promoter naturally linked to that gene or can be a heterologous promoter.

A promoter can generally be characterized as either constitutive or inducible. Constitutive promoters are generally active or function to drive expression at all times (or at certain times in the cell life cycle) at the same level. Inducible promoters, conversely, are active (or rendered inactive) or are significantly up- or down-regulated only in response to a stimulus. Both types of promoters find application in the methods of the invention. Inducible promoters useful in the invention include those that mediate transcription of an operably linked gene in response to a stimulus, such as an exogenously provided small molecule, temperature (heat or cold), lack of nitrogen in culture media, etc. Suitable promoters can activate transcription of an essentially silent gene or upregulate, preferably substantially, transcription of an operably linked gene that is transcribed at a low level.

Inclusion of termination region control sequence is optional, and if employed, then the choice is be primarily one of convenience, as the termination region is relatively interchangeable. The termination region may be native to the transcriptional initiation region (the promoter), may be native to the DNA sequence of interest, or may be obtainable from another source. See, for example, Chen and Orozco, Nucleic Acids Res. (1988) 16:8411.

2. Genes and Codon Optimization

Typically, a gene includes a promoter, coding sequence, and termination control sequences. When assembled by recombinant DNA technology, a gene may be termed an expression cassette and may be flanked by restriction sites for convenient insertion into a vector that is used to introduce the recombinant gene into a host cell. The expression cassette can be flanked by DNA sequences from the genome or other nucleic acid target to facilitate stable integration of the expression cassette into the genome by homologous recombination. Alternatively, the vector and its expression cassette may remain unintegrated (e.g., an episome), in which case, the vector typically includes an origin of replication, which is capable of providing for replication of the heterologous vector DNA.

A common gene present on a vector is a gene that codes for a protein, the expression of which allows the recombinant cell containing the protein to be differentiated from cells that do not express the protein. Such a gene, and its corresponding gene product, is called a selectable marker or selection marker. Any of a wide variety of selectable markers can be employed in a transgene construct useful for transforming the organisms of the invention.

For optimal expression of a recombinant protein, it is beneficial to employ coding sequences that produce mRNA with codons optimally used by the host cell to be transformed. Thus, proper expression of transgenes can require that the codon usage of the transgene matches the specific codon bias of the organism in which the transgene is being expressed. The precise mechanisms underlying this effect are many, but include the proper balancing of available aminoacylated tRNA pools with proteins being synthesized in the cell, coupled with more efficient translation of the transgenic messenger RNA (mRNA) when this need is met. When codon usage in the transgene is not optimized, available tRNA pools are not sufficient to allow for efficient translation of the heterologous mRNA resulting in ribosomal stalling and termination and possible instability of the transgenic mRNA.

D. Expression of Two or More Exogenous Genes

Further, a genetically engineered microorganism may comprise and express more than one exogenous gene. One or more genes can be expressed using an inducible promoter, which allows the relative timing of expression of these genes to be controlled. Expression of the two or more exogenous genes may be under control of the same inducible promoter or under control of different inducible promoters. In the latter situation, expression of a first exogenous gene can be induced for a first period of time (during which expression of a second exogenous gene may or may not be induced) and expression of a second or further exogenous gene can be induced for a second period of time (during which expression of a first exogenous gene may or may not be induced). Provided herein are vectors and methods for engineering microbes to grow on non-traditional growth media.

E. Transformation

Cells can be transformed by any suitable technique including, e.g., biolistics, electroporation, glass bead transformation and silicon carbide whisker transformation. Any convenient technique for introducing a transgene into a microorganism can be employed in the present invention. Transformation can be achieved by, for example, the method of D. M. Morrison (Methods in Enzymology 68, 326 (1979)), the method by increasing permeability of recipient cells for DNA with calcium chloride (Mandel, M. and Higa, A., J. Mol. Biol., 53, 159 (1970)), or the like.

Examples of expression of transgenes in oleaginous yeast (e.g., *Yarrowia lipolytica*) can be found in the literature (see, for example, Bordes et al., J Microbiol Methods, Jun. 27 (2007)). Examples of expression of exogenous genes in bacteria such as *E. coli* are well known; see, for example, Molecular Cloning: A Laboratory Manual, Sambrook et al. (3d edition, 2001, Cold Spring Harbor Press).

Vectors for transformation of microorganisms in accordance with the present invention can be prepared by known techniques familiar to those skilled in the art. In one embodiment, an exemplary vector design for expression of a gene in a microorganism contains a gene encoding an enzyme in operable linkage with a promoter active in the microorganism. Alternatively, if the vector does not contain a promoter in operable linkage with the gene of interest, the gene can be transformed into the cells such that it becomes operably linked to an endogenous promoter at the point of vector integration. The vector can also contain a second gene that encodes a protein. Optionally, one or both gene(s) is/are followed by a 3' untranslated sequence containing a polyadenylation signal. Expression cassettes encoding the two genes can be physically linked in the vector or on separate vectors. Co-transformation of microbes can also be used, in which distinct vector molecules are simultaneously used to transform cells (see, for example, Protist 2004 December; 155(4):381-93). The transformed cells can be optionally selected based upon the ability to grow in the presence of the antibiotic or other selectable marker under conditions in which cells lacking the resistance cassette would not grow.

Nitrogen-Containing Compounds in Feedstocks

In certain embodiments, the invention relates to use of an atypical nitrogen-containing feedstock comprising, consisting essentially of, or consisting of a nitrogen-containing compound of any one of Formulas I-III. In certain embodiments, a non-genetically engineered organism, i.e., a native organism, could not metabolize (i.e., use as a source of nitrogen) the nitrogen-containing compounds in the feedstock.

In certain embodiments, the invention relates to any one of the aforementioned nitrogen-containing feedstocks, wherein the nitrogen-containing compound is a compound of formula I or a salt thereof:

$$\text{(A)}\!-\!(R)_n \qquad \text{I}$$

wherein, independently for each occurrence, $$\text{(A)}$$

is a five-, six, nine-, or ten-membered aryl or heteroaryl group;

R is —OH, —$CO_2$H, —$NO_2$, —CN, substituted or unsubstituted amino, or substituted or unsubstituted alkyl; and n is 0, 1, 2, 3, 4, or 5.

In certain embodiments, the invention relates to any one of the aforementioned nitrogen-containing feedstocks, wherein the nitrogen-containing compound is a compound of formula II or a salt thereof:

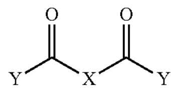

II wherein, independently for each occurrence,

X is —NH—, —N(alkyl)-, —O—, —$C(R^1)_2$—, —S—, or absent;

Y is —H, —$NH_2$, —N(H)(alkyl), —$N(alkyl)_2$, —$CO_2$H, —CN, or substituted or unsubstituted alkyl; and $R^1$ is —H, —OH, —$CO_2$H, —$NO_2$, —CN, substituted or unsubstituted amino, or substituted or unsubstituted alkyl.

In certain embodiments, the invention relates to any one of the aforementioned nitrogen-containing feedstocks, wherein the nitrogen-containing compound is a compound of formula III or a salt thereof:

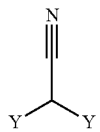

III wherein, independently for each occurrence,

Y is —H, —$NH_2$, —N(H)(alkyl), —$N(alkyl)_2$, —$CO_2$H, —CN, or substituted or unsubstituted alkyl.

In certain embodiments, the invention relates to any one of the aforementioned nitrogen-containing feedstocks, wherein the nitrogen-containing compound is selected from the group consisting of:

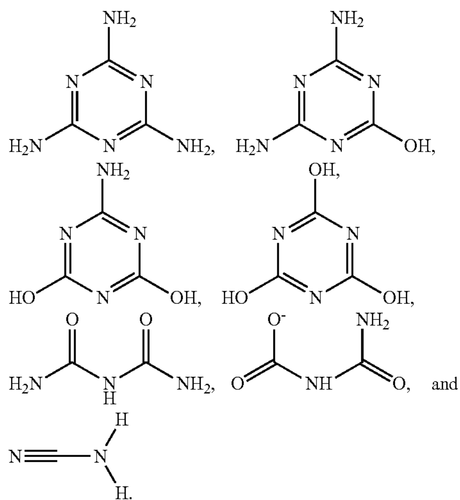

In certain embodiments, the invention relates to any one of the aforementioned nitrogen-containing feedstocks, wherein the nitrogen-containing compound is selected from the group consisting of Hydrazine, 5-Aminotetrazole, Tetrazole, Melamine, Cyanamide, 2-Cyanoguanidine, Sodium azide, Carbohydrazide, 1,2,3-Triazole, 1,2,4-Triazole, 1,3-Diaminoguanidine HCl, Ammeline, 1,3,5-triazine, Aminoacetonitrile, Cyanoethylhydrazine, Azodicarbonamide, Biurea, Formamidoxime, 1,2-Dimethylhydrazine, 1,1-Dimethylhydrazine, ethylhydrazine, Ethylenediamine, Sodium dicyanamide, Guanidine carbonate, Methylamine, Ammelide, Hydroxylamine, Malononitrile, Biuret, Diethyltriamine, Hexamethylenetetramine, Triethylenetetramine, 1,3-Diaminopropane, Triethylenetetramine, 1,3-Diaminopropane, Hydroxyurea, Tetraethylenepentamine, Thiourea, Succinonitrile, Calcium cyanamide, Cyanuric acid, Aminoethylpiperazine, Piperazine, Dimethylamine, Ethylamine, dalfampridine, Tetranitromethane, Imidazolidinyl urea, Trinitromethane, malonamide, Chloramine, Allophante, Trimethylamine, Nitromethane, Acetaldoxime, Diazolidinyl urea, 1,2-Cyclohexanedione dioxime, Acetone oxime, Thioacetamide, Sodium thiocyanate, Isothiazole, Thiazole, Dimethyl acetamide, Isothiazolinone, Methylene blue, Diethanolamine, Aspartame, Benzisothiazolinone, and Acesulfame potassium.

Exemplary Isolated Nucleic Acid Molecules and Vectors

In certain embodiments, the invention relates to an isolated nucleic acid molecule, wherein the nucleic acid molecule encodes an enzyme that provides the organism with the ability to assimilate a nitrogen source that otherwise would not have been accessible to the native organism; and the enzyme is allophanate hydrolase, biuret amidohydrolase, cyanuric acid amidohydrolase, guanine deaminase, ammeline hydrolase, ammelide hydrolyase, melamine deaminase, isopropylammelide isopropylaminohydrolase, cyanamide hydratase, urease, or urea carboxylase.

In certain embodiments, the invention relates to an isolated nucleic acid molecule, wherein the nucleic acid molecule is selected from the group consisting of trzE from *Rhodococcus* sp. strain Mel, trzE from *Rhizobium leguminosarum*, trzC MEL, trzC 12227, cah from *Fusarium oxysporum* Fo5176, cah from *F. pseudograminaearum* CS3096, cah from *Gibberella zeae* PH-1, cah from *Aspergillus kawachii* IFO 4308, cah from *A. niger* CBS 513.88, cah from *A. niger* ATCC 1015, cah from *A. oryzae* 3.042, cah from *S. cerevisiae* FostersB, atzF from *Pseudomonas* sp. strain ADP, DUR1,2 from *S. cerevisiae*, YALI0E 07271g from *Y. lipolytica* CLIB122, atzE from *Pseudomonas* sp. strain ADP, atzD from *Pseudomonas* sp. strain ADP, trzD from *Pseudomonas* sp. strain NRRLB-12227, atzD from *Rhodococcus* sp. Mel, trzD from *Rhodococcus* sp. Mel, guaD from *E. coli* K12 strain MG1566, blr3880 from *Bradyrhizobium japonicum* USDA 110, GUD1/Y DL238C from *S. cerevisiae*, YAL10E2 5740p from *Y. lipolytica* CLIB122, trzA from *Williamsia* sp. NRRL B-15444R, triA from *Pseudomonas* sp. strain NRRL B-12227, atzC from *Pseudomonas* sp. strain ADP, and cah from *Myrothecium verrucaria*.

In certain embodiments, the invention relates to an isolated nucleic acid molecule comprising any one of the sequences disclosed herein. In certain embodiments, the invention relates to an isolated nucleic acid molecule having at least 85% sequence homology with any one of the sequences disclosed herein. In certain embodiments, the invention relates to an isolated nucleic acid molecule having at least 90% sequence homology with any one of the sequences disclosed herein. In certain embodiments, the invention relates to an isolated nucleic acid molecule having at least 95% sequence homology with any one of the sequences disclosed herein. In certain embodiments, the invention relates to an isolated nucleic acid molecule having at least 99% sequence homology with any one of the sequences disclosed herein. In certain embodiments, the invention relates to an isolated nucleic acid molecule having any one of the sequences disclosed herein.

A recombinant vector comprising any one of the aforementioned nucleic acid molecules operably linked to a promoter.

In certain embodiments, the invention relates to a recombinant vector comprising any one of the sequences disclosed herein. In certain embodiments, the invention relates to a recombinant vector having at least 85% sequence homology with any one of the sequences disclosed herein. In certain embodiments, the invention relates to a recombinant vector having at least 90% sequence homology with any one of the sequences disclosed herein. In certain embodiments, the invention relates to a recombinant vector having at least 95% sequence homology with any one of the sequences disclosed herein. In certain embodiments, the invention relates to a recombinant vector having at least 99% sequence homology with any one of the sequences disclosed herein.

Exemplary Genetically Engineered Organisms of the Invention

In certain embodiments, the invention relates to a genetically engineered organism, wherein the genetically engineered organism has been transformed by a nucleic acid molecule or a recombinant vector comprising any one of the sequences disclosed herein. In certain embodiments, the nucleic acid molecule or recombinant vector has at least 85% sequence homology with any one of the sequences disclosed herein. In certain embodiments, the nucleic acid molecule or recombinant vector has at least 90% sequence homology with any one of the sequences disclosed herein. In certain embodiments, the nucleic acid molecule or recombinant vector has at least 95% sequence homology with any one of the sequences disclosed herein. In certain embodiments, the nucleic acid molecule or recombinant vector has at least 99% sequence homology with any one of the sequences disclosed herein. In certain embodiments, the invention relates to a genetically engineered organism, wherein the genetically engineered organism has been transformed by a nucleic acid molecule or a recombinant vector having any one of the sequences disclosed herein.

In certain embodiments, the invention relates to a genetically engineered organism, wherein the genetically engineered organism has been transformed by a nucleic acid molecule; the nucleic acid molecule comprises a non-native gene; and the non-native gene encodes for a non-native enzyme selected from the group consisting of allophanate hydrolase, biuret amidohydrolase, cyanuric acid amidohydrolase, guanine deaminase, ammeline hydrolase, ammelide hydrolyase, melamine deaminase, and isopropylammelide isopropylaminohydrolase, cyanamide hydratase, urease, or urea carboxylase.

In certain embodiments, the invention relates to any one of the aforementioned genetically engineered organisms, wherein the non-native gene is selected from the group consisting of atzF, DUR1,2 YALI0E 07271g, atzE, atzD, trzC, trzD, trzE, atzD, guaD, blr3880, GUD1Y DL238C, YAL10E2 5740p, trzA, triA, atzC, and cah. In certain embodiments, the invention relates to any one of the aforementioned genetically engineered organisms, wherein the non-native gene is selected from the group consisting of atzF, DUR1,2 YALI0E 07271g, atzE, atzD, trzD, atzD, guaD, blr3880, GUD1/Y DL238C, YAL10E2 5740p, trzA, triA, atzC, and cah. Any organism may be used as a source of the non-native gene, as long as the organisms has the desired enzymatic activity The non-native gene can each be obtained from chromosomal DNA of any one of the aforementioned microorganisms by isolating a DNA fragment complementing auxotrophy of a variant strain lacking the enzymatic activity. Alternatively, if the nucleotide sequence of these gene of the organism has already been elucidated (Biochemistry, Vol. 22, pp. 5243-5249, 1983; J. Biochem. Vol. 95, pp. 909-916, 1984; Gene, Vol. 27, pp. 193-199, 1984; Microbiology, Vol. 140, pp. 1817-1828, 1994; Mol. Gene Genet. Vol. 218, pp. 330-339, 1989; and Molecular Microbiology, Vol. 6, pp. 317-326, 1992), the genes can be obtained by PCR using primers synthesized based on each of the elucidated nucleotide sequences, and the chromosome DNA as a template.

In certain embodiments, the invention relates to any one of the aforementioned genetically engineered organisms, wherein the non-native gene is selected from the group consisting of trzE from *Rhodococcus* sp. strain Mel, trzE from *Rhizobium leguminosarum*, trzC MEL, trzC 12227, cah from *Fusarium oxysporum* Fo5176, cah from *F. pseudograminaearum* CS3096, cah from *Gibberella zeae* PH-1, cah from *Aspergillus kawachii* IFO 4308, cah from *A. niger* CBS 513.88, cah from *A. niger* ATCC 1015, cah from *A. oryzae* 3.042, cah from *S. cerevisiae* FostersB, atzF from *Pseudomonas* sp. strain ADP, DUR1,2 from *S. cerevisiae*, YALI0E 07271g from *Y. lipolytica* CLIB122, atzE from *Pseudomonas* sp. strain ADP, atzD from *Pseudomonas* sp. strain ADP, trzD from *Pseudomonas* sp. strain NRRLB-12227, atzD from *Rhodococcus* sp. Mel, trzD from *Rhodococcus* sp. Mel, guaD from *E. coli* K12 strain MG1566, blr3880 from *Bradyrhizobium japonicum* USDA 110, GUD1/Y DL238C from *S. cerevisiae*, YAL10E2 5740p from *Y. lipolytica* CLIB122, trzA from *Williamsia* sp. NRRL B-15444R, triA from *Pseudomonas* sp. strain NRRL B-12227, atzC from *Pseudomonas* sp. strain ADP, and cah from *Myrothecium verrucaria*.

In certain embodiments, the invention relates to any one of the aforementioned genetically engineered organisms, wherein the genetically engineered organism is a species of the genus *Yarrowia, Saccharomyces, Ogataea, Pichia*, or *Escherichia*.

In certain embodiments, the invention relates to any one of the aforementioned genetically engineered organisms, wherein the genetically engineered organism is selected from the group consisting of *Yarrowia lipolytica, Saccharomyces cerevisiae, Ogataea polymorpha, Pichia pastoris*, and *Escherichia coli*.

In certain embodiments, the genetically engineered organism is not *Rhodococcus* sp. Strain Mel.

Exemplary Methods of the Invention

In certain embodiments, the invention relates to a method, comprising the step of contacting any one of the aforementioned genetically engineered organisms with a substrate, wherein the substrate comprises a nitrogen-containing fraction and a non-nitrogen-containing fraction;

the nitrogen-containing fraction comprises, in an amount from about 10% by weight to about 100% by weight, a nitrogen-containing compound of any one of Formulas I-III;

a native organism of the same species as the genetically engineered organism could not metabolize (i.e., use as a source of nitrogen) the nitrogen-containing compound; and the genetically engineered organism converts the substrate to a product.

In certain embodiments, the invention relates to any one of the aforementioned methods, wherein the nitrogen-containing compounds have a low molecular weight. In certain embodiments, the invention relates to any one of the aforementioned methods, wherein the nitrogen-containing compounds have a molecular weight between about 30 Da and about 800 Da. In certain embodiments, the invention relates to any one of the aforementioned methods, wherein the nitrogen-containing compounds have a molecular weight between about 40 Da and about 600 Da. In certain embodiments, the invention relates to any one of the aforementioned methods, wherein the nitrogen-containing compounds have a molecular weight of about 40 Da, about 50 Da, about 60 Da, about 70 Da, about 80 Da, about 90 Da, about 100 Da, about 110 Da, about 120 Da, about 130 Da, about 140 Da, about 150 Da, about 160 Da, about 170 Da, about 180 Da, about 190 Da, about 200 Da, about 220 Da, about 240 Da, about 260 Da, about 280 Da, about 300 Da, about 320 Da, about 340 Da, about 360 Da, about 380 Da, about 400 Da, about 420 Da, about 440 Da, about 460 Da, about 480 Da, about 500 Da, about 520 Da, about 540 Da, about 560 Da, about 580 Da, or about 600 Da.

In certain embodiments, the invention relates to any one of the aforementioned methods, wherein the nitrogen-containing compounds have less than 12 carbon atoms. In certain embodiments, the invention relates to any one of the aforementioned methods, wherein the nitrogen-containing compounds have less than 8 carbon atoms. In certain embodiments, the invention relates to any one of the aforementioned methods, wherein the nitrogen-containing compounds have 1, 2, 3, 4, 5, 6, or 7 carbon atoms.

In certain embodiments, the invention relates to any one of the aforementioned methods, wherein the nitrogen-containing compounds have 1, 2, 3, 4, 5, 6, 7, 8, 9, or 10 nitrogen atoms.

In certain embodiments, the invention relates to any one of the aforementioned methods, wherein the nitrogen-containing compounds have 0, 1, 2, 3, 4, 5, 6, 7, or 8 oxygen atoms.

In certain embodiments, the invention relates to any one of the aforementioned methods, wherein the nitrogen-containing compounds have an octanol-water partition coefficient (log P) less than about 5. In certain embodiments, the invention relates to any one of the aforementioned methods, wherein the nitrogen-containing compounds have an octanol-water partition coefficient (log P) from about −0.5 to about 5. In certain embodiments, the invention relates to any one of the aforementioned methods, wherein the nitrogen-containing compounds have an octanol-water partition coefficient (log P) of about −0.5, about 0, about 0.5, about 1, about 1.5, about 2, about 2.5, about 3, about 3.5, about 4, or about 4.5.

In certain embodiments, the invention relates to any one of the aforementioned methods, wherein the nitrogen-containing compounds are soluble in water at about 20° C. at a concentration of between about 0.01 g/L to about 1000 g/L. In certain embodiments, the invention relates to any one of the aforementioned methods, wherein the nitrogen-containing compounds are soluble in water at about 20° C. at a concentration of about 0.01 g/L, about 0.05 g/L, about 0.1 g/L, about 0.5 g/L, about 1 g/L, about 5 g/L, about 10 g/L, about 15 g/L, about 20 g/L, about 25 g/L, about 30 g/L, about 35 g/L, about 40 g/L, about 45 g/L, about 50 g/L, about 55 g/L, about 60 g/L, about 65 g/L, about 70 g/L, about 75 g/L, about 80 g/L, about 85 g/L, about 90 g/L, about 95 g/L, or about 100 g/L.

In certain embodiments, the invention relates to any one of the aforementioned methods, wherein the nitrogen-containing compounds move through the cell membrane by passive transport. Passive transport includes diffusion, facilitated diffusion, and filtration.

In certain embodiments, the invention relates to any one of the aforementioned methods, wherein the nitrogen-containing compounds move through the cell membrane by active transport, such as, for example, via an ATP-Binding Cassette (ABC) transporter or other known transmembrane transporter.

In certain embodiments, the invention relates to any one of the aforementioned methods, wherein the nitrogen-containing compounds are transported through the cell membrane.

In certain embodiments, the invention relates to any one of the aforementioned methods, wherein the nitrogen-containing compounds are substantially non-biocidal.

In certain embodiments, the invention relates to any one of the aforementioned methods, wherein the nitrogen-containing compounds are substantially biodegradable.

In certain embodiments, the invention relates to any one of the aforementioned methods, wherein the nitrogen-containing fraction comprises the nitrogen-containing compound in about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% by weight.

In certain embodiments, the invention relates to a method, comprising the step of contacting any one of the aforementioned genetically engineered organisms with a substrate, wherein the substrate comprises a nitrogen-containing fraction and a non-nitrogen-containing fraction;

the nitrogen-containing fraction comprises, in an amount from about 10% by weight to about 100% by weight, a nitrogen-containing compound selected from the group consisting of triazine, urea, melamine, cyanamide, 2-cyanoguanidine, ammeline, guanidine carbonate, ethylenediamine, ammelide, biuret, diethylenetriamine, triethylenetetramine, 1,3-diaminopropane, calcium cyanamide, cyanuric acid, aminoethylpiperazine, piperazine, and allophante; and the genetically engineered organism converts the substrate to a product.'

In certain embodiments, the invention relates to any one of the aforementioned methods, wherein the nitrogen-containing fraction comprises the nitrogen-containing compound in about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% by weight.

In certain embodiments, the invention relates to a method, comprising the step of contacting any one of the aforementioned genetically engineered organisms with a substrate, wherein the substrate comprises a nitrogen-containing fraction and a non-nitrogen-containing fraction;

the nitrogen containing fraction consists essentially of a nitrogen-containing compound selected from the group consisting of triazine, urea, melamine, cyanamide, 2-cyanoguanidine, ammeline, guanidine carbonate, ethylenediamine, ammelide, biuret, diethylenetriamine, triethylenetetramine, 1,3-diaminopropane, calcium cyanamide, cyanuric acid, aminoethylpiperazine, piperazine, and allophante; and the genetically engineered organism converts the substrate to a product.

In certain embodiments, the invention relates to a method, comprising the step of contacting any one of the aforementioned genetically engineered organisms with a substrate, wherein the substrate consists of a nitrogen-containing fraction and a non-nitrogen-containing fraction;

the nitrogen containing fraction consists of a nitrogen-containing compound selected from the group consisting of triazine, urea, melamine, cyanamide, 2-cyanoguanidine, ammeline, guanidine carbonate, ethylenediamine, ammelide, biuret, diethylenetriamine, triethylenetetramine, 1,3-diaminopropane, calcium cyanamide, cyanuric acid, aminoethylpiperazine, piperazine, and allophante; and the genetically engineered organism converts the substrate to a product.

In certain embodiments, the invention relates to any one of the aforementioned methods, wherein the genetically engineered organism sequesters the product.

In certain embodiments, the invention relates to any one of the aforementioned methods, wherein a plurality of genetically engineered organisms is used.

In certain embodiments, the invention relates to any one of the aforementioned methods, wherein the substrate does not comprise an antibiotic.

In certain embodiments, the invention relates to any one of the aforementioned methods, wherein the substrate does not comprise ammonium sulfate.

In certain embodiments, the invention relates to any one of the aforementioned methods, wherein the substrate does not comprise urea.

In certain embodiments, the invention relates to any one of the aforementioned methods, wherein a non-genetically engineered organism, i.e., a native organism, could not metabolize (i.e., use as a source of nitrogen) the nitrogen-containing compound. In certain embodiments, the genetically engineered organism is not *Rhodococcus* sp. Strain Mel.

In certain embodiments, the invention relates to any one of the aforementioned methods, wherein the substrate comprises lignocellulosic material, glucose, xylose, sucrose, acetic acid, formic acid, lactic acid, butyric acid, a free fatty acid, dextrose, glycerol, fructose, lactose, galactose, mannose, rhamnose, or arabinose, or a combination thereof.

In certain embodiments, the invention relates to any one of the aforementioned methods, wherein the pH of the substrate is from about 2.5 to about 10.

In certain embodiments, the invention relates to any one of the aforementioned methods, wherein the genetically engineered organism is contacted with the substrate at a temperature of from about 15° C. to about 80° C.

In certain embodiments, the invention relates to any one of the aforementioned methods, wherein the genetically engineered organism is contacted with the substrate over a time period of from about 6 h to about 10 d.

In certain embodiments, the invention relates to any one of the aforementioned methods, wherein the genetically engineered organism is contacted with the substrate in a fermenter.

In certain embodiments, the invention relates to any one of the aforementioned methods, wherein the genetically engineered organism is contacted with the substrate in an industrial-size fermenter.

In certain embodiments, the invention relates to any one of the aforementioned methods, wherein a plurality of genetically engineered organisms is contacted with a plurality of substrates in a plurality of fermenters, wherein the plurality of fermenters are arranged in parallel.

In certain embodiments, the invention relates to any one of the aforementioned methods, wherein the product is ethanol, isopropanol, lactic acid, an isoprenoid, a lipid, a high-value specialty chemical, butanol, 1,3-propanediol, 1,4-butanediol, succinic acid, an expressed protein product, an enzyme product, a polyol, a pharmaceutical product, itaconic acid, or a high value specialty chemical.

Exemplary Products

In certain embodiments, the invention relates to a product made by any one of the aforementioned methods.

EXEMPLIFICATION

The following examples are provided to illustrate the invention. It will be understood, however, that the specific details given in each example have been selected for purpose of illustration and are not to be construed as limiting the scope of the invention. Generally, the experiments were conducted under similar conditions unless noted.

Example 1

The oleaginous yeast *Yarrowia lipolytica* may be engineered to convert melamine into ammonia. Melamine ($C_3N_6H_6$) is a highly nitrogenous compound that can only be degraded by a very limited number of organisms including *Rhodococcus* sp. Strain Mel. Incorporating the pathway for melamine degradation into *Yarrowia*, accompanied with a modification in the media composition to use melamine as the predominant nitrogen source, will generate a more robust industrial production solution applicable to a number of applications. The advantage confirmed by this modification is significant enough to provide advantage in multiple applications including situations where the core technology may be significant genetic burden on the organism.

Example 2

Genes from FIG. 3, or suitable homologs, will be cloned into a host strain such as *Yarrowia lipolytica, Saccharomyces cerevisiae*, or *Escherichia coli*. Enzymes native to the host organism, such as allophante hydrolase or guanine deaminase may be overexpressed with a heterologous promoter. Functional expression will be assayed by enzymatic activity and the ability to confer nitrogen limited growth on the appropriate pathway intermediate. Ultimately, strains able to degrade melamine will be selected for improved utilization of the pathway via melamine limited continuous culturing or other selective methods. Similar strategies can be devised for nitrogen compounds listed in FIG. 2.

Example 3—Vector Construction Via Yeast Mediated Ligation

Base Vector

Vector pNC10 contains an *E. coli* pMB1 origin of replication and ampicillin resistance gene, a *S. cerevisiae* 2 μm origin of replication and URA3 gene, and a multiple cloning site containing the 8-bp recognition sequences for PacI, PmeI, and AscI. DNA of interest is inserted in the multiple cloning site via yeast mediated homologous recombination (YML) cloning. (Shanks et al. 2006; Shanks et al. 2009). Briefly, target DNA sequences are amplified by PCR using primers with 20-40 bp overhang homology to adjacent DNA segments in the final vector. pNC10 or another suitable base vector is then restriction digested, creating a linearized plasmid. PCR products and linear plasmid are transformed in *S. cerevisiae*, and the native *S. cerevisiae* gap repair mechanism assembles an intact plasmid based on homology overhangs.

Figure 5:
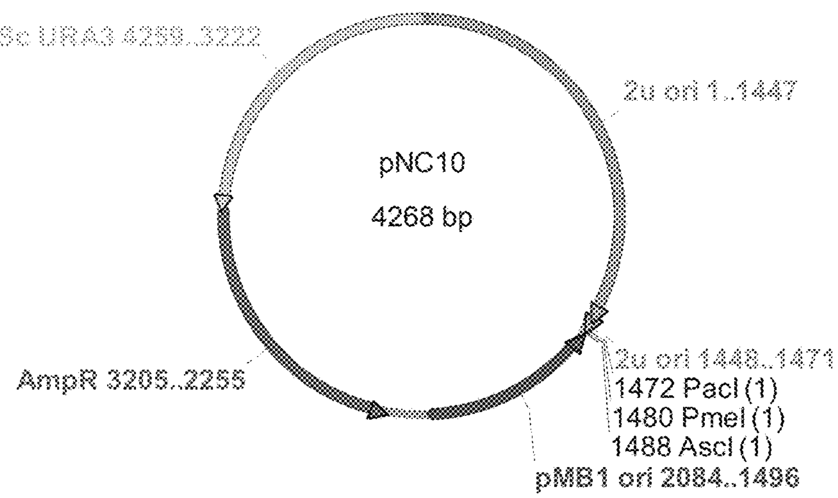
FIGS. 5-10 depict various plasmids of the invention.

The complete vector can then be isolated from *S. cerevisiae* via a DNA extraction protocol and used to transform *E. coli*. Concentrated vector can then be recovered from *E. coli* via DNA plasmid mini-prep or other suitable standard molecular biology protocols. See FIG. 5.

Example 4—*S. Cerevisiae* Transformation

Grow overnight a 5 mL culture of a *S. cerevisiae* ura3 auxotroph strain in YPD at 30 C.

Transfer 1.5 mL of overnight culture to 50 mL fresh YPD (OD ~ 0.3) and shake at 200 rpm, 30° C. in a flask. Allow to grow for approx. 4-5 hrs to an OD of 1.0.

Centrifuge cells at >5,000 rpm for 1 min, resuspend in 50 mL sterile water and repeat.

Add 1 mL of 100 mM Lithium acetate to cell pellet and transfer cells to a 1.5 mL tube.

Spin cells for 10 sec at >12,000 rpm, remove supernatant, and resuspend in 400-800 μL of 100 mM LiAc (each transformation uses 50 μL of this cell suspension).

Prepare a transformation master mix of the following, per sample

X number of transformations+1

| | |
|---|---|
| 50% PEG 3350 | 240 μL |
| 1M LiAc | 36 μL |
| Salmon sperm DNA* (2 mg/mL) | 50 μL |

*SS DNA should be first boiled for 10 min and rapidly cooled to 4° C.

Prepare one 1.5 mL tube for each transformation. Per tube, add: 5 μL of digested vector, 5 μL of each PCR insert (assuming a good PCR amplification, approx. 100-200 ng DNA), and water to bring the final volume to 34 μL. Add 326 μL master mix, and then 50 μL of cell suspension. Vortex tubes to completely mix contents.

Incubate for 30 min at 30° C., then mix by inverting and place in 42° C. water bath for 30 min. (Note optimal time at 42° C. varies strain to strain).

Spin down cells for 10 sec at >12,000 rpm, remove PEG mixture and resuspend in 1 mL sterile water. Spin down again, remove 800 μL, and use final 200 μL to resuspend and spread on SD-URA plates. Incubate at 30° C. for 2-4 days.

Example 5—Expression of Melamine Assimilation Enzymes in *S. Cerevisiae*

Melamine assimilation genes, or a subset of them, can be expressed in *S. cerevisiae* by construction of a vector using the yeast mediated ligation described above. Expression vectors consist of an *S. cerevisiae* functional promoter, a gene encoding an enzyme of the melamine assimilation pathway, and an *S. cerevisiae* functional terminator. Assemblies of the promoter-gene-terminator motif can be incorporated into a single strain, either on a replicating plasmid or integrated into a chromosome. Possible promoters and terminators are listed below, see also Sun et al. 2012. A representative plasmid, expressing the trzA melamine hydratase under control of the *Y. lipolytica* TEF1 promoter and terminator is shown below.

Figure 6:
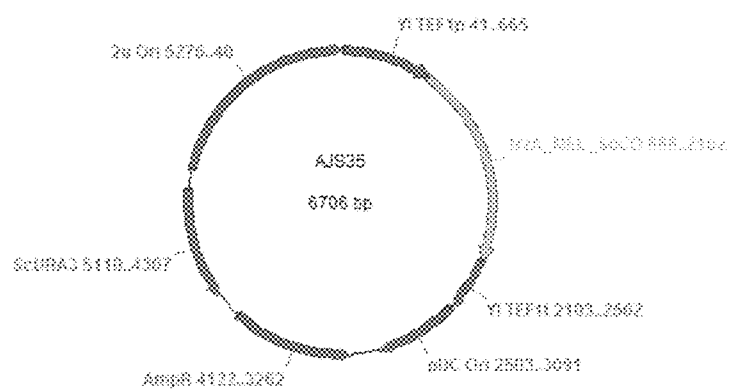

Plasmid AJS35 is an example of the melamine dehydratase trzA transcribed via the *Y. lipolytica* TEF1 promoter and terminator. See FIG. 6.

Strains NS98 and NS99 are industrial *S. cereviaie* strains carrying plasmids pNC96 (hyg$^R$, and a codon optimized trzE from *Rhodococcus* sp. MEL and pNC97 (hyg$^R$, and a codon optimized trzE from *Rhizobium leguminosarum*), respectively. Strain NS100 is the same industral *S. cerevisiae* stain carrying plasmid pNC67 (hyg$^R$, nat$^R$) which serves as a control strain.

Figures 23, 24:
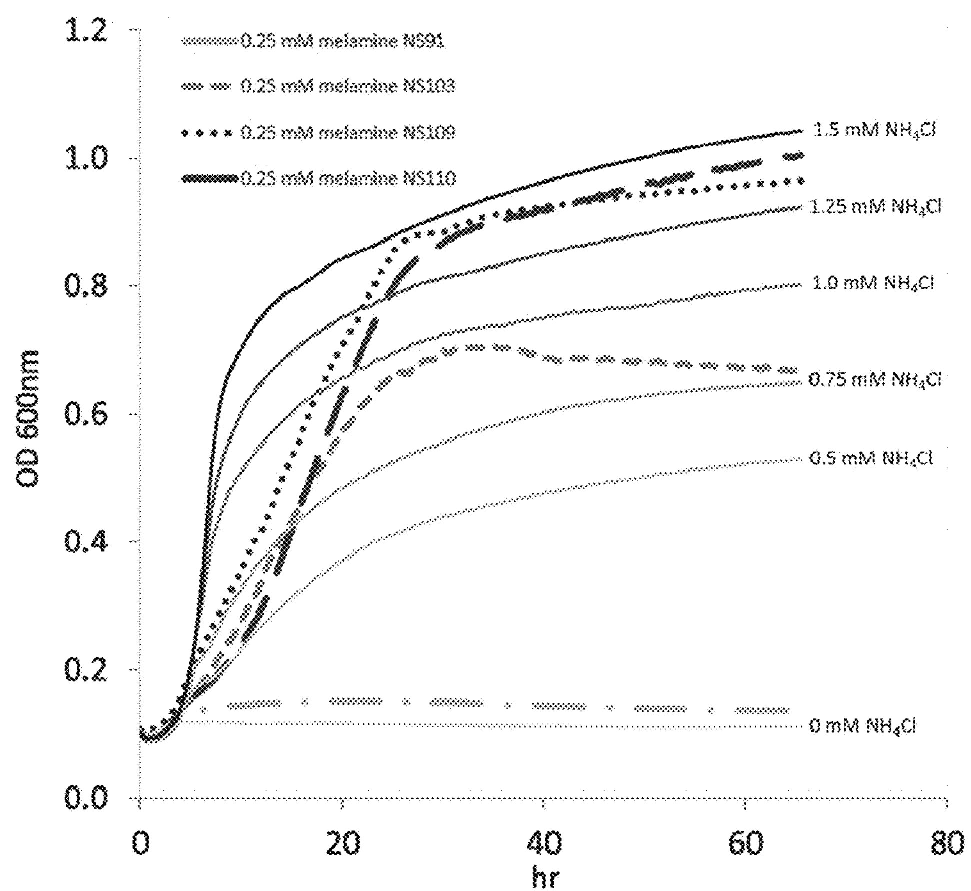
FIG. 23 tabulates the optical density at 600 nm after growth of three organisms of the invention on various media.
FIG. 24 depicts the growth of four organisms of the invention (NS91=control) on 0.25 mM melamine, as compared to the standard curves for a native organism on $NH_4Cl$. Because melamine has six nitrogen atoms, organisms having the ability to utilize melamine should be approximately six times more efficient (see, for example, NS110 on 0.25 mM melamine, as compared to a native organism on 1.5 mM $NH_4Cl$).

Strains NS98, NS99, and NS100 were grown in defined YNB medium with 10 mM urea and 100 μg/mL hygromycin to stationary phase aerobically at 30° C. 1/1000 v/v inoculations were then made into the same defined medium with either 10 mM urea, 10 mM biuret, or no additional nitrogen and grown under the same conditions. Optical density was measured after 72 hours, as shown in FIG. 23. Strains NS98 and NS99 were able to grow to an optical density approximately double that of NS100 in medium containing biuret, and also approximately double that with medium with no nitrogen supply. This shows that *S. cerevisiae* strains expressing trzE genes are advantaged in their utilization of biuret.

DNA That Can be Used as Promoters for Gene Transcription in *S. Cerevisiae*

*S. cerevisiae* TPI promoter (SEQ ID NO: 59)

```
aggaacccatcaggttggtggaaGATTACCCGTTCTAAGACTTTTCAGCT
TCCTCTATTGATGTTACACCTGGACACCCCTTTTCTGGCATCCAGTTTTT
AATCTTCAGTGGCATGTGAGATTCTCCGAAATTAATTAAAGCAATCACAC
AATTCTCTCGGATACCACCTCGGTTGAAACTGACAGGTGGTTTGTTACGC
ATGCTAATGCAAAGGAGCCTATATACCTTTGGCTCGGCTGCTGTAACAGG
GAATATAAAGGGCAGCATAATTTAGGAGTTTAGTGAACTTGCAACATTTA
CTATTTTCCCTTCTTACGTAAATATTTTTCTTTTTAATTCTAAATCAATC
TTTTTCAATTTTTTGTTTGTATTCTTTTCTTGCTTAAAtctataactaca
aaaaacacatacataaactaaaa
```

*S. cerevisiae* GPM1 promoter (SEQ ID NO: 60)

```
ttgctacgcaggctgcacaattacACGAGAATGCTCCCGCCTAGGATTTA
AGGCTAAGGGACGTGCAATGCAGACGACAGATCTAAATGACCGTGTCGGT
GAAGTGTTCGCCAAACTTTTCGGTTAACACATGCAGTGATGCACGCGCGA
TGGTGCTAAGTTACATATATATATATATATATATATATATATATATATAG
CCATAGTGATGTCTAAGTAACCTTTATGGTATATTTCTTAATGTGGAAAG
ATACTAGCGCGCGCACCCACACACAAGCTTCGTCTTTTCTTGAAGAAAAG
AGGAAGCTCGCTAAATGGGATTCCACTTTCCGTTCCCTGCCAGCTGATGG
AAAAAGGTTAGTGGAACGATGAAGAATAAAAAGAGAGATCCACTGAGGTG
AAATTTCAGCTGACAGCGAGTTTCATGATCGTGATGAACAATGGTAACGA
```

-continued

GTTGTGGCTGTTGCCAGGGAGGGTGGTTCTCAACTTTTAATGTATGGCCA

AATCGCTACTTGGGTTTGTTATATAACAAAGAAGAAATAATGAACTGATT

CTCTTCCTCCTTCTTGTCCTTTCTTAATTCTGTTGTAATTACCTTCCTTT

GTAATTTTTTTTGTAATTATTCTtcttaataatccaaacaaacacacata ttacaata

*S. cerevisiae* TDH3 promoter (SEQ ID NO: 61)

tgctgtaacccgtacatgcccaaaATAGGGGGCGGGTTACACAGAATATA

TAACATCGTAGGTGTCTGGGTGAACAGTTTATTCCTGGCATCCACTAAAT

ATAATGGAGCCCGCTTTTTAAGCTGGCATCCAGAAAAAAAAAGAATCCCA

GCACCAAAATATTGTTTTCTTCACCAACCATCAGTTCATAGGTCCATTCT

CTTAGCGCAACTACAGAGAACAGGGGCACAAACAGGCAAAAAACGGGCAC

AACCTCAATGGAGTGATGCAACCTGCCTGGAGTAAATGATGACACAAGGC

AATTGACCCACGCATGTATCTATCTCATTTTCTTACACCTTCTATTACCT

TCTGCTCTCTCTGATTTGGAAAAAGCTGAAAAAAAAGGTTGAAACCAGTT

CCCTGAAATTATTCCCCTACTTGACTAATAAGTATATAAAGACGGTAGGT

ATTGATTGTAATTCTGTAAATCTATTTCTTAAACTTCTTAAATTCTACTT

TTATAGTTAGTCTTTTTTTTAGTTTTAAAACACCAAGAacttagtttcga ataaacacacataaacaaacaaa

*S. cerevisiae* FBA1 Promoter (SEQ ID NO: 62)

gcaccgctggcttgaacaacaataCCAGCCTTCCAACTTCTGTAAATAAC

GGCGGTACGCCAGTGCCACCAGTACCGTTACCTTTCGGTATACCTCCTTT

CCCCATGTTTCCAATGCCCTTCATGCCTCCAACGGCTACTATCACAAATC

CTCATCAAGCTGACGCAAGCCCTAAGAAATGAATAACAATACTGACAGTA

CTAAATAATTGCCTACTTGGCTTCACATACGTTGCATACGTCGATATAGA

TAATAATGATAATGACAGCAGGATTATCGTAATACGTAATAGTTGAAAAT

CTCAAAAATGTGTGGGTCATTACGTAAATAATGATAGGAATGGGATTCTT

CTATTTTTCCTTTTTCCATTCTAGCAGCCGTCGGGAAAACGTGGCATCCT

CTCTTTCGGGCTCAATTGGAGTCACGCTGCCGTGAGCATCCTCTCTTTCC

ATATCTAACAACTGAGCACGTAACCAATGGAAAAGCATGAGCTTAGCGTT

GCTCCAAAAAAGTATTGGATGGTTAATACCATTTGTCTGTTCTCTTCTGA

CTTTGACTCCTCAAAAAAAAAAAATCTACAATCAACAGATCGCTTCAATT

ACGCCCTCACAAAAACTTTTTTCCTTCTTCTTCGCCCACGTTAAATTTTA

TCCCTCATGTTGTCTAACGGATTTCTGCACTTGATTTATTATAAAAAGAC

AAAGACATAATACTTCTCTATCAATTTCAGTTATTGTTCTTCCTTGCGTT

ATTCTTCTGTTCTTCTTTTTCTTTTGTcatatataaccataaccaagtaa tacatattcaaa

*Y. lipolytica* TEF1 Promoter (SEQ ID NO: 63)

tataaacggtattttcacaattgcACCCCAGCCAGACCGATAGCCGGTCG

CAATCCGCCACCCACAACCGTCTACCTCCCACAGAACCCCGTCACTTCCA

CCCTTTTCCACCAGATCATATGTCCCAACTTGCCAAATTAAAACCGTGCG

AATTTTCAAAATAAACTTTGGCAAAGAGGCTGCAAAGGAGGGGCTGGTGA

GGGCGTCTGGAAGTCGACCAGAGACCGGGTTGGCGGCGCATTTGTGTCCC

AAAAAACAGCCCCAATTGCCCCAATTGACCCCAAATTGACCCAGTAGCGG

GCCCAACCCCGGCGAGAGCCCCCTTCTCCCCACATATCAAACCTCCCCCG

GTTCCCACACTTGCCGTTAAGGGCGTAGGGTACTGCAGTCTGGAATCTAC

GCTTGTTCAGACTTTGTACTAGTTTCTTTGTCTGGCCATCCGGGTAACCC

ATGCCGGACGCAAAATAGACTACTGAAAATTTTTTTGCTTTGTGGTTGGG

ACTTTAGCCAAGGGTATAAAAGACCACCGTCCCCGAATTACCTTTCCTCT

TCTTTTCTCTCTCTCCTTGTCAACTCACACCCGAAATCGTtaagcatttc cttctgagtataagaatcattcaaa

*S. cerevisiae* PDC1 Promoter (SEQ ID NO: 64)

gcataatattgtccgctgcccgttTTTCTGTTAGACGGTGTCTTGATCTA

CTTGCTATCGTTCAACACCACCTTATTTTCTAACTATTTTTTTTTTAGCT

CATTTGAATCAGCTTATGGTGATGGCACATTTTTGCATAAACCTAGCTGT

CCTCGTTGAACATAGGAAAAAAAAATATATAAACAAGGCTCTTTCACTCT

CCTTGGAATCAGATTTGGGTTTGTTCCCTTTATTTTCATATTTCTTGTCA

TATTCTTTTCTCAATTATTATCTTCTACTCATAacctcacgcaaaataac acagtcaaatcaatcaaa

*S. cerevisiae* TEF1 Promoter (SEQ ID NO: 65)

CATAGCTTCAAAATGTTTCTACTCCTTTTTTACTCTTCCAGATTTTCTCG

GACTCCGCGCATCGCCGTACCACTTCAAAACACCCAAGCACAGCATACTA

AATTTCCCCTCTTTCTTCCTCTAGGGTGTCGTTAATTACCCGTACTAAAG

GTTTGGAAAAGAAAAAAGAGACCGCCTCGTTTCTTTTTCTTCGTCGAAAA

AGGCAATAAAAATTTTTATCACGTTTCTTTTTCTTGAAAATTTTTTTTTT

TGATTTTTTTCTCTTTCGATGACCTCCCATTGATATTTAAGTTAATAAAC

GGTCTTCAATTTCTCAAGTTTCAGTTTCATTTTTCTTGTTCTATTACAAC

TTTTTTTACTTCTTGCTCATTAGAAAGAaagcatagcaatctaatctaag ttttaattacaaa

DNA Sequences That Can be Used as Terminators of Gene Transcription

*S. cerevisiae* TPI Terminator (SEQ ID NO: 66)

taagattaatataattatataaAAATATTATCTTCTTTTCTTTATATCTA

GTGTTATGTAAAATAAATTGATGACTACGGAAAGCTTTTTATATTGTTT

-continued

CTTTTTCATTCTGAGCCACTTAAATTTCGTGAATGTTCTTGTAAGGGACG

GTAGATTTACAAGTGATACAACAAAAAGCAAGGCGCTTTTTCTAATAAAA

AGAAGAAAAGCATTTAACAATTGAACACCTCTATATCAACGAAGAATATT

ACTTTGTCTCTAAATCCTTGTAAAATGTGTACGATCTCTATATGGGTTAC

TCATAAgtgtaccgaagactgcattgaaag

*S. cerevisiae* GPM1 Terminator (SEQ ID NO: 67)

gtctgaagaatgaatgatttgaTGATTTCTTTTTCCCTCCATTTTTCTTA

CTGAATATATCAATGATATAGACTTGTATAGTTTATTATTTCAAATTAAG

TAGCTATATATAGTCAAGATAACGTTTGTTTGACACGATTACATTATTCG

TCGACATCTTTTTTCAGCCTGTCGTGGTAGCAATTTGAGGAGTATTATTA

ATTGAATAGGTTCATTTTGCGCTCGCATAAACAGTTTTCGTCAGGGACAG

TATGTTGGAATGAGTGGTAATTAATGGTGACATGACATGTTATAGCAATA

ACCTTGATGTTTACATCGTAGTTTAATGTACACCCCGCGAATTCGTTCAA

GTAggagtgcaccaattgcaaagggaa

*S. cerevisiae* TDH3 Terminator (SEQ ID NO: 68)

gtgaatttactttaaatcttgcATTTAAATAAATTTTCTTTTTATAGCTT

TATGACTTAGTTTCAATTTATATACTATTTTAATGACATTTTCGATTCAT

TGATTGAAAGCTTTGTGTTTTTTCTTGATGCGCTATTGCATTGTTCTTGT

CTTTTTCGCCACATGTAATATCTGTAGTAGATACCTGATACATTGTGGAT

GCTGAGTGAAATTTTAGTTAATAATGGAGGCGCTCTTAATAATTTTGGGG

ATATTGGCTTTTTTTTTTAAAGTTTACAAATGAATTTTTTCCGCCAGGAT

AACGATTCTGAAGTTACTCTTAGCGTTCCTATCGGTACAGCCATCAAATC

ATGCCTATAAATCATGCCTATATTTGCGTGCAGTCAGTATCATCTACATG

AAAAAAACTCCCGCAATTTCTTATAGAATACGTTGAAAATTAAATGTACG

CGCCAAGATAAGATAACATATATCTAGATGCAGTAATATACACAGATTCC

CGCGGA

*S. cerevisiae* FBA1 Terminator (SEQ ID NO: 69)

gttaattcaaattaattgatatAGTTTTTTAATGAGTATTGAATCTGTTT

AGAAATAATGGAATATTATTTTTATTTATTTATTTATATTATTGGTCGGC

TCTTTTCTTCTGAAGGTCAATGACAAAATGATATGAAGGAAATAATGATT

TCTAAAATTTTACAACGTAAGATATTTTTACAaaagcctagctcatctt

*Y. lipolytica* TEF1 Terminator (SEQ ID NO: 70)

gctgcttgtacctagtgcaaccccagtttgttaaaAATTAGTAGTCAAAA

ACTTCTGAGTTAGAAATTTGTGAGTGTAGTGAGATTGTAGAGTATCATGT

GTGTCCGTAAGTGAAGTGTTATTGACTCTTAGTTAGTTTATCTAGTACTC

GTTTAGTTGACACTGATCTAGTATTTTACGAGGCGTATGACTTTAGCCAA

-continued

GTGTTGTACTTAGTCTTCTCTCCAAACATGAGAGGGCTCTGTCACTCAGT

CGGCCTATGGGTGAGATGGCTTGGTGAGATCTTTCGATAGTCTCGTCAAG

ATGGTAGGATGATGGGGGAATACATTACTGCTCTCGTCAAGGAAACCACA

ATCAGATCACACCATCCTCCATGGTAtccgatgactctcttctccacagt

*S. cerevisiae* PDC1 Terminator (SEQ ID NO: 71)

acaagctaagttgactgctgctACCAACGCTAAGCAATAAGCGATTTAAT

CTCTAATTATTAGTTAAAGTTTTATAAGCATTTTTATGTAACGAAAAATA

AATTGGTTCATATTATTACTGCACTGTCACTTACCATGGAAAGACCAGAC

AAGAAGTTGCCGACACGACAGTCTGTTGAattggcttaagtctgggtccg ctt

*S. cerevisiae* CYC1 Terminator (SEQ ID NO: 72)

caggccccttttcctttgtcgaTATCATGTAATTAGTTATGTCACGCTTA

CATTCACGCCCTCCTCCCACATCCGCTCTAACCGAAAAGGAAGGAGTTAG

ACAACCTGAAGTCTAGGTCCCTATTTATTTTTTTTAATAGTTATGTTAGT

ATTAAGAACGTTATTTATATTTCAAATTTTTCTTTTTTTTCTGTACAAAC

GCGTGTACGCATGTAACATTATACTGAAAACCTTGCTTGAGAAGGTTTTG

GGACGCTCGAAGGCTTTAATTTGC

Example 6—Expression of Melamine Assimilation Enzymes in *E. Coli*

Melamine assimilation genes, or a subset of them, can be expressed in *E. coli* by construction of a vector using the yeast mediated ligation described above. Expression vectors consist of an *E. coli* functional promoter, a gene encoding an enzyme of the melamine assimilation pathway, and an *E. coli* functional terminator. Alternatively, several genes can be expressed from a single promoter as part of a gene operon; in this case inter-gene linker sequences are placed between genes. Sequences that can act as promoters, terminators, and linkers are listed below, as well as two representative *E. coli* expression plasmids, AJS67 (expressing genes for degradation of melamine to cyanuric acid with release of 3 $NH_3$ per melamine) and AJS68 (expressing genes for degradation of cyanuric acid to $NH_3$ and $CO_2$ with release of 3 $NH_3$ per cyanuric acid)

*E. coli* Ptach Promoter (SEQ ID NO: 73)

agctggtgacaattaatcatcggctcgtataatgtgtggaattgaatcga tataaggaggttaatca

Figure 7:
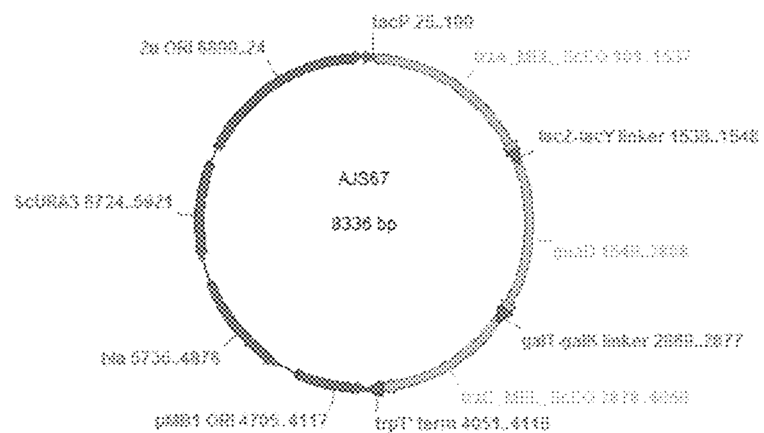
Figure 8:
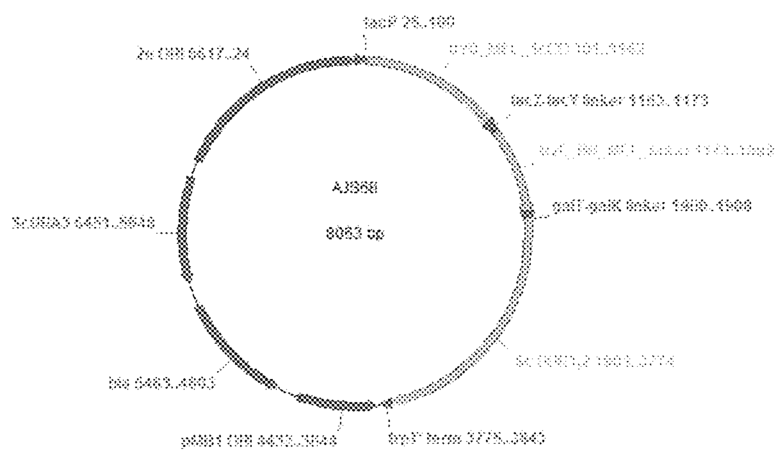

*E. coli* trpT' Terminator (SEQ ID NO: 74)

ctcaaaatatattttccctctatcttctcgttgcgcttaatttgactaa ttctcattagcgaggcgcgcctttccataggctccgcccc Inter-Gene Operon Linkers
lacZ-lacY Linker (SEQ ID NO: 75)
ggaaatccatt galT-galK Linker (SEQ ID NO: 76)
ggaacgacc See FIG. 7 and FIG. 8.

Example 7—Expression of Cyanamide Assimilation Enzyme in *S. Cerevisiae*

Figure 9:
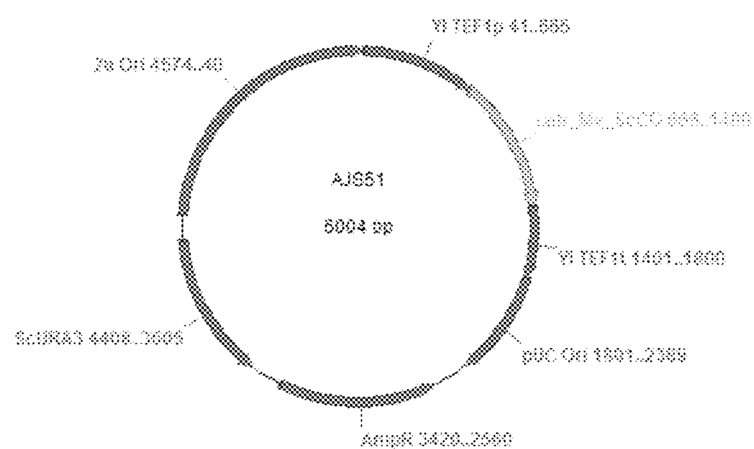

The gene expression methods described in example 5 can also be used in example 7. *S. cerevisiae* has the native ability to convert urea to $NH_3$ and $CO_2$ via the actions of urea carboxylase and allophante hydrolase, encoded in the fusion gene DUR1,2. Therefore, functional expression of cyanamide hydrolase is sufficient to convert cyanamide to $NH_3$. A representative cyanamide hydratase expression vector is shown below, with *Y. lipolytica* TEF1 promoter and terminator and a *S. cerevisiae* codon-optimized cyanamide hydratase (cah) from *Myrothecium verrucaria*. See FIG. 9.

Example 8—Expression of Cyanamide Assimilation Enzymes in *E. Coli*

Figure 10:
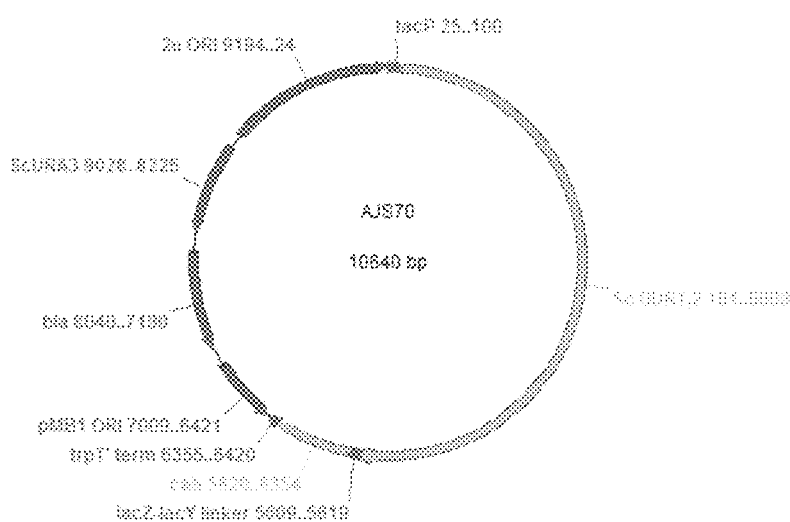

The gene expression methods described in Example 6 can also be used in example 8. Unlike *S. cerevisiae*, most *E. coli* strains are unable to utilize urea as a nitrogen source, so these additional conversion steps must also be engineered. Either a urea carboxylase/allophante hydrolase system or a urease enzyme with appropriate accessory enzymes must be expressed in addition to a cyanamide hydrolase. Urease can be found in some *E. coli* isolates (Collins and Falkow 1990) or heterologously expressed (Cussac et al. 1992). Alternatively, the DUR1,2 genes from *S. cerevisiae* could be expressed, as shown below in plasmid AJS70, along with a cyanamide hydratase. See FIG. 10.

Example 9—Expression of Melamine Assimilation Enzymes in *E. coli*

Several *E. coli* strains containing partial or complete melamine utilization pathways were constructed, as shown in FIGS. 29 and 30. Vector and strain construction was as described in example 6. All vectors contain the ampicillin resistance gene, and 100 ug/mL ampicillin was added to all culture medium. These strains were grown in MOPS defined medium with different nitrogen sources.

*E. Coli* Strains and Melamine Utilization Genes

NS88—triA (step 1)

NS89—trzA, guaD, trzC (steps 1, 2, 3)

NS90—trzD, trzE, DUR1,2 (steps 4, 5, 6)

NS91—none (control strain)

NS93—triA, native guaD selected for improved ammeline utilization (steps 1, 2)

NS103—triA, guaD, trzC (steps 1, 2, 3)

NS109—triA, guaD, trzC, trzD 12227, trzE, DUR1,2 (steps 1-6)

NS110—triA, guaD, trzC, atzD ADP, trzE, DUR1,2 (steps 1-6)

Figure 12:
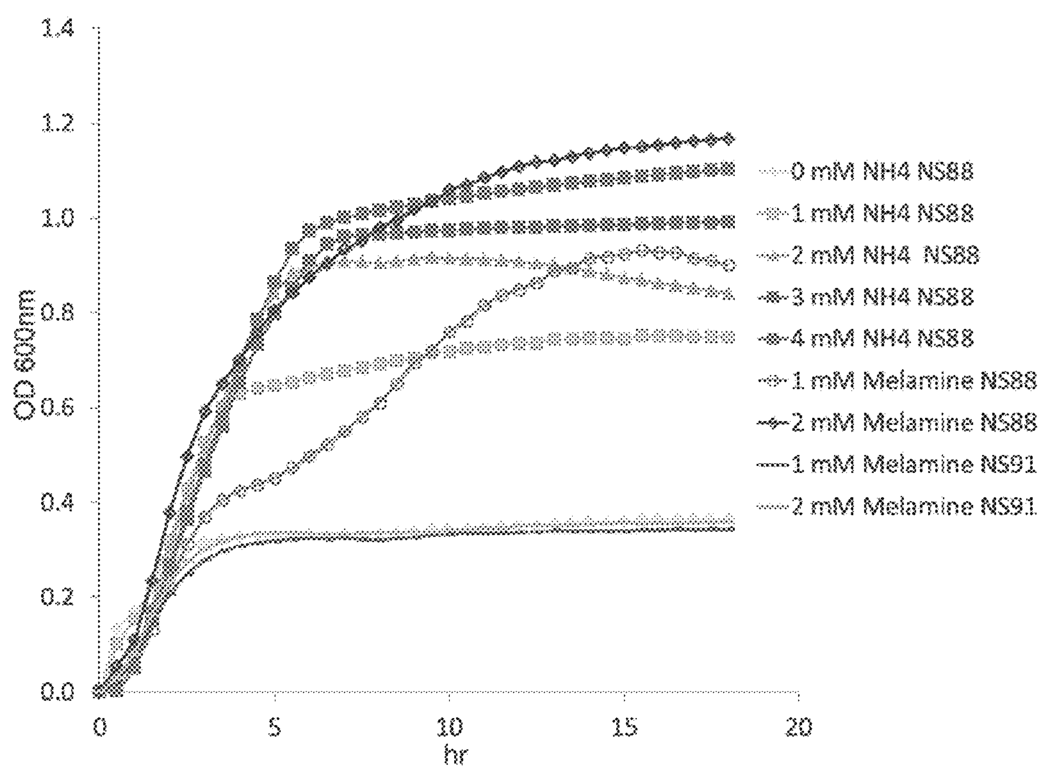
FIG. 12 depicts the growth progress of NS88 and NS91 (control) in media containing various concentrations of ammonium ion or melamine.

FIG. 12 shows the growth progress of NS88 and NS91 (control) in media containing various concentrations of ammonium chloride or melamine. NS88 grown on 1 mM melamine reaches an optical density comparable to that of the equivalent use of 2 mM ammonium chloride, suggesting that 2 mM ammonia are liberated from melamine by triA and the natively encoded guaD genes. The control strain NS91 does not grow with melamine as nitrogen source.

Figure 13:
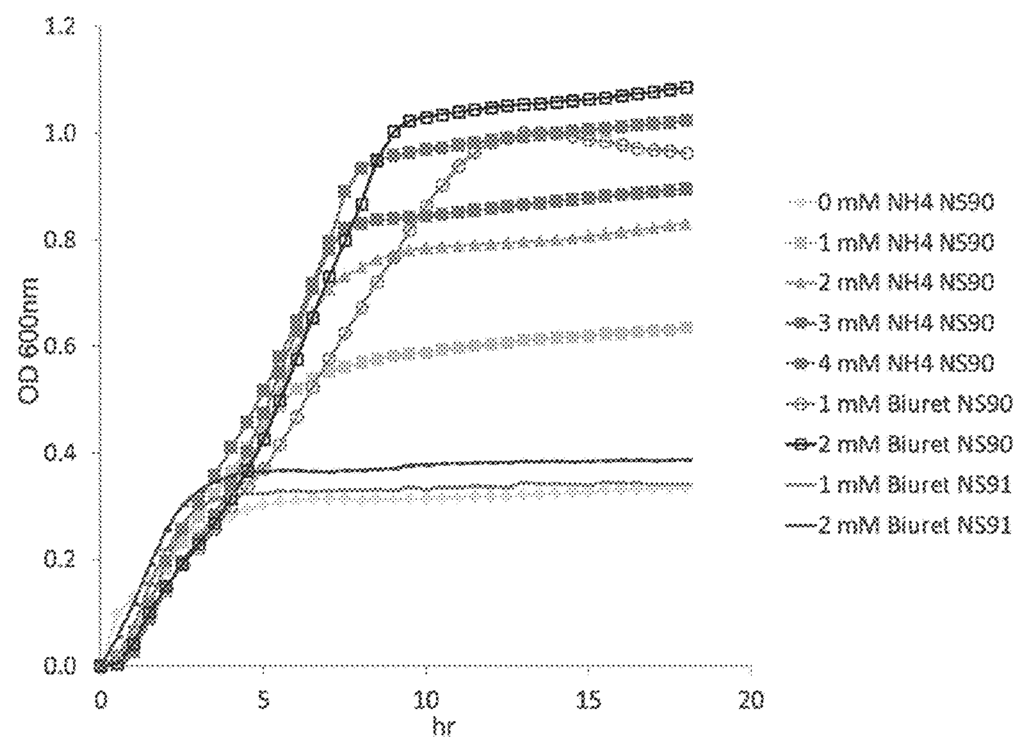
FIG. 13 depicts the growth progress of NS90 and NS91 (control) in media containing various concentrations of ammonium ion or biuret.

FIG. 13 shows the growth progress of NS90 and NS91 (control) in media containing various concentrations of ammonium chloride or biuret. NS90 grown on 1 mM biuret reaches an optical density comparable to that of the equivalent use of 3 mM ammonium chloride, suggesting that 3 mM ammonia are liberated from biuret by trzE and the DUR1,2. The control strain NS91 does not grow with biuret as nitrogen source.

FIG. 24 shows the growth progress of NS91, NS103, NS109, and NS110 in medium containing 0.25 mM melamine as sole nitrogen source. An average of all four strains grown on different ammonium chloride concentrations from 0 to 1.5 mM is also shown as a standard curve for growth with limiting nitrogen. NS91 grown on melamine is similar to the 0 mM ammonium chloride control. NS103 grown on 0.25 mM melamine is similar to 1-0.75 mM ammonium chloride, suggesting it is approximately utilizating the predicted 3 mM ammonia per 1 mM melamine. Strains NS109 and NS110 grown on 0.25 mM melamine are similar to 1.5-1.25 mM ammonium chloride, suggesting it is approximately utilizating the predicted 6 mM ammonia per 1 mM melamine.

Figure 25:
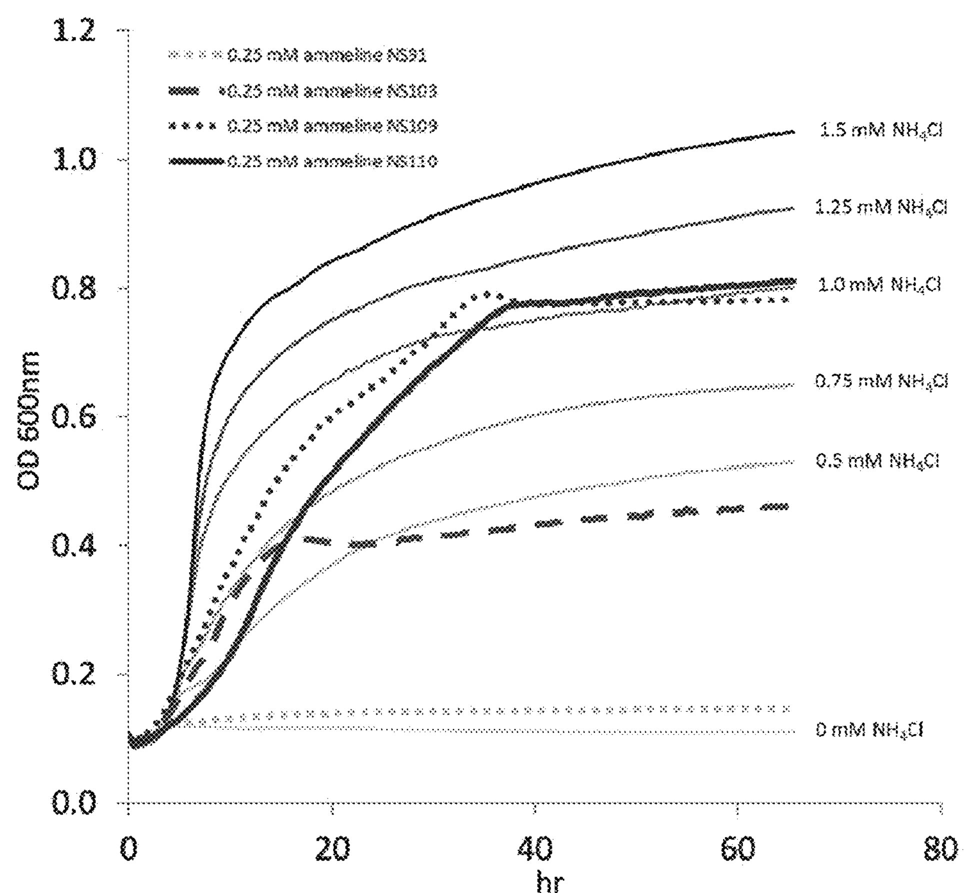
FIG. 25 depicts the growth of four organisms of the invention (NS91=control) on 0.25 mM ammeline, as compared to the standard curves for a native organism on $NH_4Cl$. Because ammeline has five nitrogen atoms, organisms having the ability to utilize melamine should be approximately five times more efficient (see, for example, NS110 on 0.25 mM ammeline, as compared to a native organism on 1.25 mM $NH_4Cl$).

FIG. 25 shows the growth progress of NS91, NS103, NS109, and NS110 in medium containing 0.25 mM ammeline as sole nitrogen source. An average of all four strains grown on different ammonium chloride concentrations from 0 to 1.5 mM is also shown as a standard curve for growth with limiting nitrogen. NS91 grown on ammeline is similar to the 0 mM ammonium chloride control. NS103 grown on 0.25 mM ammeline is similar to 0.5 mM ammonium chloride, suggesting it is approximately utilizating the predicted 2 mM ammonia per 1 mM ammeline. Strains NS109 and NS110 grown on 0.25 mM ammeline are similar to 1.25-1.0 mM ammonium chloride, suggesting it is approximately utilizating the predicted 5 mM ammonia per 1 mM ammeline.

Figure 26:
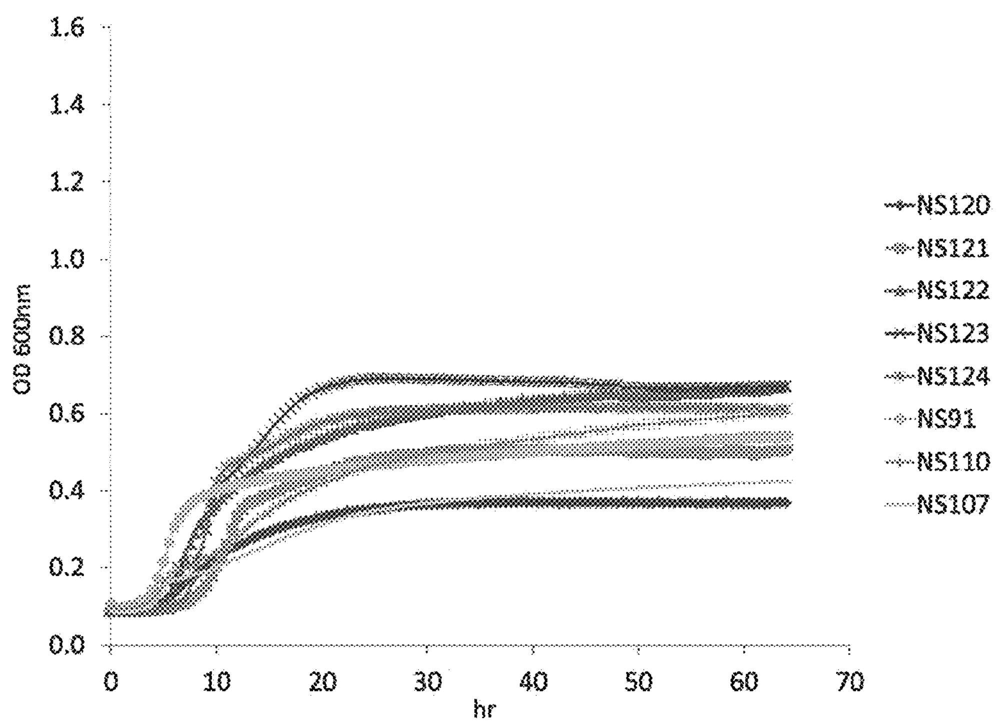
FIG. 26 depicts the growth of various organisms of the invention on 0.5 mM $NH_4Cl$. Importantly, the organisms described in FIGS. 26-28, for example NS120, NS91, NS107, and NS123, are *E. coli* strains derived from *E. coli* K12, *E. coli* B, *E. coli* Crooks, and *E. coli* MG1655 and are intended to show the breadth of the invention across various strains of *E. coli*.
Figure 27:
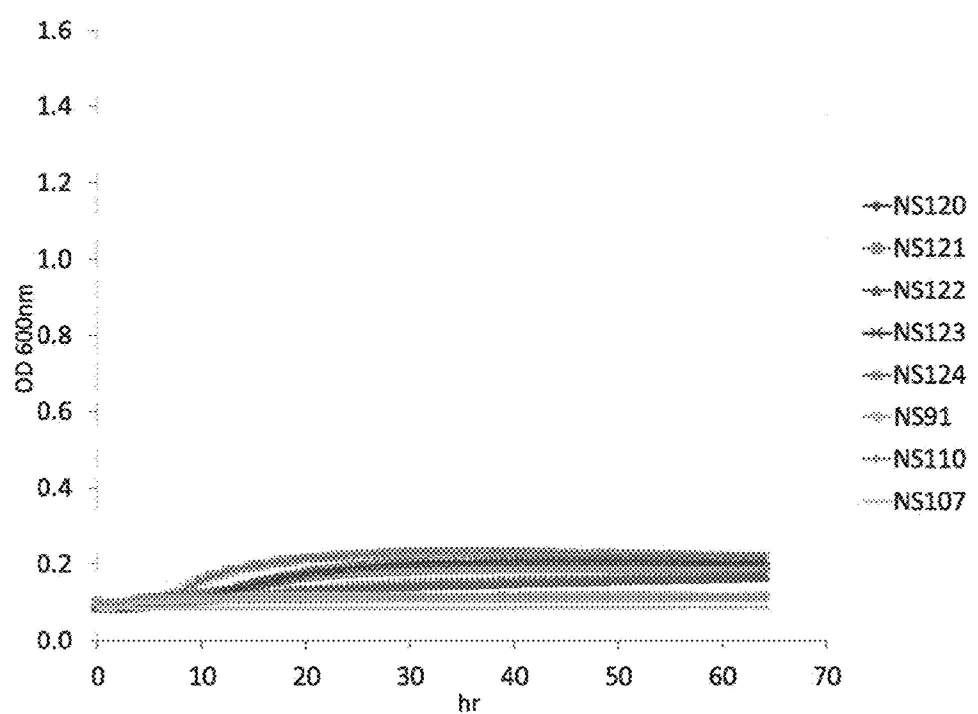
FIG. 27 depicts the growth of various organisms of the invention on a medium containing no nitrogen.
Figure 28:
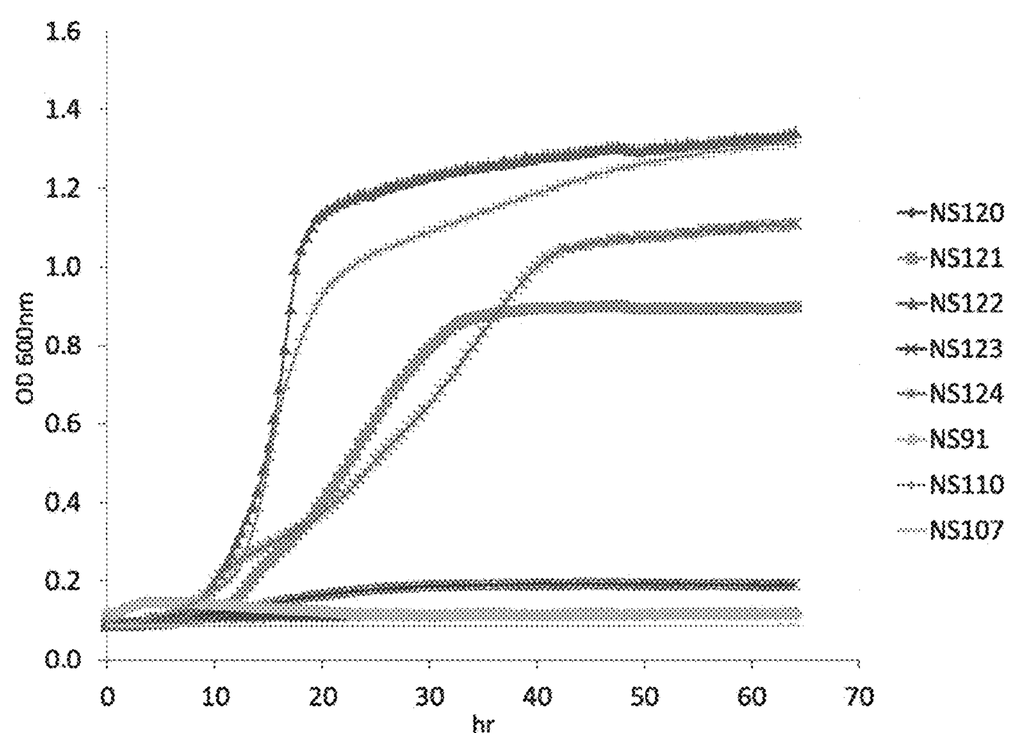
FIG. 28 depicts the growth of various organisms of the invention on a medium containing 0.5 mM melamine.

FIGS. 26, 27, and 28 show *E. coli* strains derived from *E. coli* K12, *E. coli* MG1655, *E. coli* B, and *E. coli* Crooks (C) containing either pNC121 with the complete melamine utilization pathway, or pNC53, a control vector. See FIGS. 29 and 30 for strain details. All the strains containing pNC121 are able to grow on 0.5 mM melamine as sole nitrogen source (FIG. 28). This indicates that the melamine utilization pathway is broadly applicable to *E. coli* strains that are commonly utilized for biotechnology applications.

Strains can also be selected for improved utilization of melamine derived nitrogen sources, in one example NS88 was passaged for 11 serial transfers in MOPS defined medium with 0.5 mM ammeline as sole nitrogen source. After the final passage, single colonies were isolated, and one was designated as NS93. NS93 and NS91 were grown overnight in medium with 0.5 mM ammonium chloride as sole nitrogen source, and then inoculated in medium with 0.5 mM ammeline as sole nitrogen source. NS91 exhibited a maximum growth rate of 0.024 $hr^{-1}$ on ammeline, while NS93 exhibited a maximum growth rate of 0.087 $hr^{-1}$.

Media Utilization

Cultures grown aerobically at 37° C. with 100 mg/L ampicillin. Pre-cultures were grown in LB media with 100 mg/L ampicillin, washed once with an equal volume of MOPS media containing no nitrogen, and inoculated at 5% v/v of the final fermentation volume. The content of the MOPS medium is outlined in FIG. 11.

Imaging Cultures in Various Media

Figure 14:
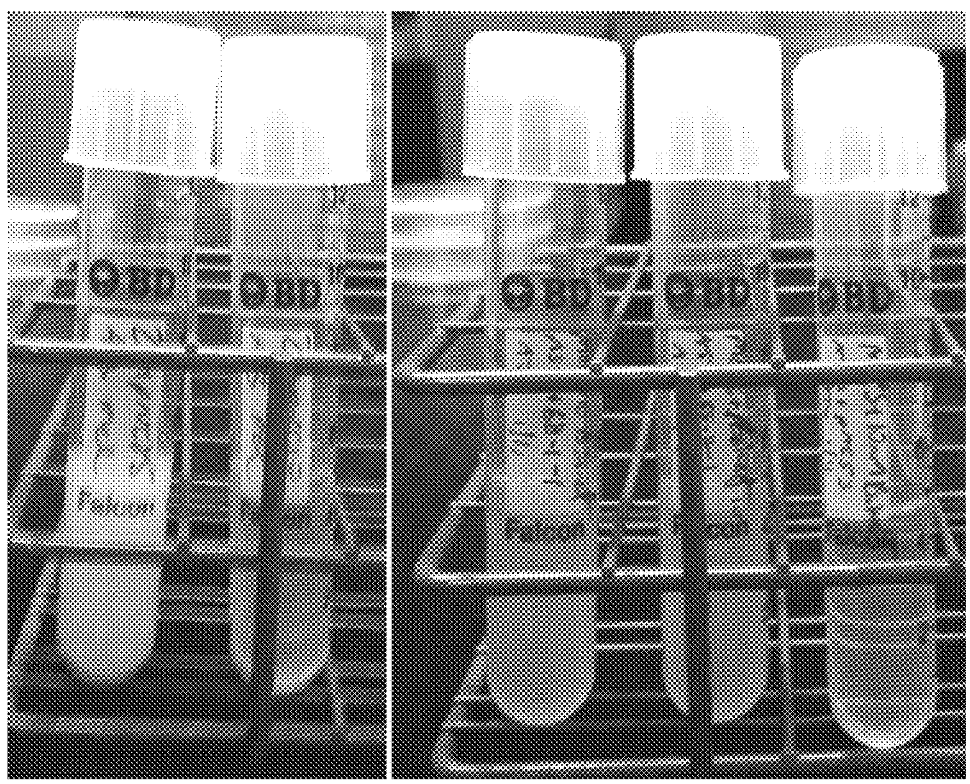
FIG. 14 depicts images, taken after 48 h, of cultures grown in MOPS media with different nitrogen sources. From left to right: NS88 with 10 mM melamine; NS91 with 10 mM melamine; NS90 with 10 mM biuret (replicate 1); NS90 with 10 mM biuret (replicate 2); and NS91 with 10 mM biuret.
Figure 15:
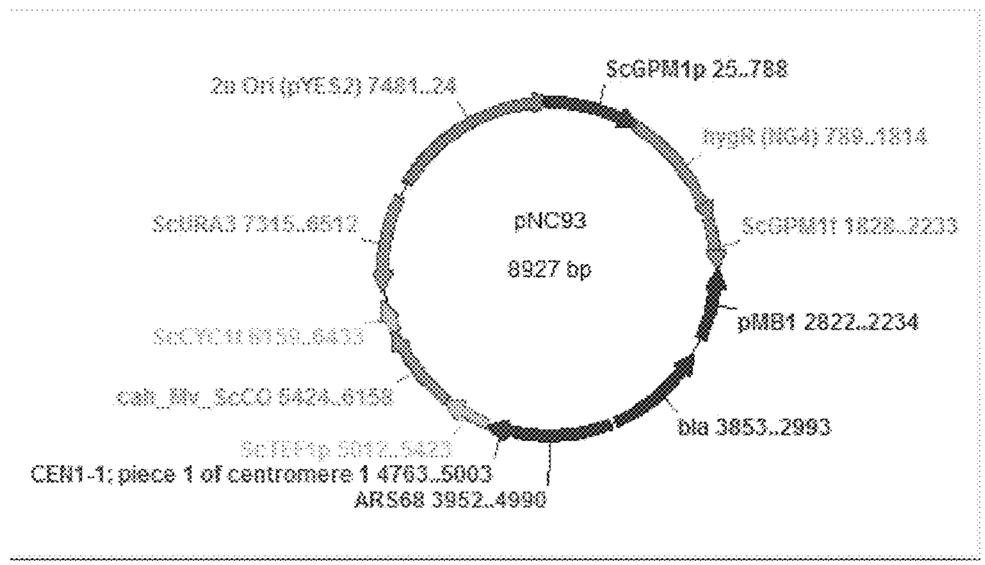
FIG. 15 depicts a plasmid of the invention.

Precultures were grown in LB media with 100 mg/L ampicillin, 0.1 mL were directly inoculated into 5 mL MOPS media with 100 mg/L ampicillin and the indicated nitrogen source. Grown at 37° C. in a drum roller at 30 rpm. See FIG. 14.

Example 10—Organisms Engineered to Utilize Cyanamide

Organisms

NS100—industrial *S. cerevisiae* strain with pNC67 ($hyg^R$, $nat^R$)

NS101—industrial *S. cerevisiae* strain with pNC93 ($hyg^R$, cah)

NS111—*S. cerevisiae* NRRL Y-2223 with pNC93 ($hyg^R$, cah)

NS112—*S. cerevisiae* NRRL Y-2223 with pNC67 ($hyg^R$, $nat^R$)

Figure 16:
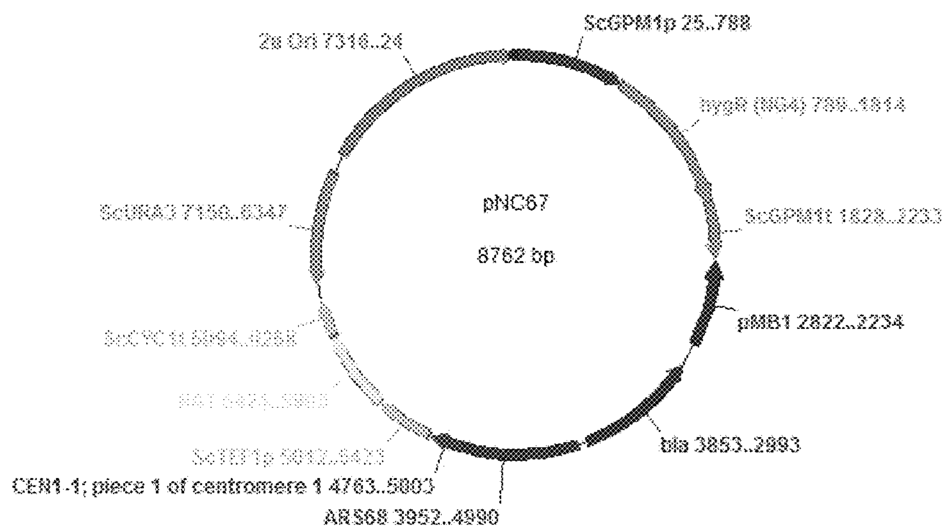
FIG. 16 depicts a plasmid of the invention.

See FIG. 16.

Utilization of Cyanamide in Defined Medium

Figure 17:
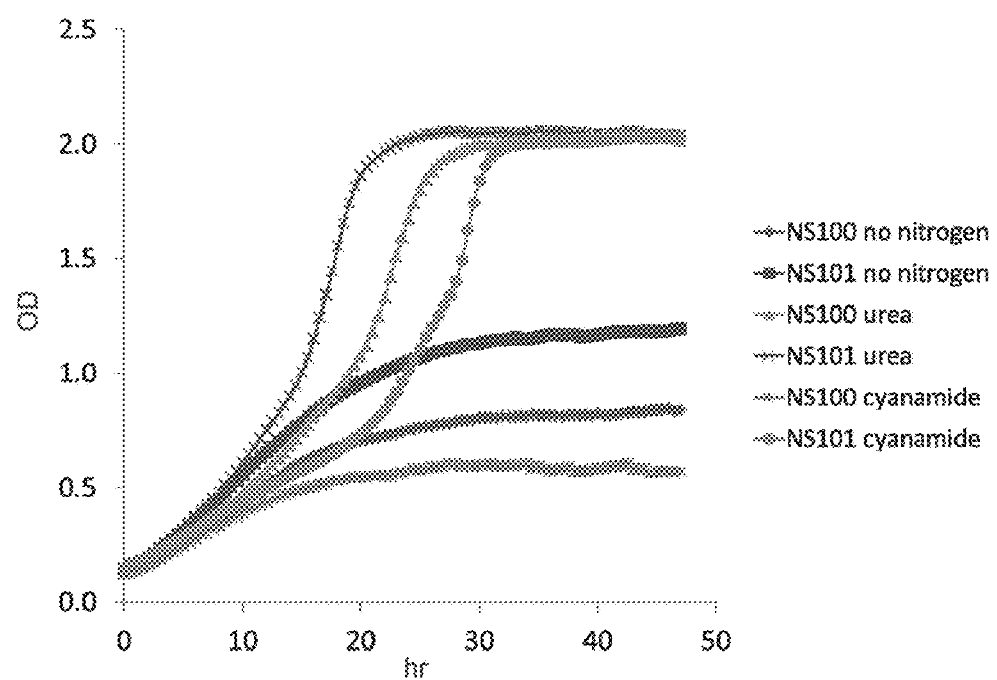
FIG. 17 depicts the growth progress of NS100 (control) and NS101 in media containing no nitrogen source, urea, or cyanamide.

Optical density of NS100 and NS101 grown in defined medium with different nitrogen sources. NS100 and NS101 were grown overnight in YPD medium, washed once in an equal volume of sterile water, and inoculated at 3.33% v/v. Strain NS101 is able to grow to an optical density with cyanamide comparable to that with urea, while NS100 grows to an optical density comparable to that with no nitrogen present in the medium. Data are averages of 3 replicate wells in a 96 well plate; 150 μL per well. 30° C., YNB medium contained 20 g/L glucose, 1.7 g/L YNB base medium without amino acids or ammonium sulfate, 5 g/L sodium sulfate, 100 μg/mL hygromycin, and either 10 mM urea, 10 mM cyanamide, or no nitrogen source. Inoculation was with 5 μL of culture pregrown for 24 hrs in the same medium with urea as nitrogen source. See FIG. 17.

Figures 21, 22:
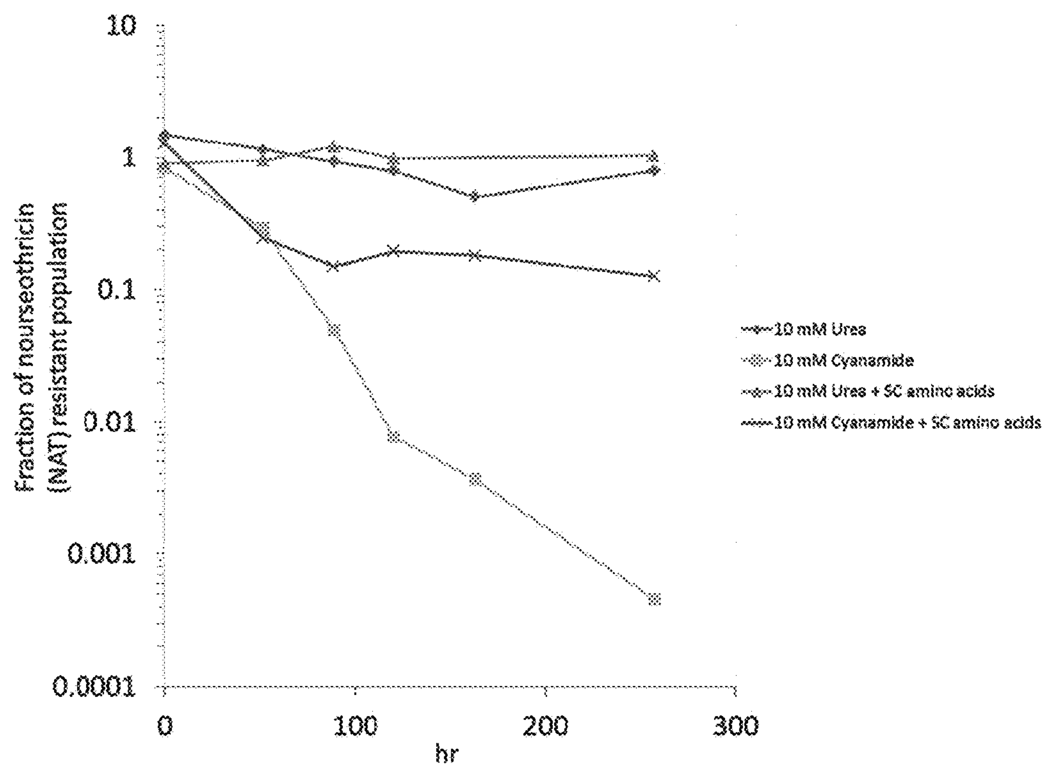
FIG. 21 depicts the growth of an organism of the invention in the presence of an antibiotic on various nitrogen-containing media (see FIG. 33 for composition of SC amino acid media).
FIG. 22 tabulates the optical density at 600 nm after growth of four organisms of the invention on various media.

Additionally, strains NS100, NS101, NS111, and NS112 were grown in defined YNB medium with 10 mM urea and 100 μg/mL hygromycin to stationary phase aerobically at 30° C. 1/1000 v/v inoculations were then made into the same defined medium with either 10 mM urea, 10 mM cyanamide, or no additional nitrogen and grown under the same conditions. Optical density was measured after 72 hours, as shown in FIG. 22. Strains NS101 and NS111, two different *S. cerevisiae* strains carrying the cah gene, were able to grow to an optical density comparable to that with urea; however, NS100 and NS112 only were able to grow to an optical density equal to or lower than in media with no nitrogen source. This shows that multiple *S. cerevisiae* strains are able to utilize cyanamide in the presence of the cah gene.

Competition in Defined Medium

Figure 18:
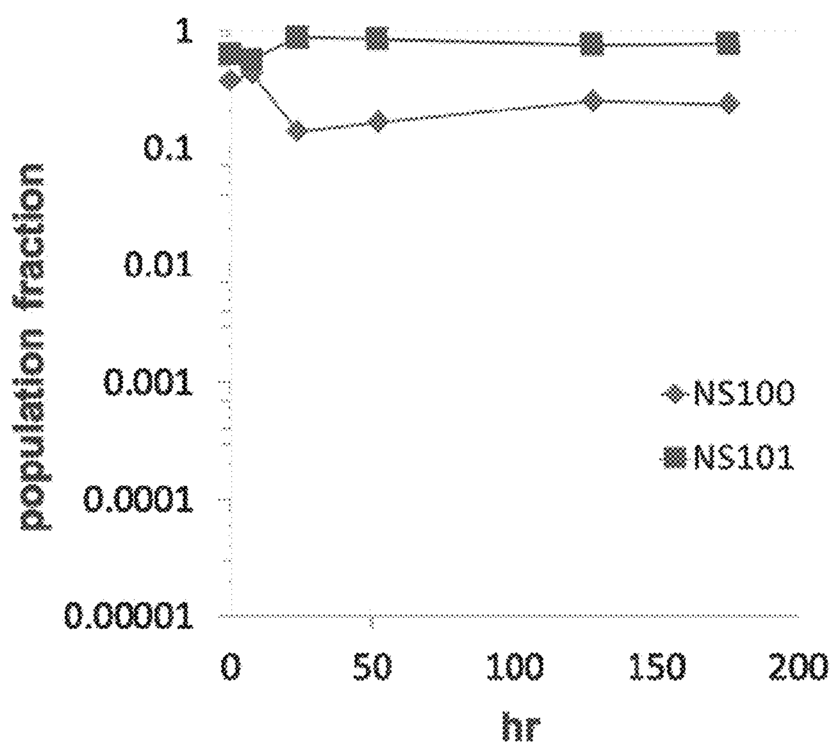
FIG. 18 depicts the population fraction of NS100 (control) and NS101 in a urea-containing medium.
Figure 19:
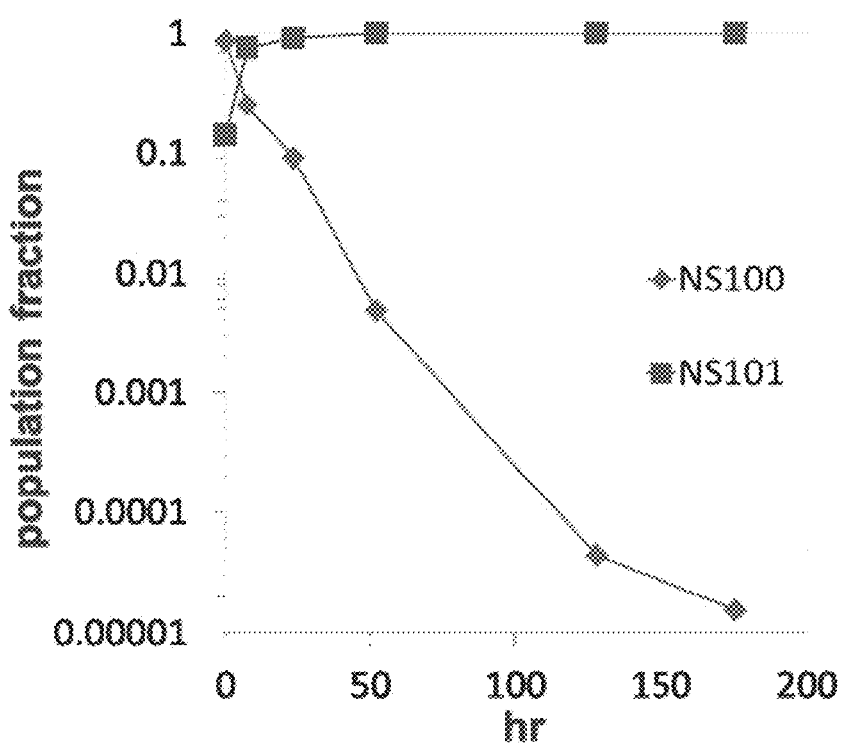
FIG. 19 depicts the population fraction of NS100 (control) and NS101 in a cyanamide-containing medium.

Strains NS100 ($hyg^R$, $nat^R$) and NS101 ($hyg^R$, cah) were grown in defined medium with 100 μg/mL hygromycin with urea as nitrogen source, and then both inoculated into defined medium containing either 10 mM urea or 10 mM cyanamide as nitrogen source. Upon growth to stationary phase, 1/100 v/v serial transfers were made to fresh medium with the same composition. The culture population was monitored via counting the number of $hyg^R$, $nat^R$ colony forming units and subtracting from the number of $hyg^R$ colony forming units. See FIG. 18 and FIG. 19 for one experiment in defined minimal medium. A second experiment is shown in FIG. 21. The second experiment included both defined minimal (YNB) and defined complex (YNB+SC amino acids) medium compositions. The defined YNB medium contained 20 g/L glucose, 1.7 g/L YNB base medium without amino acids or ammonium sulfate, 5 g/L sodium sulfate, and either 10 mM urea, 10 mM cyanamide, or no nitrogen source. Medium compositions are additionally given in FIGS. 32 and 33. Growth occurred aerobically at 30° C. Colony forming units were counted by serial dilutions in YPD media with either 300 μg/mL hygromycin or 100 μg/mL nourseothricin, and are the average of 3 dilution counts. See FIG. 18 and FIG. 19.

Utilization of Cyanamide in Rich Medium

Optical density of NS100 and NS101 grown in rich YPD medium with 100 μg/mL hydgromycin and with and without 10 mM cyanamide. NS100 and NS101 were grown overnight in YNB medium, and inoculated at 3.33% v/v. NS101 experiences a shorter lag phase than NS100 in the presence of 10 mM cyanamide. Thus, cyanamide, in addition to functioning as a sole source of nitrogen, can also act as a deterrent for microbial growth. Data are averages of 3 replicate wells in a 96 well plate; 150 μL per well. 30° C., YPD medium or YPD medium with 10 mM cyanamide. Inoculation was with 5 μL of culture pregrown for 24 hrs in the YNB medium with urea as nitrogen source.

Figure 20:
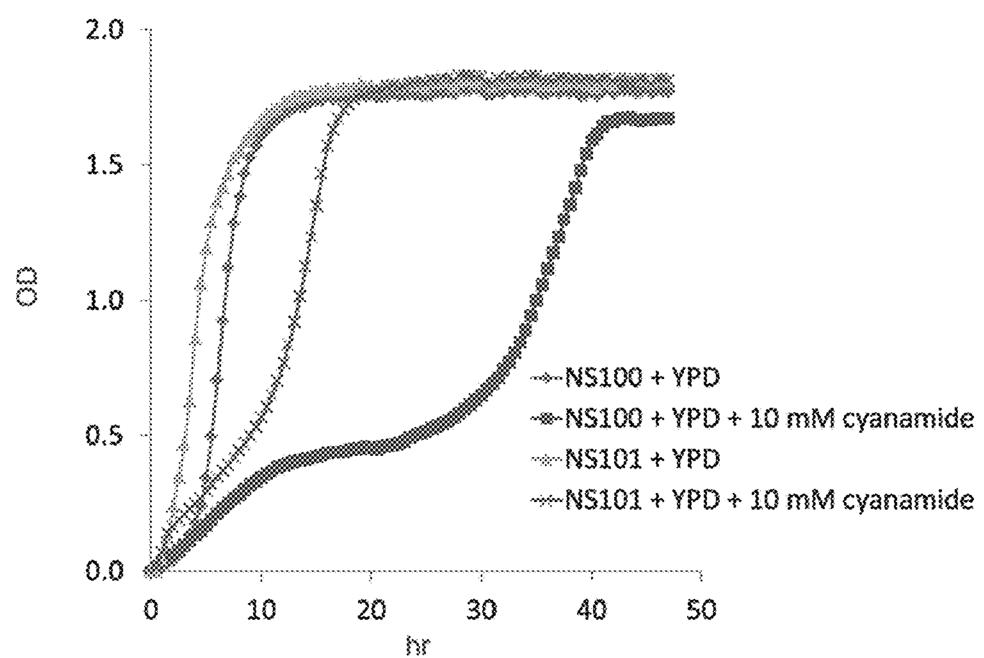
FIG. 20 depicts the growth progress of NS100 (control) and NS101 in media containing no nitrogen source, or media containing cyanamide.

See FIG. 20.

Example 11—Cyanamide Hydratase Activity Assay

This assay measured the conversion rate of cyanamide to urea. In the first step, cyanamide was hydrated to urea by cyanamide hydratase, which was detected in cell free extract of a *S. cerevisiae* strain expressing the cah gene and a control strain without cah. In the second step of the assay, a commercial kit (Megazyme, Ireland) was used to detect urea via enzymatic conversion of urea to ammonia followed by NADPH linked conversion of ammonia and 2-oxoglutarate to NADP+, $H_2O$, and glutamic acid.

Cell free extracts were prepared by growing *S. cerevisiae* strains in 50 mL yeast extract, peptone, dextrose (YPD) medium with 300 μg/mL hygromycin to an optical density between 1-2. Cells were harvested by centrifugation, washed once in an equal volume of water, and re-suspended in Y-PER lysis buffer (Thermo Scientific, USA) following the manufacturer's instructions. After incubation at room temperature for 20 minutes, the lysate was centrifuged at 14,000×g for 10 min and the supernatant was recovered as the cell free extract. Total protein was measured by a Nanodrop spectrophotometer (Thermo Scientific, USA).

Protocol

Add together in a 100 μL volume:

10 μL of 50 mM NaPO4, pH 7.7;

10 μL of 200 mM cyanamide made fresh 5-20 μL cell free extract balance water (60 μL for 20 μL CFE)

add 100 uL of above sample to 2.9 mL Megazyme urea/ammonia assay reagents and monitor at 340 nm.

| | | Cyanamide hydratase activity | |
|---|---|---|---|
| Strain | Genotype | μmol $min^{-1}$ $mg^{-1}$ | Standard Deviation |
| NS100 | $hyg^R$ $nat^R$ | 0.019 | 0.001 |
| NS101 | $hyg^R$ cah | 0.073 | 0.002 |

Example 12—Exemplary Sequences of the Invention

Sequence 1 is the DNA sequence of the allophanate hydrolase atzF gene in *Pseudomonas* sp. strain ADP.

Sequence 2 is the DNA sequence of allophanate hydrolase DUR1,2 gene in *S. cerevisiae*.

Sequence 3 is the DNA sequence of allophanate hydrolase YALI0E07271g gene in *Y. lipolytica* CLIB122.

Sequence 4 is the DNA sequence of the biuret amidohydrolase atzE gene in *Pseudomonas* sp. strain ADP.

Sequence 5 is the DNA sequence of the cyanuric acid amidohydrolase atzD gene in *Pseudomonas* sp. strain ADP.

Sequence 6 is the DNA sequence of the cyanuric acid amidohydrolase trzD gene in *Pseudomonas* sp. strain NRRLB-12227 (formerly *Acidovorax citrulli*).

Sequence 7 is the DNA sequence of the cyanuric acid amidohydrolase atzD trzD gene in *Rhodococcus* sp. Mel.

Sequence 8 is the DNA sequence of the guanine deaminase guaD gene in *E. coli* K12 strain MG1566.

Sequence 9 is the DNA sequence of the guanine deaminase blr3880 gene in *Bradyrhizobium japonicum* USDA 110.

Sequence 10 is the DNA sequence of the guanine deaminase GUD1/YDL238C gene in *S. cerevisiae*.

Sequence 11 is the DNA sequence of the guanine deaminase YALI0E25740p gene in *Y. lipolytica* CLIB122.

Sequence 12 is the DNA sequence of the melamine deaminase trzA gene in *Williamsia* sp. NRRL B-15444R (formerly *R. corallinus*).

Sequence 13 is the DNA sequence of the melamine deaminase triA gene in *Pseudomonas* sp. strain NRRL B-12227 (formerly *Acidovorax citrulli*).

Sequence 14 is the DNA sequence of the isopropylammelide isopropylaminohydrolase atzC gene in *Pseudomonas* sp. strain ADP.

Sequence 15 is the cDNA sequence of the *Myrothecium verrucaria* cyanamide hydratase (cah) gene.

Sequences 16-21 are DNA sequences of the invention.

Sequences 22-37 are the sequences of various cyanamide hydratase (cah) genes for use in the invention.

Sequences 38 and 39 are the sequences of various trzC genes for use in the invention.

Sequences 40 and 41 are the sequences of various trzE genes for use in the invention.

Sequence 42 is the sequence of plasmid pNC10.

Sequence 43 is the sequence of plasmid pNC53.

Sequence 44 is the sequence of plasmid pNC67.

Sequence 45 is the sequence of plasmid pNC85.

Sequence 46 is the sequence of plasmid pNC86.

Sequence 47 is the sequence of plasmid pNC87.

Sequence 48 is the sequence of plasmid pNC93.

Sequence 49 is the sequence of plasmid pNC96.

Sequence 50 is the sequence of plasmid pNC97.

Sequence 51 is the sequence of plasmid pNC101.

Sequence 52 is the sequence of plasmid pNC120.

Sequence 53 is the sequence of plasmid pNC121.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A fermentation method of culturing a genetically engineered microbial a cell comprising:

providing a cell comprising a non-native nucleic acid molecule encoding a melamine deaminase enzyme:

contacting the cell with a substrate, wherein the substrate comprises a nitrogen-containing fraction and a non-nitrogen-containing fraction and wherein the nitrogen-containing fraction comprises, in an amount from about 10% by weight to about 100% by weight, a nitrogen-containing compound of Formula I, or a salt thereof; and culturing the cell, wherein the cell can, unlike a cell of the same species that lacks the nucleic acid molecule, metabolize the nitrogen-containing compound and wherein, the compound of formula I is $$\text{(A)}\!-\!\!(R)_n \qquad \text{I}$$

wherein, independently for each occurrence, $$\text{(A)}$$

is a five-, or a six-membered aryl or heteroaryl group;

R is —OH, —$CO_2$H, —$NO_2$, —CN, substituted or unsubstituted amino, or substituted or unsubstituted alkyl; and n is 0, 1, 2, 3, 4, or 5.

2. The method of claim 1, wherein the nitrogen-containing compound is selected from the group consisting of 5-Aminotetrazole, Melamine, Ammeline, and Ammelide.

3. The method of claim 1, wherein the substrate does not comprise an antibiotic.

4. The method claim 1, wherein the substrate does not comprise ammonium or urea.

5. The method of claim 1, wherein the substrate comprises lignocellulosic material, glucose, xylose, sucrose, acetic acid, formic acid, lactic acid, butyric acid, a free fatty acid, dextrose, glycerol, fructose, lactose, galactose, mannose, rhamnose, or arabinose, or a combination thereof.

6. The method of claim 1, wherein the genetically engineered cell is contacted with the substrate in a fermentor.

7. The method of claim 1, wherein the non-native nucleic acid molecule comprises SEQ ID NO: 12 or SEQ ID NO: 13 or the non-native molecule comprises a sequence having at least 85% sequence identity with SEQ ID NO:12 or SEQ ID NO:13.

* * * * *